United States Patent
Iyer et al.

(10) Patent No.: US 8,513,425 B2
(45) Date of Patent: Aug. 20, 2013

(54) HETEROARYL PYRROLIDINYL AND PIPERIDINYL KETONE DERIVATIVES AND USES THEREOF

(75) Inventors: Pravin Iyer, Mountain View, CA (US); Clara Jeou Jen Lin, Palo Alto, CA (US); Stephen M. Lynch, San Jose, CA (US); Matthew C. Lucas, Sunnyvale, CA (US); Ann Marie Madera, Dublin, CA (US); Kerem Erol Ozboya, Mountain View, CA (US); Robert James Weikert, Boulder Creek, CA (US); Ryan Craig Schoenfeld, San Jose, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 13/301,605

(22) Filed: Nov. 21, 2011

(65) Prior Publication Data
US 2012/0065225 A1    Mar. 15, 2012

Related U.S. Application Data

(62) Division of application No. 12/002,696, filed on Dec. 18, 2007, now Pat. No. 8,084,623.

(60) Provisional application No. 60/875,969, filed on Dec. 19, 2006, provisional application No. 60/999,561, filed on Oct. 19, 2007.

(51) Int. Cl.
*C07D 211/30* (2006.01)
*A61K 31/445* (2006.01)

(52) U.S. Cl.
USPC .......................... 546/225; 514/330

(58) Field of Classification Search
USPC .......................... 546/225; 514/330
See application file for complete search history.

(56) References Cited

PUBLICATIONS

Schaumann (CAPLUS Abstract of: Archiv fuer Experimentelle Pathologie und Pharmakologie (1940), 196, 109-36).*
Kubinyi (3D QSAR in Drug Design: Ligand-Protein Interactions and Molecular Similarity, vol. 2-3, Springer, 1998, 800 pages). pp. 243-244 provided.*
Rhoden et al. (J. Bioorg. Med. Chem. 13 (2005) 5623-34).*

* cited by examiner

*Primary Examiner* — Robert Havlin
(74) *Attorney, Agent, or Firm* — Robert C. Hall

(57) ABSTRACT

Compounds of the formula:

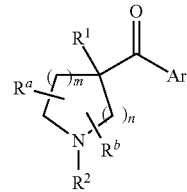

or pharmaceutically acceptable salts thereof, wherein m, n, Ar, $R^1$, $R^2$, $R^a$ and $R^b$ are defined herein. Also provided are pharmaceutical compositions, methods of using, and methods of preparing the compounds.

12 Claims, No Drawings

HETEROARYL PYRROLIDINYL AND PIPERIDINYL KETONE DERIVATIVES AND USES THEREOF

CROSS REFERENCE TO RELATED APPLICATIONS

This application is a Divisional of U.S. application Ser. No. 12/002,696 filed on Dec. 18, 2007, which claims benefit of priority of U.S. Provisional Application No. 60/875,969, filed on Dec. 19, 2006 and U.S. Provisional Application No. 60/999,561, filed on Oct. 19, 2007, the disclosures of which are hereby incorporated by reference in their entirety.

FIELD OF THE INVENTION

This invention pertains to heteroaryl pyrrolidinyl and piperidinyl ketone compounds and methods for using the same. In particular, compounds of the present invention are useful for treatment of diseases associated with monoamine reuptake inhibitors.

BACKGROUND OF THE INVENTION

Monoamine deficiency has been long been linked to depressive, anxiolytic and other disorders (see, e.g.: Charney et al., *J. Clin. Psychiatry* (1998) 59, 1-14; Delgado et al., *J. Clin. Psychiatry* (2000) 67, 7-11; Resser et al., *Depress. Anxiety* (2000) 12 (Suppl 1) 2-19; and Hirschfeld et al., *J. Clin. Psychiatry* (2000) 61, 4-6. In particular, serotonin (5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Masand et al., *Harv. Rev. Psychiatry* (1999) 7, 69-84). Noradrenaline or norepinephrine reuptake inhibitors such as reboxetine, atomoxetine, desipramine and nortryptyline have provided effective treatments for depressive, attention deficit and hyperactivity disorders (Scates et al., *Ann. Pharmacother.* (2000) 34, 1302-1312; Tatsumi et al., *Eur. J. Pharmacol.* (1997) 340, 249-258).

Enhancement of serotonin and norepinephrine neurotransmission is recognized as synergistic in the pharmacotherapy of depressive and anxiolytic disorders, in comparison with enhancement of only serotonin or norepinephrine neurotransmission alone (Thase et al., *Br. J. Psychiatry* (2001) 178, 234, 241; Tran et al., *J. Clin. Psychopharmacology* (2003) 23, 78-86). Dual reuptake inhibitors of both serotonin and norepinephrine, such as duloxetine, milnacipran and venlafaxine are currently marketed for treatment of depressive and anxiolytic disorders (Mallinckrodt et al., *J. Clin. Psychiatry* (2003) 5(1) 19-28; Bymaster et al., *Expert Opin. Investig. Drugs* (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behaviour, attention deficit disorders, panic attacks, social phobias, eating disorders such as obesity, anorexia, bulimia and "binge-eating", stress, hyperglycaemia, hyperlipidemia, non-insulin-dependent diabetes, seizure disorders such as epilepsy, and treatment of conditions associated with neurological damage resulting from stroke, brain trauma, cerebral ischaemia, head injury and hemorrhage. Dual reuptake inhibitors of serotonin and norepinephrine also offer potential treatments for disorders and disease states of the urinary tract, and for pain and inflammation.

More recently, "triple reuptake" inhibitors ("broad-spectrum antidepressants") which inhibit the reuptake of norepinephrine, serotonin, and dopamine, have been recognized as useful for the treatment of depression and other CNS indications (Beer et al., *J. Clinical Pharmacology* (2004) 44:1360-1367; Skolnick et al., *Eur J Pharmacol.* (2003) Feb. 14; 461(2-3):99-104.

Monamine reuptake inhibitors also have use in pain treatment. Serotonin has been found to have a role in pain processing in the peripheral nervous system and to contribute to peripheral sensitization and hyperalgesia in inflammation and nerve injury (Sommer et al., *Molecular Neurobiology* (2004) 30(2), 117-125. The serotonin-norepinephrine reuptake inhibitor duloxetine has been shown effective in treatment of pain in animal models (Iyengar et al., *J. Pharm. Exper. Therapeutics* (20040, 311, 576-584).

There is accordingly a need for compounds that are effective as serotonin reuptake inhibitors, norepinephrine reuptake inhibitors, dopamine reuptake inhibitors, and/or dual reuptake inhibitors of serotonin, norepinephrine and/or dopamine, or triple reuptake inhibitors of norepinephrine, serotonin, and dopamine, as well as methods of making and using such compounds in the treatment of depressive, anxiolytic, genitourinary, pain, and other disorders. The present invention satisfies these needs.

SUMMARY OF THE INVENTION

One aspect of the invention provides compounds of formula I:

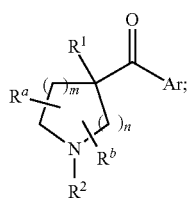

or a pharmaceutically acceptable salt thereof,
wherein:
m is from 0 to 3;
n is from 0 to 2;
Ar is:
  optionally substituted indolyl;
  optionally substituted indazolyl;
  optionally substituted azaindolyl;
  optionally substituted azaindazolyl;
  optionally substituted 2,3-dihydro-indolyl;
  optionally substituted 1,3-dihydro-indol-2-one-yl;
  optionally substituted benzothiophenyl;
  optionally substituted benzimidazolyl;
  optionally substituted benzoxazolyl;
  optionally substituted benzisoxazolyl;
  optionally substituted benzothiazolyl;
  optionally substituted benzisothiazolyl;
  optionally substituted quinolinyl;
  optionally substituted 1,2,3,4-tetrahydroquinolinyl;
  optionally substituted quinolin-2-one-yl;
  optionally substituted isoquinolinyl;
  optionally substituted naphthalenyl;
  optionally substituted pyridinyl;
  optionally substituted thiophenyl;
  optionally substituted pyrrolyl; or optionally substituted phenyl;
R¹ is:
C$_{1-6}$alkyl;
C$_{2-6}$alkenyl;
C$_{2-6}$alkynyl;
hetero-C$_{1-6}$alkyl;
halo-C$_{1-6}$alkyl;
halo-C$_{2-6}$alkenyl;
C$_{3-7}$cycloalkyl;
C$_{3-7}$cycloalkyl-C$_{1-6}$alkyl;
C$_{1-6}$alkyl-C$_{3-6}$cycloalkyl-C$_{1-6}$alkyl;
C$_{1-6}$alkoxy;
C$_{1-6}$alkylsulfonyl;
C$_{1-6}$alkylsulfanyl;
optionally substituted aryl;
optionally substituted heteroaryl;
heterocyclyl-C$_{1-6}$alkyl;
aryl-C$_{1-3}$alkyl wherein the aryl portion is optionally substituted;
heteroaryl-C$_{1-3}$alkyl wherein the heteroaryl portion is optionally substituted;
aryloxy;
aryl-C$_{1-6}$alkoxy;
heteroaryloxy; or
heteroaryl-C$_{1-6}$alkoxy;
R² is:
hydrogen; or
C$_{1-6}$alkyl; and
R$^a$ and R$^b$ each independently is:
hydrogen;
C$_{1-6}$alkyl;
C$_{1-6}$alkoxy;
halo;
hydroxy; or
oxo;
or R$^a$ and R$^b$ together form a C$_{1-2}$alkylene;
provided that when m is 1, n is 2 and Ar is optionally substituted phenyl, then R¹ is not methyl or ethyl.

The invention also provides pharmaceutical compositions, methods of using, and methods of preparing the aforementioned compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. C$_1$-C$_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —C(O)—R, where R' is alkyl as defined herein.

"Alkylsulfonyl" means a moiety of the formula —SO$_2$—R' where R' is alkyl as defined herein.

"Alkylsulfanyl" means a moiety of the formula —S—R' where R' is alkyl as defined herein.

"Alkylsulfonylalkyl" means a moiety of the formula —R$^b$—SO$_2$—R$^a$, where R$^a$ is alkyl and R$^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfanylalkyl" means a moiety of the formula —R$^b$—S—R$^a$, where R$^a$ is alkyl and R$^b$ is alkylene as defined herein.

"Alkylsulfonyloxy" means a moiety of the formula R$^a$—SO$_2$—O—, where R$^a$ is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Alkylcarbonylamino" means a group of the formula —NR—C(O)—R' wherein R is hydrogen or alkyl and R' is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, azulenyl, oxydiphenyl, biphenyl, methylenediphenyl, aminodiphenyl, diphenylsulfidyl, diphenylsulfonyl, diphenylisopropylidenyl, benzodioxanyl, benzodioxylyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like. Preferred aryl include optionally substituted phenyl and optionally substituted naphthyl.

"Aryloxy" means a moiety of the formula —OR, wherein R is an aryl moiety as defined herein.

"Arylalkyl" and "Aralkyl", which may be used interchangeably, mean a radical —R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Azaindolyl" means a group of the formula

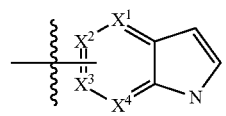

wherein one or two of any of $X^1$, $X^2$, $X^3$ and $X^4$ is N (aza), and the others are carbon. "Azaindoles" may be optionally substituted, as defined herein for heteroaryls, at position 1, 2 and 3, and at any of positions 4-through seven that are not nitrogen. "Azaindolyl" thus includes: "pyrrolopyrimidines" of the above formula wherein $X^2$ and $X^4$ are N; "pyrrolopyrimidines" of the above formula wherein $X^1$ and $X^3$ are N; "pyrrolopyrazines" of the above formula wherein $X^1$ and $X^4$ are N; "pyrrolopyridines" of the above formula wherein $X^1$ is N; "pyrrolopyridines" of the above formula wherein $X^2$ is N; "pyrrolopyridines" of the above formula wherein $X^3$ is N; and "pyrrolopyridines" of the above formula wherein $X^4$ is N. One preferred azaindolyl is 7-azaindolyl ($X^1$, $X^2$, $X^3$=C and $X^4$=N) or pyrrolo[2,3-b]pyridinyl. Another preferred azaindole is 4-azaindolyl or pyrrolo[3,2-b]pyridinyl.

"Azaindazolyl" means a group of the formula

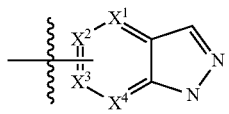

wherein one or two of any of $X^1$, $X^2$, $X^3$ and $X^4$ is N (aza), and the others are carbon. "Azaindazoles" may be optionally substituted, as defined herein for heteroaryls, at position 1, 2 and 3, and at any of positions 4-through seven that are not nitrogen. "Azaindaolyl" thus includes: "pyrazolopyrimidines" of the above formula wherein $X^2$ and $X^4$ are N; "pyrazolopyrimidines" of the above formula wherein $X^1$ and $X^3$ are N; "pyrazolopyrazines" of the above formula wherein $X^1$ and $X^4$ are N; "pyrazolopyridines" of the above formula wherein $X^1$ is N; "pyrazolopyridines" of the above formula wherein $X^2$ is N; "pyrazolopyridines" of the above formula wherein $X^3$ is N; and "pyrazolopyridines" of the above formula wherein $X^4$ is N.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R", where R' is alkylene and R" is cycloalkyl as defined herein.

"Alkylcycloalkylalkyl" means a moiety of the formula

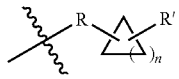

wherein n is from 1 to 4, R is alkylene and R' is alkyl as defined herein. An exemplary alkylcycloalkylalkyl is 2-(1-methyl-cyclopropyl)-ethyl. Exemplary alkylcycloalkylalkyl include 2-(1-methyl-cyclopropyl)-ethyl and 3-(1-methyl-cyclopropylmethyl.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, amino sulfonylpropyl, methylaminosulfonylmethyl, methylaminosulfonylethyl, methylaminosulfonylpropyl, and the like.

"Heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, pyridazinyl, thiophenyl, furanyl, pyranyl, pyridinyl, pyrrolyl, pyrazolyl, pyrimidyl, quinolinyl, isoquinolinyl, quinazolinyl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, heterocyclyl ring may be optionally substituted as defined herein. Examples of heterocyclyl moieties include, but are not limited to, optionally substituted piperidinyl, piperazinyl, homopiperazinyl, azepanyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, benzothiazolidinyl, benzoazolylidinyl, dihydrofuranyl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like. Preferred heterocyclyl include tetrahydropyranyl, tetrahydrofuranyl, pipiridinyl, piperazinyl and pyrrolidinyl.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thiophenyl, optionally substituted pyrazolyl, optionally substituted pyridinyl, morpholinocarbonyl, $-(CH_2)_q-S(O)_rR^f$; $-(CH_2)_q-NR^gR^h$; $-(CH_2)_qC(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy. Certain preferred optional substituents for "aryl", phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin, norepinephrine and/or dopamine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract. "Disease states" associated with serotonin, norepinephrine and/or dopamine neurotransmission also include inflammation conditions in a subject. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions.

"Depression" as used herein includes, but is not limited to, major depression, long-term depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, $28^{th}$ Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
  (i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen, sulfur or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention or a pharmaceutically acceptable salt thereof,
wherein:
m is from 0 to 3;
n is from 0 to 2;
Ar is:
optionally substituted indolyl;
optionally substituted indazolyl;
optionally substituted azaindolyl;
optionally substituted azaindazolyl;
optionally substituted 2,3-dihydro-indolyl;
optionally substituted 1,3-dihydro-indol-2-one-yl;
optionally substituted benzothiophenyl;
optionally substituted benzimidazolyl;
optionally substituted benzoxazolyl;
optionally substituted benzisoxazolyl;
optionally substituted benzothiazolyl;
optionally substituted benzisothiazolyl;
optionally substituted quinolinyl;
optionally substituted 1,2,3,4-tetrahydroquinolinyl;
optionally substituted quinolin-2-one-yl;
optionally substituted isoquinolinyl;
optionally substituted naphthalenyl;
optionally substituted pyridinyl;
optionally substituted thiophenyl;
optionally substituted pyrrolyl; or
optionally substituted phenyl;

$R^1$ is:
$C_{1-6}$alkyl;
$C_{2-6}$alkenyl;
$C_{2-6}$alkynyl;
hetero-$C_{1-6}$alkyl;
halo-$C_{1-6}$alkyl;
halo-$C_{2-6}$alkenyl;
$C_{3-7}$cycloalkyl;
$C_{3-7}$cycloalkyl-$C_{1-6}$alkyl;
$C_{1-6}$alkyl-$C_{3-6}$cycloalkyl-$C_{1-6}$alkyl;
$C_{1-6}$alkoxy;
$C_{1-6}$alkylsulfonyl;
$C_{1-6}$alkylsulfanyl;
optionally substituted aryl;
optionally substituted heteroaryl;
heterocyclyl-$C_{1-6}$alkyl;
aryl-$C_{1-3}$alkyl wherein the aryl portion is optionally substituted;
heteroaryl-$C_{1-3}$alkyl wherein the heteroaryl portion is optionally substituted;
aryloxy;
aryl-$C_{1-6}$alkoxy;
heteroaryloxy; or
heteroaryl-$C_{1-6}$alkoxy;
$R^2$ is:
hydrogen; or
$C_{1-6}$alkyl; and
$R^a$ and $R^b$ each independently is:
hydrogen;
$C_{1-6}$alkyl;
$C_{1-6}$alkoxy;
halo;
hydroxy; or
oxo;
or $R^a$ and $R^b$ together form a $C_{1-2}$alkylene;
provided that when m is 1, n is 2 and Ar is optionally substituted phenyl, then $R^1$ is not methyl or ethyl.

In certain embodiments of formula I, Ar is:
optionally substituted indolyl;
optionally substituted indazolyl;
optionally substituted 2,3-dihydro-indolyl;
optionally substituted 1,3-dihydro-indol-2-one-yl;
optionally substituted benzothiophenyl;
optionally substituted quinolinyl;
optionally substituted 1,2,3,4-tetrahydroquinolinyl;
optionally substituted azaindolyl;
optionally substituted naphthalenyl;
optionally substituted benzothiazolyl;
optionally substituted benzisothiazolyl;
optionally substituted thiophenyl; or
optionally substituted phenyl.

In certain embodiments of formula I, Ar is:
optionally substituted indolyl; or
optionally substituted indazolyl;

In certain embodiments of formula I, Ar is:
optionally substituted naphthalenyl; or
optionally substituted phenyl.

In certain embodiments of formula I, Ar is optionally substituted indolyl.

In certain embodiments of formula I, Ar is optionally substituted indazolyl.

In certain embodiments of formula I, Ar is optionally substituted azaindolyl.

In certain embodiments of formula I, Ar is optionally substituted benzothiophenyl.

In certain embodiments of formula I, Ar is optionally substituted benzimidazolyl.

In certain embodiments of formula I, Ar is optionally substituted benzoxazolyl.

In certain embodiments of formula I, Ar is optionally substituted benzothiazolyl.

In certain embodiments of formula I, Ar is optionally substituted quinolinyl.

In certain embodiments of formula I, Ar is optionally substituted isoquinolinyl.

In certain embodiments of formula I, Ar is optionally substituted naphthalenyl.

In certain embodiments of formula I, Ar is optionally substituted 2,3-dihydro-indolyl.

In certain embodiments of formula I, Ar is optionally substituted azaindazolyl.

In certain embodiments of formula I, Ar is optionally substituted pyridinyl.

In certain embodiments of formula I, Ar is optionally substituted thiophenyl.

In certain embodiments of formula I, Ar is optionally substituted pyrrolyl.

In certain embodiments of formula I, Ar is optionally substituted benzothiazolyl.

In certain embodiments of formula I, Ar is optionally substituted benzisothiazolyl.

In certain embodiments of formula I, Ar is optionally substituted phenyl.

In certain embodiments of formula I, Ar is substituted phenyl.

In certain embodiments of formula I, Ar is phenyl substituted two or three times.

In certain embodiments of formula I, Ar is indol-2-yl, indol-3-yl, indol-4-yl, indol-5-yl or indol-6-yl, each optionally substituted.

In certain embodiments of formula I, Ar is indol-2-yl, indol-5-yl or indol-6-yl, each optionally substituted.

In certain embodiments of formula I, Ar is optionally substituted indol-5-yl.

In certain embodiments of formula I, Ar is optionally substituted indazol-5-yl.

In certain embodiments of formula I, Ar is optionally substituted benzothiophen-5-yl.

In certain embodiments of formula I, Ar is optionally substituted benzothiophen-2-yl.

In certain embodiments of formula I, Ar is optionally substituted benzothiophen-3-yl.

In certain embodiments of formula I, Ar is optionally substituted benzothiophen-5-yl.

In certain embodiments of formula I, Ar is optionally substituted benzothiophen-6-yl.

In certain embodiments of formula I, Ar is optionally substituted thien-2-yl.

In certain embodiments of formula I, Ar is optionally substituted thien-3-yl.

In certain embodiments of formula I, Ar is optionally substituted benzothiazol-2-yl.

In certain embodiments of formula I, Ar is optionally substituted benzisothiazol-3-yl.

In certain embodiments of formula I, Ar is optionally substituted naphthalen-2-yl.

In certain embodiments of formula I, Ar is optionally substituted quinolin-6-yl.

In certain embodiments of formula I, Ar is optionally substituted quinolin-2-yl.

In certain embodiments of formula I, Ar is optionally substituted isoquinolin-6-yl.

In certain embodiments of formula I, Ar is optionally substituted 2,3-dihydro-indol-5-yl.

In certain embodiments of formula I, Ar is optionally substituted 1,3-dihydro-indol-2-one-5-yl.

In certain embodiments of formula I, Ar is optionally substituted benzimidazol-5-yl.

In certain embodiments of formula I, Ar is optionally substituted benzoxazol-5-yl.

In certain embodiments of formula I, Ar is optionally substituted benzothiazol-5-yl.

In certain embodiments of formula I, Ar is optionally substituted 1,2,3,4-tetrahydroquinolin-6-yl.

In certain embodiments of formula I, Ar is optionally substituted quinolin-2-one-6-yl.

In certain embodiments of formula I, Ar is optionally substituted pyridin-2-yl.

In embodiments of formula I where Ar is optionally substituted azaindolyl, such azaindolyl is preferably pyrrolo[2,3-b]pyridin-yl.

In certain embodiments of formula I where Ar is optionally substituted azaindolyl, such azaindolyl is preferably pyrrolo[2,3-b]pyridin-5-yl.

Where Ar is any of indolyl, indazolyl, azaindolyl, azaindazolyl, 2,3-dihydro-indolyl, 1,3-dihydro-indol-2-one-yl, benzothiophenyl, benzimidazolyl, benzoxazolyl, benzisoxazolyl, benzothiazolyl, benzisothiazolyl, quinolinyl, 1,2,3,4-tetrahydroquinolinyl, quinolin-2-one-yl, isoquinolinyl, pyridinyl, thiophenyl, pyrrolyl, naphthalenyl or phenyl that is optionally substituted, such optional substituents may comprise one, two or three groups each independently selected from:

halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
nitro;
amino;
N—$C_{1-6}$alkyl-amino;
N,N-di-$C_{1-6}$alkylamino; or
—$(CH_2)_n$—Y—$(CH_2)_s$—Z—$(CH_2)_t$—Q-$(CH_2)_u$—$R^c$;
wherein
r, s, t and u each independently is 0 or 1;
Z is —C(O)— or —SO$_2$—;
X and Y each independently is —O—, —NR$^d$— or a bond;
$R^c$ is:
hydrogen;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
amino;
$C_{1-6}$alkyl-amino; or
N,N-di-$C_{1-6}$alkylamino; and
$R^d$ is:
hydrogen; or
$C_{1-6}$alkyl.

Where Ar is any of indolyl, indazolyl, azaindolyl, azaindazolyl, 2,3-dihydro-indolyl, 1,3-dihydro-indol-2-one-yl, benzothiophenyl, benzimidazolyl, benzoxazolyl, benzisoxazolyl, benzothiazolyl, benzisothiazolyl, quinolinyl, 1,2,3,4-tetrahydroquinolinyl, quinolin-2-one-yl, isoquinolinyl, pyridinyl, thiophenyl, pyrrolyl, naphthalenyl or phenyl that is optionally substituted, such optional substituents may comprise one, two or three groups each independently selected from:
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl selected from:
hydroxy-$C_{1-6}$alkyl;
$C_{1-6}$alkylsulfonyl-$C_{1-6}$alkyl; and
$C_{1-6}$alkoxy-$C_{1-6}$alkyl;
cyano;
nitro;
amino;
N—$C_{1-6}$alkyl-amino;
N,N-di-$C_{1-6}$alkylamino;
$C_{1-6}$alkyl-sulfonyl; or
—C(O)R$^c$ wherein R$^c$ is:
$C_{1-6}$alkyl;
amino;
$C_{1-6}$alkyl-amino; or
N,N-di-$C_{1-6}$alkylamino.

Where Ar is any of indolyl, indazolyl, azaindolyl, azaindazolyl, 2,3-dihydro-indolyl, 1,3-dihydro-indol-2-one-yl, benzothiophenyl, benzimidazolyl, benzoxazolyl, benzisoxazolyl, benzothiazolyl, benzisothiazolyl, quinolinyl, 1,2,3,4-tetrahydroquinolinyl, quinolin-2-one-yl, isoquinolinyl, pyridinyl, thiophenyl, pyrrolyl, naphthalenyl or phenyl that is optionally substituted, such optional substituents may comprise one or two groups each independently selected from:
halo;
amino;
$C_{1-6}$alkyl;
halo-$C_{1-6}$alkyl;
$C_{1-6}$alkoxy;
hydroxy; or
cyano.

Preferably, where Ar is any of indolyl, indazolyl, azaindolyl, azaindazolyl, 2,3-dihydro-indolyl, 1,3-dihydro-indol-2-one-yl, benzothiophenyl, benzimidazolyl, benzoxazolyl, benzisoxazolyl, benzothiazolyl, benzisothiazolyl, quinolinyl, 1,2,3,4-tetrahydroquinolinyl, quinolin-2-one-yl, isoquinolinyl, pyridinyl, thiophenyl, pyrrolyl, naphthalenyl or phenyl that is optionally substituted, such optional substituents may comprise one or two groups each independently selected from halo, amino, $C_{1-6}$alkyl, and halo-$C_{1-6}$alkyl. In some embodiments Ar is substituted once or twice with halo, preferably fluoro.

In certain embodiments of formula I, Ar is phenyl substituted one, two or three times with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy;
phenylsulfonyl; or
optionally substituted heteroaryl.

In certain embodiments of formula I, Ar is phenyl substituted two or three times with groups independently selected from:
halo;
amino;
$C_{1-6}$alkyl;
halo-$C_{1-6}$alkyl;
$C_{1-6}$alkoxy;
hydroxy; or cyano.

In certain embodiments of formula I, Ar is phenyl substituted two or three times with halo.

In certain embodiments of formula I, Ar is phenyl substituted at the 3- and 4-positions, and optionally substituted at the 2- or 5-position, with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl.

In certain embodiments of formula I, Ar is phenyl substituted at the 3- and 4-positions, and optionally substituted at the 2- or 5-position, with groups independently selected from:
halo;
amino;
$C_{1-6}$alkyl;
halo-$C_{1-6}$alkyl;
$C_{1-6}$alkoxy;
hydroxy; or
cyano.

In certain embodiments of formula I, Ar is phenyl substituted at the 3- and 4-positions, and optionally substituted at the 2- or 5-position, with halo.

In certain embodiments of formula I, Ar is phenyl substituted at the 3- and 4-positions, and optionally substituted at the 2- or 5-position, with halo or amino.

In certain embodiments of formula I, Ar is pyridinyl substituted one or two times with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl.

In certain embodiments of formula I, Ar is pyridinyl substituted one or two times with groups independently selected from:
halo;
amino;
$C_{1-6}$alkyl;
halo-$C_{1-6}$alkyl;
$C_{1-6}$alkoxy;
hydroxy; or
cyano.

In certain embodiments of formula I, Ar is thiophenyl substituted once, twice or three times with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl.

In certain embodiments of formula I, Ar is thiophenyl substituted once or twice with groups independently selected from:
halo;
amino;
$C_{1-6}$alkyl;
halo-$C_{1-6}$alkyl;
$C_{1-6}$alkoxy;
hydroxy; or
cyano.

In certain embodiments of formula I, Ar is thiophenyl substituted once or twice with halo.

In certain embodiments of formula I, Ar is thiophen-2-yl substituted at the 4- and 5-positions, and optionally substituted at the 3-position, with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl.

In certain embodiments of formula I, Ar is thiophen-2-yl substituted at the 4- and 5-positions, and optionally substituted at the 3-position, with groups independently selected from:
halo;
amino;
$C_{1-6}$alkyl;
halo-$C_{1-6}$alkyl;
$C_{1-6}$alkoxy;
hydroxy; or
cyano.

In certain embodiments of formula I, Ar is thiophen-2-yl substituted at the 4- and 5-positions, and optionally substituted at the 3-position, with halo.

In certain embodiments of formula I, Ar is thiophen-2-yl substituted at the 4- and 5-positions, and optionally substituted at the 3-position, with halo or amino.

In certain embodiments of formula I, Ar is pyrrolyl substituted once, twice or three times with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl.

In certain embodiments of formula I, Ar is pyrrolyl substituted once or twice with groups independently selected from:
halo;
amino;
$C_{1-6}$alkyl;
halo-$C_{1-6}$alkyl;
$C_{1-6}$alkoxy;
hydroxy; or
cyano.

In certain embodiments of formula I, Ar is pyrrolyl substituted once or twice with halo.

In certain embodiments of formula I, Ar is pyrrol-2-yl substituted at the 4- and 5-positions, and optionally substituted at the 3-position, with groups independently selected from:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl.

In certain embodiments of formula I, Ar is pyrrol-2-yl substituted at the 4- and 5-positions, and optionally substituted at the 3-position, with groups independently selected from:

halo;
amino;
$C_{1-6}$alkyl;
halo-$C_{1-6}$alkyl;
$C_{1-6}$alkoxy;
hydroxy; or
cyano.

In certain embodiments of formula I, Ar is pyrrol-2-yl substituted at the 4- and 5-positions, and optionally substituted at the 3-position, with halo.

In certain embodiments of formula I, Ar is pyrrol-2-yl substituted at the 4- and 5-positions, and optionally substituted at the 3-position, with halo or amino.

In certain embodiments of formula I, Ar is pyridinyl substituted one or two times with halo.

In certain embodiments of formula I, Ar is: 3,4-dichlorophenyl; 4-methoxy-phenyl; 4-methyl-phenyl; 4-fluoro-phenyl; 3-chloro-phenyl; 4-chloro-phenyl; 4-iodo-phenyl; 4-cyano-phenyl; 4-isopropyl-phenyl; 4-phenyl-phenyl (biphenyl-4-yl); 4-(pyrazol-3-yl-phenyl; 4-chloro-3-methoxy-phenyl; 4-chloro-3-ethyl-phenyl; 4-chloro-3-cyano-phenyl; 4-chloro-3-phenyl-phenyl (6-chloro-biphenyl-3-yl); 3-chloro-4-methoxy-phenyl; 3-chloro-4-methoxymethyl-phenyl; 3-chloro-4-hydroxy-phenyl; 3-chloro-4-methylsulfanyl-phenyl; 3-chloro-4-methylsulfonyl-phenyl; 4-acetyl-3-chloro-phenyl; 4-chloro-3-fluoro-phenyl; 4-chloro-3-cyclopropyl-phenyl; 4-chloro-3-acetyl-phenyl; 4-chloro-3-cyano-phenyl; 3-chloro-4-fluoro-phenyl; 3-chloro-5-fluoro-phenyl; 2,3-dichloro-phenyl; 3,5-dichloro-phenyl; 3,4-difluoro-phenyl; 3,4-dibromo-phenyl; 3,4-di-cyano-phenyl; 3-chloro-4-methyl-phenyl; 3-bromo-4-chloro-phenyl; 4-chloro-3-methyl-phenyl; 4-chloro-3-trifluoromethyl-phenyl; 4-trifluoromethyl-phenyl; 4-trifluoromethoxy-phenyl; 3,4,5-trifluoro-phenyl; 3,4,5-trichloro-phenyl; 3,4-dichloro-5-fluoro-phenyl; 3,4-dichloro-5-methyl-phenyl; 4,5-dichloro-2-fluoro-phenyl; 4-bromo-3-chloro-phenyl; 4-chloro-3-isopropoxy-phenyl; 3-(4-fluoro-phenoxy)-phenyl; 4-amino-3-chloro-phenyl; 4-amino-3-fluoro-phenyl; 4-bromo-3-methyl-phenyl; 4-amino-3-chloro-5-fluoro-phenyl; 2-amino-3,4-dichloro-phenyl; 4-bromo-3-chloro-5-fluoro-phenyl; 3-chloro-5-fluoro-4-hydroxy-phenyl; 4-chloro-3-phenoxy-phenyl; or 3-chloro-4-phenoxy-phenyl.

In certain embodiments of formula I, Ar is: 3,4-dichlorophenyl; 4-chloro-3-fluoro-phenyl; 3-chloro-4-fluoro-phenyl; 3,4-difluoro-phenyl; 3,4-dibromo-phenyl; 3-bromo-4-chloro-phenyl; 3,4,5-trifluoro-phenyl; 3,4,5-trichloro-phenyl; 3,4-dichloro-5-fluoro-phenyl; 4,5-dichloro-2-fluoro-phenyl; 4-bromo-3-chloro-phenyl; 4-chloro-3-isopropoxy-phenyl; 4-amino-3-chloro-phenyl; 4-amino-3-fluoro-phenyl; 4-amino-3-chloro-5-fluoro-phenyl; 2-amino-3,4-dichloro-phenyl; or 4-bromo-3-chloro-5-fluoro-phenyl.

In certain embodiments of formula I, Ar is: 3,4-dichlorophenyl; 3,4-dichloro-5-fluoro-phenyl; 4-amino-3-chloro-phenyl; or 4-amino-3-chloro-5-fluoro-phenyl.

In certain embodiments of formula I, Ar is 3,4-dichlorophenyl.

In certain embodiments of formula I, Ar is 3,4-dichloro-5-fluoro-phenyl.

In certain embodiments of formula I, Ar is 4-amino-3-chloro-phenyl.

In certain embodiments of formula I, Ar is 4-amino-3-chloro-5-fluoro-phenyl.

In certain embodiments of formula I, Ar is: indol-5-yl; 1-methyl-indol-5-yl; 7-fluoro-indol-5-yl; 2-methyl-indol-5-yl; indol-4-yl; 7-chloro-indol-5-yl; indol-3-yl; 7-trifluoromethyl-indol-5-yl; 6-fluoro-indol-5-yl; 6,7-difluoro-indol-5-yl; indol-2-yl; 5-fluoro-indol-2-yl; 1-phenylsulfonyl-indol-2-yl; 1-methyl-indol-2-yl; 6-fluoro-indol-2-yl; 7-fluoro-indol-2-yl; or 4-fluoro-indol-2-yl.

In certain embodiments of formula I, Ar is: benzothiophen-5-yl; benzothiophen-2-yl; benzothiophen-3-yl; 5-fluoro-benzothiophen-2-yl; 6-fluoro-benzothiophen-2-yl; 5-chloro-benzothiophen-2-yl; 7-fluoro-benzothiophen-2-yl; or 4-fluoro-benzothiophen-2-yl.

In certain embodiments of formula I, Ar is: 4,5-dichloro-thiophen-2-yl; 4-chloro-thiophen-2-yl; 3-chloro-thiophen-2-yl; or 4-chloro-5-methyl-thiophen-2-yl.

In certain embodiments of formula I, $R^2$ is hydrogen.

In certain embodiments of formula I, $R^2$ is $C_{1-6}$alkyl.

In certain embodiments of formula I, $R^2$ is methyl.

In certain embodiments of formula I where Ar is optionally substituted phenyl, Ar preferably is phenyl substituted once, twice, or three times, and more preferably two or three times, with any of halo, $C_{1-6}$alkyl, $C_{1-6}$alkoxy, hydroxy or cyano.

In certain embodiments of formula I, m is 1, n is 1, Ar is optionally substituted indol-5-yl, $R^1$ is optionally substituted benzyl, and $R^2$ is hydrogen.

In certain embodiments of formula I, m is 1, n is 1, Ar is optionally substituted indol-5-yl, $R^1$ is $C_{3-6}$alkyl, and $R^2$ is hydrogen.

In certain embodiments of formula I, m is 1, n is 2, Ar is optionally substituted indol-5-yl, $R^1$ is optionally substituted benzyl, and $R^2$ is hydrogen.

In certain embodiments of formula I, m is 1, n is 2, Ar is optionally substituted indol-5-yl, $R^1$ is $C_{3-6}$alkyl, and $R^2$ is hydrogen.

In certain embodiments of formula I, m is 2, n is 1, Ar is optionally substituted indol-5-yl, $R^1$ is optionally substituted benzyl, and $R^2$ is hydrogen.

In certain embodiments of formula I, m is 2, n is 1, Ar is optionally substituted indol-5-yl, $R^1$ is $C_{3-6}$alkyl, and $R^2$ is hydrogen.

In certain embodiments of formula I, m is 1, n is 1, Ar is optionally substituted indazol-5-yl, $R^1$ is optionally substituted benzyl, and $R^2$ is hydrogen.

In certain embodiments of formula I, m is 1, n is 1, Ar is optionally substituted indazol-5-yl, $R^1$ is $C_{3-6}$alkyl, and $R^2$ is hydrogen.

In certain embodiments of formula I, m is 1, n is 2, Ar is optionally substituted indazol-5-yl, $R^1$ is optionally substituted benzyl, and $R^2$ is hydrogen.

In certain embodiments of formula I, m is 1, n is 2, Ar is optionally substituted indazol-5-yl, $R^1$ is $C_{3-6}$alkyl, and $R^2$ is hydrogen.

In certain embodiments of formula I, m is 2, n is 1, Ar is optionally substituted indazol-5-yl, $R^1$ is optionally substituted benzyl, and $R^2$ is hydrogen.

In certain embodiments of formula I, m is 2, n is 1, Ar is optionally substituted indazol-5-yl, $R^1$ is $C_{3-6}$alkyl, and $R^2$ is hydrogen.

In certain embodiments of formula I, m is 1, n is 1, Ar is optionally substituted phenyl, $R^1$ is optionally substituted benzyl, and $R^2$ is hydrogen.

In certain embodiments of formula I, m is 1, n is 1, Ar is optionally substituted phenyl, $R^1$ is $C_{3-6}$alkyl, and $R^2$ is hydrogen.

In certain embodiments of formula I, m is 1, n is 2, Ar is optionally substituted indazol-5-yl, $R^1$ is optionally substituted benzyl, and $R^2$ is hydrogen.

In certain embodiments of formula I, m is 1, n is 2, Ar is optionally substituted phenyl, $R^1$ is $C_{3-6}$alkyl, and $R^2$ is hydrogen.

In certain embodiments of formula I, m is 2, n is 1, Ar is optionally substituted phenyl, $R^1$ is optionally substituted benzyl, and $R^2$ is hydrogen.

In certain embodiments of formula I, m is 2, n is 1, Ar is optionally substituted phenyl, $R^1$ is $C_{3-6}$alkyl, and $R^2$ is hydrogen.

In certain embodiments of formula I, $R^a$ and $R^b$ are hydrogen.

In certain embodiments of formula I, one of $R^a$ and $R^b$ is hydrogen and the other is $C_{1-6}$alkoxy, halo, oxo or hydroxy.

In certain embodiments of formula I, $R^a$ and $R^b$ together form a $C_{1-2}$alkylene;

In certain embodiments of formula I, the subject compounds may be of formula II:

wherein:
p is from 0 to 3;
X is N or $CR^e$;
$R^3$ is:
hydrogen; or
$C_{1-6}$alkyl;
$R^4$, $R^5$ and $R^e$ each independently is:
hydrogen;
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
nitro;
amino;
N—$C_{1-6}$alkyl-amino;
N,N-di-$C_{1-6}$alkylamino; or
—$(CH_2)_r$—Y—$(CH_2)_s$—Z—$(CH_2)_t$-Q-$(CH_2)_u$—$R^c$;
wherein
r, s, t and u each independently is 0 or 1;
Z is —C(O)— or —$SO_2$—;
X and Y each independently is —O—, —$NR^d$— or a bond;
$R^c$ is:
hydrogen;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
amino;
$C_{1-6}$alkyl-amino; or
N,N-di-$C_{1-6}$alkylamino; and
$R^d$ is:
hydrogen; or
$C_{1-6}$alkyl; and
m, n and $R^1$ are as defined herein for formula I.

In certain embodiments of formula II, X is N.
In certain embodiments of formula II, X is $CR^e$.
In certain embodiments of formula II, X is CH.
In certain embodiments of formula II, $R^3$ is hydrogen.
In certain embodiments of formula II, $R^3$ is $C_{1-6}$alkyl.
In certain embodiments of formula II, $R^3$ is methyl.
In certain embodiments of formula II, m is 1, n is 1, X is CH, $R^1$ is optionally substituted benzyl, and $R^3$ is hydrogen.
In certain embodiments of formula II, m is 1, n is 1, X is N, $R^1$ is $C_{3-6}$ alkyl, and $R^3$ is hydrogen.
In certain embodiments of formula II, m is 1, n is 1, X is CH, $R^1$ is optionally substituted benzyl, and $R^3$ is hydrogen.
In certain embodiments of formula II, m is 1, n is 1, X is N, $R^1$ is $C_{3-6}$alkyl, and $R^3$ is hydrogen.

In certain embodiments of formula I, the subject compounds may be of formula III:

wherein m, n, p, $R^1$, $R^4$ and $R^5$ are as defined herein for formula I.

In certain embodiments of formula II or III, p is 0, 1 or 2.
In certain embodiments of formula II or III, p is 0, 1 or 2 and $R^6$ is halo.
In certain embodiments of formula II or III, p is 0, 1 or 2 and $R^6$ is fluoro.
In certain embodiments of formula II or III, p is 1 and $R^6$ is fluoro.
In certain embodiments of formula II or III, p is 0.

In certain embodiments of formula I, the subject compounds may be of formula IV:

wherein:
q is 0 or 1;
$R^6$, $R^7$ and $R^8$ each independently is:
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;

optionally substituted phenoxy; or
optionally substituted heteroaryl;
or $R^6$ and $R^7$ together form $C_{1-2}$alkylene or $C_{1-2}$alkylenedioxy;
or $R^7$ and $R^8$ together form $C_{1-2}$alkylene or $C_{1-2}$alkylenedioxy;
and wherein m, n and $R^1$ are as defined herein for formula I.

In certain embodiments of formula IV, $R^6$, $R^7$ and $R^8$ each independently is: halo; amino; $C_{1-6}$alkyl; $C_{1-6}$alkylcarbonyl; halo-$C_{1-6}$alkyl; $C_{1-6}$alkoxy; halo-$C_{1-6}$alkoxy; hydroxy; or cyano.

In certain embodiments of formula IV, one of $R^6$, $R^7$ and $R^8$ is amino, and the others are halo.

In certain embodiments of formula IV, q is 1, one of $R^6$, $R^7$ and $R^8$ is amino, and the others are halo.

In certain embodiments of formula N, q is 1 and $R^6$, $R^7$ and $R^8$ are halo.

In certain embodiments of formula N, q is 0, one of $R^6$ and $R^7$ is amino, and the other is halo.

In certain embodiments of formula N, q is 0 and $R^6$ and $R^7$ are halo.

In certain embodiments of formula N, one of $R^6$, $R^7$ and $R^8$ is fluoro, and the others are chloro.

In certain embodiments of formula N, q is 1, one of $R^6$, $R^7$ and $R^8$ is amino, and the others are chloro or fluoro.

In certain embodiments of formula N, q is 0.

In certain embodiments of formula N, q is 1.

In certain embodiments of formula N, $R^6$, $R^7$ and $R^8$ are halo.

In certain embodiments of formula N, q is 1, $R^7$ is amino, and $R^6$ and $R^8$ are independently fluoro or chloro.

In certain embodiments of formula N, q is 0, $R^7$ is amino, and $R^6$ is fluoro or chloro.

In certain embodiments of formula I, the subject compounds may be of formula V:

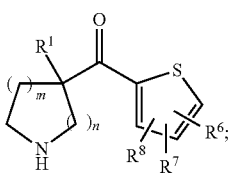

V wherein:
$R^6$, $R^7$ and $R^8$ each independently is:
hydrogen;
halo;
amino;
$C_{1-6}$alkyl;
$C_{3-6}$cycloalkyl;
$C_{1-6}$alkylcarbonyl;
$C_{1-6}$alkylsulfonyl;
$C_{1-6}$alkylsulfanyl;
halo-$C_{1-6}$alkyl;
$C_{1-6}$alkoxy;
halo-$C_{1-6}$alkoxy;
$C_{1-6}$alkoxy-$C_{1-6}$alkyl;
hydroxy;
cyano;
optionally substituted phenyl;
optionally substituted phenoxy; or
optionally substituted heteroaryl;
or $R^7$ and $R^8$ together form $C_{1-2}$alkylene or $C_{1-2}$alkylenedioxy;
and wherein m, n and $R^1$ are as defined herein for formula I.

In certain embodiments of formula V, $R^8$ is hydrogen, and $R^6$ and $R^7$ each independently is: halo; amino; $C_{1-6}$alkyl; $C_{1-6}$alkylcarbonyl; halo-$C_{1-6}$alkyl; $C_{1-6}$alkoxy; halo-$C_{1-6}$alkoxy; hydroxy; or cyano.

In certain embodiments of formula V, $R^8$ is hydrogen, and $R^6$ and $R^7$ are halo.

In certain embodiments of formula V, $R^8$ is hydrogen, and $R^6$ and $R^7$ are chloro or fluoro.

In certain embodiments of formula V, $R^8$ is hydrogen, and $R^6$ and $R^7$ are chloro.

In certain embodiments of formula V, $R^8$ is hydrogen, one of $R^6$ and $R^7$ is amino, and the other is halo.

In certain embodiments of formula V, $R^6$ is halo, and $R^7$ and $R^8$ are hydrogen.

In certain embodiments of formula V, one of $R^6$, $R^7$ and $R^8$ is amino, and the others are halo.

In certain embodiments of any of formulas I, II, III, IV or V, m is 0.

In certain embodiments of any of formulas I, II, III, IV or V, m is 1.

In certain embodiments of any of formulas I, II, III, IV or V, m is 2.

In certain embodiments of any of formulas I, II, III, IV or V, m is 3.

In certain embodiments of any of formulas I, II, III, IV or V, n is 0.

In certain embodiments of any of formulas I, II, III, IV or V, n is 1.

In certain embodiments of any of formulas I, II, III, IV or V, n is 2.

In certain embodiments of any of formulas I, II, III, IV or V, m is 1 and n is 1.

In certain embodiments of any of formulas I, II, III, IV or V, m is 2 and n is 1.

In certain embodiments of any of formulas I, II, III, N or V, m is 2 and n is 0.

In certain embodiments of any of formulas I, II, III, N or V, m is 3 and n is 0.

In certain embodiments of any of formulas I, II, III, N or V, m is 1 and n is 0.

In certain embodiments of any of formulas I, II, III, N or V, m is 1 and n is 2.

In certain embodiments of any of formulas I, II, III, N or V, m is 0 and n is 1.

In certain embodiments of any of formulas I, II, III, N or V, $R^1$ is:
$C_{1-6}$alkyl;
$C_{1-6}$alkenyl;
$C_{1-6}$alkynyl;
$C_{1-6}$alkoxy;
$C_{3-7}$cycloalkyl-$C_{1-6}$alkyl;
hetero-$C_{1-6}$alkyl;
halo-$C_{1-6}$alkyl;
optionally substituted aryl;
aryl-$C_{1-3}$alkyl wherein the aryl portion is optionally substituted;
heteroaryl-$C_{1-3}$alkyl wherein the heteroaryl portion is optionally substituted;

In certain embodiments of any of formulas I, II, III, N or V, $R^1$ is:
$C_{1-6}$alkyl;
$C_{1-6}$alkenyl; or
aryl-$C_{1-3}$alkyl wherein the aryl portion is optionally substituted.

In certain embodiments of any of formulas I, II, III, IV or V, $R^1$ is:
- $C_{3-6}$alkyl;
- $C_{3-6}$haloalkyl;
- $C_{3-6}$cycloalkyl-$C_{1-3}$alkyl;
- $C_{1-2}$alkoxy-$C_{1-3}$alkyl;
- $C_{1-2}$alkyl-$C_{3-6}$cycloalkyl-$C_{1-3}$alkyl;
- optionally substituted benzyl.

In certain embodiments of any of formulas I, II, III, IV or V, $R^1$ is:
n-propyl; isopropyl; tert-butyl; n-butyl; isobutyl; n-pentyl; isopentyl; 2,2-dimethyl-propyl; 3,3-dimethyl-butyl; cyclopentyl; cyclopropyl-methyl; cyclobutyl-methyl; cyclopentyl-methyl; cyclohexyl-methyl; cyclopropyl-ethyl; cyclohexyl-ethyl; 2-(1-methyl-cyclopropyl)-ethyl; 3-(1-methyl-cyclopropylmethyl; 3,3,3-trifluoro-propyl; 4,4,4-trifluoro-butyl; 3,3-difluoro-allyl; benzyl; 3-fluoro-benzyl; 4-fluoro-benzyl; 3-methoxy-benzyl; 4-methoxy-benzyl; 3,4-dichloro-benzyl; 3,4-difluoro-benzyl; pyrazin-2-yl-methyl; thiazol-4-yl-methyl; pyrazol-1-yl-methyl; methoxy-methyl; ethoxy-methyl; isopropoxy-methyl; 2-methoxy-ethyl; 2-ethoxy-ethyl; 3-methoxy-3-methyl-butyl; 3-ethanesulfonyl-methyl; or tetrahydropyran-4-ylmethyl.

In certain embodiments of any of formulas I, II, III, IV or V, $R^1$ is:
n-propyl; isopropyl; tert-butyl; n-butyl; isobutyl; n-pentyl; isopentyl; 2,2-dimethyl-propyl; 3,3-dimethyl-butyl; cyclopentyl; cyclopropyl-methyl; cyclobutyl-methyl; cyclopentyl-methyl; cyclohexyl-methyl; cyclopropyl-ethyl; cyclohexyl-ethyl; 2-(1-methyl-cyclopropyl)-ethyl; 3-(1-methyl-cyclopropylmethyl; 3,3,3-trifluoro-propyl; or 4,4,4-trifluoro-butyl.

In certain embodiments of any of formulas I, II, III, IV or V, $R^1$ is:
n-propyl; isopropyl; tert-butyl; n-butyl; isobutyl; isopentyl; 2,2-dimethyl-propyl; 3,3-dimethyl-butyl; cyclopentyl; cyclopropyl-methyl; cyclobutyl-methyl; cyclopentyl-methyl; cyclohexyl-methyl; cyclopropyl-ethyl; cyclohexyl-ethyl; 2-(1-methyl-cyclopropyl)-ethyl; or 3-(1-methyl-cyclopropylmethyl.

In certain embodiments of any of formulas I, II, III, IV or V wherein $R^1$ is heteroaryl-$C_{1-3}$alkyl, heteroaryloxy, heteroaryl-$C_{1-6}$alkoxy, the heteroaryl moiety may be pyridinyl, pyrazinyl, thiazolyl or pyrazolyl.

In certain embodiments of any of formulas I, II, III, IV or V, $R^1$ is: $C_{1-6}$alkyl; aryl-$C_{1-6}$alkyl; $C_{3-6}$cycloalkyl-$C_{1-6}$alkyl; hetero-$C_{1-6}$alkyl; halo-$C_{1-6}$alkyl; or $C_{1-6}$-alkyl-$C_{1-3}$cycloalkyl-$C_{1-6}$alkyl.

In certain embodiments of any of formulas I, II, III, IV or V, $R^1$ is: $C_{1-6}$alkyl; aryl-$C_{1-6}$alkyl; $C_{3-6}$cycloalkyl-$C_{1-6}$alkyl; or $C_{1-6}$-alkyl-$C_{1-3}$cycloalkyl-$C_{1-6}$alkyl.

In certain embodiments of any of formulas I, II, III, IV or V, $R^1$ is $C_{3-6}$alkyl.

In certain embodiments of any of formulas I, II, III, IV or V, $R^1$ is $C_{3-6}$alkenyl.

In certain embodiments of any of formulas I, II, III, IV or V, $R^1$ is $C_{3-6}$alkynyl.

In certain embodiments of any of formulas I, II, III, IV or V, $R^1$ is $C_{2-6}$alkoxy.

In certain embodiments of any of formulas I, II, III, IV or V, $R^1$ is $C_{3-7}$cycloalkyl-$C_{1-6}$alkyl.

In certain embodiments of any of formulas I, II, III, IV or V, $R^1$ is $C_{3-7}$cycloalkyl.

In certain embodiments of any of formulas I, II, III, IV or V, $R^1$ is $C_{1-6}$alkyl-$C_{3-6}$-cycloalkyl-$C_{1-6}$alkyl In certain embodiments of any of formulas I, II, III, IV or V, $R^1$ is hetero-$C_{1-6}$alkyl.

In certain embodiments of any of formulas I, II, III, IV or V, $R^1$ is heterocyclyl-$C_{1-6}$alkyl.

In certain embodiments of any of formulas I, II, III, IV or V, $R^1$ is heterocyclyl-$C_{1-6}$alkyl selected from tetrahydropyranylmethyl, tetrahydrofuranylmethyl and piperidinylmethyl.

In certain embodiments of any of formulas I, II, III, IV or V, $R^1$ is tetrahydropyranylmethyl.

In certain embodiments of any of formulas I, II, III, IV or V, $R^1$ is hetero-$C_{1-6}$alkyl selected from:
- hydroxy-$C_{1-6}$alkyl;
- $C_{1-6}$alkylsulfonyl-$C_{1-6}$alkyl;
- $C_{1-6}$alkylsulfanyl-$C_{1-6}$alkyl; and
- $C_{1-6}$alkoxy-$C_{1-6}$alkyl.

In certain embodiments of any of formulas I, II, III, IV or V, $R^1$ is hydroxy-$C_{1-6}$alkyl.

In certain embodiments of any of formulas I, II, III, IV or V, $R^1$ is $C_{1-6}$alkylsulfonyl-$C_{1-6}$alkyl.

In certain embodiments of any of formulas I, II, III, IV or V, $R^1$ is $C_{1-6}$alkylsulfanyl-$C_{1-6}$alkyl.

In certain embodiments of any of formulas I, II, III, IV or V, $R^1$ is $C_{1-6}$alkoxy-$C_{1-6}$alkyl.

In certain embodiments of any of formulas I, II, III, IV or V, $R^1$ is halo-$C_{1-6}$alkyl.

In certain embodiments of any of formulas I, II, III, IV or V, $R^1$ is optionally substituted aryl.

In certain embodiments of any of formulas I, II, III, IV or V, $R^1$ is optionally substituted heteroaryl.

In certain embodiments of any of formulas I, II, III, IV or V, $R^1$ is aryl-$C_{1-3}$alkyl wherein the aryl portion is optionally substituted.

In certain embodiments of any of formulas I, II, III, IV or V, $R^1$ is heteroaryl-$C_{1-3}$ alkyl wherein the heteroaryl portion is optionally substituted.

In certain embodiments of any of formulas I, II, III, IV or V, $R^1$ is heteroaryl-$C_{1-3}$alkyl selected from pyridinyl-$C_{1-3}$alkyl, pyrazinyl-$C_{1-3}$alkyl, thiazolyl-$C_{1-3}$alkyl and pyrazolyl-$C_{1-3}$alkyl.

In certain embodiments of any of formulas I, II, III, IV or V, $R^1$ is n-propyl, isopropyl, n-butyl, isobutyl, n-pentyl or isopentyl.

In certain embodiments of any of formulas I, II, III, IV or V, $R^1$ is n-propyl.

In certain embodiments of any of formulas I, II, III, IV or V, $R^1$ is isopropyl.

In certain embodiments of any of formulas I, II, III, IV or V, $R^1$ is n-butyl.

In certain embodiments of any of formulas I, II, III, IV or V, $R^1$ is isobutyl.

In certain embodiments of any of formulas I, II, III, IV or V, $R^1$ is tert-butyl.

In certain embodiments of any of formulas I, II, III, IV or V, $R^1$ is n-pentyl.

In certain embodiments of any of formulas I, II, III, IV or V, $R^1$ is isopentyl.

In certain embodiments of any of formulas I, II, III, IV or V, $R^1$ is 2,2-dimethyl-propyl.

In certain embodiments of any of formulas I, II, III, IV or V, $R^1$ is 3,3-dimethyl-butyl.

In certain embodiments of any of formulas I, II, III, IV or V, $R^1$ is cyclopropyl-methyl.

In certain embodiments of any of formulas I, II, III, IV or V, $R^1$ is 2-(1-methyl-cyclopropyl)-ethyl.

In certain embodiments of any of formulas I, II, III, IV or V, $R^1$ is 3-(1-methyl-cyclopropylmethyl.

In certain embodiments of any of formulas I, II, III, IV or V, $R^1$ is:
optionally substituted benzyl;
thiazolylmethyl;
pyrazinylmethyl;
optionally substituted phenyl; or
$C_{1-6}$alkyl.

In certain embodiments of any of formulas I, II, III, IV or V, $R^1$ is:
optionally substituted benzyl;
optionally substituted phenyl; or
$C_{3-6}$alkyl.

In certain embodiments of any of formulas I, II, III, IV or V, $R^1$ is optionally substituted benzyl.

In certain embodiments of any of formulas I, II, III, IV or V, $R^1$ is optionally substituted phenyl.

In certain embodiments of any of formulas I, II, III, N or V, $R^1$ is $C_{3-6}$ alkyl.

In certain embodiments of any of formulas I, II, III, IV or V, $R^1$ is optionally substituted phenylethyl.

In certain embodiments of any of formulas I, II, III, IV or V, $R^1$ is optionally substituted heteroaryl-$C_{1-6}$alkyl selected from thiazolylmethyl and pyrazolylmethyl.

In certain embodiments of formula II, $R^4$, $R^5$ and $R^c$ each preferably is independently selected from:
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl selected from:
hydroxy-$C_{1-6}$alkyl;
$C_{1-6}$ alkylsulfonyl-$C_{1-6}$alkyl; and
$C_{1-6}$alkoxy-$C_{1-6}$alkyl;
cyano;
nitro;
amino;
N—$C_{1-6}$alkyl-amino;
N,N-di-$C_{1-6}$alkylamino;
$C_{1-6}$alkyl-sulfonyl; or
—C(O)$R^e$ wherein $R^e$ is:
$C_{1-6}$alkyl;
amino;
$C_{1-6}$alkyl-amino; or
N,N-di-$C_{1-6}$alkylamino.

In certain embodiments of any of formula II, $R^4$, $R^5$ and $R^c$ each more preferably is independently selected from:
halo;
$C_{1-6}$alkyl;
halo-$C_{1-6}$alkyl;
$C_{1-6}$alkoxy;
hydroxy; or
cyano.

In embodiments of formulas I, II, III, IV or V where $R^1$ is optionally substituted aryl, optionally substituted heteroaryl, optionally substituted aryl-$C_{1-3}$ alkyl (including optionally substituted benzyl) or optionally substituted heteroaryl-$C_{1-3}$alkyl, such optionally substituents may comprise one, two or three groups each independently selected from:
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
nitro;
amino;
N—$C_{1-6}$alkyl-amino;
N,N-di-$C_{1-6}$alkylamino; or
—(CH$_2$)$_r$—Y—(CH$_2$)$_s$—Z—(CH$_2$)$_t$-Q-(CH$_2$)$_u$—$R^c$;
wherein
r, s, t and u each independently is 0 or 1;
Z is —C(O)— or —SO$_2$—;
X and Y each independently is —O—, —NR$^d$— or a bond;
$R^c$ is:
hydrogen;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl;
cyano;
amino;
$C_{1-6}$alkyl-amino; or
N,N-di-$C_{1-6}$alkylamino; and
$R^d$ is:
hydrogen; or
$C_{1-6}$alkyl.

In embodiments of formulas I, II, III, IV or V where $R^1$ is optionally substituted aryl, optionally substituted heteroaryl, optionally substituted aryl-$C_{1-3}$ alkyl (including optionally substituted benzyl) or optionally substituted heteroaryl-$C_{1-3}$alkyl, such optionally substituents more preferably comprise one, two or three groups each independently selected from:
halo;
$C_{1-6}$alkyl;
halo-$C_{1-6}$alkyl;
halo-$C_{1-6}$alkoxy;
$C_{1-6}$alkoxy;
hydroxy;
hetero-$C_{1-6}$alkyl selected from:
hydroxy-$C_{1-6}$alkyl;
$C_{1-6}$alkylsulfonyl-$C_{1-6}$alkyl; and
$C_{1-6}$alkoxy-$C_{1-6}$alkyl;
cyano;
nitro;
amino;
N—$C_{1-6}$alkyl-amino
N,N-di-$C_{1-6}$alkylamino;
$C_{1-6}$alkyl-sulfonyl; or
—C(O)$R^e$ wherein $R^e$ is:
$C_{1-6}$alkyl;
amino;
$C_{1-6}$alkyl-amino; or
N,N-di-$C_{1-6}$alkylamino.

In embodiments of formulas I, II, III, IV or V where $R^1$ is optionally substituted aryl, optionally substituted heteroaryl, optionally substituted aryl-$C_{1-3}$ alkyl (including optionally substituted benzyl) or optionally substituted heteroaryl-$C_{1-3}$alkyl, such optionally substituents still more preferably comprise one or two groups each independently selected from:
halo;
$C_{1-6}$alkyl;
halo-$C_{1-6}$alkyl;
$C_{1-6}$alkoxy;
hydroxy; or
cyano.

In certain embodiments of formula I, the subject compounds may be more specifically of formula VI:

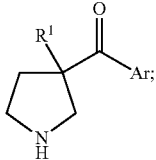

VI wherein Ar and R¹ are as defined herein for formula I.

In certain embodiments of formula VI, the subject compounds may be more specifically of formula VIa or formula VIb:

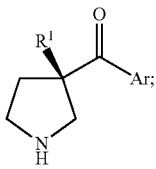

VIa

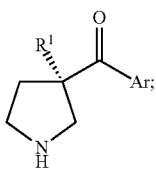

VIb wherein Ar and R¹ are as defined herein for formula I.

In certain embodiments of formula I, the subject compounds may be more specifically of formula VII:

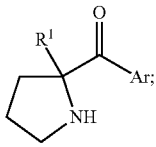

VII wherein Ar and R¹ are as defined herein for formula I.

In certain embodiments of formula VII, the subject compounds may be more specifically of formula VIIa or formula VIIb:

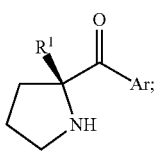

VIIa

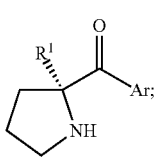

VIIb wherein Ar and R¹ are as defined herein for formula I.

In certain embodiments of formula I, the subject compounds may be more specifically of formula VIII:

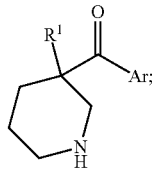

VIII wherein Ar and R¹ are as defined herein for formula I.

In certain embodiments of formula VIII, the subject compounds may be more specifically of formula VIIIa or formula VIIIb:

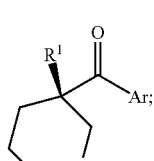

VIIIa

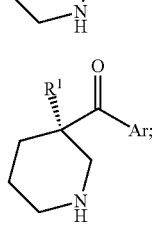

VIIIb wherein Ar and R¹ are as defined herein for formula I.

In certain embodiments of formula I, the subject compounds may be more specifically of formula IX:

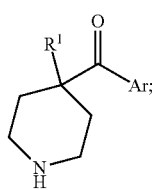

IX wherein Ar and R¹ are as defined herein for formula I.

In certain embodiments of formula I, the subject compounds may be more specifically of formula X:

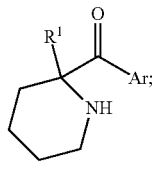

X wherein Ar and R¹ are as defined herein for formula I.

In certain embodiments of formula X, the subject compounds may be more specifically of formula Xa or formula Xb:

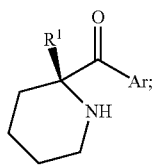

Xa

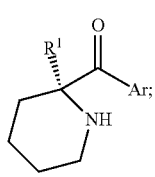

Xb wherein Ar and R[1] are as defined herein for formula I.

Representative compounds in accordance with the methods of the invention are shown in Table 1. Melting points (° C.) in Table 1 are for hydrochloride salts unless indicated otherwise.

TABLE 1

| # | Structure | Name | mp/M + H |
|---|-----------|------|----------|
| 1 | 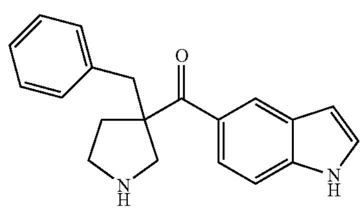 [SMILES: O=C(c1ccc2[nH]ccc2c1)C1(Cc2ccccc2)CCNC1] | (3-Benzyl-pyrrolidin-3-yl)-(1H-indol-5-yl)-methanone | 305 |
| 2 | 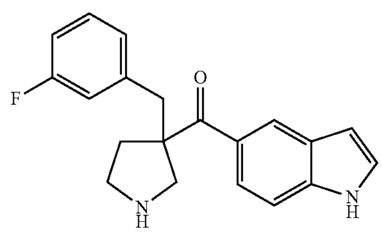 [SMILES: O=C(c1ccc2[nH]ccc2c1)C1(Cc2cccc(F)c2)CCNC1] | [3-(3-Fluoro-benzyl)-pyrrolidin-3-yl]-(1H-indol-5-yl)-methanone | 323 |
| 3 | 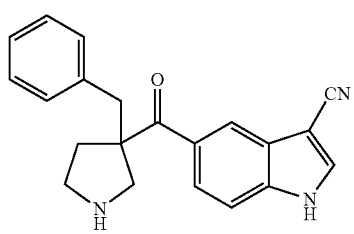 [SMILES: N#Cc1c[nH]c2ccc(C(=O)C3(Cc4ccccc4)CCNC3)cc12] | 5-(3-Benzyl-pyrrolidine-3-carbonyl)-1H-indole-3-carbonitrile | 330 |
| 4 | 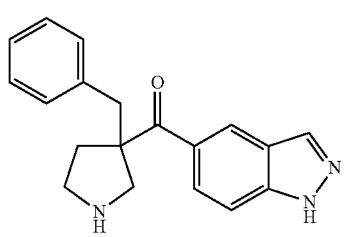 [SMILES: O=C(c1ccc2[nH]ncc2c1)C1(Cc2ccccc2)CCNC1] | (3-Benzyl-pyrrolidin-3-yl)-(1H-indazol-5-yl)-methanone | 306 |

TABLE 1-continued

| # | Structure | Name | mp/M + H |
|---|---|---|---|
| 5 | 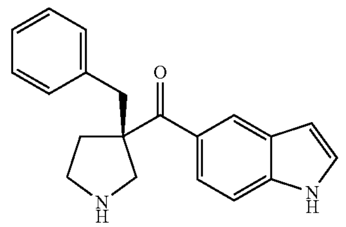 [SMILES: O=C(c1ccc2[nH]ccc2c1)[C@@]1(Cc2ccccc2)CCNC1] | (S)-3-Benzyl-pyrrolidin-3-yl)-(1H-indol-5-yl)-methanone | 305 |
| 6 | 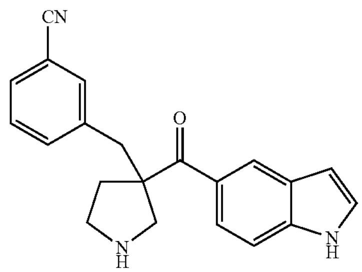 [SMILES: N#Cc1cccc(CC2(C(=O)c3ccc4[nH]ccc4c3)CCNC2)c1] | 3-[3-(1H-Indole-5-carbonyl)-pyrrolidin-3-ylmethyl]-benzonitrile | 330 |
| 7 | 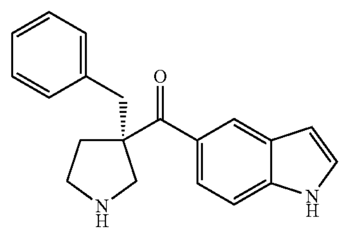 [SMILES: O=C(c1ccc2[nH]ccc2c1)[C@]1(Cc2ccccc2)CCNC1] | ((R)-3-Benzyl-pyrrolidin-3-yl)-(1H-indol-5-yl)-methanone | 305 |
| 8 | 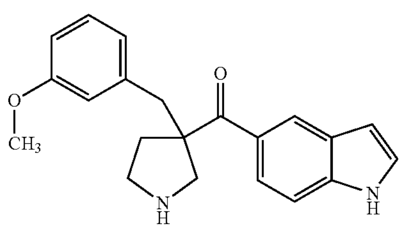 [SMILES: COc1cccc(CC2(C(=O)c3ccc4[nH]ccc4c3)CCNC2)c1] | (1H-Indol-5-yl)-[3-(3-methoxy-benzyl)-pyrrolidin-3-yl]-methanone | 335 |
| 9 | 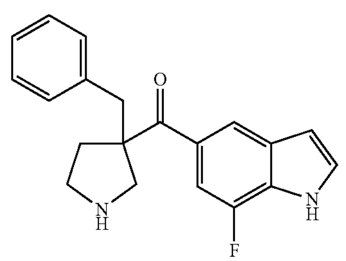 [SMILES: O=C(c1cc(F)c2[nH]ccc2c1)C1(Cc2ccccc2)CCNC1] | (3-Benzyl-pyrrolidin-3-yl)-(7-fluoro-1H-indol-5-yl)-methanone | 323 |
| 10 | 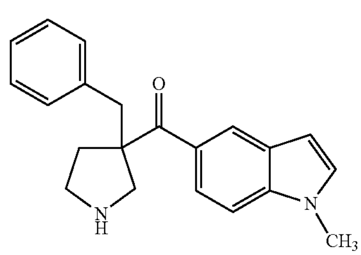 [SMILES: Cn1ccc2cc(C(=O)C3(Cc4ccccc4)CCNC3)ccc21] | (3-Benzyl-pyrrolidin-3-yl)-(1-methyl-1H-indol-5-yl)-methanone | 319 |

TABLE 1-continued
| # | Structure | Name | mp/M + H |
|---|---|---|---|
| 11 | 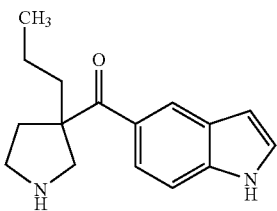 | (1H-Indol-5-yl)-(3-propyl-pyrrolidin-3-yl)-methanone | 257 |
| 12 | 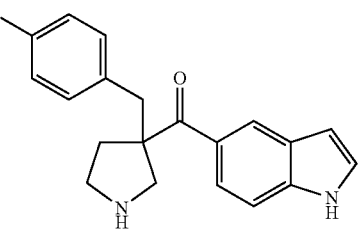 | [3-(4-Fluoro-benzyl)-pyrrolidin-3-yl]-(1H-indol-5-yl)-methanone | 323 |
| 13 | 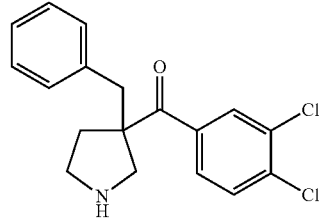 [SMILES: O=C(c1ccc(Cl)c(Cl)c1)C1(Cc2ccccc2)CCNC1] | (3-Benzyl-pyrrolidin-3-yl)-(3,4-dichloro-phenyl)-methanone | 334 |
| 14 | 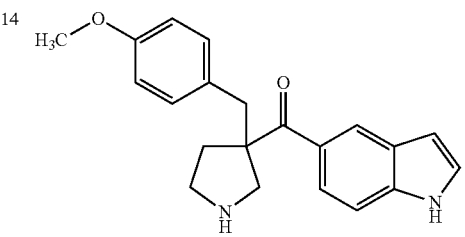 | (1H-Indol-5-yl)-[3-(4-methoxy-benzyl)-pyrrolidin-3-yl]-methanone | 335 |
| 15 | 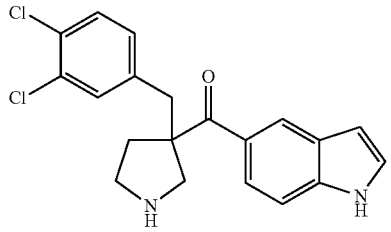 [SMILES: O=C(c1ccc2[nH]ccc2c1)C1(Cc2ccc(Cl)c(Cl)c2)CCNC1] | [3-(3,4-Dichloro-benzyl)-pyrrolidin-3-yl]-(1H-indol-5-yl)-methanone | 373 |
| 16 | 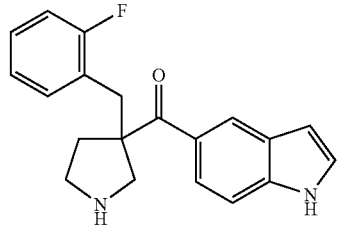 [SMILES: O=C(c1ccc2[nH]ccc2c1)C1(Cc2ccccc2F)CCNC1] | [3-(2-Fluoro-benzyl)-pyrrolidin-3-yl]-(1H-indol-5-yl)methanone | 323 |

TABLE 1-continued

| # | Structure | Name | mp/M + H |
|---|---|---|---|
| 17 | 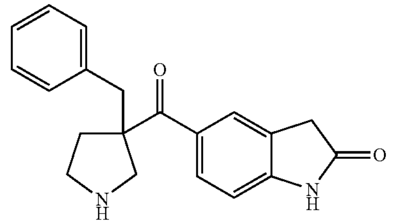 [SMILES: O=C1Cc2cc(C(=O)C3(Cc4ccccc4)CCNC3)ccc2N1] | 5-(3-Benzyl-pyrrolidine-3-carbonyl)-1,3-dihydro-indol-2-one | 321 |
| 18 | 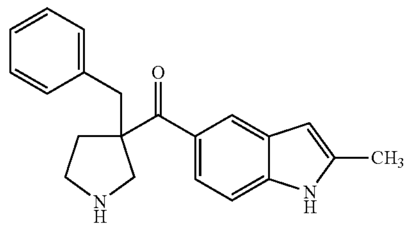 [SMILES: Cc1cc2cc(C(=O)C3(Cc4ccccc4)CCNC3)ccc2[nH]1] | (3-Benzyl-pyrrolidin-3-yl)-(2-methyl-1H-indol-5-yl)-methnanone | 319 |
| 19 | 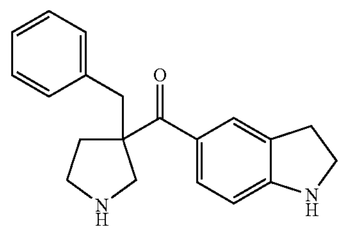 [SMILES: O=C(c1ccc2c(c1)CCN2)C1(Cc2ccccc2)CCNC1] | (3-Benzyl-pyrrolidin-3-yl)-(2,3-dihydro-1H-indol-5-yl)-methanone | 307 |
| 20 | 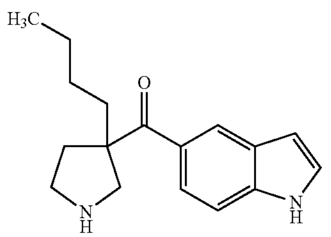 [SMILES: CCCCC1(C(=O)c2ccc3[nH]ccc3c2)CCNC1] | (3-Butyl-pyrrolidin-3-yl)-(1H-indol-5-yl)-methanone | 271 |
| 21 | 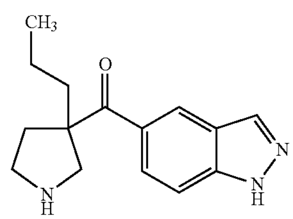 [SMILES: CCCC1(C(=O)c2ccc3[nH]ncc3c2)CCNC1] | (1H-Indazol-5-yl)-(3-propyl-pyrrolidin-3-yl)-methonone | 258 |
| 22 | 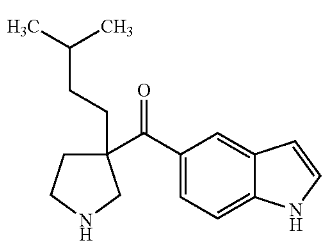 [SMILES: CC(C)CCC1(C(=O)c2ccc3[nH]ccc3c2)CCNC1] | (1H-Indol-5-yl)-[3-(3-methyl-butyl)-pyrrolidin-3-yl]-methanone | 285 |
| 23 | 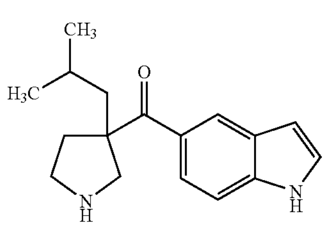 [SMILES: CC(C)CC1(C(=O)c2ccc3[nH]ccc3c2)CCNC1] | (1H-Indol-5-yl)-(3-isobutyl-pyrrolidin-3-yl)-methanone | 271 |

TABLE 1-continued

| # | Structure | Name | mp/M + H |
|---|---|---|---|
| 24 | 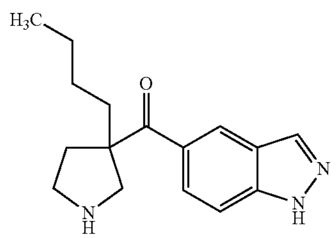 [SMILES: CCCCC1(C(=O)c2ccc3[nH]ncc3c2)CCNC1] | (3-Butyl-pyrrolidin-3-yl)-(1H-indazol-5-yl)-methanone | 272 |
| 25 | 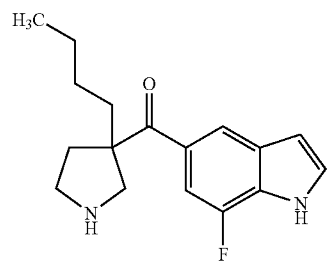 [SMILES: CCCCC1(C(=O)c2cc(F)c3[nH]ccc3c2)CCNC1] | (3-Butyl-pyrrolidin-3-yl)-(7-fluoro-1H-indol-5-yl)-methanone | 289 |
| 26 | 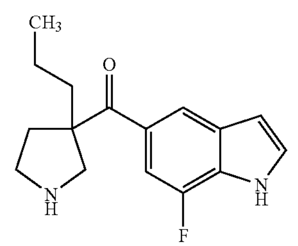 [SMILES: CCCC1(C(=O)c2cc(F)c3[nH]ccc3c2)CCNC1] | (7-Fluoro-1H-indol-5-yl)-(3-propyl-pyrrolidin-3-yl)-methanone | 275 |
| 27 | 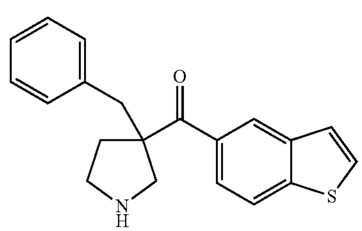 [SMILES: O=C(c1ccc2sccc2c1)C1(Cc2ccccc2)CCNC1] | Benzo[b]thiophen-5-yl-(3-benzyl-pyrrolidin-3-yl)-methanone | 322 |
| 28 | 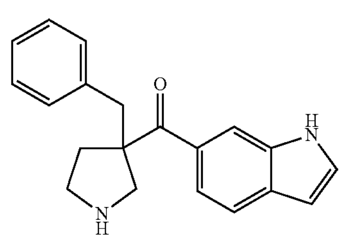 [SMILES: O=C(c1ccc2cc[nH]c2c1)C1(Cc2ccccc2)CCNC1] | (3-Benzyl-pyrrolidin-3-yl)-(1H-indol-6-yl)-methanone | 305 |
| 29 | 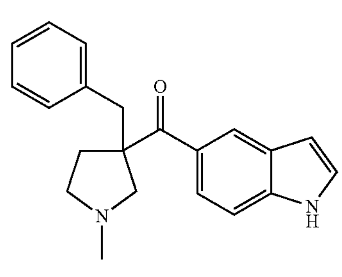 [SMILES: CN1CCC(Cc2ccccc2)(C(=O)c2ccc3[nH]ccc3c2)C1] | (3-Benzyl-1-methyl-pyrrolidin-3-yl)-(1H-indol-5-yl)-methanone | 319 |

TABLE 1-continued

| # | Structure | Name | mp/M + H |
|---|---|---|---|
| 30 | 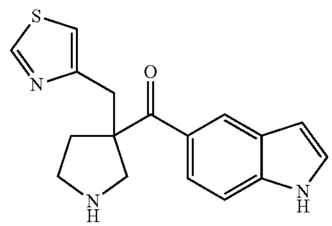 [SMILES: O=C(c1ccc2[nH]ccc2c1)C1(Cc2cscn2)CCNC1] | (1H-Indol-5-yl)-(3-thiazol-4-ylmethyl-pyrrolidin-3-yl)-methanone | 312 |
| 31 | 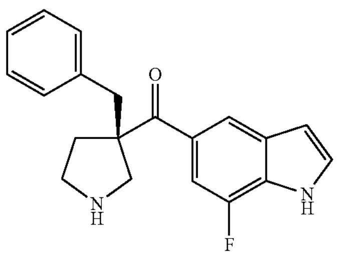 [SMILES: O=C(c1cc(F)c2[nH]ccc2c1)[C@@]1(Cc2ccccc2)CCNC1] | ((S)-3-Benzyl-pyrrolidin-3-yl)-(7-fluoro-1H-indol-5-yl)-methanone | 323 |
| 32 | 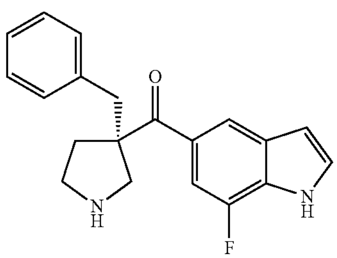 [SMILES: O=C(c1cc(F)c2[nH]ccc2c1)[C@]1(Cc2ccccc2)CCNC1] | ((R)-3-Benzyl-pyrrolidin-3-yl)-(7-fluoro-1H-indol-5-yl)-methanone | 323 |
| 33 | 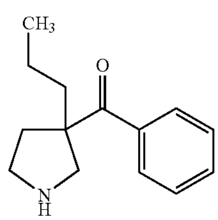 [SMILES: CCCC1(C(=O)c2ccccc2)CCNC1] | Phenyl-(3-propyl-pyrrolidin-3-yl)-methanone | 218 |
| 34 | 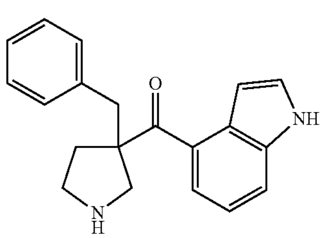 [SMILES: O=C(c1cccc2[nH]ccc12)C1(Cc2ccccc2)CCNC1] | (3-Benzyl-pyrrolidin-3-yl)-(1H-indol-4-yl)-methanone | 305 |
| 35 | 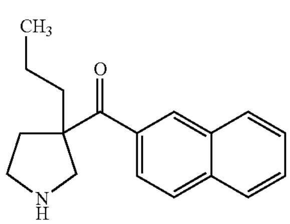 | Naphthalen-2-yl-(3-propyl-pyrrolidin-3-yl)-methanone | 268 |

TABLE 1-continued

| # | Structure | Name | mp/M + H |
|---|---|---|---|
| 36 | 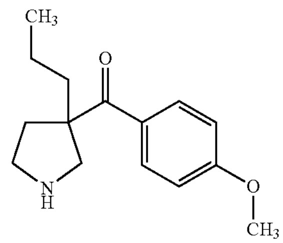 [SMILES: CCCC1(C(=O)c2ccc(OC)cc2)CCNC1] | (4-Methoxy-phenyl)-(3-propyl-pyrrolidin-3-yl)-methanone | 248 |
| 37 | 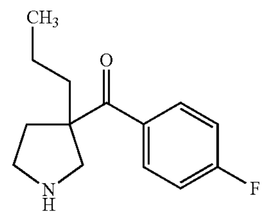 [SMILES: CCCC1(C(=O)c2ccc(F)cc2)CCNC1] | (4-Fluoro-phenyl)-(3-propyl-pyrrolidin-3-yl)-methanone | 236 |
| 38 | 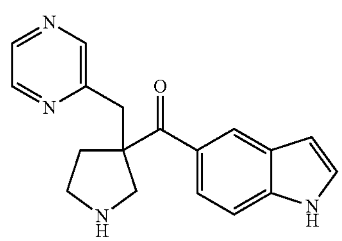 [SMILES: O=C(c1ccc2[nH]ccc2c1)C1(Cc2cnccn2)CCNC1] | (1H-Indol-5-yl)-(3-pyrazin-2-ylmethyl-pyrrolidin-3-yl)-methanone | 307 |
| 39 | 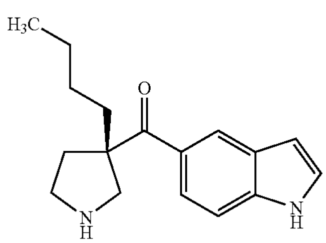 [SMILES: CCCC[C@]1(C(=O)c2ccc3[nH]ccc3c2)CCNC1] | ((S)-3-Butyl-pyrrolidin-3-yl)-(1H-indol-5-yl)-methanone | 271 |
| 40 | 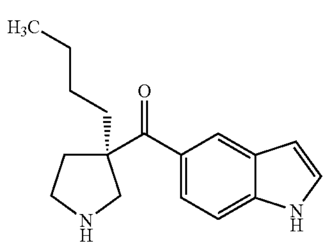 | ((R)-3-Butyl-pyrrolidin-3-yl)-(1H-indol-5-yl)-methanone | 271 |
| 41 | 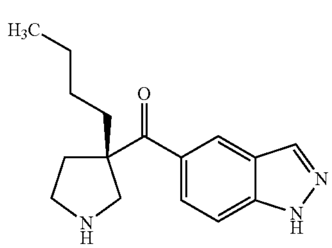 [SMILES: CCCC[C@]1(C(=O)c2ccc3[nH]ncc3c2)CCNC1] | ((S)-3-Butyl-pyrrolidin-3-yl)-(1H-indazol-5-yl)-methanone | 272 |

TABLE 1-continued

| # | Structure | Name | mp/M + H |
|---|---|---|---|
| 42 | 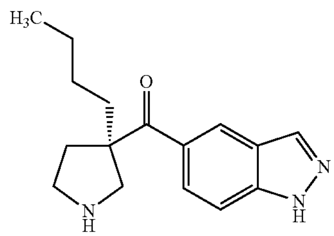 [SMILES: CCCC[C@@]1(C(=O)c2ccc3[nH]ncc3c2)CCNC1] | ((R)-3-Butyl-pyrrolidin-3-yl)-(1H-indazol-5-yl)-methanone | 272 |
| 43 | 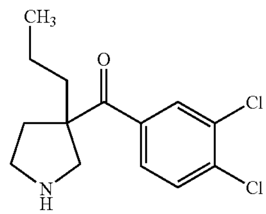 | (3,4-Dichloro-phenyl)-(3-propyl-pyrrolidin-3-yl)-methanone | 286 |
| 44 | 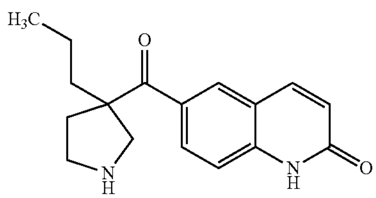 [SMILES: CCCC1(C(=O)c2ccc3[nH]c(=O)ccc3c2)CCNC1] | 6-(3-Propyl-pyrrolidine-3-carbonyl)-1H-quinolin-2-one | 285 |
| 45 | 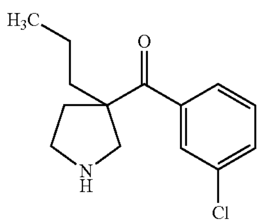 [SMILES: CCCC1(C(=O)c2cccc(Cl)c2)CCNC1] | (3-Chloro-phenyl)-(3-propyl-pyrrolidin-3-yl)-methanone | 252 |
| 46 | 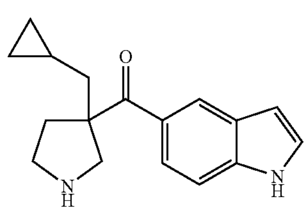 [SMILES: O=C(c1ccc2[nH]ccc2c1)C1(CC2CC2)CCNC1] | (3-Cyclopropylmethyl-pyrrolidin-3-yl)-(1H-indol-5-yl)-methanone | 269 |
| 47 | 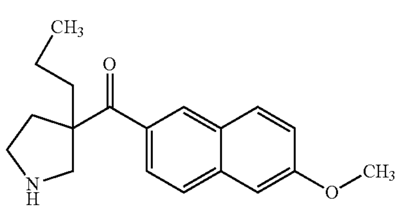 [SMILES: CCCC1(C(=O)c2ccc3cc(OC)ccc3c2)CCNC1] | (6-Methoxy-naphthalen-2-yl)-(3-propyl-pyrrolidin-3-yl)-methanone | 298 |
| 48 | 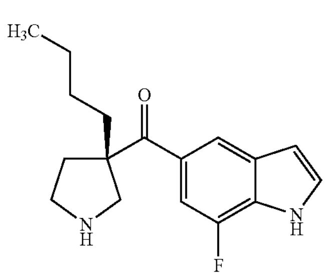 [SMILES: CCCC[C@]1(C(=O)c2cc(F)c3[nH]ccc3c2)CCNC1] | ((S)-3-Butyl-pyrrolidin-3-yl)-(7-fluoro-1H-indol-5-yl)-methanone | 119.0-120.0 |

TABLE 1-continued

| # | Structure | Name | mp/M + H |
|---|---|---|---|
| 49 | 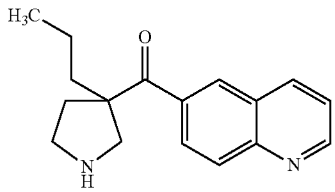 [SMILES: CCCC1(C(=O)c2ccc3ncccc3c2)CCNC1] | (3-Propyl-pyrrolidin-3-yl)-quinolin-6-yl-methanone | 269 |
| 50 | 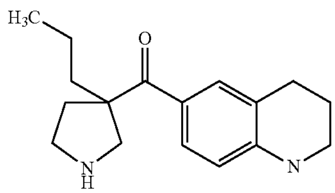 [SMILES: CCCC1(C(=O)c2ccc3c(c2)CCCN3)CCNC1] | (3-Propyl-pyrrolidin-3-yl)-(1,2,3,4-tetrahydro-quinolin-6-yl)-methanone | 273 |
| 51 | 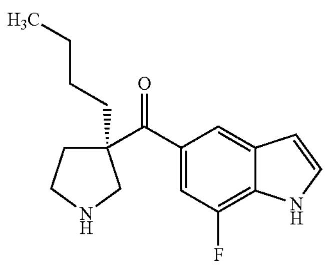 | ((R)-3-Butyl-pyrrolidin-3-yl)-(7-fluoro-1H-indol-5-yl)-methanone | 112.0-113.0 |
| 52 | 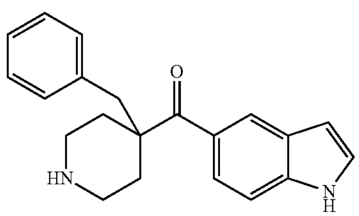 [SMILES: O=C(c1ccc2[nH]ccc2c1)C1(Cc2ccccc2)CCNCC1] | (4-Benzyl-piperidin-4-yl)-(1H-indol-5-yl)-methanone | 319 |
| 53 | 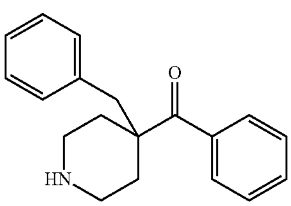 [SMILES: O=C(c1ccccc1)C1(Cc2ccccc2)CCNCC1] | (4-Benzyl-piperidin-4-yl)-phenyl-methanone | 280 |
| 54 | 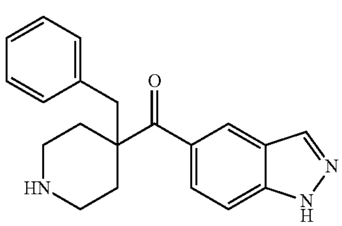 [SMILES: O=C(c1ccc2[nH]ncc2c1)C1(Cc2ccccc2)CCNCC1] | (4-Benzyl-piperidin-4-yl)-(1H-indazol-5-yl)-methanone | 320 |
| 55 | 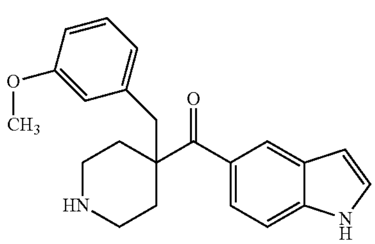 [SMILES: COc1cccc(CC2(C(=O)c3ccc4[nH]ccc4c3)CCNCC2)c1] | (1H-Indol-5-yl)-[4-(3-methoxy-benzyl)-piperidin-4-yl]-methanone | 349 |

TABLE 1-continued

| # | Structure | Name | mp/M + H |
|---|---|---|---|
| 56 | 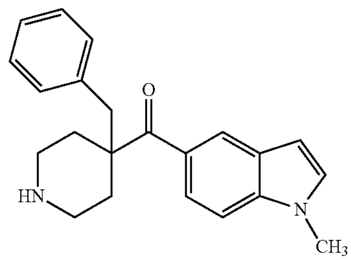 [SMILES: Cn1ccc2cc(C(=O)C3(Cc4ccccc4)CCNCC3)ccc21] | (4-Benzyl-piperidin-4-yl)-(1-methyl-1H-indol-5-yl)-methnanone | 333 |
| 57 | 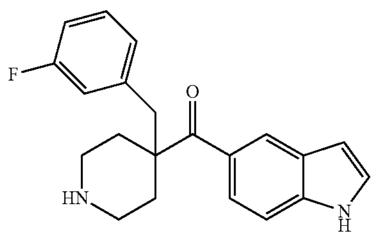 [SMILES: O=C(c1ccc2[nH]ccc2c1)C1(Cc2cccc(F)c2)CCNCC1] | 4-(3-Fluoro-benzyl)-piperidin-4-yl]-(1H-indol-5-yl)-methanone | 337 |
| 58 | 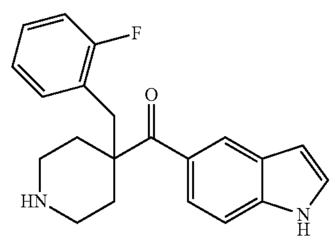 [SMILES: O=C(c1ccc2[nH]ccc2c1)C1(Cc2ccccc2F)CCNCC1] | [4-(2-Fluoro-benzyl)-piperidin-4-yl]-(1H-indol-5-yl)-methanone | 337 |
| 59 | 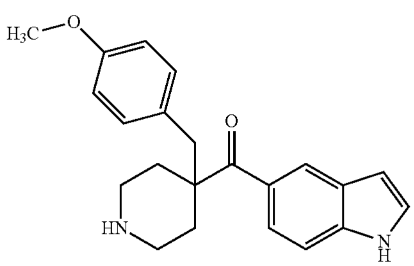 [SMILES: COc1ccc(CC2(C(=O)c3ccc4[nH]ccc4c3)CCNCC2)cc1] | (1H-Indol-5-yl)-[4-(4-methoxy-benzyl)-piperidin-4-yl]-methanone | 349 |
| 60 | 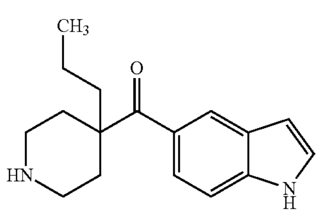 [SMILES: CCCC1(C(=O)c2ccc3[nH]ccc3c2)CCNCC1] | (1H-Indol-5-yl)-(4-propyl-piperidin-4-yl)-methanone | 163.9-165.1 |
| 61 | 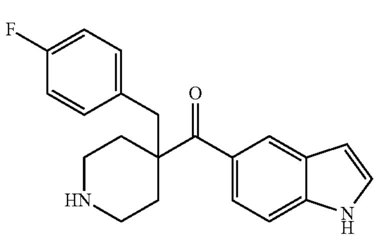 [SMILES: O=C(c1ccc2[nH]ccc2c1)C1(Cc2ccc(F)cc2)CCNCC1] | [4-(4-Fluoro-benzyl)-piperidin-4-yl]-(1H-indol-5-yl)-methanone | 337 |

TABLE 1-continued

| # | Structure | Name | mp/M + H |
|---|---|---|---|
| 62 | 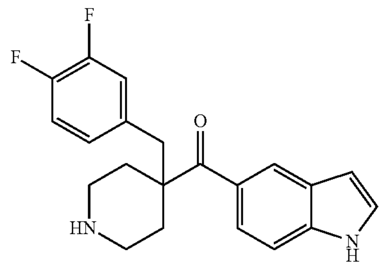 [SMILES: O=C(c1ccc2[nH]ccc2c1)C1(Cc2ccc(F)c(F)c2)CCNCC1] | [4-(3,4-Difluoro-benzyl)-piperidin-4-yl]-(1H-indol-5-yl)-methanone | 355 |
| 63 | 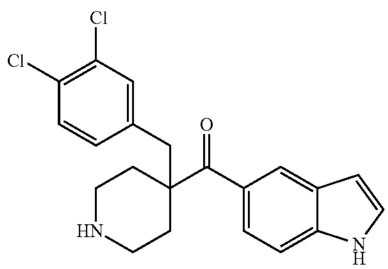 [SMILES: O=C(c1ccc2[nH]ccc2c1)C1(Cc2ccc(Cl)c(Cl)c2)CCNCC1] | [4-(3,4-Dichloro-benzyl)-piperidin-4-yl]-(1H-indol-5-yl)-methanone | 387 |
| 64 | 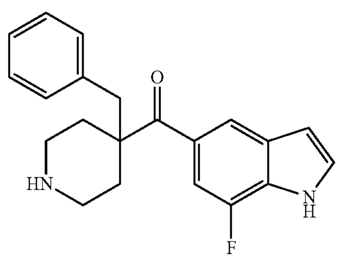 [SMILES: O=C(c1cc(F)c2[nH]ccc2c1)C1(Cc2ccccc2)CCNCC1] | (4-Benzyl-piperidin-4-yl)-(7-fluoro-1H-indol-5-yl)-methanone | 337 |
| 65 | 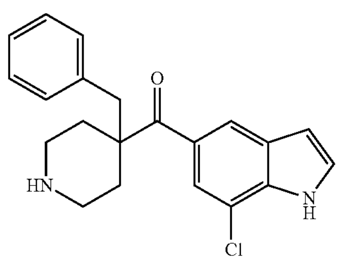 [SMILES: O=C(c1cc(Cl)c2[nH]ccc2c1)C1(Cc2ccccc2)CCNCC1] | (4-Benzyl-piperidin-4-yl)-(7-chloro-1H-indol-5-yl)-methanone | 353 |
| 66 | 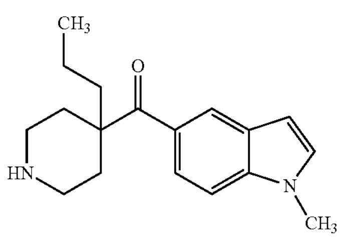 [SMILES: CCCC1(C(=O)c2ccc3c(ccn3C)c2)CCNCC1] | (1-Methyl-1H-indol-5-yl)-(4-propyl-piperidin-4-yl)-methanone | 184.4-186.3 |
| 67 | 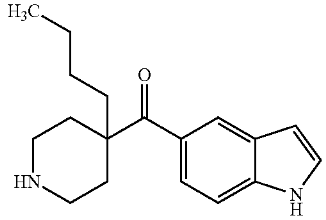 [SMILES: CCCCC1(C(=O)c2ccc3[nH]ccc3c2)CCNCC1] | (4-Butyl-piperidin-4-yl)-(1H-indol-5-yl)-methanone | 130.6-133.9 |

TABLE 1-continued

| # | Structure | Name | mp/M + H |
|---|-----------|------|----------|
| 68 | 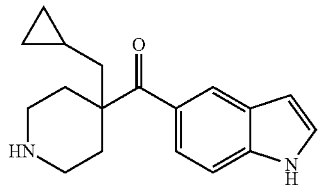 [SMILES: O=C(c1ccc2[nH]ccc2c1)C1(CC2CC2)CCNCC1] | (4-Cyclopropylmethyl-piperidin-4-yl)-(1H-indol-5-yl)-methanone | 169.4-170.2 |
| 69 | 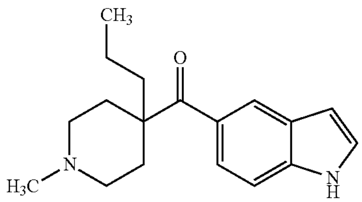 [SMILES: CCCC1(C(=O)c2ccc3[nH]ccc3c2)CCN(C)CC1] | (1H-Indol-5-yl)-(1-methyl-4-propyl-piperidin-4-yl)-methanone | 285 |
| 70 | 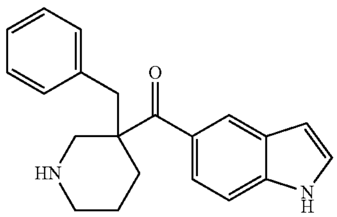 | (3-Benzyl-piperidin-3-yl)-(1H-indol-5-yl)-methanone | 319 |
| 71 | 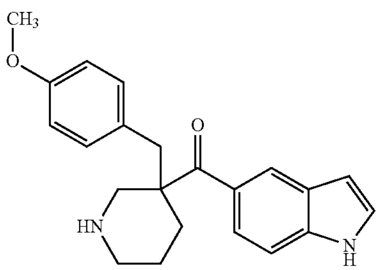 [SMILES: COc1ccc(CC2(C(=O)c3ccc4[nH]ccc4c3)CCCNC2)cc1] | (1H-Indol-5-yl)-[3-(4-methoxy-benzyl)-piperidin-3-yl]-methanone | 349 |
| 72 | 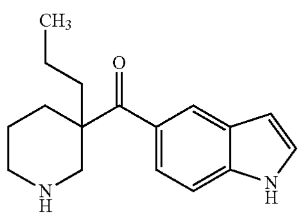 [SMILES: CCCC1(C(=O)c2ccc3[nH]ccc3c2)CCCNC1] | (1H-Indol-5-yl)-(3-propyl-piperidin-3-yl)-methanone | 132.0-137.0 |
| 73 | 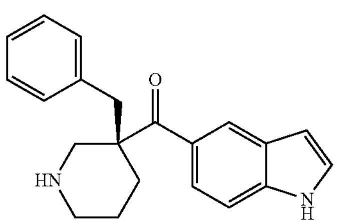 [SMILES: O=C(c1ccc2[nH]ccc2c1)[C@]1(Cc2ccccc2)CCCNC1] | ((S)-3-Benzyl-piperidin-3-yl)-(1H-indol-5-yl)-methanone | 319 |
| 74 | 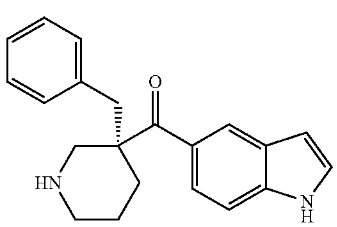 [SMILES: O=C(c1ccc2[nH]ccc2c1)[C@@]1(Cc2ccccc2)CCCNC1] | ((R)-3-Benzyl-piperidin-3-yl)-(1H-indol-5-yl)-methanone | 319 |

TABLE 1-continued

| # | Structure | Name | mp/M + H |
|---|---|---|---|
| 75 | 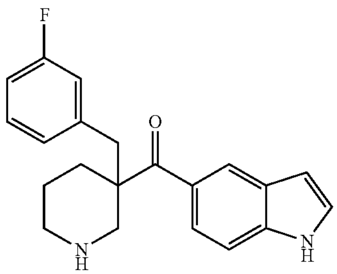 [SMILES: O=C(c1ccc2[nH]ccc2c1)C1(Cc2cccc(F)c2)CCCNC1] | [3-(3-Fluoro-benzyl)-piperidin-3-yl]-(1H-indol-5-yl)-methanone | 337 |
| 76 | 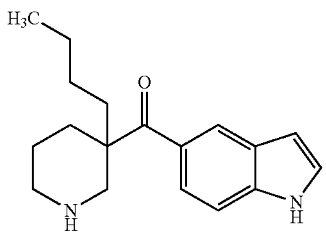 [SMILES: CCCCC1(C(=O)c2ccc3[nH]ccc3c2)CCCNC1] | (3-Butyl-piperidin-3-yl)-(1H-indol-5-yl)-methanone | 166.8-170.8 |
| 77 | 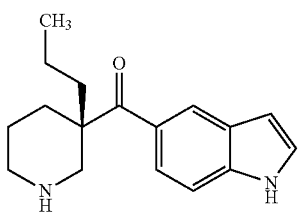 [SMILES: CCC[C@]1(C(=O)c2ccc3[nH]ccc3c2)CCCNC1] | (1H-Indol-5-yl)-((S)-3-propyl-piperidin-3-yl)-methanone | 115.0-117.0 |
| 78 | 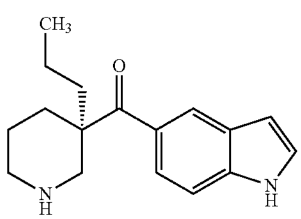 | (1H-Indol-5-yl)-((R)-3-propyl-piperidin-3-yl)-methanone | 271 |
| 79 | 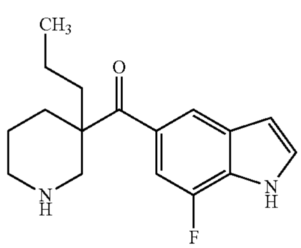 [SMILES: CCCC1(C(=O)c2cc(F)c3[nH]ccc3c2)CCCNC1] | (7-Fluoro-1H-indol-5-yl)-(3-propyl-piperidin-3-yl)-methanone | 289 |
| 80 | 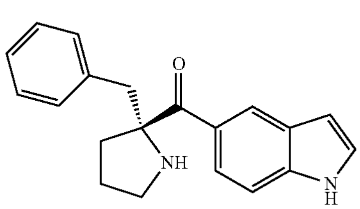 [SMILES: O=C(c1ccc2[nH]ccc2c1)[C@]1(Cc2ccccc2)CCCN1] | (2-Benzyl-pyrrolidin-2-yl)-(1H-indol-5-yl)-methanone | 405 |

TABLE 1-continued

| # | Structure | Name | mp/M + H |
|---|---|---|---|
| 81 | 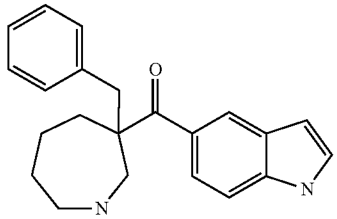 [SMILES: O=C(c1ccc2[nH]ccc2c1)C1(Cc2ccccc2)CCCCNC1] | (3-Benzyl-azepan-3-yl)-(1H-indol-5-yl)-methanone | 333 |
| 82 | 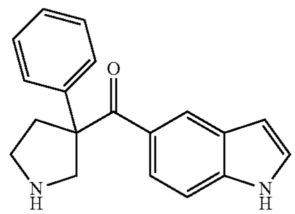 [SMILES: O=C(c1ccc2[nH]ccc2c1)C1(c2ccccc2)CCNC1] | (1H-Indol-5-yl)-(3-phenyl-pyrrolidin-3-yl)-methanone | 291 |
| 83 | 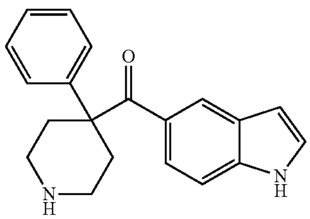 [SMILES: O=C(c1ccc2[nH]ccc2c1)C1(c2ccccc2)CCNCC1] | (1H-Indol-5-yl)-(4-phenyl-piperidin-4-yl)-methanone | 305 |
| 84 | 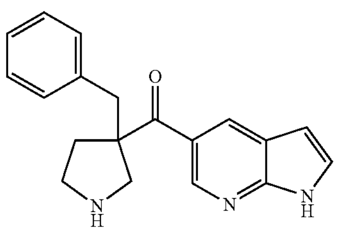 [SMILES: O=C(c1cnc2[nH]ccc2c1)C1(Cc2ccccc2)CCNC1] | (3-Benzyl-pyrrolidin-3-yl)-(1H-pyrrolo[2,3-b]pyridin-5-yl)-methanone | 306 |
| 85 | 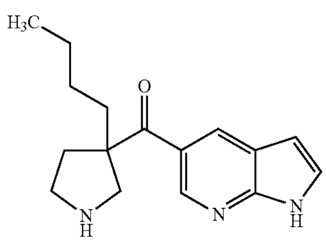 [SMILES: CCCCC1(C(=O)c2cnc3[nH]ccc3c2)CCNC1] | (3-Butyl-pyrrolidin-3-yl)-(1H-pyrrolo[2,3-b]pyridin-5-yl)-methanone | 272 |
| 86 | 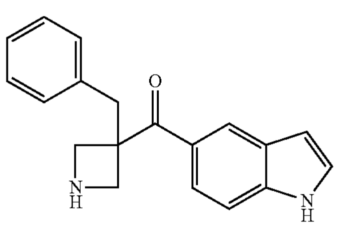 [SMILES: O=C(c1ccc2[nH]ccc2c1)C1(Cc2ccccc2)CNC1] | (3-Benzyl-azetidin-3-yl)-(1H-indol-5-yl)-methanone | 291 |
| 87 | 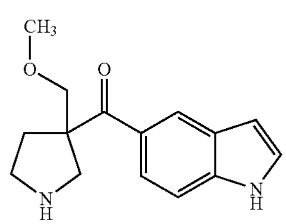 [SMILES: COCC1(C(=O)c2ccc3[nH]ccc3c2)CCNC1] | (1H-Indol-5-yl)-(3-methoxymethyl-pyrrolidin-3-yl)-methanone | 59.1-61.0 |

TABLE 1-continued

| # | Structure | Name | mp/M + H |
|---|-----------|------|----------|
| 88 | 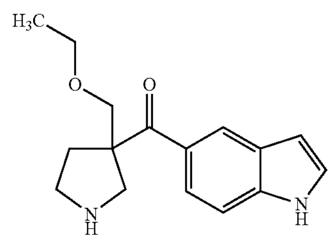 [SMILES: CCOCC1(C(=O)c2ccc3[nH]ccc3c2)CCNC1] | (3-Ethoxymethyl-pyrrolidin-3-yl)-(1H-indol-5-yl)-methanone | 98.6-99.6 |
| 89 | 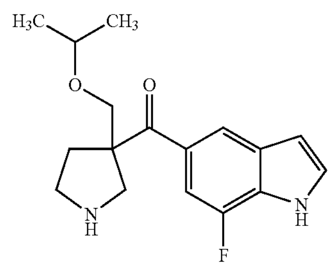 [SMILES: CC(C)OCC1(C(=O)c2cc(F)c3[nH]ccc3c2)CCNC1] | (7-Fluoro-1H-indol-5-yl)-(3-isopropoxymethyl-pyrrolidin-3-yl)-methanone | 154.5-155.4 |
| 90 | 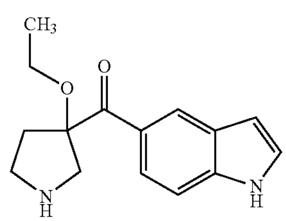 [SMILES: CCOC1(C(=O)c2ccc3[nH]ccc3c2)CCNC1] | (3-Ethoxy-pyrrolidin-3-yl)-(1H-indol-5-yl)-methanone | 259 |
| 91 | 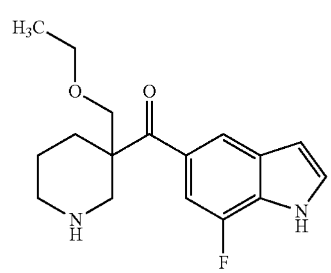 [SMILES: CCOCC1(C(=O)c2cc(F)c3[nH]ccc3c2)CCCNC1] | (3-Ethoxymethyl-piperidin-3-yl)-(7-fluoro-1H-indol-5-yl)-methanone | 291 |
| 92 | 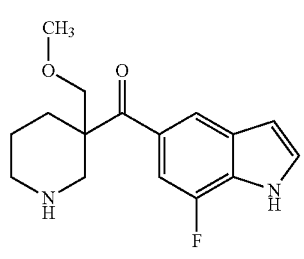 [SMILES: COCC1(C(=O)c2cc(F)c3[nH]ccc3c2)CCCNC1] | (7-Fluoro-1H-indol-5-yl)-(3-methoxymethyl-piperidin-3-yl)-methanonemethanone | 277 |
| 93 | 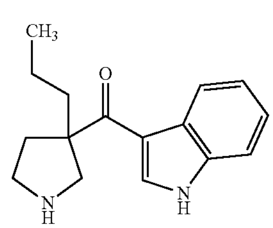 [SMILES: CCCC1(C(=O)c2c[nH]c3ccccc23)CCNC1] | (1H-Indol-3-yl)-(3-propyl-pyrrolidin-3-yl)-methanone | 257 |

TABLE 1-continued

| # | Structure | Name | mp/M + H |
|---|---|---|---|
| 94 | 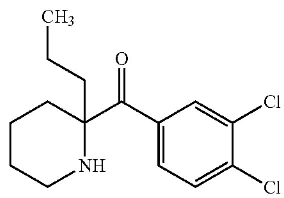 [SMILES: CCCC1(C(=O)c2ccc(Cl)c(Cl)c2)CCCCN1] | (3,4-Dichloro-phenyl)-(2-propyl-piperidin-2-yl)-methanone | 300 |
| 95 | 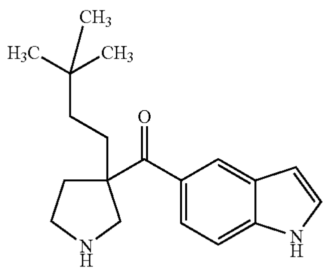 [SMILES: CC(C)(C)CCC1(C(=O)c2ccc3[nH]ccc3c2)CCNC1] | [3-(3,3-Dimethyl-butyl)-pyrrolidin-3-yl]-(1H-indol-5-yl)-methanone | 299 |
| 96 | 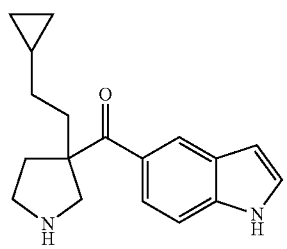 [SMILES: O=C(c1ccc2[nH]ccc2c1)C1(CCC2CC2)CCNC1] | [3-(2-Cyclopropyl-ethyl)-pyrrolidin-3-yl]-(1H-indol-5-yl)-methanone | 283 |
| 97 | 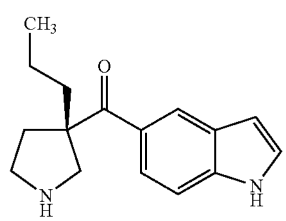 [SMILES: CCC[C@]1(C(=O)c2ccc3[nH]ccc3c2)CCNC1] | (1H-Indol-5-yl)-((S)-3-propyl-pyrrolidin-3-yl)-methanone | 257 |
| 98 | 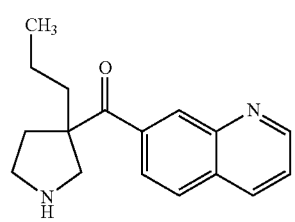 [SMILES: CCCC1(C(=O)c2ccc3cccnc3c2)CCNC1] | (3-Propyl-pyrrolidin-3-yl)-quinolin-7-yl-methanone | 269 |
| 99 | 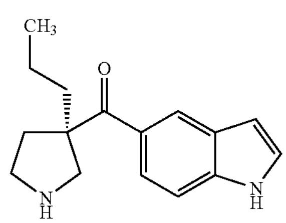 [SMILES: CCC[C@@]1(C(=O)c2ccc3[nH]ccc3c2)CCNC1] | (1H-Indol-5-yl)-((R)-3-propyl-pyrrolidin-3-yl)-methanone | 257 |

TABLE 1-continued

| # | Structure | Name | mp/M + H |
|---|---|---|---|
| 100 | 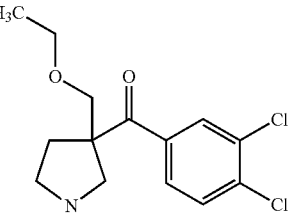 | (3,4-Dichloro-phenyl)-(3-ethoxymethyl-pyrrolidin-3-yl)-methanone | 303 |
| 101 | 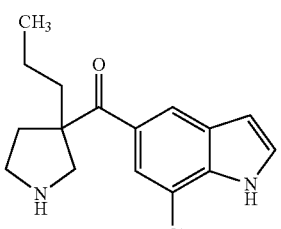 | (7-Chloro-1H-indol-5-yl)-(3-propyl-pyrrolidin-3-yl)-methanone | 291 |
| 102 | 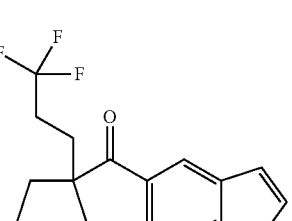 | (1H-Indol-5-yl)-[3-(3,3,3-trifluoro-propyl)-pyrrolidin-3-yl]-methanone | 311 |
| 103 | 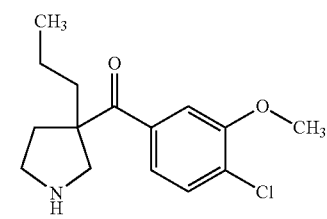 [SMILES: CCCC1(C(=O)c2ccc(Cl)c(OC)c2)CCNC1] | (4-Chloro-3-methoxy-phenyl)-(3-propyl-pyrrolidin-3-yl)-methanone | 282 |
| 104 | 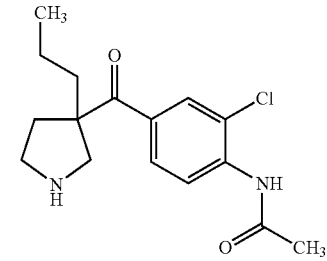 [SMILES: CCCC1(C(=O)c2ccc(NC(C)=O)c(Cl)c2)CCNC1] | N-[2-Chloro-4-(3-propyl-pyrrolidine-3-carbonyl)-phenyl]-acetamide | 309 |
| 105 | 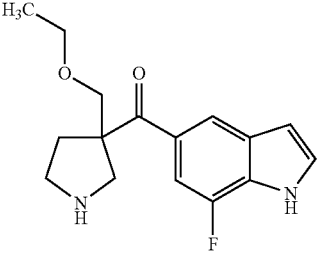 | (3-Ethoxymethyl-pyrrolidin-3-yl)-(7-fluoro-1H-indol-5-yl)-methanone | 162.5-163.0 |

TABLE 1-continued

| # | Structure | Name | mp/M + H |
|---|---|---|---|
| 106 | 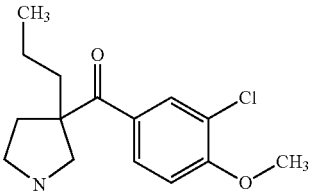 | (3-Chloro-4-methoxy-phenyl)-(3-propyl-pyrrolidin-3-yl)-methanone | 282 |
| 107 | 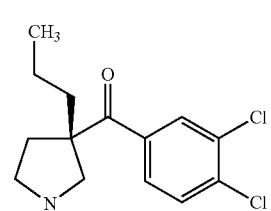 | (3,4-Dichloro-phenyl)-((S)-3-propyl-pyrrolidin-3-yl)-methanone | 136.6-138.2 |
| 108 | 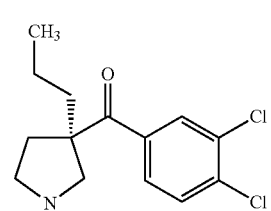 | (3,4-Dichloro-phenyl)-((R)-3-propyl-pyrrolidin-3-yl)-methanone | 287 |
| 109 | 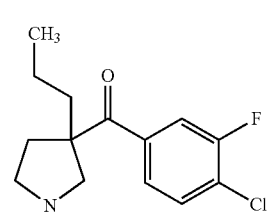 | (4-Chloro-3-fluoro-phenyl)-(3-propyl-pyrrolidin-3-yl)-methanone | 270 |
| 110 | 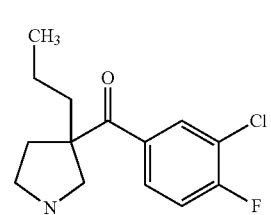 | (3-Chloro-4-fluoro-phenyl)-(3-propyl-pyrrolidin-3-yl)-methanone | 270 |
| 111 | 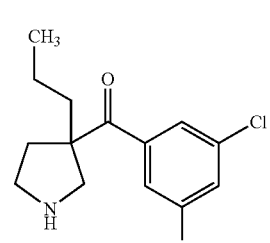 | (3,5-Dichloro-phenyl)-(3-propyl-pyrrolidin-3-yl)-methanone | 287 |
| 112 | 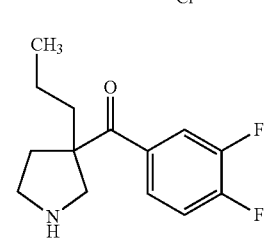 | (3,4-Difluoro-phenyl)-(3-propyl-pyrrolidin-3-yl)-methanone | 254 |

TABLE 1-continued

| # | Structure | Name | mp/M + H |
|---|---|---|---|
| 113 | 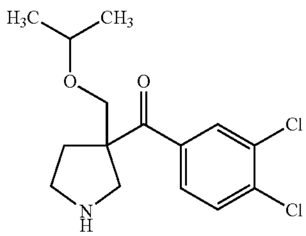 [SMILES: CC(C)OCC1(C(=O)c2ccc(Cl)c(Cl)c2)CCNC1] | (3,4-Dichoro-phenyl)-(3-isopropoxymethyl-pyrrolidin-3-yl)-methanone | 317 |
| 114 | 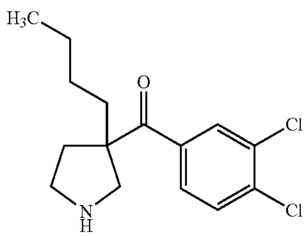 [SMILES: CCCCC1(C(=O)c2ccc(Cl)c(Cl)c2)CCNC1] | (3-Butyl-pyrrolidin-3-yl)-(3,4-dichloro-phenyl)-methanone | 301 |
| 115 | 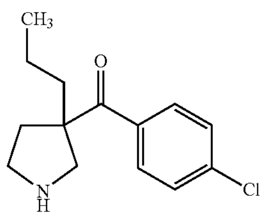 [SMILES: CCCC1(C(=O)c2ccc(Cl)cc2)CCNC1] | (4-Chloro-phenyl)-(3-propyl-pyrrolidin-3-yl)-methanone | 252 |
| 116 | 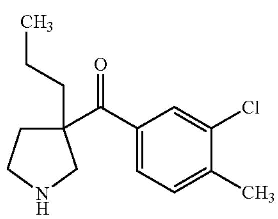 [SMILES: CCCC1(C(=O)c2ccc(C)c(Cl)c2)CCNC1] | (3-Chloro-4-methyl-phenyl)-(3-propyl-pyrrolidin-3-yl)-methanone | 266 |
| 117 | 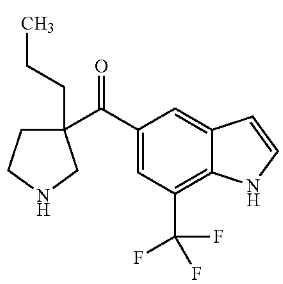 [SMILES: CCCC1(C(=O)c2cc(C(F)(F)F)c3[nH]ccc3c2)CCNC1] | (3-Propyl-pyrrolidin-3-yl)-(7-trifluoromethyl-1H-indol-5-yl)-methanone | 325 |
| 118 | 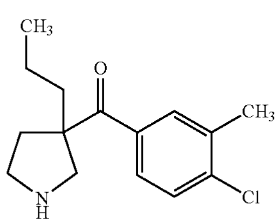 [SMILES: CCCC1(C(=O)c2ccc(Cl)c(C)c2)CCNC1] | (4-Chloro-3-methyl-phenyl)-(3-propyl-pyrrolidin-3-yl)-methanone | 266 |

TABLE 1-continued

| # | Structure | Name | mp/M + H |
|---|---|---|---|
| 119 | 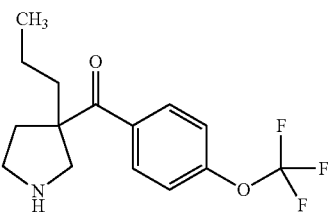 [SMILES: CCCC1(C(=O)c2ccc(OC(F)(F)F)cc2)CCNC1] | (3-Propyl-pyrrolidin-3-yl)-(4-trifluoromethoxy-phenyl)-methanone | 302 |
| 120 | 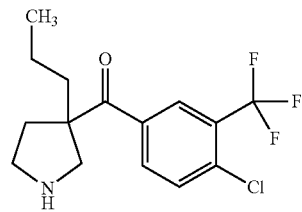 [SMILES: CCCC1(C(=O)c2ccc(Cl)c(C(F)(F)F)c2)CCNC1] | (4-Chloro-3-trifluoromethyl-phenyl)-(3-propyl-pyrrolidin-3-yl)-methanone | 320 |
| 121 | 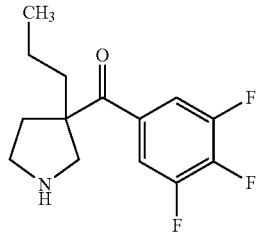 [SMILES: CCCC1(C(=O)c2cc(F)c(F)c(F)c2)CCNC1] | (3-Propyl-pyrrolidin-3-yl)-(3,4,5-trifluoro-phenyl)-methanone | 172.0-173.5 |
| 122 | 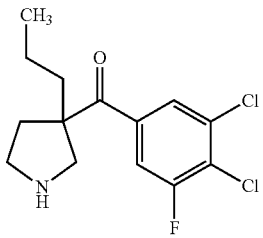 [SMILES: CCCC1(C(=O)c2cc(F)c(Cl)c(Cl)c2)CCNC1] | (3,4-Dichloro-5-fluoro-phenyl)-(3-propyl-pyrrolidin-3-yl)-methanone | 305 |
| 123 | 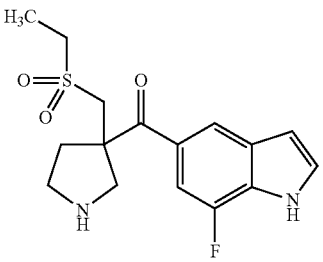 [SMILES: CCS(=O)(=O)CC1(C(=O)c2cc(F)c3[nH]ccc3c2)CCNC1] | (3-Ethanesulfonylmethyl-pyrrolidin-3-yl)-(7-fluoro-1H-indol-5-yl)-methanone | 339 |
| 124 | 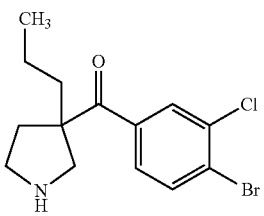 [SMILES: CCCC1(C(=O)c2ccc(Br)c(Cl)c2)CCNC1] | (4-Bromo-3-chloro-phenyl)-(3-propyl-pyrrolidin-3-yl)-methanone | 331 |

TABLE 1-continued

| # | Structure | Name | mp/M + H |
|---|-----------|------|----------|
| 125 | 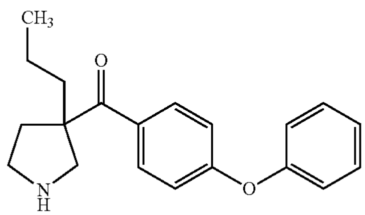 [SMILES: CCCC1(C(=O)c2ccc(Oc3ccccc3)cc2)CCNC1] | (4-Phenoxy-phenyl)-(3-propyl-pyrrolidin-3-yl)-methanone | 310 |
| 126 | 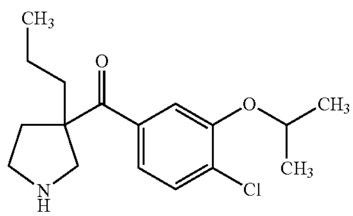 [SMILES: CCCC1(C(=O)c2ccc(Cl)c(OC(C)C)c2)CCNC1] | (4-Chloro-3-isopropoxy-phenyl)-(3-propyl-pyrrolidin-3-yl)-methanone | 310 |
| 127 | 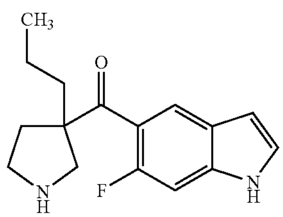 [SMILES: CCCC1(C(=O)c2cc3cc[nH]c3cc2F)CCNC1] | (6-Fluoro-1H-indol-5-yl)-(3-propyl-pyrrolidin-3-yl)-methanone | 275 |
| 128 | 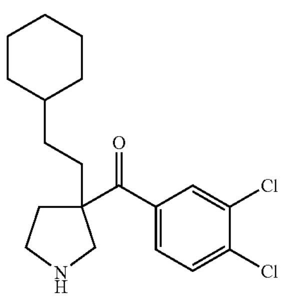 [SMILES: O=C(c1ccc(Cl)c(Cl)c1)C1(CCC2CCCCC2)CCNC1] | [3-(2-Cyclohexyl-ethyl)-pyrrolidin-3-yl]-(3,4-dichloro-phenyl)-methanone | 355 |
| 129 | 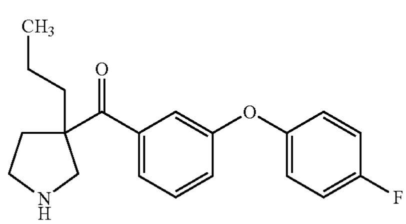 [SMILES: CCCC1(C(=O)c2cccc(Oc3ccc(F)cc3)c2)CCNC1] | [3-(4-Fluoro-phenoxy]-phenyl]-(3-propyl-pyrrolidin-3-yl)-methanone | 328 |
| 130 | 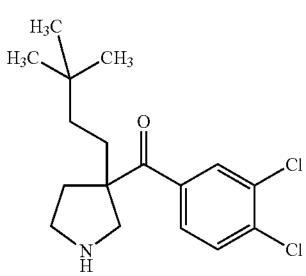 [SMILES: CC(C)(C)CCC1(C(=O)c2ccc(Cl)c(Cl)c2)CCNC1] | (3,4-Dichloro-phenyl)-[3-(3,3-dimethyl-butyl)-pyrrolidin-3-yl]-methanone | 152.5-154.0 |

TABLE 1-continued

| # | Structure | Name | mp/M + H |
|---|---|---|---|
| 131 | 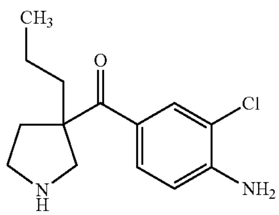 [SMILES: CCCC1(C(=O)c2ccc(N)c(Cl)c2)CCNC1] | (4-Amino-3-chloro-phenyl)-(3-propyl-pyrrolidin-3-yl)-methanone | 81.0-82.0 |
| 132 | 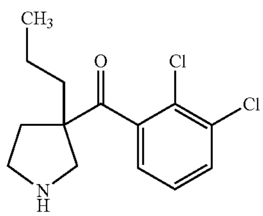 [SMILES: CCCC1(C(=O)c2cccc(Cl)c2Cl)CCNC1] | (2,3-Dichloro-phenyl)-(3-propyl-pyrrolidin-3-yl)-methanone | 287 |
| 133 | 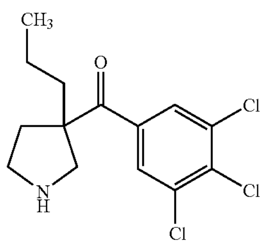 [SMILES: CCCC1(C(=O)c2cc(Cl)c(Cl)c(Cl)c2)CCNC1] | (3-Propyl-pyrrolidin-3-yl)-(3,4,5-trichloro-phenyl)-methanone | 174.0-175.0 |
| 134 | 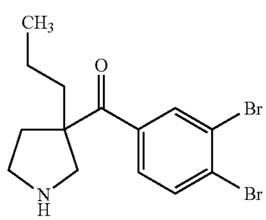 [SMILES: CCCC1(C(=O)c2ccc(Br)c(Br)c2)CCNC1] | (3,4-Dibromo-phenyl)-(3-propyl-pyrrolidin-3-yl)-methanone | 82.5-83.0 |
| 135 | 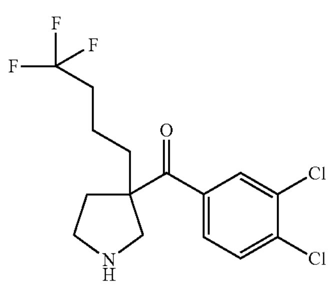 [SMILES: O=C(c1ccc(Cl)c(Cl)c1)C1(CCCC(F)(F)F)CCNC1] | (3,4-Dichloro-phenyl)-[3-(4,4,4-trifluoro-butyl)-pyrrolidin-3-yl]-methanone | 355 |
| 136 | 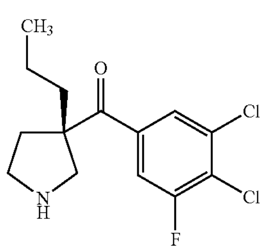 [SMILES: CCC[C@]1(C(=O)c2cc(F)c(Cl)c(Cl)c2)CCNC1] | (3,4-Dichloro-5-fluoro-phenyl)-((S)-3-propyl-pyrrolidin-3-yl)-methanone | 149.5-150.5 |

TABLE 1-continued

| # | Name | mp/M + H |
|---|------|----------|
| 137 | (3,4-Dichloro-5-fluoro-phenyl)-((R)-3-propyl-pyrrolidin-3-yl)-methanone | 305 |
| 138 | (4-Chloro-3-ethyl-phenyl)-(3-propyl-pyrrolidin-3-yl)-methanone | 280 |
| 139 | (3-Bromo-4-chloro-phenyl)-(3-propyl-pyrrolidin-3-yl)-methanone | 331 |
| 140 | (3-Cyclopropylmethyl-pyrrolidin-3-yl)-(3,4-dichloro-phenyl)-methanone | 299 |
| 141 | (3,4-Dichloro-phenyl)-[3-(tetrahydro-pyran-4-ylmethyl)-pyrrolidin-3-yl]-methanone | 186.0-187.0 |
| 142 | (4-Bromo-3-methyl-phenyl)-(3-propyl-pyrrolidin-3-yl)-methanone | 311 |
| 143 | (7-Fluoro-1H-indol-5-yl)-((S)-3-propyl-pyrrolidin-3-yl)-methanone | 140.0-141.0 |

TABLE 1-continued

| # | Structure | Name | mp/M + H |
|---|---|---|---|
| 144 | 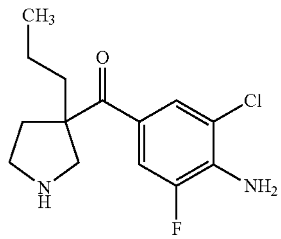 [SMILES: CCCC1(C(=O)c2cc(F)c(N)c(Cl)c2)CCNC1] | (4-Amino-3-chloro-5-fluoro-phenyl)-(3-propyl-pyrrolidin-3-yl)-methanone | 65.0-67.0 |
| 45 | 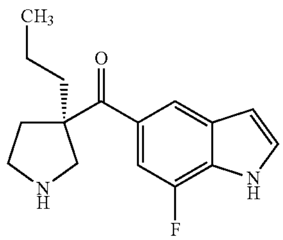 | (7-Fluoro-1H-indol-5-yl)-((R)-3-propyl-pyrrolidin-3-yl)-methanone | 100.0-101.0 |
| 146 | 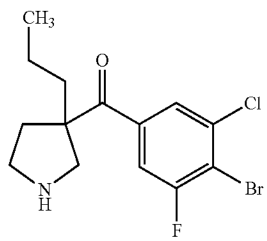 [SMILES: CCCC1(C(=O)c2cc(F)c(Br)c(Cl)c2)CCNC1] | (4-Bromo-3-chloro-5-fluoro-phenyl)-(3-propyl-pyrrolidin-3-yl)-methanone | 349 |
| 147 | 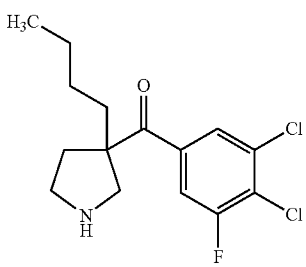 [SMILES: CCCCC1(C(=O)c2cc(F)c(Cl)c(Cl)c2)CCNC1] | (3-Butyl-pyrrolidin-3-yl)-(3,4-dichloro-5-fluoro-phenyl)-methanone | 319 |
| 148 | 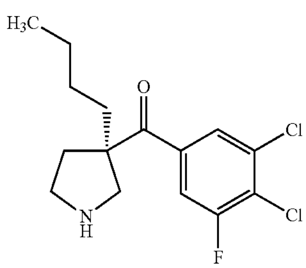 [SMILES: CCCC[C@@]1(C(=O)c2cc(F)c(Cl)c(Cl)c2)CCNC1] | ((R)-3-Butyl-pyrrolidin-3-yl)-(3,4-dichloro-5-fluoro-phenyl)-methanone | 129.0-130.0 |
| 149 | 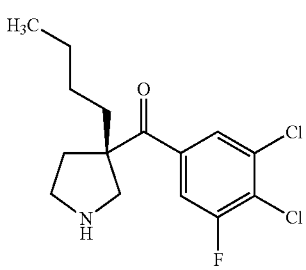 [SMILES: CCCC[C@]1(C(=O)c2cc(F)c(Cl)c(Cl)c2)CCNC1] | ((S)-3-Butyl-pyrrolidin-3-yl)-(3,4-dichloro-5-fluoro-phenyl)-methanone | 319 |

TABLE 1-continued

| # | Structure | Name | mp/M + H |
|---|---|---|---|
| 150 | 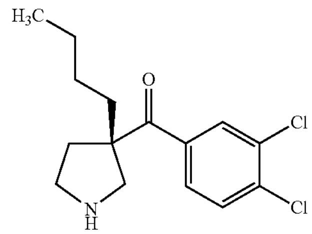 [SMILES: CCCC[C@]1(C(=O)c2ccc(Cl)c(Cl)c2)CCNC1] | ((S)-3-Butyl-pyrrolidin-3-yl)-(3,4-dichloro-phenyl)-methanone | 154.7-155.5 |
| 151 | 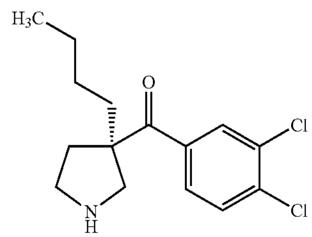 | ((R)-3-Butyl-pyrrolidin-3-yl)-(3,4-dichloro-phenyl)-methanone | 153.8-154.8 |
| 152 | 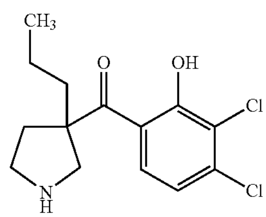 [SMILES: CCCC1(C(=O)c2ccc(Cl)c(Cl)c2O)CCNC1] | (3,4-Dichloro-2-hydroxy-phenyl)-(3-propyl-pyrrolidin-3-yl)-methanone | 180.0-181.0 |
| 153 | 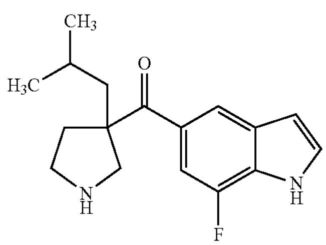 | (7-Fluoro-1H-indol-5-yl)-(3-isobutyl-pyrrolidin-3-yl)-methanone | 119.0-120.0 |
| 154 | 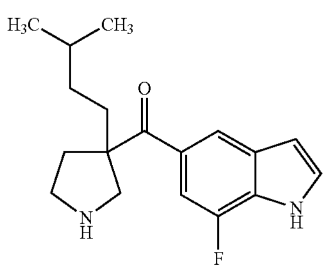 [SMILES: CC(C)CCC1(C(=O)c2cc(F)c3[nH]ccc3c2)CCNC1] | (7-Fluoro-1H-indol-5-yl)-[3-(3-methyl-butyl)-pyrrolidin-3-yl]-methanone | 109.0-110.0 |
| 155 | 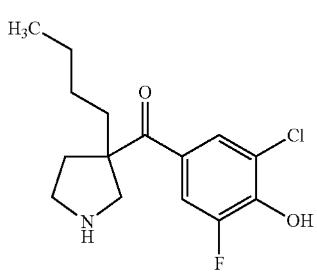 [SMILES: CCCCC1(C(=O)c2cc(F)c(O)c(Cl)c2)CCNC1] | (3-Butyl-pyrrolidin-3-yl)-(3-chloro-5-fluoro-4-hydroxy-phenyl)-methanone | 300 |

TABLE 1-continued

| # | Structure | Name | mp/M + H |
|---|---|---|---|
| 156 | 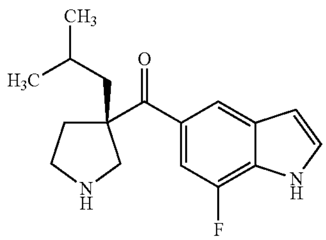 [SMILES: CC(C)C[C@]1(C(=O)c2cc(F)c3[nH]ccc3c2)CCNC1] | (7-Fluoro-1H-indol-5-yl)-((S)-3-isobutyl-pyrrolidin-3-yl)-methanone | 141.8-143.0 |
| 157 | 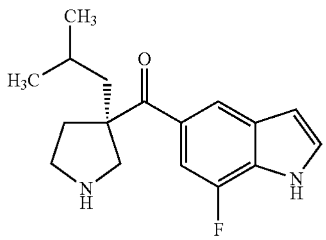 [SMILES: CC(C)C[C@@]1(C(=O)c2cc(F)c3[nH]ccc3c2)CCNC1] | (7-Fluoro-1H-indol-5-yl)-((R)-3-isobutyl-pyrrolidin-3-yl)-methanone | 196.2-197.8 |
| 158 | 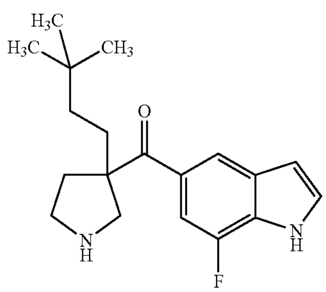 [SMILES: CC(C)(C)CCC1(C(=O)c2cc(F)c3[nH]ccc3c2)CCNC1] | [3-(3,3-Dimethyl-butyl)-pyrrolidin-3-yl]-(7-fluoro-1H-indol-5-yl)-methanone | 135.0-136.0 |
| 159 | 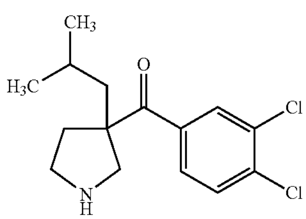 [SMILES: CC(C)CC1(C(=O)c2ccc(Cl)c(Cl)c2)CCNC1] | (3,4-Dichloro-phenyl)-(3-isobutyl-pyrrolidin-3-yl)-methanone | 301 |
| 160 | 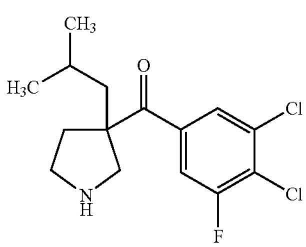 [SMILES: CC(C)CC1(C(=O)c2cc(F)c(Cl)c(Cl)c2)CCNC1] | (3,4-Dichloro-5-fluoro-phenyl)-(3-isobutyl-pyrrolidin-3-yl)-methanone | 319 |
| 161 | 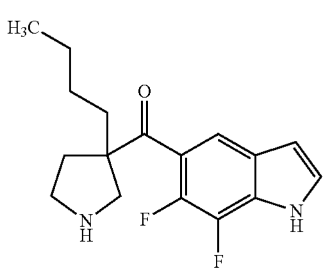 [SMILES: CCCCC1(C(=O)c2cc3cc[nH]c3c(F)c2F)CCNC1] | (3-Butyl-pyrrolidin-3-yl)-(6,7-difluoro-1H-indol-5-yl)-methanone | 70.0-71.0 |

TABLE 1-continued

| # | Structure | Name | mp/M + H |
|---|---|---|---|
| 162 | 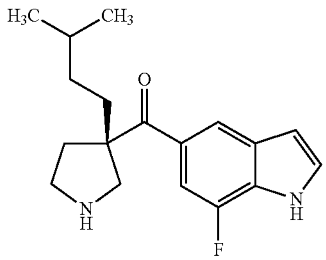 [SMILES: CC(C)CC[C@]1(C(=O)c2cc(F)c3[nH]ccc3c2)CCNC1] | (7-Fluoro-1H-indol-5-yl)-[(S)-3-(3-methyl-butyl)-pyrrolidin-3-yl]-methanone | 106.0-107.0 |
| 163 | 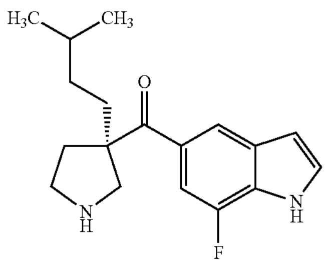 [SMILES: CC(C)CC[C@@]1(C(=O)c2cc(F)c3[nH]ccc3c2)CCNC1] | (7-Fluoro-1H-indol-5-yl)-[(R)-3-(3-methyl-butyl)-pyrrolidin-3-yl]-methanone | 109.0-110.0 |
| 164 | 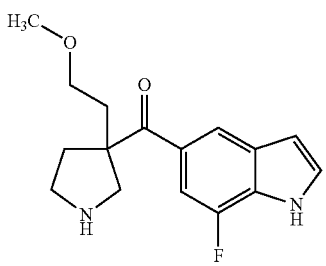 | (7-Fluoro-1H-indol-5-yl)-[3-(2-methoxy-ethyl)-pyrrolidin-3-yl]-methanone | 291 |
| 165 | 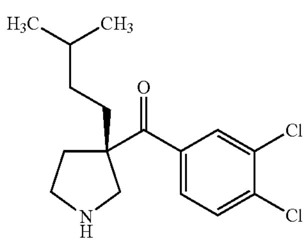 [SMILES: CC(C)CC[C@]1(C(=O)c2ccc(Cl)c(Cl)c2)CCNC1] | (3,4-Dichloro-phenyl)-[(S)-3-(3-methyl-butyl)-pyrrolidin-3-yl]-methanone | 315 |
| 166 | 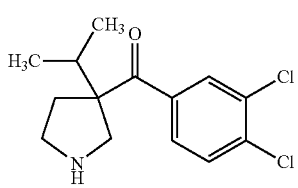 [SMILES: CC(C)C1(C(=O)c2ccc(Cl)c(Cl)c2)CCNC1] | (3,4-Dichloro-phenyl)-(3-isopropyl-pyrrolidin-3-yl)-methanone | 287 |
| 167 | 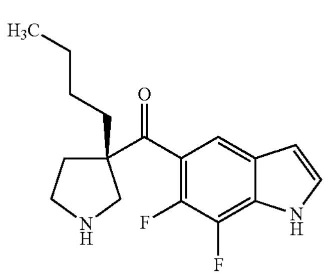 [SMILES: CCCC[C@]1(C(=O)c2cc3cc[nH]c3c(F)c2F)CCNC1] | ((S)-3-Butyl-pyrrolidin-3-yl)-(6,7-difluoro-1H-indol-5-yl)-methanone | 100.0-101.0 |

TABLE 1-continued

| # | Structure | Name | mp/M + H |
|---|---|---|---|
| 168 | 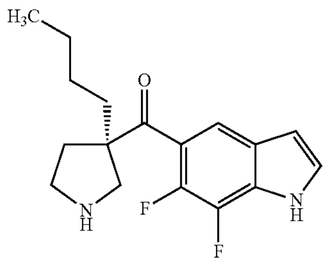 [SMILES: CCCC[C@@]1(C(=O)c2cc3cc[nH]c3c(F)c2F)CCNC1] | ((R)-3-Butyl-pyrrolidin-3-yl)-(6,7-difluoro-1H-indol-5-yl)-methanone | 99.0-100.0 |
| 169 | 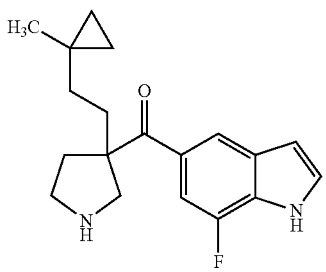 [SMILES: CC1(CCC2(C(=O)c3cc(F)c4[nH]ccc4c3)CCNC2)CC1] | (7-Fluoro-1H-indol-5-yl)-{3-[2-(1-methyl-cyclopropyl)-ethyl]-pyrrolidin-3-yl}-methanone | 119.0-120.0 |
| 170 | 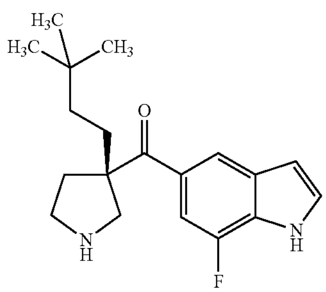 [SMILES: CC(C)(C)CC[C@]1(C(=O)c2cc(F)c3[nH]ccc3c2)CCNC1] | [(S)-3-(3,3-Dimethyl-butyl)-pyrrolidin-3-yl]-(7-fluoro-1H-indol-5-yl)-methanone | 198.7-199.9 |
| 171 | 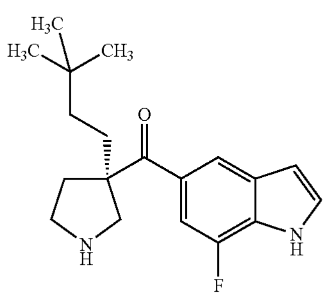 [SMILES: CC(C)(C)CC[C@@]1(C(=O)c2cc(F)c3[nH]ccc3c2)CCNC1] | [(R)-3-(3,3-Dimethyl-butyl)-pyrrolidin-3-yl]-(7-fluoro-1H-indol-5-yl)-methanone | 135.5-138.9 |
| 172 | 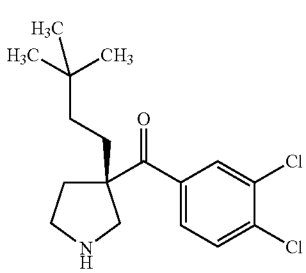 [SMILES: CC(C)(C)CC[C@]1(C(=O)c2ccc(Cl)c(Cl)c2)CCNC1] | (3,4-Dichloro-phenyl)-[(S)-3-(3,3-dimethyl-butyl)-pyrrolidin-3-yl]-methanone | 190.0-191.0 |

TABLE 1-continued

| # | Structure | Name | mp/M + H |
|---|---|---|---|
| 173 | 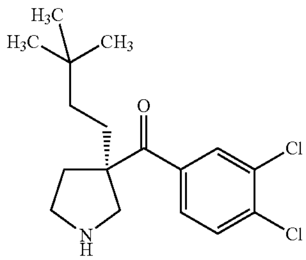 [SMILES: CC(C)(C)CC[C@@]1(C(=O)c2ccc(Cl)c(Cl)c2)CCNC1] | (3,4-Dichloro-phenyl)-[(R)-3-(3,3-dimethyl-butyl)-pyrrolidin-3-yl]-methanone | 188.0-189.0 |
| 174 | 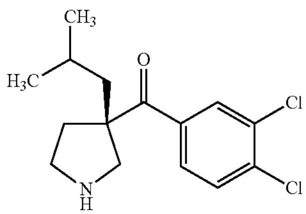 [SMILES: CC(C)C[C@]1(C(=O)c2ccc(Cl)c(Cl)c2)CCNC1] | (3,4-Dichloro-phenyl)-((S)-3-isobutyl-pyrrolidin-3-yl)-methanone | 167.5-168.5 |
| 175 | 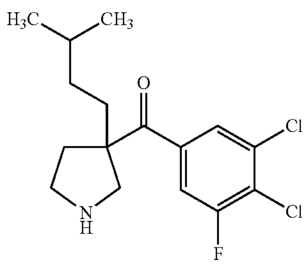 [SMILES: CC(C)CCC1(C(=O)c2cc(F)c(Cl)c(Cl)c2)CCNC1] | (3,4-Dichloro-5-fluoro-phenyl)-[3-(3-methyl-butyl)-pyrrolidin-3-yl]-methanone | 333 |
| 176 | 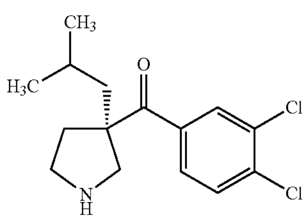 [SMILES: CC(C)C[C@@]1(C(=O)c2ccc(Cl)c(Cl)c2)CCNC1] | (3,4-Dichloro-phenyl)-((R)-3-isobutyl-pyrrolidin-3-yl)-methanone | 166.5-167.5 |
| 177 | 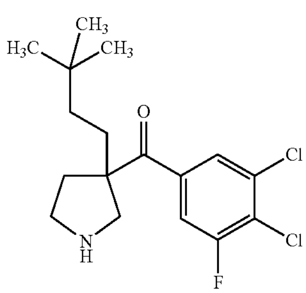 [SMILES: CC(C)(C)CCC1(C(=O)c2cc(F)c(Cl)c(Cl)c2)CCNC1] | (3,4-Dichloro-5-fluoro-phenyl)-[3-(3,3-dimethyl-butyl)-pyrrolidin-3-yl]-methanone | 347 |
| 178 | 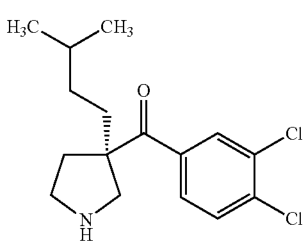 [SMILES: CC(C)CC[C@@]1(C(=O)c2ccc(Cl)c(Cl)c2)CCNC1] | (3,4-Dichloro-phenyl)-[(R)-3-(3-methyl-butyl)-pyrrolidin-3-yl]-methanone | 154.0-155.0 |

TABLE 1-continued

| # | Structure | Name | mp/M + H |
|---|-----------|------|----------|
| 179 | 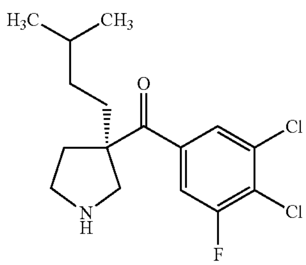 | (3,4-Dichloro-5-fluoro-phenyl)-[(R)-3-(3-methyl-butyl)-pyrrolidin-3-yl]-methanone | 119.0-120.0 |
| 180 | 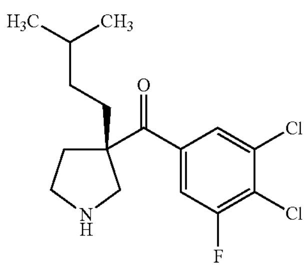 [SMILES: CC(C)CC[C@]1(C(=O)c2cc(F)c(Cl)c(Cl)c2)CCNC1] | (3,4-Dichloro-5-fluoro-phenyl)-[(S)-3-(3-methyl-butyl)-pyrrolidin-3-yl]-methanone | 119.0-120.0 |
| 181 | 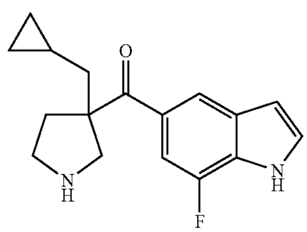 [SMILES: O=C(c1cc(F)c2[nH]ccc2c1)C1(CC2CC2)CCNC1] | (3-Cyclopropylmethyl-pyrrolidin-3-yl)-(7-fluoro-1H-indol-5-yl)-methanone | 109.0-110.0 |
| 182 | 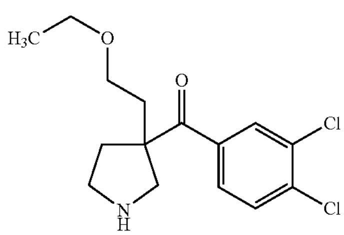 [SMILES: CCOCCC1(C(=O)c2ccc(Cl)c(Cl)c2)CCNC1] | (3,4-Dichloro-phenyl)-[3-(2-ethoxy-ethyl)-pyrrolidin-3-yl]-methanone | 317 |
| 183 | 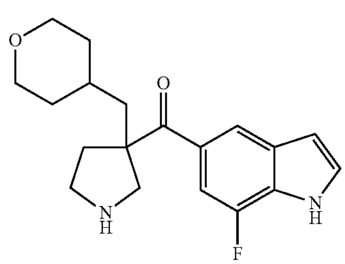 [SMILES: O=C(c1cc(F)c2[nH]ccc2c1)C1(CC2CCOCC2)CCNC1] | (7-Fluoro-1H-indol-5-yl)-[3-(tetrahydro-pyran-4-ylmethyl)-pyrrolidin-3-yl]-methanone | 139.0-140.0 |
| 184 | 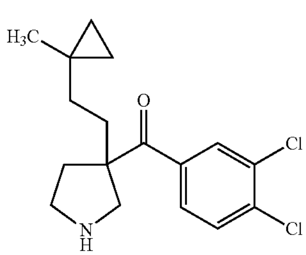 [SMILES: CC1(CCC2(C(=O)c3ccc(Cl)c(Cl)c3)CCNC2)CC1] | (3,4-Dichloro-phenyl)-{3-[2-(1-methyl-cyclopropyl)-ethyl]-pyrrolidin-3-yl}-methanone | 188.0-189.0 |

TABLE 1-continued

| # | Structure | Name | mp/M + H |
|---|---|---|---|
| 185 | 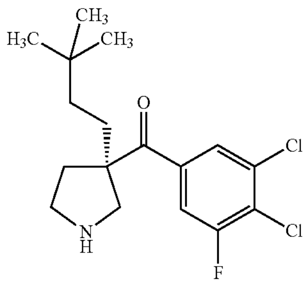 [SMILES: CC(C)(C)CC[C@@]1(C(=O)c2cc(F)c(Cl)c(Cl)c2)CCNC1] | (3,4-Dichloro-5-fluoro-phenyl)-[(R)-3-(3,3-dimethyl-butyl)-pyrrolidin-3-yl]-methanone | 171.0-172.0 |
| 186 | 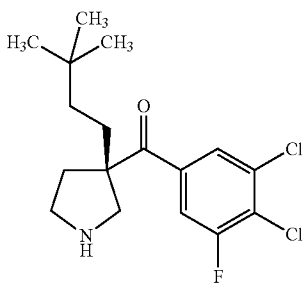 [SMILES: CC(C)(C)CC[C@]1(C(=O)c2cc(F)c(Cl)c(Cl)c2)CCNC1] | (3,4-Dichloro-5-fluoro-phenyl)-[(S)-3-(3,3-dimethyl-butyl)-pyrrolidin-3-yl]-methanone | 347 |
| 187 | 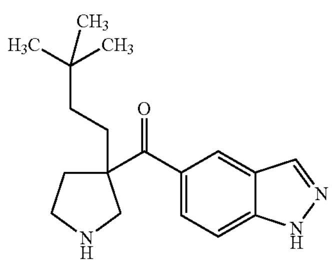 [SMILES: CC(C)(C)CCC1(C(=O)c2ccc3[nH]ncc3c2)CCNC1] | [3-(3,3-Dimethyl-butyl)-pyrrolidin-3-yl]-(1H-indazol-5-yl)-methanone | 240.0-241.0 |
| 188 | 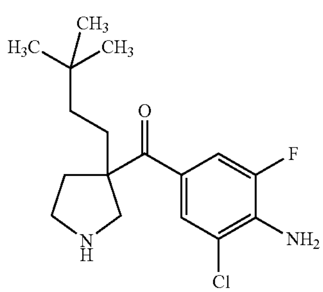 [SMILES: CC(C)(C)CCC1(C(=O)c2cc(F)c(N)c(Cl)c2)CCNC1] | (4-Amino-3-chloro-5-fluoro-phenyl)-[3-(3,3-dimethyl-butyl)-pyrrolidin-3-yl]-methanone | 327 |
| 189 | 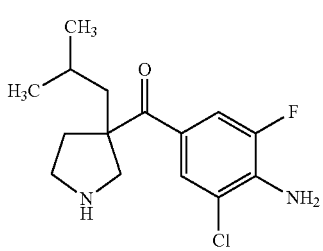 [SMILES: CC(C)CC1(C(=O)c2cc(F)c(N)c(Cl)c2)CCNC1] | (4-Amino-3-chloro-5-fluoro-phenyl)-(3-isobutyl-pyrrolidin-3-yl)-methanone | 299 |

TABLE 1-continued

| # | Structure | Name | mp/M + H |
|---|---|---|---|
| 190 | 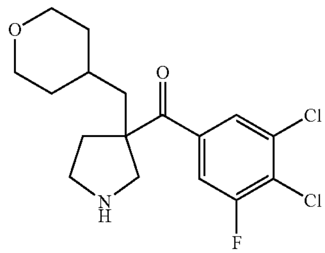 [SMILES: O=C(c1cc(F)c(Cl)c(Cl)c1)C1(CC2CCOCC2)CCNC1] | (3,4-Dichloro-5-fluoro-phenyl)-[3-(tetrahydro-pyran-4-ylmethyl)-pyrrolidin-3-yl]-methanone | 153.0-154.0 |
| 191 | 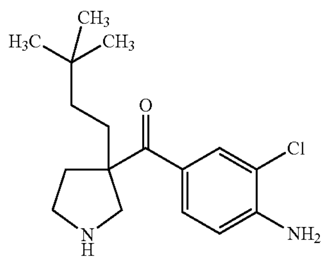 | (4-Amino-3-chloro-phenyl)-[3-(3,3-dimethyl-butyl)-pyrrolidin-3-yl]-methanone | 309 |
| 192 | 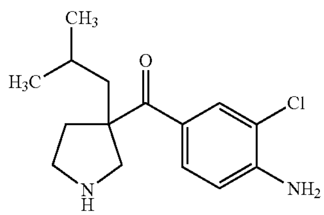 [SMILES: CC(C)CC1(C(=O)c2ccc(N)c(Cl)c2)CCNC1] | (4-Amino-3-chloro-phenyl)-(3-isobutyl-pyrrolidin-3-yl)-methanone | 281 |
| 193 | 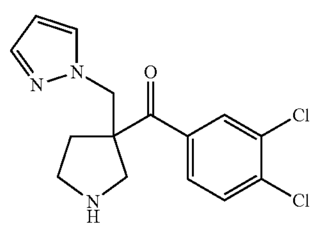 [SMILES: O=C(c1ccc(Cl)c(Cl)c1)C1(Cn2cccn2)CCNC1] | (3,4-Dichloro-phenyl-(3-pyrazol-1-ylmethyl-pyrrolidin-3-yl)-methanone | 325 |
| 194 | 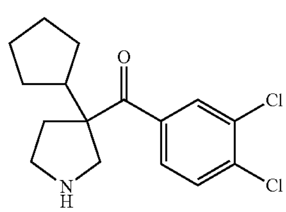 [SMILES: O=C(c1ccc(Cl)c(Cl)c1)C1(C2CCCC2)CCNC1] | (3-Cyclopentyl-pyrrolidin-3-yl)-(3,4-dichloro-phenyl)-methanone | 313 |
| 195 | 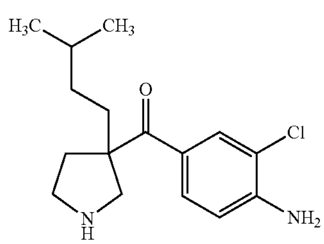 [SMILES: CC(C)CCC1(C(=O)c2ccc(N)c(Cl)c2)CCNC1] | (4-Amino-3-chloro-phenyl)-[3-(3-methyl-butyl)-pyrrolidin-3-yl]-methanone | 100.0-101.0 |

TABLE 1-continued

| # | Structure | Name | mp/M + H |
|---|---|---|---|
| 196 | 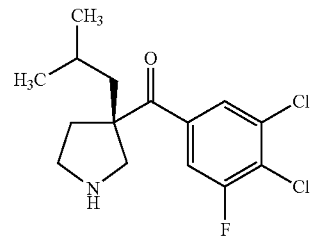 [SMILES: CC(C)C[C@]1(C(=O)c2cc(F)c(Cl)c(Cl)c2)CCNC1] | (3,4-Dichloro-5-fluoro-phenyl)-((S)-3-isobutyl-pyrrolidin-3-yl)-methanone | 153.0-154.0 |
| 197 | 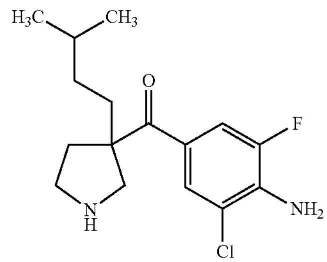 [SMILES: CC(C)CCC1(C(=O)c2cc(F)c(N)c(Cl)c2)CCNC1] | (4-Amino-3-chloro-5-fluoro-phenyl)-[3-(3-methyl-butyl)-pyrrolidin-3-yl]-methanone | 92.0-93.0 |
| 198 | 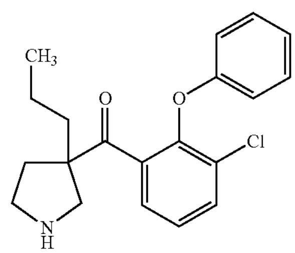 [SMILES: CCCC1(C(=O)c2cccc(Cl)c2Oc2ccccc2)CCNC1] | (3-Chloro-2-phenoxy-phenyl)-(3-propyl-pyrrolidin-3-yl)-methanone | 344 |
| 199 | 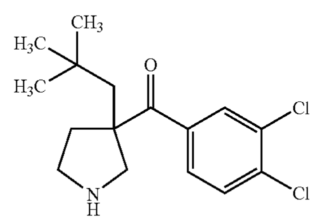 [SMILES: CC(C)(C)CC1(C(=O)c2ccc(Cl)c(Cl)c2)CCNC1] | (3,4-Dichloro-phenyl)-[3-(2,2-dimethyl-propyl)-pyrrolidin-3-yl]-methanone | 199.0-202.0 |
| 200 | 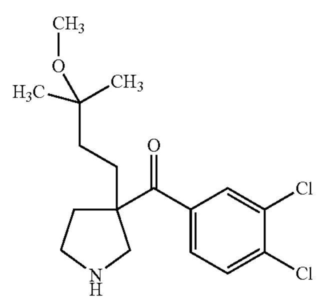 [SMILES: COC(C)(C)CCC1(C(=O)c2ccc(Cl)c(Cl)c2)CCNC1] | (3,4-Dichloro-phenyl)-[3-(3-methoxy-3-methyl-butyl)-pyrrolidin-3-yl]-methanone | 145.0-146.8 |
| 201 | 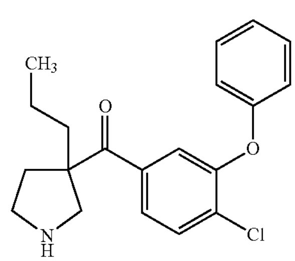 [SMILES: CCCC1(C(=O)c2ccc(Cl)c(Oc3ccccc3)c2)CCNC1] | (4-Chloro-3-phenoxy-phenyl)-(3-propyl-pyrrolidin-3-yl)-methanone | 344 |

TABLE 1-continued

| # | Structure | Name | mp/M + H |
|---|---|---|---|
| 202 | 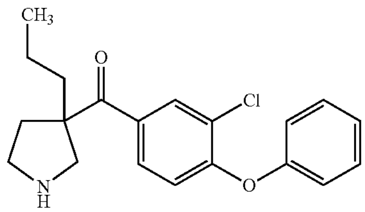 [SMILES: CCCC1(C(=O)c2ccc(Oc3ccccc3)c(Cl)c2)CCNC1] | (3-Chloro-4-phenoxy-phenyl)-(3-propyl-pyrrolidin-3-yl)-methanone | 344 |
| 203 | 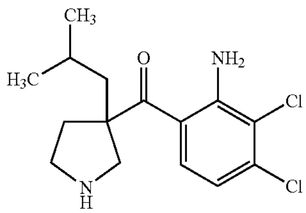 [SMILES: CC(C)CC1(C(=O)c2ccc(Cl)c(Cl)c2N)CCNC1] | (2-Amino-3,4-dichloro-phenyl)-(3-isobutyl-pyrrolidin-3-yl)-methanone | 316 |
| 204 | 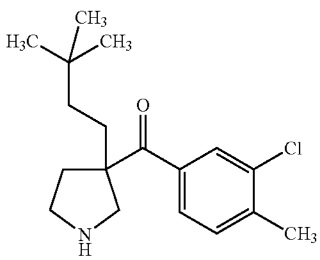 | (3-Chloro-4-methyl-phenyl)-[3-(3,3-dimethyl-butyl)-pyrrolidin-3-yl]-methanone | 176.7-178.6 |
| 205 | 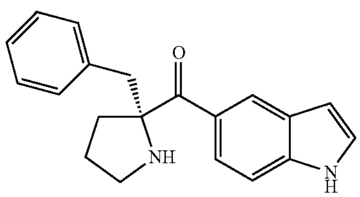 [SMILES: O=C(c1ccc2[nH]ccc2c1)[C@]1(Cc2ccccc2)CCCN1] | ((R)-2-Benzyl-pyrrolidin-2-yl)-(1H-indol-5-yl)-methanone | 305 |
| 206 | 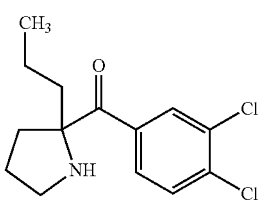 | (3,4-Dichloro-phenyl)-(2-propyl-pyrrolidin-2-yl)-methanone | 287 |
| 207 | 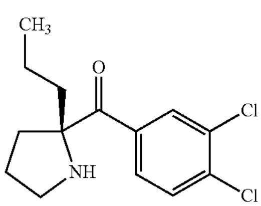 [SMILES: CCC[C@]1(C(=O)c2ccc(Cl)c(Cl)c2)CCCN1] | (3,4-Dichloro-phenyl)-((R)-2-propyl-pyrrolidin-2-yl)-methanone | 287 |
| 208 | 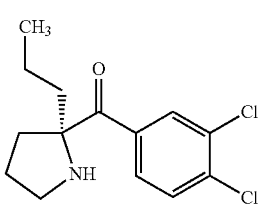 | (3,4-Dichloro-phenyl)-((S)-2-propyl-pyrrolidin-2-yl)-methanone | 154.0-155.0 |

TABLE 1-continued

| # | Structure | Name | mp/M + H |
|---|---|---|---|
| 209 | 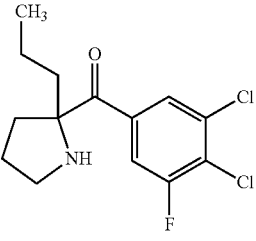 [SMILES: CCCC1(C(=O)c2cc(F)c(Cl)c(Cl)c2)CCCN1] | (3,4-Dichloro-5-fluoro-phenyl)-(2-propyl-pyrrolidin-2-yl)-methanone | 202.0-203.5 |
| 210 | 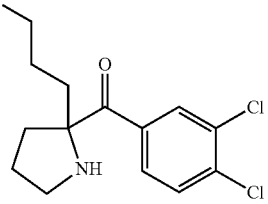 | (2-Butyl-pyrrolidin-2-yl)-(3,4-dichloro-phenyl)-methanone | 119.5-120.0 |
| 211 | 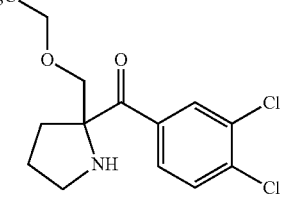 | (3,4-Dichloro-phenyl)-(2-ethoxymethyl-pyrrolidin-2-yl)-methanone | 303 |
| 212 | 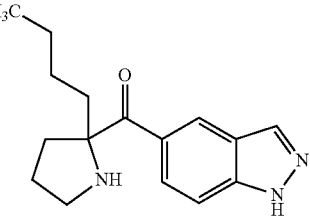 | (2-Butyl-pyrrolidin-2-yl)-(1H-indazol-5-yl)-methanone | >300 |
| 213 | 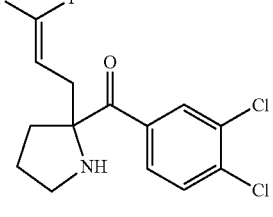 | (3,4-Dichloro-phenyl)-[2-(3,3-difluoro-allyl)-pyrrolidin-2-yl]-methanone | 321 |
| 214 | 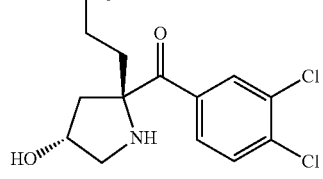 | (3,4-Dichloro-phenyl)-((2R,4R)-4-hydroxy-2-propyl-pyrrolidin-2-yl)-methanone | 302 |
| 215 | 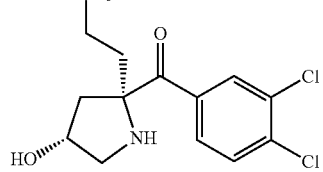 | (3,4-Dichloro-phenyl)-((2S,4R)-4-hydroxy-2-propyl-pyrrolidin-2-yl)-methanone | 108.0-109.0 |

TABLE 1-continued

| # | Structure | Name | mp/M + H |
|---|---|---|---|
| 216 | 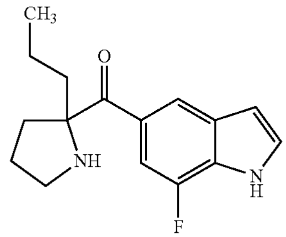 [SMILES: CCCC1(C(=O)c2cc(F)c3[nH]ccc3c2)CCCN1] | (7-Fluoro-1H-indol-5-yl)-(2-propyl-pyrrolidin-2-yl)-methanone | 264.0-265.0 |
| 217 | 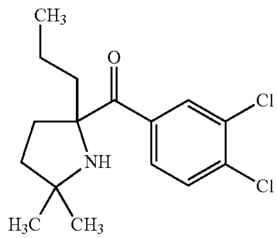 [SMILES: CCCC1(C(=O)c2ccc(Cl)c(Cl)c2)CCC(C)(C)N1] | (3,4-Dichloro-phenyl)-(5,5-dimethyl-2-propyl-pyrrolidin-2-yl)-methanone | 244.0-246.0 |
| 218 | 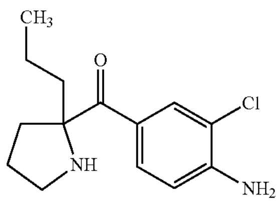 [SMILES: CCCC1(C(=O)c2ccc(N)c(Cl)c2)CCCN1] | (4-Amino-3-chloro-phenyl)-(2-propyl-pyrrolidin-2-yl)-methanone | 267 |
| 219 | 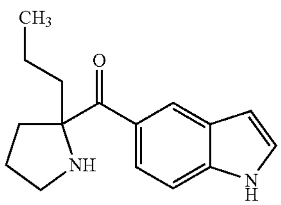 [SMILES: CCCC1(C(=O)c2ccc3[nH]ccc3c2)CCCN1] | (1H-Indazol-5-yl)-(2-propyl-pyrrolidin-2-yl)-methanone | 208.0-209.0 |
| 220 | 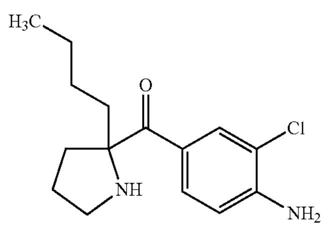 [SMILES: CCCCC1(C(=O)c2ccc(N)c(Cl)c2)CCCN1] | (4-Amino-3-chloro-phenyl)-(2-butyl-pyrrolidin-2-yl)-methanone | 281 |
| 221 | 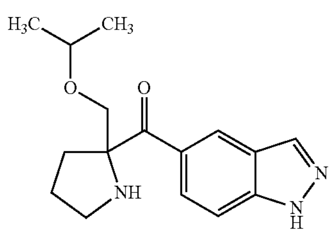 [SMILES: CC(C)OCC1(C(=O)c2ccc3[nH]ncc3c2)CCCN1] | (1H-Indazol-5-yl)-(2-isopropoxymethyl-pyrrolidin-2-yl)-methanone | 288 |
| 222 | 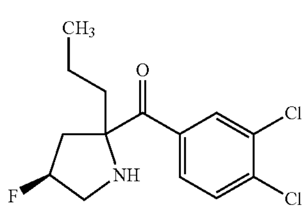 [SMILES: CCCC1(C(=O)c2ccc(Cl)c(Cl)c2)C[C@H](F)CN1] | (3,4-Dichloro-phenyl)-((S)-4-fluoro-2-propyl-pyrrolidin-2-yl)-methanone | 305 |

TABLE 1-continued

| # | Structure | Name | mp/M + H |
|---|---|---|---|
| 223 | 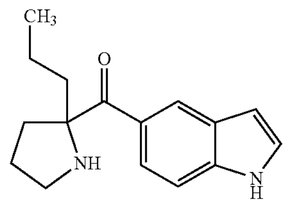 [SMILES: CCCC1(C(=O)c2ccc3[nH]ccc3c2)CCCN1] | (1H-Indol-5-yl)-(2-propyl-pyrrolidin-2-yl)-methanone | 257 |
| 224 | 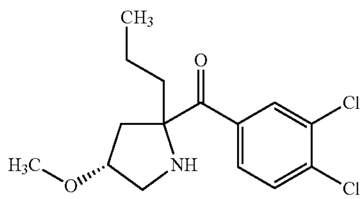 [SMILES: CCCC1(C(=O)c2ccc(Cl)c(Cl)c2)C[C@@H](OC)CN1] | (3,4-Dichloro-phenyl)-((R)-4-methoxy-2-propyl-pyrrolidin-2-yl)-methanone | 317 |
| 225 | 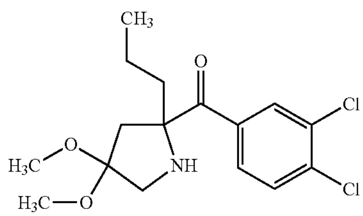 [SMILES: CCCC1(C(=O)c2ccc(Cl)c(Cl)c2)CC(OC)(OC)CN1] | (3,4-Dichloro-phenyl)-(4,4-dimethoxy-2-propyl-pyrrolidin-2-yl)-methanone | 347 |
| 226 | 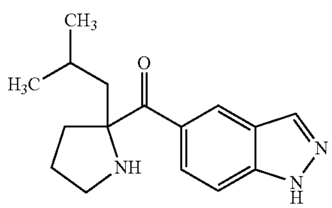 [SMILES: CC(C)CC1(C(=O)c2ccc3[nH]ncc3c2)CCCN1] | (1H-Indazol-5-yl)-(2-isobutyl-pyrrolidin-2-yl)-methanone | >300 |
| 227 | 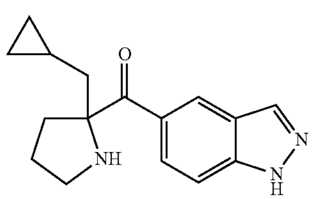 [SMILES: O=C(c1ccc2[nH]ncc2c1)C1(CC2CC2)CCCN1] | (2-Cyclopropylmethyl-pyrrolidin-2-yl)-(1H-indazol-5-yl)-methanone | 291.0-292.0 |
| 228 | 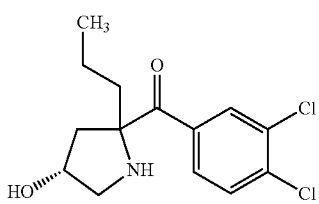 [SMILES: CCCC1(C(=O)c2ccc(Cl)c(Cl)c2)C[C@@H](O)CN1] | (3,4-Dichloro-phenyl)-((R)-4-hydroxy-2-propyl-pyrrolidin-2-yl)-methanone | 110.0-111.0 |
| 229 | 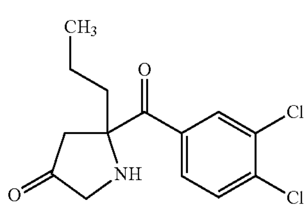 [SMILES: CCCC1(C(=O)c2ccc(Cl)c(Cl)c2)CC(=O)CN1] | 5-(3,4-Dichloro-benzoyl)-5-propyl-pyrrolidin-3-one | 301 |

TABLE 1-continued

| # | Name | mp/M + H |
|---|------|----------|
| 230 | (4-Amino-3-chloro-phenyl)-(2-isobutyl-pyrrolidin-2-yl)-methanone | 149.0–140.0 |
| 231 | (1H-Indazol-5-yl)-((R)-2-propyl-pyrrolidin-2-yl)methanone | 258 |
| 232 | (1H-Indazol-5-yl)-((S)-2-propyl-pyrrolidin-2-yl)-methanone | 258 |
| 233 | (4-Amino-3-chloro-phenyl)-(2-cyclopropylmethyl-pyrrolidin-2-yl)-methanone | 146.0–147.0 |
| 234 | (3,4-Dichloro-phenyl)-((S)-4-hydroxy-2-propyl-pyrrolidin-2-yl)-methanone | 303 |
| 235 | (2-Ethoxymethyl-pyrrolidin-2-yl)-(1H-indazol-5-yl)-methanone | 274 |
| 236 | [2-(3,3-Dimethyl-butyl)-pyrrolidin-2-yl]-(1H-indazol-5-yl)-methanone | 300 |

TABLE 1-continued

| # | Structure | Name | mp/M + H |
|---|---|---|---|
| 237 | 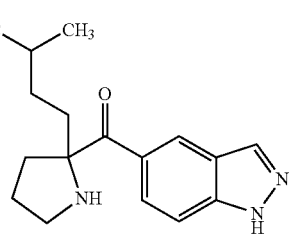 | (1H-Indazol-5-yl)-[2-(3-methyl-butyl)-pyrrolidin-2-yl]-methanone | 126.0-127.0 |
| 238 | 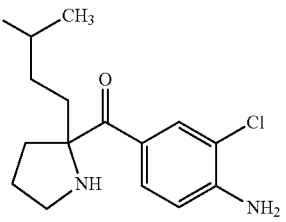 | (4-Amino-3-chloro-phenyl)-[2-(3-methyl-butyl)-pyrrolidin-2-yl]-methanone | 119.0-120.0 |
| 239 | 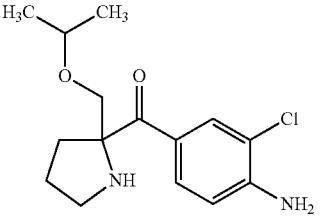 [SMILES: CC(C)OCC1(C(=O)c2ccc(N)c(Cl)c2)CCCN1] | (4-Amino-3-chloro-phenyl)-(2-isopropoxymethyl-pyrrolidin-2-yl)-methanone | 297 |
| 240 | 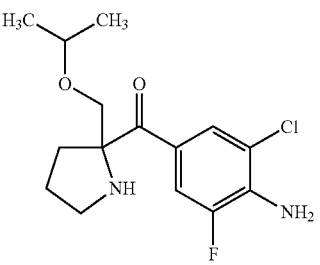 [SMILES: CC(C)OCC1(C(=O)c2cc(F)c(N)c(Cl)c2)CCCN1] | (4-Amino-3-chloro-5-fluoro-phenyl)-(2-isopropoxymethyl-pyrrolidin-2-yl)-methanone | 315 |
| 241 | 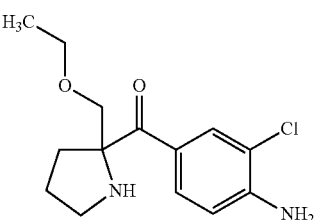 | (4-Amino-3-chloro-phneyl)-(2-ethoxymethyl-pyrrolidin-2-yl)-methanone | 283 |
| 242 | 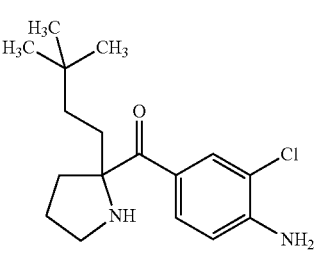 [SMILES: CC(C)(C)CCC1(C(=O)c2ccc(N)c(Cl)c2)CCCN1] | (4-Amino-3-chloro-phenyl)-[2-(3,3-dimethyl-butyl)-pyrrolidin-2-yl]-methanone | 309 |

TABLE 1-continued

| # | Structure | Name | mp/M + H |
|---|---|---|---|
| 243 | 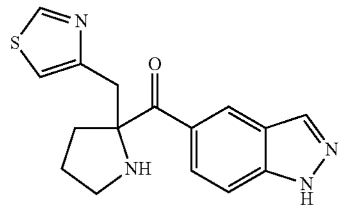 [SMILES: O=C(c1ccc2[nH]ncc2c1)C1(Cc2cscn2)CCCN1] | (1H-Indazol-5-yl)-(2-thiazol-4-ylmethyl-pyrrolidin-2-yl)-methanone | 313 |
| 244 | 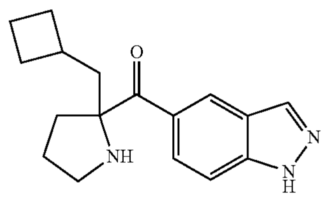 [SMILES: O=C(c1ccc2[nH]ncc2c1)C1(CC2CCC2)CCCN1] | (2-Cyclobutylmethyl-pyrrolidin-2-yl)-(1H-indazol-5-yl)-methanone | >300 |
| 245 | 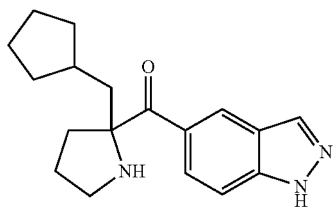 [SMILES: O=C(c1ccc2[nH]ncc2c1)C1(CC2CCCC2)CCCN1] | (2-Cyclopentylmethyl-pyrrolidin-2-yl)-(1H-indazol-5-yl)-methanone | >300 |
| 246 | 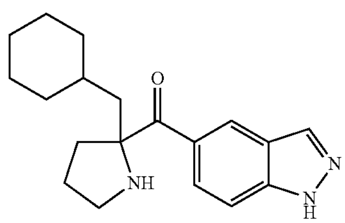 [SMILES: O=C(c1ccc2[nH]ncc2c1)C1(CC2CCCCC2)CCCN1] | (2-Cyclohexylmethyl-pyrrolidin-2-yl)-(1H-indazol-5-yl)-methanone | 104.0-105.0 |
| 247 | 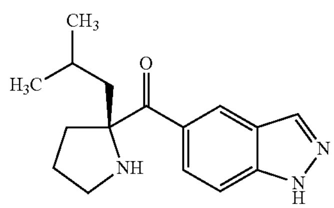 [SMILES: CC(C)C[C@]1(C(=O)c2ccc3[nH]ncc3c2)CCCN1] | (1H-Indazol-5-yl)-((S)-2-isobutyl-pyrrolidin-2-yl)-methanone | 272 |
| 248 | 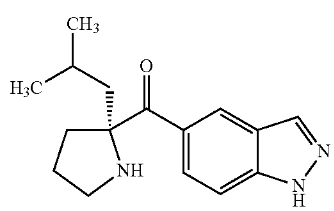 | (1H-Indazol-5-yl)-((R)-2-isobutyl-pyrrolidin-2-yl)-methanone | 272 |
| 249 | 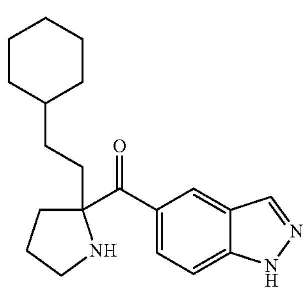 [SMILES: O=C(c1ccc2[nH]ncc2c1)C1(CCC2CCCCC2)CCCN1] | [2-(2-Cyclohexyl-ethyl)-pyrrolidin-2-yl]-(1H-indazol-5-yl)-methanone | 326 |

TABLE 1-continued

| # | Structure | Name | mp/M + H |
|---|---|---|---|
| 250 | 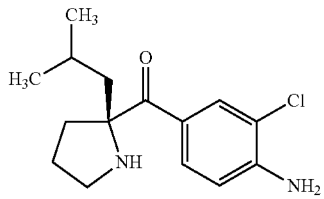 [SMILES: CC(C)C[C@]1(C(=O)c2ccc(N)c(Cl)c2)CCCN1] | (4-Amino-3-chloro-phenyl)-((S)-2-isobutyl-pyrrolidin-2-yl)-methanone | 114.0-115.0 |
| 251 | 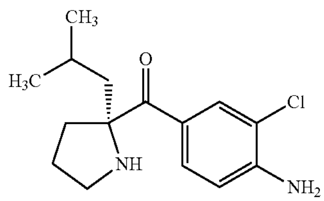 [SMILES: CC(C)C[C@@]1(C(=O)c2ccc(N)c(Cl)c2)CCCN1] | (4-Amino-3-chloro-phenyl)-((R)-2-isobutyl-pyrrolidin-2-yl)-methanone | 114.0-115.0 |
| 252 | 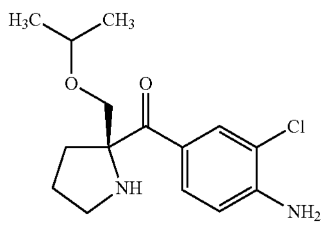 [SMILES: CC(C)OC[C@]1(C(=O)c2ccc(N)c(Cl)c2)CCCN1] | (4-Amino-3-chloro-phenyl)-((S)-2-isopropoxymethyl-pyrrolidin-2-yl)-methanone | 297 |
| 253 | 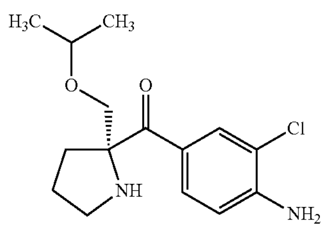 [SMILES: CC(C)OC[C@@]1(C(=O)c2ccc(N)c(Cl)c2)CCCN1] | (4-Amino-3-chloro-phenyl)-((R)-2-isopropoxymethyl-pyrrolidin-2-yl)-methanone | 297 |
| 254 | 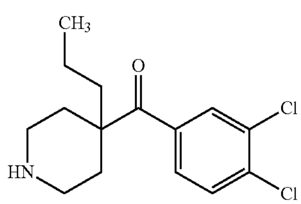 [SMILES: CCCC1(C(=O)c2ccc(Cl)c(Cl)c2)CCNCC1] | (3,4-Dichloro-phenyl)-(4-propyl-piperidin-4-yl)-methanone | 130.0-131.0 |
| 255 | 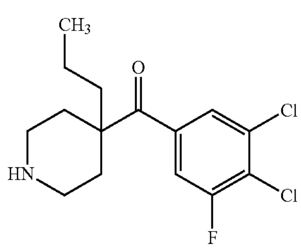 [SMILES: CCCC1(C(=O)c2cc(F)c(Cl)c(Cl)c2)CCNCC1] | (3,4-Dichloro-5-fluoro-phenyl)-(4-propyl-piperidin-4-yl)-methanone | 319 |
| 256 | 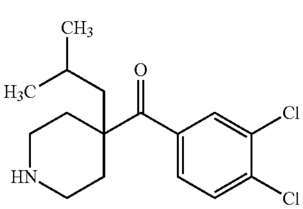 [SMILES: CC(C)CC1(C(=O)c2ccc(Cl)c(Cl)c2)CCNCC1] | (3,4-Dichloro-phenyl)-(4-isobutyl-piperidin-4-yl)-methanone | 185.0-186.0 |

TABLE 1-continued

| # | Structure | Name | mp/M + H |
|---|---|---|---|
| 257 | 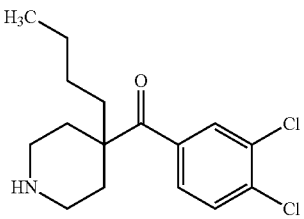 [SMILES: CCCCC1(C(=O)c2ccc(Cl)c(Cl)c2)CCNCC1] | (4-Butyl-piperidin-4-yl)-(3,4-dichloro-phenyl)-methanone | 115.0-116.0 |
| 258 | 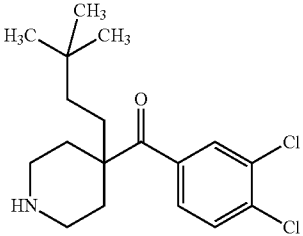 [SMILES: CC(C)(C)CCC1(C(=O)c2ccc(Cl)c(Cl)c2)CCNCC1] | (3,4-Dichloro-phenyl)-[4-(3,3-dimethyl-butyl)-piperidin-4-yl]-methanone | 231.0-232.0 |
| 259 | 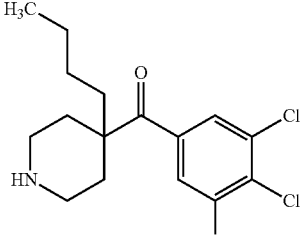 | (4-Butyl-piperidin-4-yl)-(3,4-dichoro-5-fluoro-phenyl)-methanone | 141.0-142.0 |
| 260 | 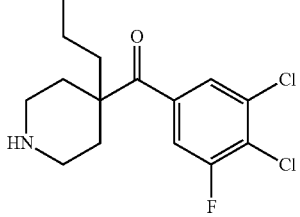 | (3,4-Dichloro-5-fluoro-phenyl)-[4-(3-methyl-butyl)-piperidin-4-yl]-methanone | 181.0-182.0 |
| 261 | 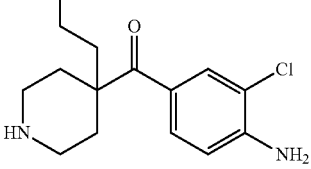 | (4-Amino-3-chloro-phenyl)-[4-(3-methyl-butyl)-piperidin-4-yl]-methanone | 180.0-181.0 |
| 262 | 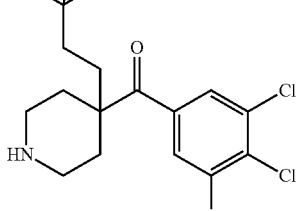 | (3,4-Dichloro-5-fluoro-phenyl)-[4-(3,3-dimethyl-butyl)-piperidin-4-yl]-methanone | 205.0-206.0 |

TABLE 1-continued

| # | Name | mp/M + H |
|---|------|----------|
| 263 | (4-Amino-3-chloro-5-fluoro-phenyl)-(4-butyl-piperidin-4-yl)-methanone | 184.0-185.0 |
| 264 | (4-Amino-3-fluoro-phenyl)-[4-(3,3-dimethyl-butyl)-piperidin-4-yl]-methanone | 236.0-237.0 |
| 265 | (4-Amino-3-chloro-phenyl)-(4-butyl-piperidin-4-yl)-methanone | 135.0-136.0 |
| 266 | (4-Amino-3-chloro-phenyl)-(4-isobutyl-piperidin-4-yl)-methanone | 159.0-160.0 |
| 267 | (3,4-Dichloro-5-fluoro-phenyl)-(4-isobutyl-piperidin-4-yl)-methanone | 166.0-167.0 |
| 268 | (4-Amino-3-chloro-phenyl)-[4-(3,3-dimethyl-butyl)-piperidin-4-yl]-methanone | 260.0-261.0 |

TABLE 1-continued

| # | Structure | Name | mp/M + H |
|---|---|---|---|
| 269 | 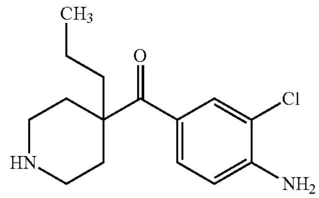 [SMILES: CCCC1(C(=O)c2ccc(N)c(Cl)c2)CCNCC1] | (4-Amino-3-chloro-phenyl)-(4-propyl-piperidin-4-yl)-methanone | 108.0-109.0 |
| 270 | 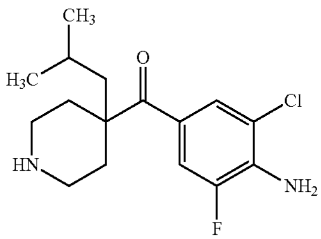 [SMILES: CC(C)CC1(C(=O)c2cc(F)c(N)c(Cl)c2)CCNCC1] | (4-Amino-3-chloro-5-fluoro-phenyl)-(4-isobutyl-piperidin-4-yl)-methanone | 208.0-209.0 |
| 271 | 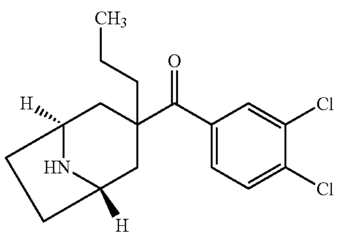 [SMILES: CCCC1(C(=O)c2ccc(Cl)c(Cl)c2)C[C@@H]2CC[C@@H](C1)N2] | (3,4-Dichloro-phenyl)-((1R,5S)-3-propyl-8-aza-bicyclo[3.2.1]oct-3-yl)-methanone | 230.0-231.0 |
| 272 | 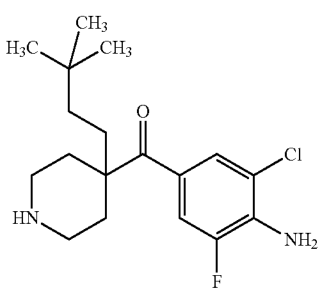 [SMILES: CC(C)(C)CCC1(C(=O)c2cc(F)c(N)c(Cl)c2)CCNCC1] | (4-Amino-3-chloro-5-fluoro-phenyl)-[4-(3,3-dimethyl-butyl)-piperidin-4-yl]-methanone | 341 |
| 723 | 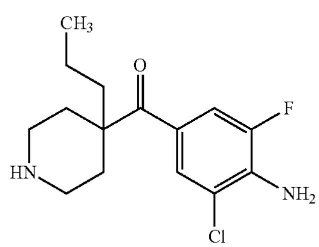 [SMILES: CCCC1(C(=O)c2cc(F)c(N)c(Cl)c2)CCNCC1] | (4-Amino-3-chloro-5-fluoro-phenyl)-(4-propyl-piperidin-4-yl)-methanone | 299 |
| 274 | 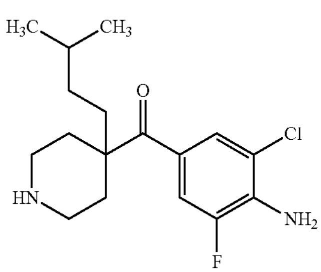 [SMILES: CC(C)CCC1(C(=O)c2cc(F)c(N)c(Cl)c2)CCNCC1] | (4-Amino-3-chloro-5-fluoro-phenyl)-[4-(3-methyl-butyl)-piperidin-4-yl]-methanone | 197.0-205.0 |

TABLE 1-continued

| # | Structure | Name | mp/M + H |
|---|---|---|---|
| 275 | 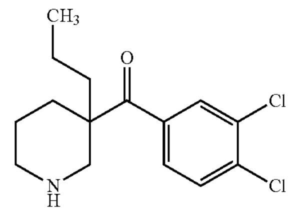 [SMILES: CCCC1(C(=O)c2ccc(Cl)c(Cl)c2)CCCNC1] | (3,4-Dichloro-phenyl)-(3-propyl-piperidin-3-yl)-methanone | 191.0-192.6 |
| 276 | 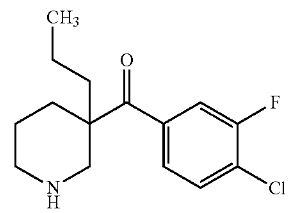 [SMILES: CCCC1(C(=O)c2ccc(Cl)c(F)c2)CCCNC1] | (4-Chloro-3-fluoro-phenyl)-(3-propyl-piperidin-3-yl)-methanone | 284 |
| 277 | 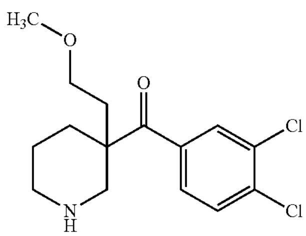 [SMILES: COCCC1(C(=O)c2ccc(Cl)c(Cl)c2)CCCNC1] | (3,4-Dichloro-phenyl)-(3-ethoxymethyl-piperidin-3-yl)-methanone | 317 |
| 278 | 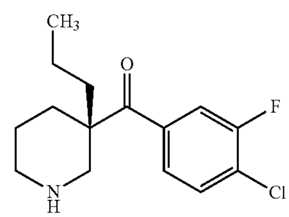 [SMILES: CCC[C@]1(C(=O)c2ccc(Cl)c(F)c2)CCCNC1] | (3,4-Dichloro-phenyl)-((S)-3-propyl-piperidin-3-yl)-methanone | 167.0-170.0 |
| 279 | 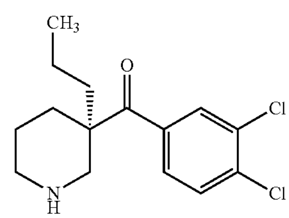 [SMILES: CCC[C@@]1(C(=O)c2ccc(Cl)c(Cl)c2)CCCNC1] | (3,4-Dichloro-phenyl)-((R)-3-propyl-piperidin-3-yl)-methanone | 162.0-164.0 |
| 280 | 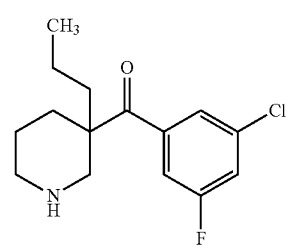 [SMILES: CCCC1(C(=O)c2cc(F)cc(Cl)c2)CCCNC1] | (3-Chloro-5-fluoro-phenyl)-(3-propyl-piperidin-3-yl)-methanone | 196.0-197.0 |
| 281 | 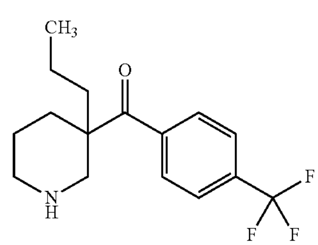 [SMILES: CCCC1(C(=O)c2ccc(C(F)(F)F)cc2)CCCNC1] | (3-Propyl-piperidin-3-yl)-(4-trifluoromethyl-phenyl)-methanone | 300 |

US 8,513,425 B2

TABLE 1-continued

| # | Structure | Name | mp/M + H |
|---|---|---|---|
| 282 | 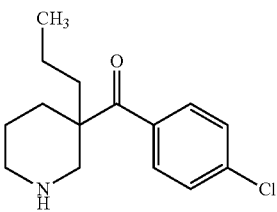 | (4-Chloro-phenyl)-(3-propyl-piperidin-3-yl)-methanone | 266 |
| 283 | 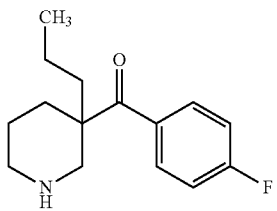 [SMILES: CCCC1(C(=O)c2ccc(F)cc2)CCCNC1] | (4-Fluoro-phenyl)-(3-propyl-piperidin-3-yl)-methanone | 250 |
| 284 | 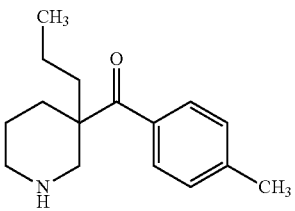 [SMILES: CCCC1(C(=O)c2ccc(C)cc2)CCCNC1] | (3-Propyl-piperidin-3-yl)-p-tolyl-methanone | 246 |
| 285 | 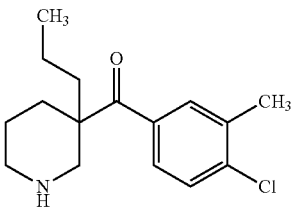 [SMILES: CCCC1(C(=O)c2ccc(Cl)c(C)c2)CCCNC1] | (4-Chloro-3-methyl-phenyl)-(3-propyl-piperidin-3-yl)-methanone | 280 |
| 286 | 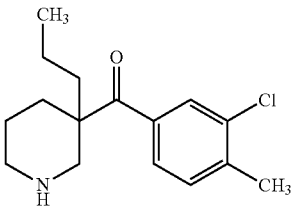 [SMILES: CCCC1(C(=O)c2ccc(C)c(Cl)c2)CCCNC1] | (3-Chloro-4-methyl-phenyl)-(3-propyl-piperidin-3-yl)-methanone | 182.0-183.0 |
| 287 | 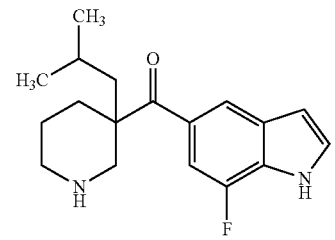 [SMILES: CC(C)CC1(C(=O)c2cc(F)c3[nH]ccc3c2)CCCNC1] | (7-Fluoro-1H-indol-5-yl)-(3-isobutyl-piperidin-3-yl)-methanone | 186.5-187.9 |
| 288 | 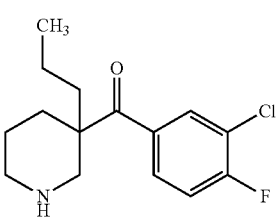 | (3-Chloro-4-fluoro-phenyl)-(3-propyl-piperidin-3-yl)-methanone | 284 |

TABLE 1-continued

| # | Structure | Name | mp/M + H |
|---|---|---|---|
| 289 | 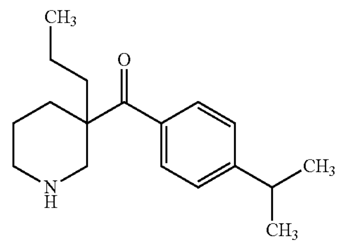 [SMILES: CCCC1(C(=O)c2ccc(C(C)C)cc2)CCCNC1] | (4-Isopropyl-phenyl-(3-propyl-piperidin-3-yl)-methanone | 274 |
| 290 | 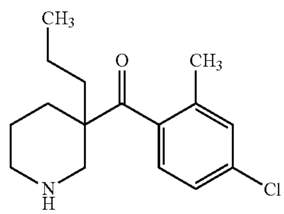 [SMILES: CCCC1(C(=O)c2ccc(Cl)cc2C)CCCNC1] | (4-Chloro-2-methyl-phenyl)-(3-propyl-piperidin-3-yl)-methanone | 214.5-215.0 |
| 291 | 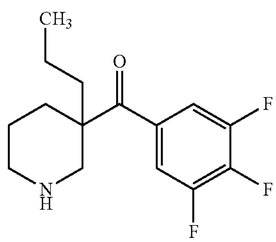 [SMILES: CCCC1(C(=O)c2cc(F)c(F)c(F)c2)CCCNC1] | (3-Propyl-piperidin-3-yl)-(3,4,5-trifluoro-phenyl)-methanone | 168.4-169.5 |
| 292 | 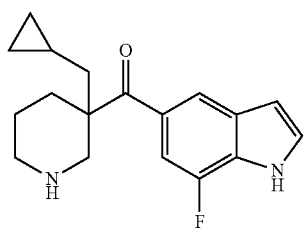 [SMILES: O=C(c1cc(F)c2[nH]ccc2c1)C1(CC2CC2)CCCNC1] | (3-Cyclopropylmethyl-piperidin-3-yl)-(7-fluoro-1H-indol-5-yl)-methanone | 223.0-224.0 |
| 293 | 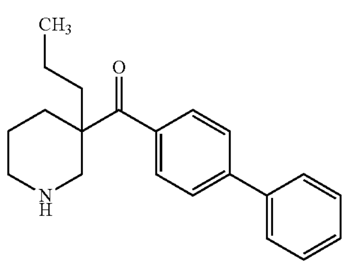 [SMILES: CCCC1(C(=O)c2ccc(-c3ccccc3)cc2)CCCNC1] | Biphenyl-4-yl-(3-propyl-piperidin-3-yl)-methanone | 129.0-130.0 |
| 294 | 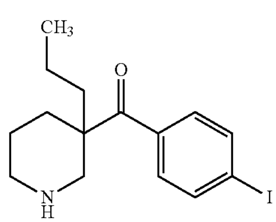 [SMILES: CCCC1(C(=O)c2ccc(I)cc2)CCCNC1] | (4-Iodo-phenyl)-(3-propyl-piperidin-3-yl)-methanone | 135.0-136.0 |

TABLE 1-continued

| # | Structure | Name | mp/M + H |
|---|---|---|---|
| 295 | 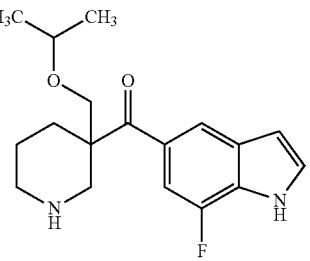 | (7-Fluoro-1H-indol-5-yl)-(3-isopropoxymethyl-piperidin-3-yl)-methanone | 319 |
| 296 | 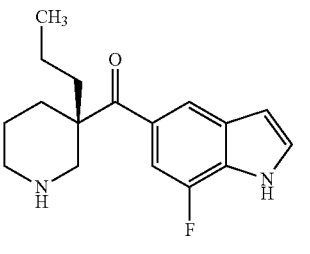 [SMILES: CCC[C@]1(C(=O)c2cc(F)c3[nH]ccc3c2)CCCNC1] | (7-Fluoro-1H-indol-5-yl)-((S)-3-propyl-piperidin-3-yl)-methanone | 319.6-320.7 |
| 297 | 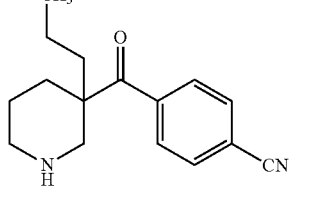 | 4-(3-Propyl-piperidine-3-carbonyl)-benzonitrile | 115.0-116.0 |
| 298 | 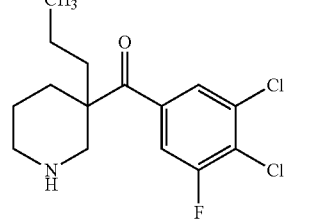 | (3,4-Dichloro-5-fluoro-phenyl)-(3-propyl-piperidin-3-yl)-methanone | 199.0-200.0 |
| 299 | 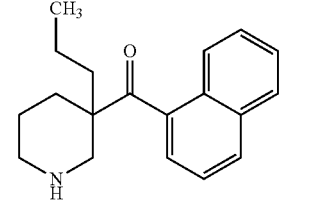 [SMILES: CCCC1(C(=O)c2cccc3ccccc23)CCCNC1] | Naphthalen-1-yl-(3-propyl-piperidin-3-yl)-methanone | 109.0-110.0 |
| 300 | 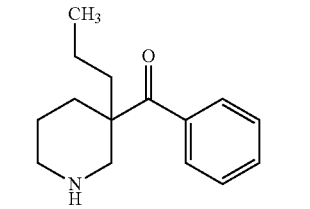 [SMILES: CCCC1(C(=O)c2ccccc2)CCCNC1] | Phenyl-(3-propyl-piperidin-3-yl)-methanone | 232 |
| 301 | 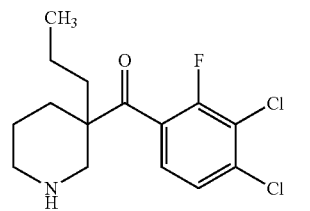 [SMILES: CCCC1(C(=O)c2ccc(Cl)c(Cl)c2F)CCCNC1] | (3,4-Dichloro-2-fluoro-phenyl)-(3-propyl-piperidin-3-yl)-methanone | 130.0-132.0 |

TABLE 1-continued

| # | Structure | Name | mp/M + H |
|---|---|---|---|
| 302 | 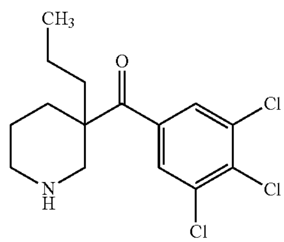 [SMILES: CCCC1(C(=O)c2cc(Cl)c(Cl)c(Cl)c2)CCCNC1] | (3-Propyl-piperidin-3-yl)-(3,4,5-trichloro-phenyl)-methanone | 241.0-215.0 |
| 303 | 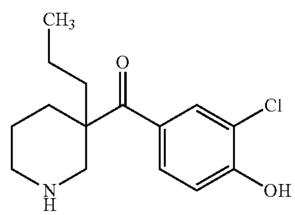 [SMILES: CCCC1(C(=O)c2ccc(O)c(Cl)c2)CCCNC1] | (3-Chloro-4-hydroxy-phenyl)-(3-propyl-piperidin-3-yl)-methanone | 265.6-266.9 |
| 304 | 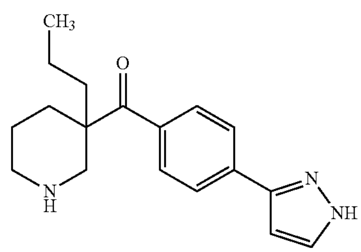 [SMILES: CCCC1(C(=O)c2ccc(-c3cc[nH]n3)cc2)CCCNC1] | (3-Propyl-piperidin-3-yl)-[4-(1H-pyrazol-3-yl)-phenyl]-methanone; compound with (E)-but-2-enedioic acid | 154.0-155.0 (succinate salt) |
| 305 | 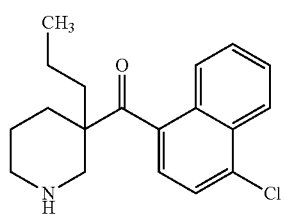 [SMILES: CCCC1(C(=O)c2ccc(Cl)c3ccccc23)CCCNC1] | (4-Chloro-naphthalen-1-yl)-(3-propyl-piperidin-3-yl)-methanone | 131.0-132.0 |
| 306 | 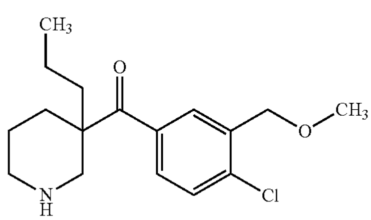 [SMILES: CCCC1(C(=O)c2ccc(Cl)c(COC)c2)CCCNC1] | (4-Chloro-3-methoxymethyl-phenyl)-(3-propyl-piperidin-3-yl)-methanone | 310 |
| 307 | 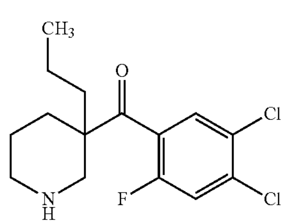 | (4,5-Dichloro-2-fluoro-phenyl)-(3-propyl-piperidin-3-yl)-methanone | 182.0-182.5 |
| 308 | 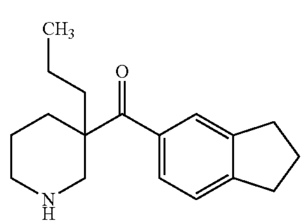 [SMILES: CCCC1(C(=O)c2ccc3c(c2)CCC3)CCCNC1] | Indan-5-yl-(3-propyl-piperidin-3-yl)-methanone | 76.0-77.0 |

TABLE 1-continued

| # | Structure | Name | mp/M + H |
|---|---|---|---|
| 309 | 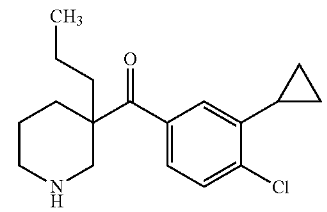 [SMILES: CCCC1(C(=O)c2ccc(Cl)c(C3CC3)c2)CCCNC1] | (4-Chloro-3-cyclopropyl-phenyl)-(3-propyl-piperidin-3-yl)-methanone | 84.5-85.5 |
| 310 | 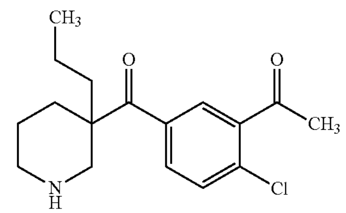 [SMILES: CCCC1(C(=O)c2ccc(Cl)c(C(C)=O)c2)CCCNC1] | 1-[2-Chloro-5-(3-propyl-piperidine-3-carbonyl)-phenyl]-ethanone | 308 |
| 311 | 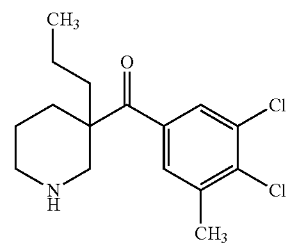 [SMILES: CCCC1(C(=O)c2cc(C)c(Cl)c(Cl)c2)CCCNC1] | (3,4-Dichloro-5-methyl-phenyl)-(3-propyl-piperidin-3-yl)-methanone | 220.0-221.0 |
| 312 | 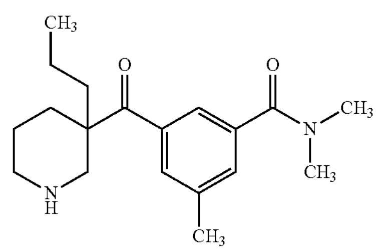 [SMILES: CCCC1(C(=O)c2cc(C)cc(C(=O)N(C)C)c2)CCCNC1] | 2-Chloro-N,N-dimethyl-5-(3-propyl-piperidine-3-carbonyl)-benzamide | 337 |
| 313 | 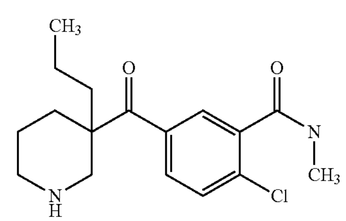 [SMILES: CCCC1(C(=O)c2ccc(Cl)c(C(=O)NC)c2)CCCNC1] | 2-Chloro-N-methyl-5-(3-propyl-piperidine-3-carbonyl)-benzamide | 323 |
| 314 | 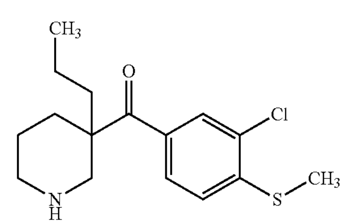 [SMILES: CCCC1(C(=O)c2ccc(SC)c(Cl)c2)CCCNC1] | (3-Chloro-4-methylsulfanyl-phenyl)-(3-propyl-piperidin-3-yl)-methanone | 312 |

TABLE 1-continued

| # | Structure | Name | mp/M + H |
|---|-----------|------|----------|
| 315 | 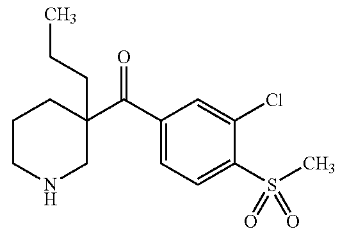 [SMILES: CCCC1(C(=O)c2ccc(S(C)(=O)=O)c(Cl)c2)CCCNC1] | (3-Chloro-4-methanesulfonyl-phenyl)-(3-propyl-piperidin-3-yl)-methanone | 344 |
| 316 | 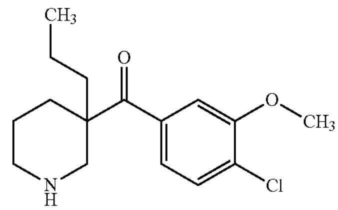 [SMILES: CCCC1(C(=O)c2ccc(Cl)c(OC)c2)CCCNC1] | (4-Chloro-3-methoxy-phenyl)-(3-propyl-piperidin-3-yl)-methanone | 296 |
| 317 | 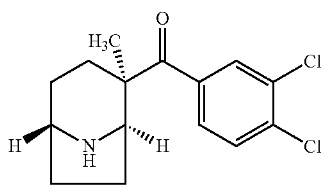 [SMILES: C[C@@]1(C(=O)c2ccc(Cl)c(Cl)c2)CC[C@H]2CC[C@H]1N2] | (3,4-Dichloro-phenyl)-((1R,2S,5R)-2-methyl-8-aza-bicyclo[3.2.1]oct-2-yl)-methanone | 299 |
| 318 | 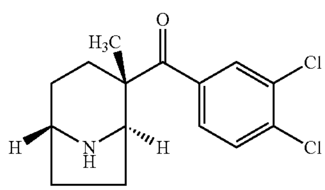 [SMILES: C[C@]1(C(=O)c2ccc(Cl)c(Cl)c2)CC[C@H]2CC[C@H]1N2] | (3,4-Dichloro-phenyl)-((1R,2R,5R)-2-methyl-8-aza-bicyclo[3.2.1]oct-2-yl)-methanone | 299 |
| 319 | 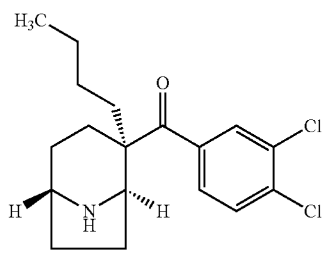 [SMILES: CCCC[C@@]1(C(=O)c2ccc(Cl)c(Cl)c2)CC[C@H]2CC[C@H]1N2] | ((1R,2S,5R)-2-Butyl-8-aza-bicyclo[3.2.1]oct-2-yl)-(3,4-dichloro-phenyl)-methanone | 90.0-91.0 |
| 320 | 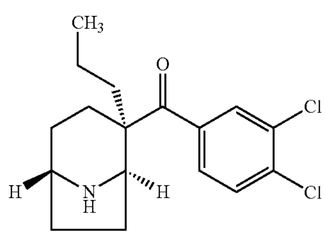 [SMILES: CCC[C@@]1(C(=O)c2ccc(Cl)c(Cl)c2)CC[C@H]2CC[C@H]1N2] | (3,4-Dichloro-phenyl)-((1R,2S,5R)-2-propyl-8-aza-bicyclo[3.2.1]oct-2-yl)-methanone | 145.0-146.0 |
| 321 | 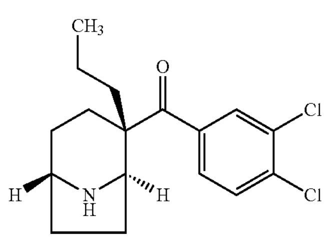 [SMILES: CCC[C@]1(C(=O)c2ccc(Cl)c(Cl)c2)CC[C@H]2CC[C@H]1N2] | (3,4-Dichloro-phenyl)-((1R,2R,5R)-2-propyl-8-aza-bicyclo[3.2.1]oct-2-yl)-methanone | 238.0-239.0 |

TABLE 1-continued

| # | Structure | Name | mp/M + H |
|---|---|---|---|
| 322 | 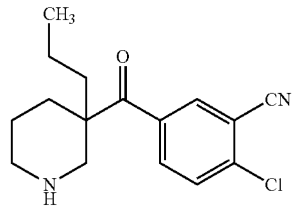 [SMILES: CCCC1(C(=O)c2ccc(Cl)c(C#N)c2)CCCNC1] | 2-Chloro-5-(3-propyl-piperidine-3-carbonyl)-benzonitrile | 197.0-198.0 |
| 323 | 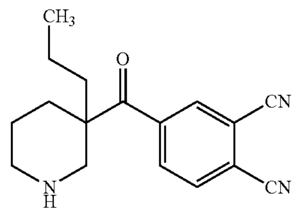 [SMILES: CCCC1(C(=O)c2ccc(C#N)c(C#N)c2)CCCNC1] | 4-(3-Propyl-piperidine-3-carbonyl)-phthalonitrile | 186.0-187.0 |
| 324 | 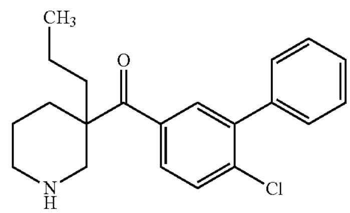 [SMILES: CCCC1(C(=O)c2ccc(Cl)c(-c3ccccc3)c2)CCCNC1] | (6-Chloro-biphenyl-3-yl)-(3-propyl-piperidin-3-yl)-methanone | 210.0-202.0 |
| 325 | 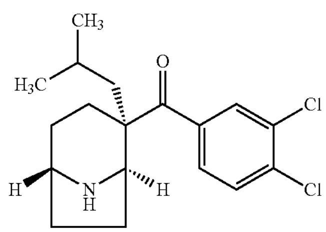 [SMILES: CC(C)C[C@@]1(C(=O)c2ccc(Cl)c(Cl)c2)CC[C@H]2CC[C@H]1N2] | (3,4-Dichloro-phenyl)-((1R,2R,5R)-2-isobutyl-8-aza-bicyclo[3.2.1]oct-2-yl)-methanone | 341 |
| 326 | 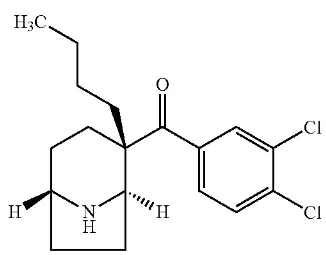 [SMILES: CCCC[C@]1(C(=O)c2ccc(Cl)c(Cl)c2)CC[C@H]2CC[C@H]1N2] | ((1R,2R,5R)-2-Butyl-8-aza-bicyclo[3.2.1]oct-2-yl)-(3,4-dichloro-phenyl)-methanone | 100.0-114.0 |
| 363 | 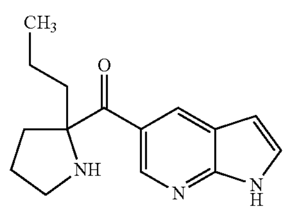 [SMILES: CCCC1(C(=O)c2cnc3[nH]ccc3c2)CCCN1] | (2-Propyl-pyrrolidin-2-yl)-(1H-pyrrolo[2,3-b]pyridin-5-yl)-methanone | 258 |
| 364 | 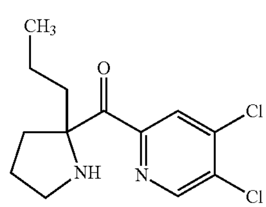 [SMILES: CCCC1(C(=O)c2cc(Cl)c(Cl)cn2)CCCN1] | (4,5-Dichloro-pyridin-2-yl)-(2-propyl-pyrrolidin-2-yl)-methanone | 288 |

TABLE 1-continued

| # | Structure | Name | mp/M + H |
|---|---|---|---|
| 365 | 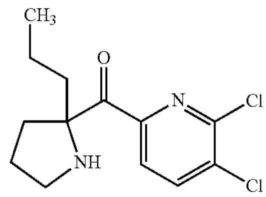 [SMILES: CCCC1(C(=O)c2ccc(Cl)c(Cl)n2)CCCN1] | (5,6-Dichloro-pyridin-2-yl)-(2-propyl-pyrrolidin-2-yl)-methanone | 288 |
| 366 | 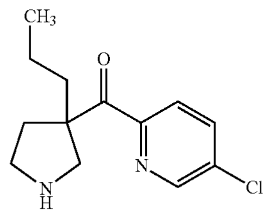 [SMILES: CCCC1(C(=O)c2ccc(Cl)cn2)CCNC1] | (5-Chloro-pyridin-2-yl)-(3-propyl-pyrrolidin-3-yl)-methanone | 253 |
| 367 | 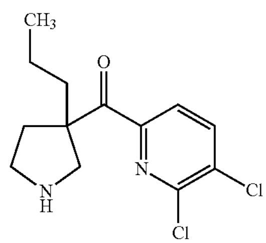 [SMILES: CCCC1(C(=O)c2ccc(Cl)c(Cl)n2)CCNC1] | (5,6-Dichloro-pyridin-2-yl)-(3-propyl-pyrrolidin-3-yl)-methanone | 288 |
| 368 | 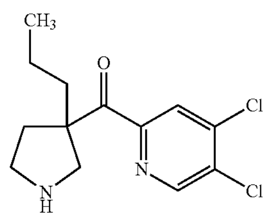 [SMILES: CCCC1(C(=O)c2cc(Cl)c(Cl)cn2)CCNC1] | (4,5-Dichloro-pyridin-2-yl)-(3-propyl-pyrrolidin-3-yl)-methanone | 288 |
| 369 | 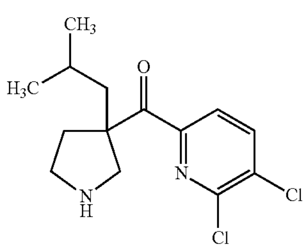 [SMILES: CC(C)CC1(C(=O)c2ccc(Cl)c(Cl)n2)CCNC1] | (5,6-Dichloro-pyridin-2-yl)-(3-isobutyl-pyrrolidin-3-yl)-methanone | 302 |
| 370 | 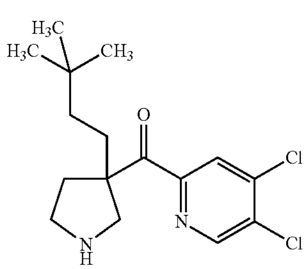 [SMILES: CC(C)(C)CCC1(C(=O)c2cc(Cl)c(Cl)cn2)CCNC1] | (4,5-Dichloro-pyridin-2-yl)-[3-(3,3-dimethyl-butyl)-pyrrolidin-3-yl]-methanone | 330 |

TABLE 1-continued

| # | Structure | Name | mp/M + H |
|---|---|---|---|
| 371 | 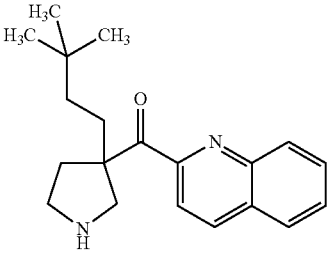 [SMILES: CC(C)(C)CCC1(C(=O)c2ccc3ccccc3n2)CCNC1] | [3-(3,3-Dimethyl-butyl)-pyrrolidin-3-yl]-quinolin-2-yl-methanone | 311 |
| 372 | 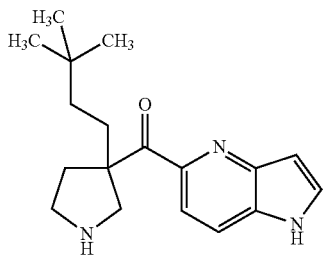 [SMILES: CC(C)(C)CCC1(C(=O)c2ccc3[nH]ccc3n2)CCNC1] | [3-(3,3-Dimethyl-butyl)-pyrrolidin-3-yl]-(1H-pyrrolo[3,2-b]pyridin-5-yl)-methanone | 300 |
| 373 | 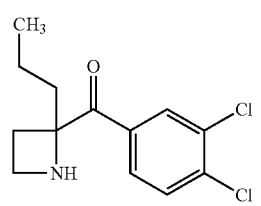 [SMILES: CCCC1(C(=O)c2ccc(Cl)c(Cl)c2)CCN1] | (3,4-Dichloro-phenyl)-(2-propyl-azetidin-2-yl)-methanone | 252.6-254.0 |
| 374 | 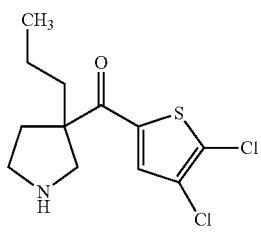 [SMILES: CCCC1(C(=O)c2cc(Cl)c(Cl)s2)CCNC1] | (4,5-Dichloro-phenyl-thiophen-2-yl)-(3-propyl-pyrrolidin-3-yl)-methanone | 293 |
| 375 | 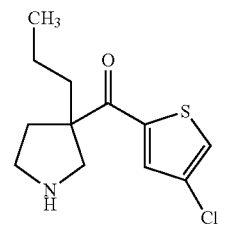 [SMILES: CCCC1(C(=O)c2cc(Cl)cs2)CCNC1] | (4-Chloro-thiophen-2-yl)-(3-propyl-pyrrolidin-3-yl)-methanone | 258 |
| 376 | 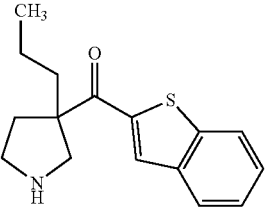 [SMILES: CCCC1(C(=O)c2cc3ccccc3s2)CCNC1] | Benzo[b]thiophen-2-yl-(3-propyl-pyrrolidin-3-yl)-methanone | 274 |

TABLE 1-continued

| # | Structure | Name | mp/M + H |
|---|---|---|---|
| 377 | 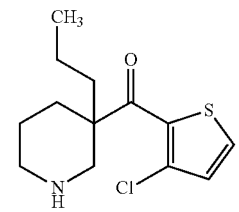 [SMILES: CCCC1(C(=O)c2sccc2Cl)CCCNC1] | (3-Chloro-thiophen-2-yl)-(3-propyl-piperidin-3-yl)-methanone | 272 |
| 378 | 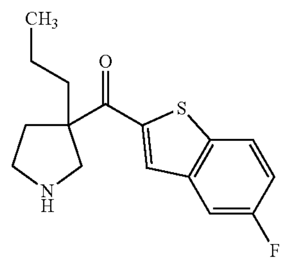 [SMILES: CCCC1(C(=O)c2cc3cc(F)ccc3s2)CCNC1] | (5-Fluoro-benzo[b]thiophen-2-yl)-(3-propyl-pyrrolidin-3-yl)-methanone | 292 |
| 379 | 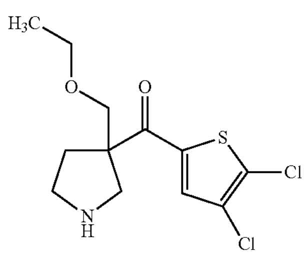 [SMILES: CCOCC1(C(=O)c2cc(Cl)c(Cl)s2)CCNC1] | (4,5-Dichloro-thiophen-2-yl)-(3-ethoxymethyl-pyrrolidin-3-yl)-methanone | 309 |
| 380 | 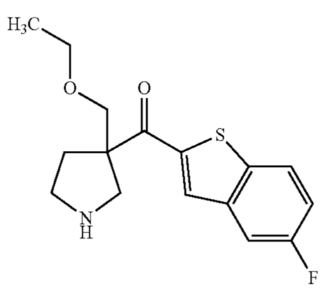 [SMILES: CCOCC1(C(=O)c2cc3cc(F)ccc3s2)CCNC1] | (3-Ethoxymethyl-pyrrolidin-3-yl)-(5-fluoro-benzo[b]thiophen-2-yl)-methanone | 308 |
| 381 | 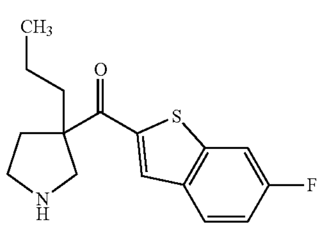 [SMILES: CCCC1(C(=O)c2cc3ccc(F)cc3s2)CCNC1] | (6-Fluoro-benzyl[b]thiophen-2-yl)-(3-propyl-pyrrolidin-3-yl)-methanone | 292 |
| 382 | 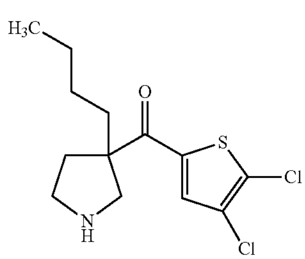 [SMILES: CCCCC1(C(=O)c2cc(Cl)c(Cl)s2)CCNC1] | (3-Butyl-pyrrolidin-3-yl)-(4,5-dichloro-thiophen-2-yl)-methanone | 307 |

TABLE 1-continued

| # | Structure | Name | mp/M + H |
|---|---|---|---|
| 383 | 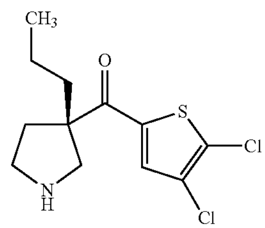 [SMILES: CCC[C@]1(C(=O)c2cc(Cl)c(Cl)s2)CCNC1] | (4,5-Dichloro-thiophen-2-yl)-((S)-3-propyl-pyrrolidin-3-yl)-methanone | 293 |
| 384 | 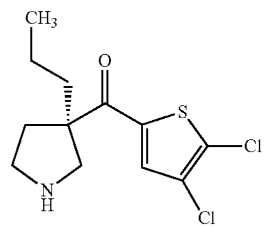 | (4,5-Dichoro-thiophen-2-yl)-((R)-3-propyl-pyrrolidin-3-yl)-methanone | 293 |
| 385 | 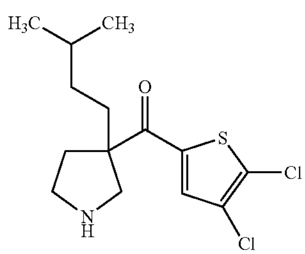 [SMILES: CC(C)CCC1(C(=O)c2cc(Cl)c(Cl)s2)CCNC1] | (4,5-Dichloro-thiophen-2-yl)-[3-(3-methyl-butyl)-pyrrolidin-3-yl]-methanone | 321 |
| 386 | 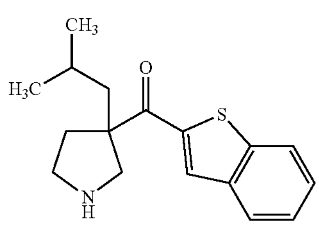 [SMILES: CC(C)CC1(C(=O)c2cc3ccccc3s2)CCNC1] | Benzo[b]thiophen-2-yl-(3-isobutyl-pyrrolidin-3-yl)-methanone | 288 |
| 387 | 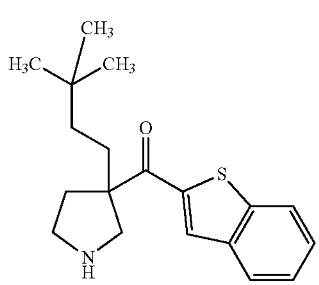 [SMILES: CC(C)(C)CCC1(C(=O)c2cc3ccccc3s2)CCNC1] | Benzo[b]thiophen-2-yl-[3-(3,3-dimethyl-butyl)-pyrrolidin-3-yl]-methanone | 316 |
| 388 | 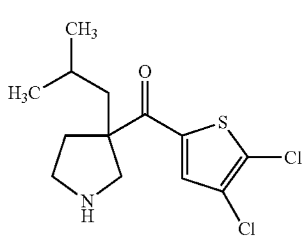 [SMILES: CC(C)CC1(C(=O)c2cc(Cl)c(Cl)s2)CCNC1] | (4,5-Dichloro-thiophen-2-yl)-(3-isobutyl-pyrrolidin-3-yl)-methanone | 307 |

TABLE 1-continued

| # | Structure | Name | mp/M + H |
|---|---|---|---|
| 389 | 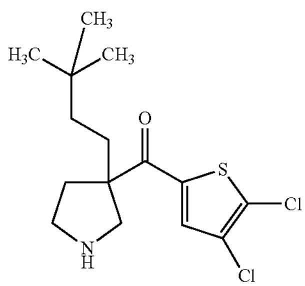 [SMILES: CC(C)(C)CCC1(C(=O)c2cc(Cl)c(Cl)s2)CCNC1] | (4,5-Dichloro-thiophen-2-yl)-[3-(3,3-dimethyl-butyl)-pyrrolidin-3-yl]-methnanone | 335 |
| 390 | 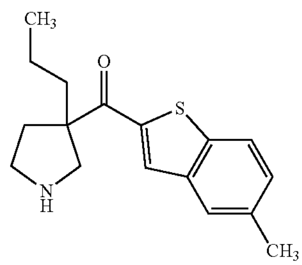 [SMILES: CCCC1(C(=O)c2cc3cc(C)ccc3s2)CCNC1] | (5-Methyl-benzo[b]thiophen-2-yl)-(3-propyl-pyrrolidin-3-yl)-methanone | 288 |
| 391 | 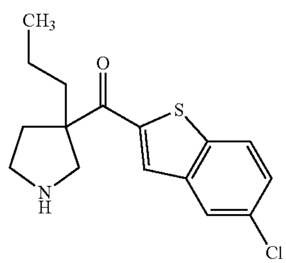 [SMILES: CCCC1(C(=O)c2cc3cc(Cl)ccc3s2)CCNC1] | (5-Chloro-benzo[b]thiophen-2-yl)-(3-propyl-pyrrolidin-3-yl)-methanone | 308 |
| 392 | 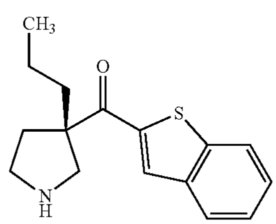 [SMILES: CCC[C@]1(C(=O)c2cc3ccccc3s2)CCNC1] | Benzo[b]thiophen-2-yl-((S)-3-propyl-pyrrolidin-3-yl)-methanone | 274 |
| 393 | 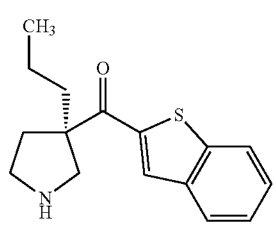 [SMILES: CCC[C@@]1(C(=O)c2cc3ccccc3s2)CCNC1] | Benzo[b]thiophen-2-yl-((R)-3-propyl-pyrrolidin-3-yl)-methanone | 274 |
| 394 | 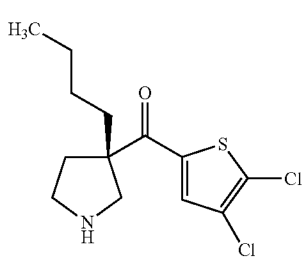 [SMILES: CCCC[C@]1(C(=O)c2cc(Cl)c(Cl)s2)CCNC1] | ((S)-3-Butyl-pyrrolidin-3-yl)-(4,5-dichloro-thiophen-2-yl)-methanone | 307 |

TABLE 1-continued

| # | Structure | Name | mp/M + H |
|---|---|---|---|
| 395 | 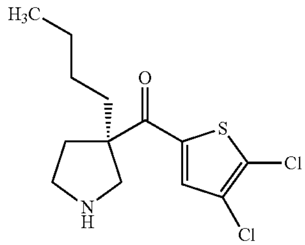 [SMILES: CCCC[C@@]1(C(=O)c2cc(Cl)c(Cl)s2)CCNC1] | ((R)-3-Butyl-pyrrolidin-3-yl)-(4,5-dichloro-thiophen-2-yl)-methanone | 307 |
| 396 | 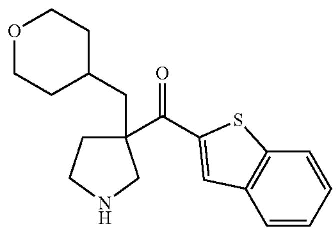 [SMILES: O=C(c1cc2ccccc2s1)C1(CC2CCOCC2)CCNC1] | Benzo[b]thiophen-2-yl-[3-(tetrahydro-pyran-4-ylmethyl)-pyrrolidin-3-yl]-methanone | 330 |
| 397 | 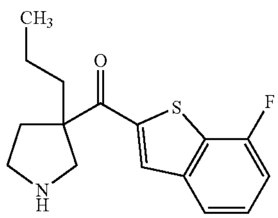 [SMILES: CCCC1(C(=O)c2cc3cccc(F)c3s2)CCNC1] | (7-Fluoro-benzo[b]thiophen-2-yl)-(3-propyl-pyrrolidin-3-yl)-methanone | 292 |
| 398 | 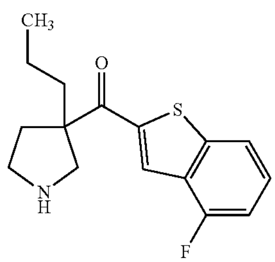 [SMILES: CCCC1(C(=O)c2cc3c(F)cccc3s2)CCNC1] | (4-Fluoro-benzo[b]thiophen-2-yl)-(3-propyl-pyrrolidin-3-yl)-methanone | 292 |
| 399 | 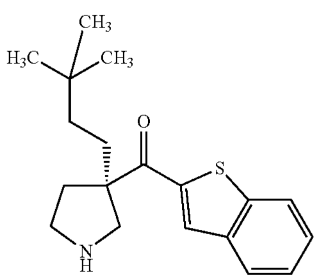 [SMILES: CC(C)(C)CC[C@@]1(C(=O)c2cc3ccccc3s2)CCNC1] | Benzo[b]thiophen-2-yl-[(R)-3-(3,3-dimethyl-butyl)-pyrrolidin-3-yl]-methanone | 217.0-218.0 |
| 400 | 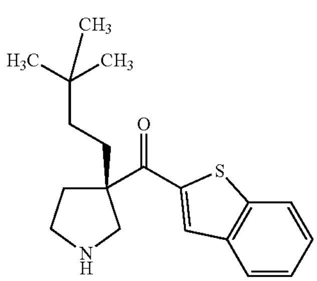 [SMILES: CC(C)(C)CC[C@]1(C(=O)c2cc3ccccc3s2)CCNC1] | Benzo[b]thiophen-2-yl-[(S)-3-(3,3-dimethyl-butyl)-pyrrolidin-3-yl]-methanone | 219.0-220.0 |

TABLE 1-continued

| # | Structure | Name | mp/M + H |
|---|---|---|---|
| 401 | 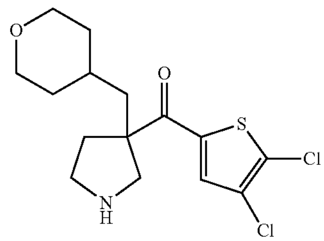 [SMILES: O=C(c1cc(Cl)c(Cl)s1)C1(CC2CCOCC2)CCNC1] | (4,5-Dichloro-thiophen-2-yl)-[3-(tetrahydro-pyran-4-ylmethyl)-pyrrolidin-3-yl]-methanone | 349 |
| 402 | 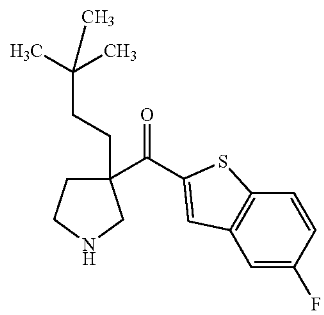 [SMILES: CC(C)(C)CCC1(C(=O)c2cc3cc(F)ccc3s2)CCNC1] | [3-(3,3-Dimethyl-butyl)-pyrrolidin-3-yl]-(5-fluoro-benzo[b]thiophen-2-yl)-methanone | 209.0-210.0 |
| 403 | 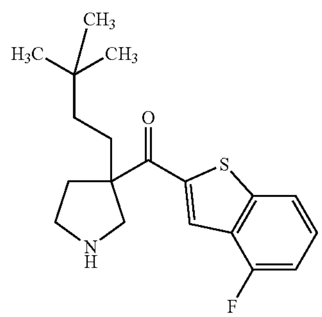 [SMILES: CC(C)(C)CCC1(C(=O)c2cc3c(F)cccc3s2)CCNC1] | [3-(3,3-Dimethyl-butyl)-pyrrolidin-3-yl]-(4-fluoro-benzyl[b]thiophen-2-yl)-methanone | 334 |
| 404 | 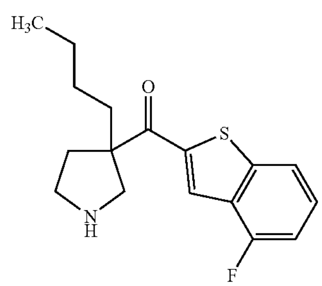 [SMILES: CCCCC1(C(=O)c2cc3c(F)cccc3s2)CCNC1] | (3-Butyl-pyrrolidin-3-yl)-(4-fluoro-benzo[b]thiophen-2-yl)-methanone | 306 |
| 405 | 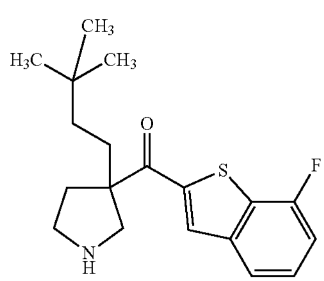 [SMILES: CC(C)(C)CCC1(C(=O)c2cc3cccc(F)c3s2)CCNC1] | [3-(3,3-Dimethyl-butyl)-pyrrolidin-3-yl]-(7-fluoro-benzyl[b]thiophen-2-yl)-methanone | 334 |

TABLE 1-continued

| # | Name | mp/M + H |
|---|---|---|
| 406 | (3-Butyl-pyrrolidin-3-yl)-(7-fluoro-benzo[b]thiophen-2-yl)-methanone | 306 |
| 407 | (4-Fluoro-benzo[b]thiophen-2-yl)-[3-(tetrahydro-pyran-4-ylmethyl)-pyrrolidin-3-yl]-methanone | 116.0-117.0 |
| 408 | Benzo[b]thiophen-2-yl-(3-ethylamino-pyrrolidin-3-yl)-methanone | 289 |
| 409 | (7-Fluoro-benzo[b]thiophen-2-yl)-(3-isobutyl-pyrrolidin-3-yl)-methanone | 306 |
| 410 | (7-Fluoro-benzo[b]thiophen-2-yl)-[3-(tetrahydro-pyran-4-ylmethyl)-pyrrolidin-3-yl]-methanone | 348 |
| 411 | (4-Fluoro-benzo[b]thiophen-2-yl)-(3-isobutyl-pyrrolidin-3-yl)-methanone | 174.0-175.0 |

TABLE 1-continued

| # | Structure | Name | mp/M + H |
|---|---|---|---|
| 412 | 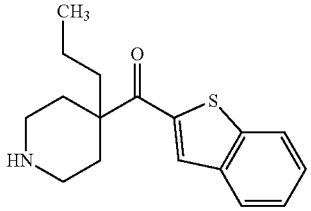 [SMILES: CCCC1(C(=O)c2cc3ccccc3s2)CCNCC1] | Benzo[b]thiophen-2-yl-(4-propyl-piperidin-4-yl)-methanone | 288 |
| 413 | 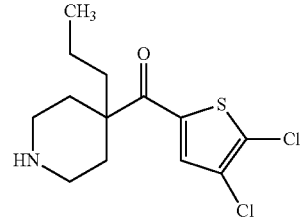 [SMILES: CCCC1(C(=O)c2cc(Cl)c(Cl)s2)CCNCC1] | (4,5-Dichloro-thiophen-2-yl)-(4-propyl-piperidin-4-yl)-methanone | 307 |
| 414 | 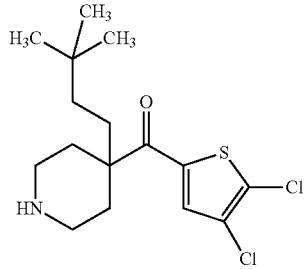 [SMILES: CC(C)(C)CCC1(C(=O)c2cc(Cl)c(Cl)s2)CCNCC1] | (4,5-Dichloro-thiophen-2-yl)-[4-(3,3-dimethyl-butyl)-piperidin-4-yl]-methanone | 349 |
| 415 | 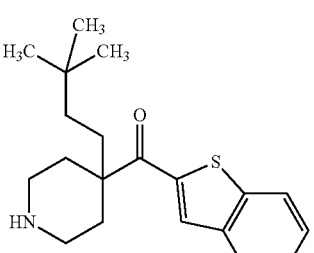 | Benzo[b]thiophen-2-yl-[4-(3,3-dimethyl-butyl)-piperidin-4-yl]-methanone | 330 |
| 416 | 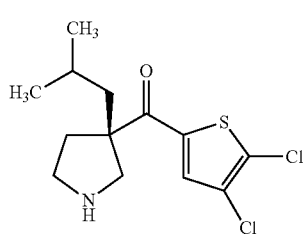 [SMILES: CC(C)C[C@]1(C(=O)c2cc(Cl)c(Cl)s2)CCNC1] | (4,5-Dichloro-thiophen-2-yl)-((S)-3-isobutyl-pyrrolidin-3-yl)-methanone | 166.0-168.0 |
| 417 | 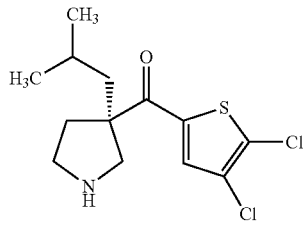 | (4,5-Dichloro-thiophen-2-yl)-((R)-3-isobutyl-pyrrolidin-3-yl)-methanone | 165.0-167.0 |

TABLE 1-continued

| # | Structure | Name | mp/M + H |
|---|---|---|---|
| 418 | 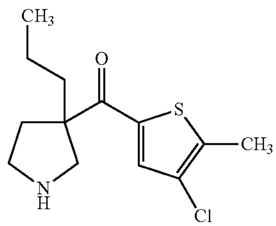 [SMILES: CCCC1(C(=O)c2cc(Cl)c(C)s2)CCNC1] | (4-Chloro-5-methyl-thiophen-2-yl)-(3-propyl-pyrrolidin-3-yl)-methanone | 272 |
| 419 | 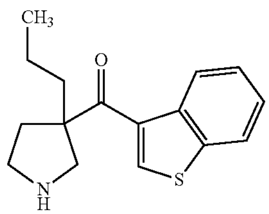 [SMILES: CCCC1(C(=O)c2csc3ccccc23)CCNC1] | Benzo[b]thiophen-3-yl-(3-propyl-pyrrolidin-3-yl)-methanone | 274 |
| 420 | 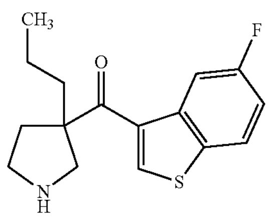 [SMILES: CCCC1(C(=O)c2csc3ccc(F)cc23)CCNC1] | (5-Fluoro-benzo[b]thiophen-3-yl)-(3-propyl-pyrrolidin-3-yl)-methanone | 292 |
| 421 | 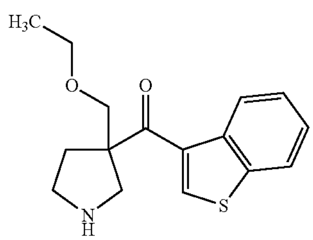 [SMILES: CCOCC1(C(=O)c2csc3ccccc23)CCNC1] | Benzo[b]thiophen-3-yl-(3-ethoxymethyl-pyrrolidin-3-yl)-methanone | 290 |
| 422 | 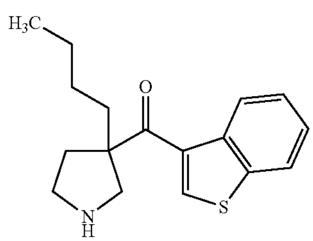 [SMILES: CCCCC1(C(=O)c2csc3ccccc23)CCNC1] | Benzo[b]thiophen-3-yl-(3-butyl-pyrrolidin-3-yl)-methanone | 288 |
| 423 | 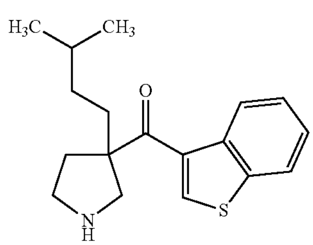 [SMILES: CC(C)CCC1(C(=O)c2csc3ccccc23)CCNC1] | Benzo[b]thiophen-3-yl-[3-(3-methyl-butyl)-pyrrolidin-3-yl]-methanone | 302 |
| 424 | 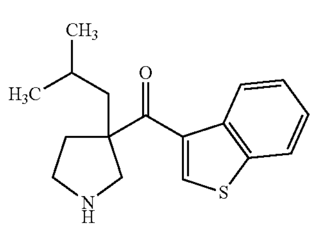 [SMILES: CC(C)CC1(C(=O)c2csc3ccccc23)CCNC1] | Benzo[b]thiophen-3-yl-(3-isobutyl-pyrrolidin-3-yl)-methanone | 288 |

TABLE 1-continued

| # | Structure | Name | mp/M + H |
|---|---|---|---|
| 425 | 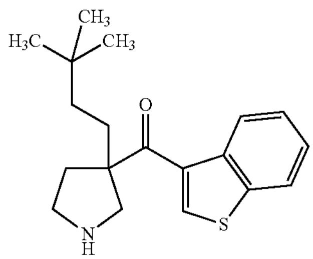 [SMILES: CC(C)(C)CCC1(C(=O)c2csc3ccccc23)CCNC1] | Benzo[b]thiophen-3-yl-[3-(3,3-dimethyl-butyl)-pyrrolidin-3-yl]-methanone | 316 |
| 426 | 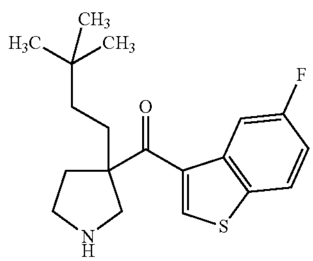 [SMILES: CC(C)(C)CCC1(C(=O)c2csc3ccc(F)cc23)CCNC1] | [3-(3,3-Dimethyl-butyl)-pyrrolidin-3-yl]-(5-fluoro-benzo[b]thiophen-3-yl)-methanone | 334 |
| 427 | 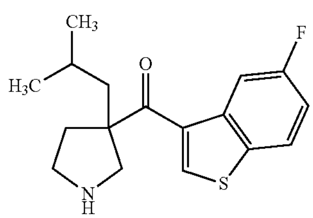 [SMILES: CC(C)CC1(C(=O)c2csc3ccc(F)cc23)CCNC1] | (5-Fluoro-benzo[b]thiophen-3-yl)-(3-isobutyl-pyrrolidin-3-yl)-methanone | 306 |
| 428 | 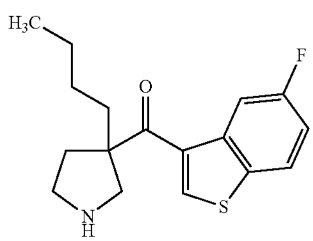 [SMILES: CCCCC1(C(=O)c2csc3ccc(F)cc23)CCNC1] | (3-Butyl-pyrrolidin-3-yl)-(5-fluoro-benzo[b]thiophen-3-yl)-methanone | 306 |
| 429 | 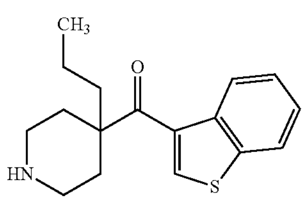 [SMILES: CCCC1(C(=O)c2csc3ccccc23)CCNCC1] | Benzo[b]thiophen-3-yl-(4-propyl-piperidin-4-yl)-methanone | 288 |
| 430 | 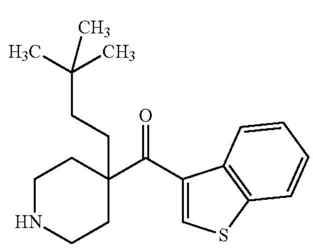 [SMILES: CC(C)(C)CCC1(C(=O)c2csc3ccccc23)CCNCC1] | Benzo[b]thiophen-3-yl-[4-(3,3-dimethyl-butyl)-piperidin-4-yl]-methanone | 330 |

TABLE 1-continued

| # | Structure | Name | mp/M + H |
|---|---|---|---|
| 431 | 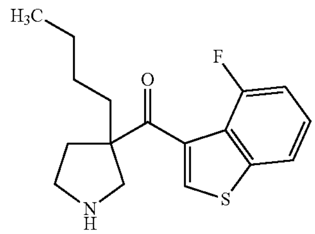 [SMILES: CCCCC1(C(=O)c2csc3cccc(F)c23)CCNC1] | (3-Butyl-pyrrolidin-3-yl)-(4-fluoro-benzo[b]thiophen-3-yl)-methanone | 306 |
| 432 | 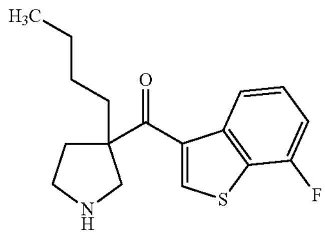 [SMILES: CCCCC1(C(=O)c2csc3c(F)cccc23)CCNC1] | (3-Butyl-pyrrolidin-3-yl)-(7-fluoro-benzo[b]thiophen-3-yl)-methanone | 306 |
| 433 | 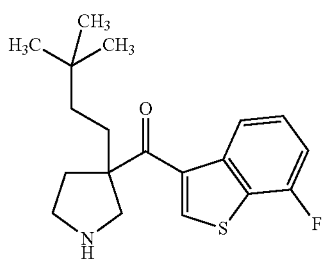 [SMILES: CC(C)(C)CCC1(C(=O)c2csc3c(F)cccc23)CCNC1] | [3-(3,3-Dimethyl-butyl)-pyrrolidin-3-yl]-(7-fluoro-benzo[b]thiophen-3-yl)-methanone | 334 |
| 434 | 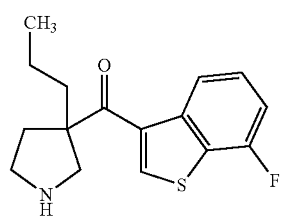 [SMILES: CCCC1(C(=O)c2csc3c(F)cccc23)CCNC1] | (7-Fluoro-benzo[b]thiophen-3-yl)-(3-propyl-pyrrolidin-3-yl)-methanone | 292 |
| 435 | 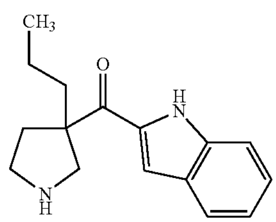 | (1H-Indol-2-yl)-(3-propyl-pyrrolidin-3-yl)-methanone | 257 |
| 436 | 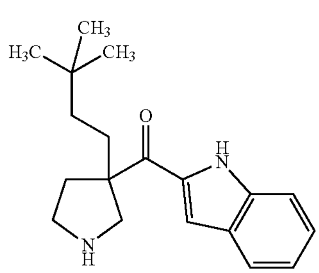 [SMILES: CC(C)(C)CCC1(C(=O)c2cc3ccccc3[nH]2)CCNC1] | [3-(3,3-Dimethyl-butyl)-pyrrolidin-3-yl]-(1H-indol-2-yl)-methanone | 299 |

TABLE 1-continued

| # | Structure | Name | mp/M + H |
|---|---|---|---|
| 437 | 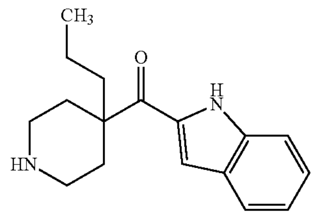 [SMILES: CCCC1(C(=O)c2cc3ccccc3[nH]2)CCNCC1] | (1H-Indol-2-yl)-(4-propyl-piperidin-4-yl)-methanone | 271 |
| 438 | 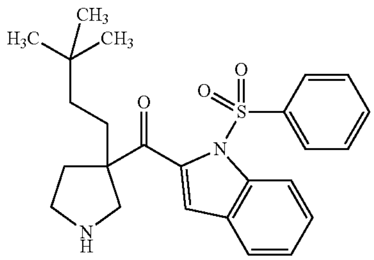 [SMILES: CC(C)(C)CCC1(C(=O)c2cc3ccccc3n2S(=O)(=O)c2ccccc2)CCNC1] | (1-Benzenesulfonyl-1H-indol-2-yl)-[4-(3,3-dimethyl-butyl)-piperidin-4-yl]-methanone | 439 |
| 439 | 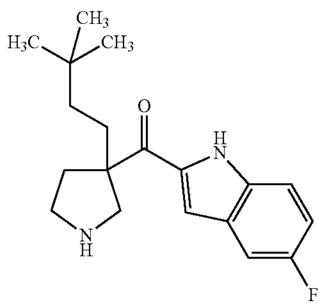 [SMILES: CC(C)(C)CCC1(C(=O)c2cc3cc(F)ccc3[nH]2)CCNC1] | [3-(3,3-Dimethyl-butyl)-pyrrolidin-3-yl]-(5-fluoro-1H-indol-2-yl)-methanone | 317 |
| 440 | 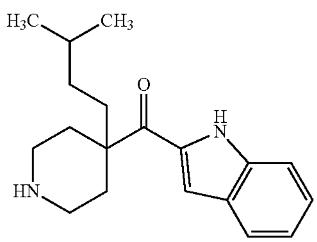 [SMILES: CC(C)CCC1(C(=O)c2cc3ccccc3[nH]2)CCNCC1] | (1H-Indol-2-yl)-[4-(3-methyl-butyl)-piperidin-4-yl]-methanone | 299 |
| 441 | 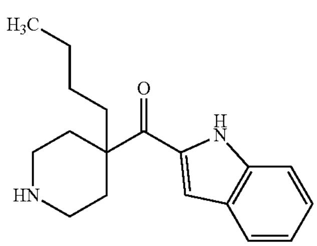 [SMILES: CCCCC1(C(=O)c2cc3ccccc3[nH]2)CCNCC1] | (4-Butyl-piperidin-4-yl)-(1H-indol-2-yl)-methanone | 285 |
| 442 | 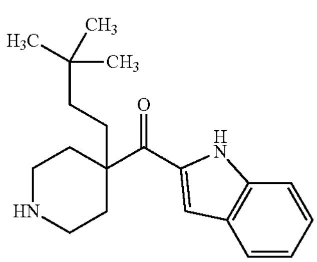 [SMILES: CC(C)(C)CCC1(C(=O)c2cc3ccccc3[nH]2)CCNCC1] | [4-(3,3-Dimethyl-butyl)-piperidin-4-yl]-(1H-indol-2-yl)-methanone | 313 |

TABLE 1-continued

| # | Structure | Name | mp/M + H |
|---|---|---|---|
| 443 | 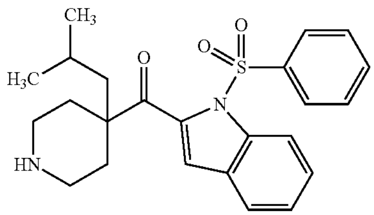 [SMILES: CC(C)CC1(C(=O)c2cc3ccccc3n2S(=O)(=O)c2ccccc2)CCNCC1] | (1-Benzenesulfonyl-1H-indol-2-yl)-(4-isobutyl-piperidin-4-yl)-methanone | 425 |
| 444 | 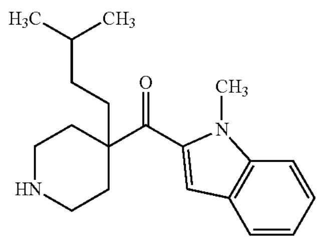 [SMILES: CC(C)CCC1(C(=O)c2cc3ccccc3n2C)CCNCC1] | [4-(3-Methyl-butyl)-piperidin-4-yl]-(1-methyl-1H-indol-2-yl)-methanone | 313 |
| 445 | 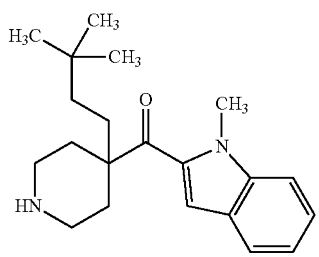 [SMILES: Cn1c(C(=O)C2(CCC(C)(C)C)CCNCC2)cc2ccccc21] | [4-(3,3-Dimethyl-butyl)-piperidin-4-yl]-(1-methyl-1H-indol-2-yl)-methanone | 327 |
| 446 | 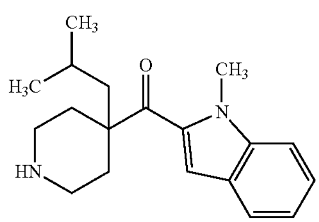 [SMILES: CC(C)CC1(C(=O)c2cc3ccccc3n2C)CCNCC1] | (1H-Indol-2-yl)-(4-isobutyl-piperidin-4-yl)-methanone | 299 |
| 447 | 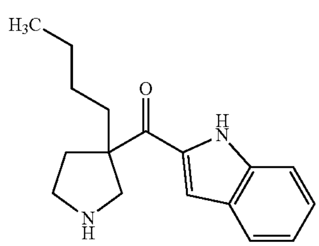 [SMILES: CCCCC1(C(=O)c2cc3ccccc3[nH]2)CCNC1] | (2-Butyl-pyrrolidin-2-yl)-(1H-indol-2-yl)-methanone | 271 |
| 448 | 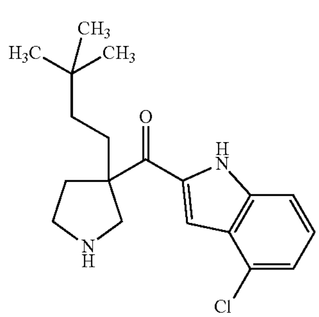 [SMILES: CC(C)(C)CCC1(C(=O)c2cc3c(Cl)cccc3[nH]2)CCNC1] | (4-Chloro-1H-indol-2-yl)-[3-(3,3-dimethyl-butyl)-pyrrolidin-3-yl]-methanone | 333 |

TABLE 1-continued

| # | Structure | Name | mp/M + H |
|---|---|---|---|
| 449 | 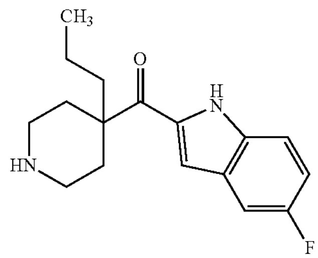 [SMILES: CCCC1(C(=O)c2cc3cc(F)ccc3[nH]2)CCNCC1] | (5-Fluoro-1H-indol-2-yl)-(4-propyl-piperidin-4-yl)-methanone | 289 |
| 450 | 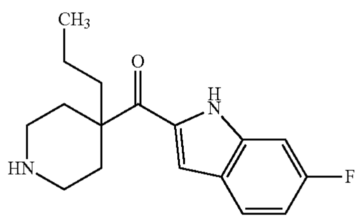 [SMILES: CCCC1(C(=O)c2cc3ccc(F)cc3[nH]2)CCNCC1] | (6-Fluoro-1H-indol-2-yl)-(4-propyl-piperidin-4-yl)-methanone | 289 |
| 451 | 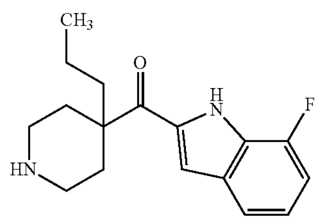 [SMILES: CCCC1(C(=O)c2cc3cccc(F)c3[nH]2)CCNCC1] | (7-Fluoro-1H-indol-2-yl)-(4-propyl-piperidin-4-yl)-methanone | 289 |
| 452 | 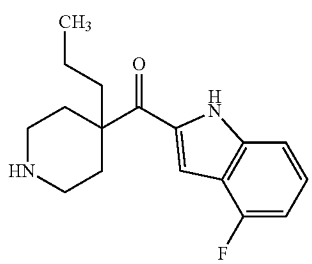 [SMILES: CCCC1(C(=O)c2cc3c(F)cccc3[nH]2)CCNCC1] | (4-Fluoro-1H-indol-2-yl)-(4-propyl-piperidin-4-yl)-methanone | 289 |
| 453 | 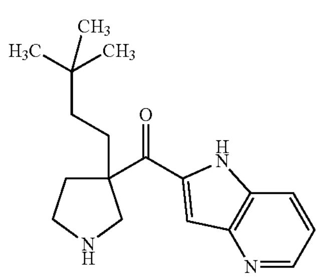 [SMILES: CC(C)(C)CCC1(C(=O)c2cc3ncccc3[nH]2)CCNC1] | [3-(3,3-Dimethyl-butyl)-pyrrolidin-3-yl]-(1H-pyrrolo[3,2-b]pyridin-2-yl)-methanone | 300 |
| 454 | 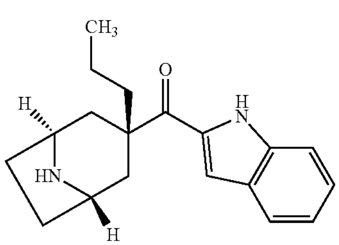 | (1H-Indol-2-yl)-((1R,2R,5R)-2-propyl-8-aza-bicyclo[3.2.1]oct-2-yl)-methanone | 297 |

TABLE 1-continued

| # | Structure | Name | mp/M + H |
|---|---|---|---|
| 455 | 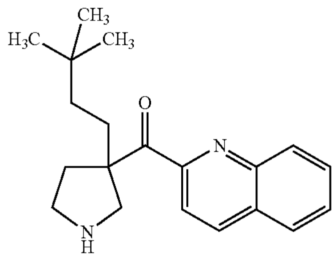 [SMILES: CC(C)(C)CCC1(C(=O)c2ccc3ccccc3n2)CCNC1] | [3-(3,3-Dimethyl-butyl)-pyrrolidin-3-yl]-quinolin-2-yl-methanone | 311 |
| 456 | 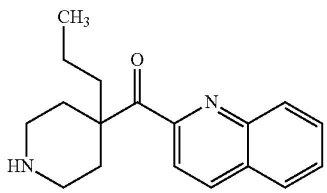 [SMILES: CCCC1(C(=O)c2ccc3ccccc3n2)CCNCC1] | (4-Propyl-piperidin-4-yl)-quinolin-2-yl-methanone | 283 |
| 457 | 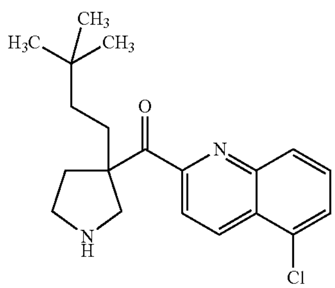 [SMILES: CC(C)(C)CCC1(C(=O)c2ccc3c(Cl)cccc3n2)CCNC1] | (5-Chloro-quinolin-2-yl)-[3-(3,3-dimethyl-butyl)-pyrrolidin-3-yl]-methanone | 345 |
| 458 | 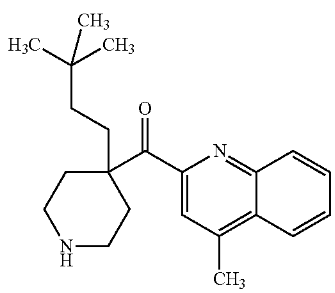 [SMILES: Cc1cc(C(=O)C2(CCC(C)(C)C)CCNCC2)nc2ccccc12] | [4-(3,3-Dimethyl-butyl)-piperidin-4-yl]-(4-methyl-quinolin-2-yl)-methanone | 339 |
| 459 | 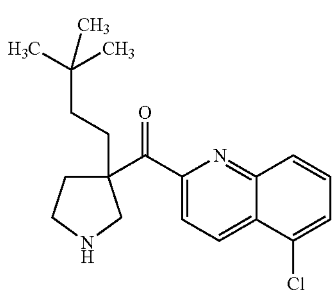 [SMILES: CC(C)(C)CCC1(C(=O)c2ccc3c(Cl)cccc3n2)CCNC1] | [3-(3,3-Dimethyl-butyl)-pyrrolidin-3-yl]-(4-methyl-quinolin-2-yl)-methanone | 345 |
| 460 | 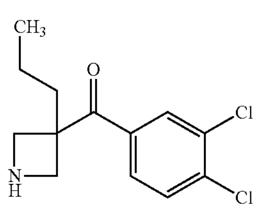 [SMILES: CCCC1(C(=O)c2ccc(Cl)c(Cl)c2)CNC1] | (3,4-Dichloro-phenyl)-(3-propyl-azetidin-3-yl)-methanone | 59.0-60.0 |

TABLE 1-continued

| # | Structure | Name | mp/M + H |
|---|---|---|---|
| 461 | 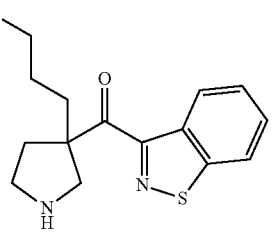 | Benzo[d]isothiazol-3-yl-(3-butyl-pyrrolidin-3-yl)-methanone | 289 |
| 462 | 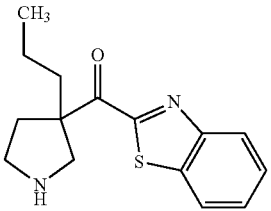 [SMILES: CCCC1(C(=O)c2nc3ccccc3s2)CCNC1] | Benzothiazol-2-yl-(3-propyl-pyrrolidin-3-yl)-methanone | 275 |
| 463 | 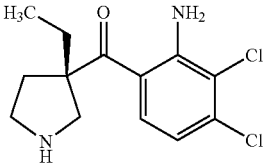 [SMILES: CC[C@]1(C(=O)c2ccc(Cl)c(Cl)c2N)CCNC1] | (2-Amino-3,4-dichloro-phenyl)-((S)-3-ethyl-pyrrolidin-3-yl)-methanone | 288 |
| 464 | 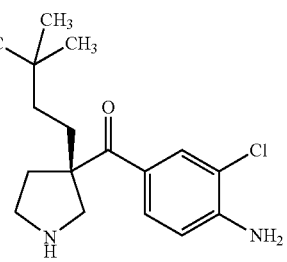 | (4-Amino-3-chloro-phenyl)-[((S)-3-(3,3-dimethyl-butyl)-pyrrolidin-3-yl]-methanone | 226.2-232.5 |
| 465 | 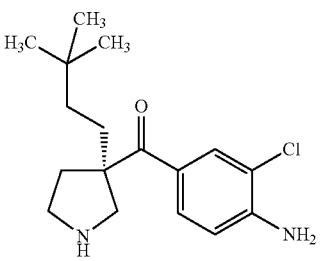 [SMILES: CC(C)(C)CC[C@@]1(C(=O)c2ccc(N)c(Cl)c2)CCNC1] | (4-Amino-3-chloro-phenyl)-[(R)-3-(3,3-dimethyl-butyl)-pyrrolidin-3-yl]-methanone | 223.3-231.0 |
| 466 | 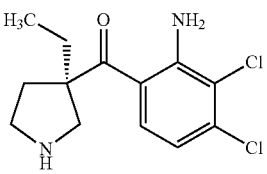 [SMILES: CC[C@@]1(C(=O)c2ccc(Cl)c(Cl)c2N)CCNC1] | (2-Amino-3,4-dichloro-phenyl)-((R)-3-ethyl-pyrrolidin-3-yl)-methanone | 288 |
| 467 | 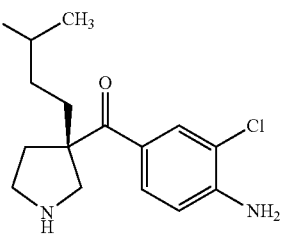 | (4-Amino-3-chloro-phenyl)-[(S)-3-(3-methyl-butyl)-pyrrolidin-3-yl]-methanone | 193.1-199.2 |

TABLE 1-continued

| # | Structure | Name | mp/M + H |
|---|---|---|---|
| 468 | 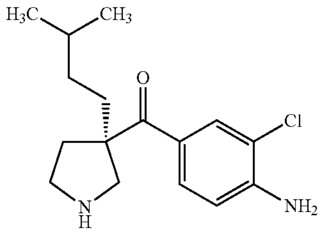 [SMILES: CC(C)CC[C@@]1(C(=O)c2ccc(N)c(Cl)c2)CCNC1] | (4-Amino-3-chloro-phenyl)-[(R)-3-(3-methyl-butyl)-pyrrolidin-3-yl]-methanone | 295 |
| 469 | 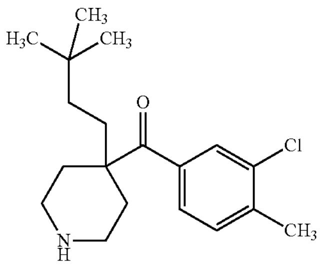 [SMILES: Cc1ccc(C(=O)C2(CCC(C)(C)C)CCNCC2)cc1Cl] | (3-Chloro-4-methyl-phenyl)-[4-(3,3-dimethyl-butyl)-piperidin-4-yl]-methanone | 237.6-238.6 |
| 470 | 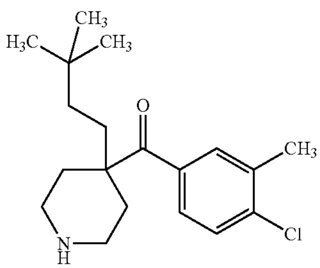 [SMILES: Cc1cc(C(=O)C2(CCC(C)(C)C)CCNCC2)ccc1Cl] | (4-Chloro-3-methyl-phenyl)-[4-(3,3-dimethyl-butyl)-piperidin-4-yl]-methanone | 223.0-225.2 |
| 471 | 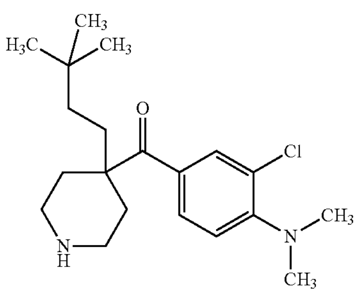 [SMILES: CN(C)c1ccc(C(=O)C2(CCC(C)(C)C)CCNCC2)cc1Cl] | (3-Chloro-4-dimethylamino-phenyl)-[4-(3,3-dimethyl-butyl)-piperidin-4-yl]-methanone | 351 |
| 472 | 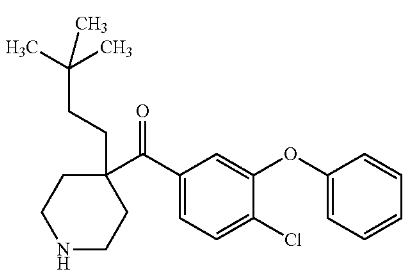 [SMILES: CC(C)(C)CCC1(C(=O)c2ccc(Cl)c(Oc3ccccc3)c2)CCNCC1] | (4-Chloro-3-phenoxy-phenyl)-[4-(3,3-dimethyl-butyl)-piperidin-4-yl]-methanone | 400 |
| 473 | 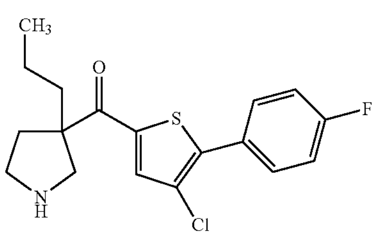 [SMILES: CCCC1(C(=O)c2cc(Cl)c(-c3ccc(F)cc3)s2)CCNC1] | [4-Chloro-5-(4-fluoro-phenyl)-thiophen-2-yl]-(3-propyl-pyrrolidin-3-yl)-methanone | 60.0-71.0 |

TABLE 1-continued

| # | Structure | Name | mp/M + H |
|---|---|---|---|
| 474 | 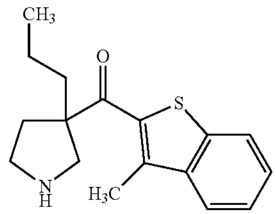 [SMILES: CCCC1(C(=O)c2sc3ccccc3c2C)CCNC1] | (3-Methyl-benzo[b]thiophen-2-yl)-(3-propyl-pyrrolidin-3-yl)-methanone | 288 |
| 475 | 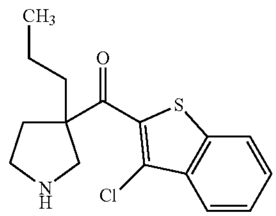 [SMILES: CCCC1(C(=O)c2sc3ccccc3c2Cl)CCNC1] | (3-Chloro-benzo[b]thiophen-2-yl)-(3-propyl-pyrrolidin-3-yl)-methanone | 308 |
| 476 | 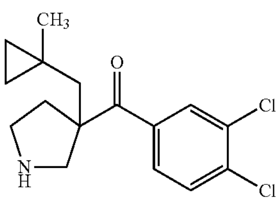 [SMILES: CC1(CC2(C(=O)c3ccc(Cl)c(Cl)c3)CCNC2)CC1] | (3,4-Dichloro-phenyl)-[3-(1-methyl-cyclopropylmethyl)-pyrrolidin-3-yl]-methanone | 313 |
| 477 | 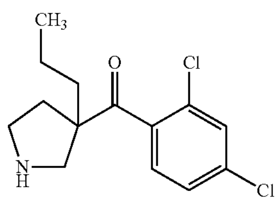 [SMILES: CCCC1(C(=O)c2ccc(Cl)cc2Cl)CCNC1] | (2,4-Dichloro-phenyl)-(3-propyl-pyrrolidin-3-yl)-methanone | 287 |
| 478 | 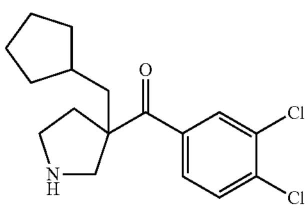 [SMILES: O=C(c1ccc(Cl)c(Cl)c1)C1(CC2CCCC2)CCNC1] | (3-Cyclopentylmethyl-pyrrolidin-3-yl)-(3,4-dichloro-phenyl)-methanone | 327 |
| 479 | 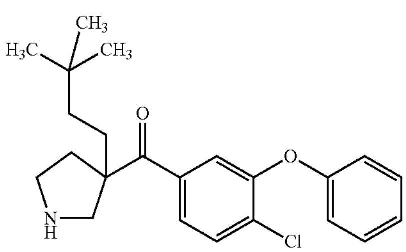 [SMILES: CC(C)(C)CCC1(C(=O)c2ccc(Cl)c(Oc3ccccc3)c2)CCNC1] | (4-Chloro-3-phenoxy-phenyl)-[3-(3,3-dimethyl-butyl)-pyrrolidin-3-yl]-methanone | 386 |
| 480 | 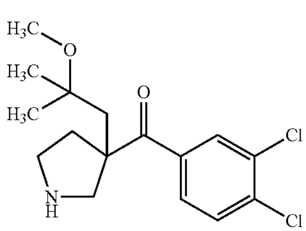 [SMILES: COC(C)(C)CC1(C(=O)c2ccc(Cl)c(Cl)c2)CCNC1] | (3,4-Dichloro-phenyl)-[3-(2-methoxy-2-methyl-propyl)-pyrrolidin-3-yl]-methanone | 331 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds, Elsevier Science Publishers,* 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein X is halo or other leaving group and may be the same or different in each occurrence, PG is a protecting group, and m, n, Ar and $R^1$ are as defined herein.

In step 1 of Scheme A, an aryl compound a, such as an aryl halide, is reacted with an N-protected heterocyclic amide compound b in the presence of strong base, such as alkyl lithium reagent, to afford aryl heterocyclic ketone c. The values of m an n in compound b may be selected to provide pyrrolidinyl, piperidinyl, azetidinyl, azepinyl, or like heterocyclic moieties. In step 2 an alkylation is carried out by reacting aryl heterocyclic ketone c with alkylating agent d, to afford compound e. Alkylating agent d may comprise, for example, a benzyl halide, alkenyl halide or other alkylating reagent. The compound e may then be deprotected in step 3 to afford compound f, which is a compound of formula I in accordance with the invention.

Numerous variations on the procedures of Scheme A are possible and will be readily apparent to those skilled in the art. For example, N-alkylation of compound f can provide compounds where $R^2$ is alkyl. Where the $R^1$ group introduced in step 2 is alkenyl or alkynyl, a hydrogenation reaction may be carried out to change the $R^1$ to alkyl.

Scheme B shows another synthetic route to the compounds of the invention, wherein R is lower alkyl, PG is a protecting group, X is a leaving group, and m, n, Ar and $R^1$ are as defined herein.

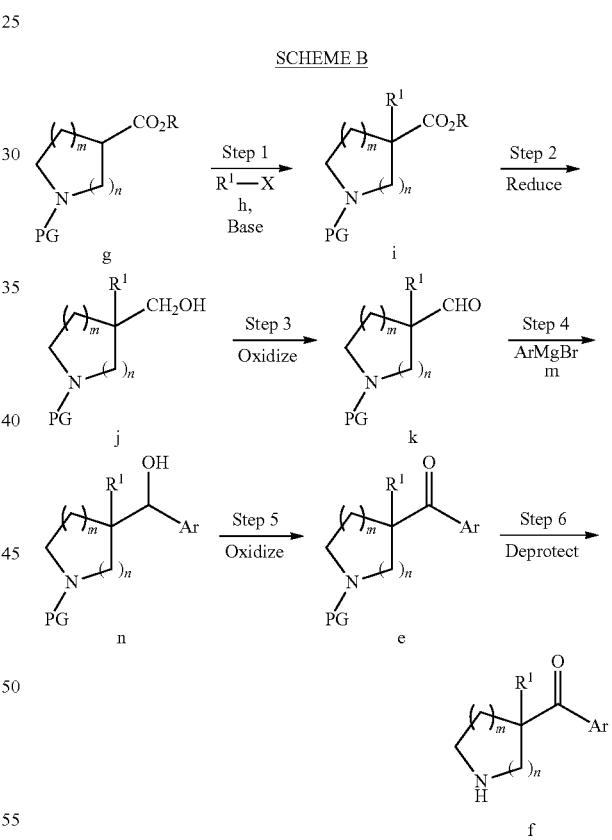

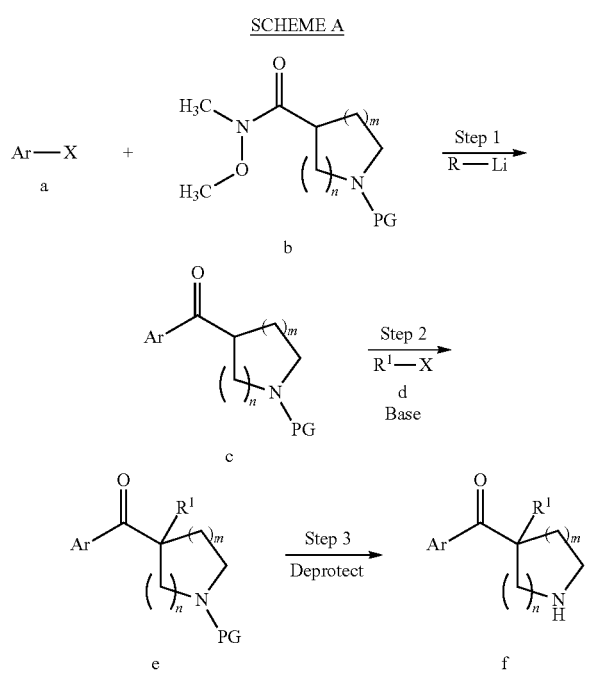

In step 1 of Scheme B, cyclic amine carboxylic acid ester g is treated with alkylating agent h in the presence of strong base, such as an alkyl lithium reagent, to provide alkylated cyclic amine i. The cyclic amine g may be pyrrolidinyl, piperidinyl, azetidinyl, azepinyl, or the like according to the values of m and n, as noted above. In step 2 the ester group of compound i is reduced to afford the primary alcohol compound i. The reduction of step 2 may be achieved, for example, using $LiAlH_4$. Alcohol compound i then undergoes a partial oxidation in step 4 to yield aldehyde compound k.

The oxidation of step 3 may be carried out, for example, using Dess Martin Periodinane or a chromate reagent. An alkylation is carried out in step 4 by reaction of aldehyde compound k with aryl magnesium bromide m. to afford aryl alcohol compound n. In step 5 alcohol n is oxidized to the corresponding aryl ketone compound e. The oxidation may be carried out, for example, using $MnO_2$, Swern's reagent, or like oxidizing agent. In step 6 the aryl ketone compound e is deprotected to provide compound f which is a compound of formula I in accordance with the invention.

Many variations on the procedure of Scheme B are possible and are considered to be within the scope of this invention. For example, an aryl lithium reagent may be used in step 4. Specific details for producing compounds of the invention are described in the Examples section below.

Utility

The compounds of the invention are usable for the treatment of diseases or conditions associated with serotonin neurotransmission, norepinephrine neuortransmission and/or dopamine neurotransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The compounds of the invention are also usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The compounds of the invention also possess anti-inflammatory and/or analgesic properties in vivo, and accordingly, are expected to find utility in the treatment of disease states associated with pain conditions from a wide variety of causes, including, but not limited to, neuropathic pain, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Compounds of the invention are also useful for treatment of arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

ABBREVIATIONS

| | |
|---|---|
| AcOH | Acetic acid |
| Bn | Benzyl |
| (BOC)$_2$O | di-tert-Butyl dicarbonate |
| t-BuLi | tert-Butyllithium |
| t-BuOH | tert-Butyl alcohol |
| m-CPBA | 3-Chloroperoxybenzoic acid |
| DCM | Dichloromethane/Methylene chloride |
| DEA | Diethylamine |
| DIPEA | Diisopropylethylamine |
| DIBALH | Diisobutylaluminum hydride |
| DMF | N,N-Dimethylformamide |
| DMP | Dess Martin Periodinane (acetic acid 1,1-diacetoxy-3-oxo-1lambda*5*-ioda-2-oxa-indan-l-yl ester) |
| Dppf | 1,1'-Bis(diphenylphosphino)ferrocene |
| EDC | 1-(3-Dimethylaminopropyl)-3-ethylcarbodiimide hydrochloride |
| EtOAc | Ethyl acetate |
| HPLC | High pressure liquid chromatography |
| HOBt | 1-Hydroxybenzotriazole |
| LAH | Lithium aluminum hydride |
| LHMDS | Lithium bis(trimethylsilyl)amide |
| MeOH | Methanol |
| MsCl | Methanesulfonyl chloride |
| NBS | N-bromosuccinimide |
| PFBSF | Perfluorobutanesulfonyl fluoride |
| TBAF | Tetrabutylammonium fluoride |
| TBAHS | Tetrabutyl ammonium hydrogen sulfate |
| TBDMS | tert-Butyldimethylsilyl |
| TMSI | Iodotrimethylsilane |
| TEA | Triethylamine |
| TIPS | Triisopropylsilyl |
| TFA | Trifluoroacetic acid |
| THF | Tetrahydrofuran |
| TMAF | Tetramethylammonium fluoride |
| TMS | trimethylsilyl |

Preparation 1

5-Bromo-1-triisopropylsilanyl-1H-indole

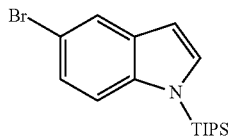

Lithium bis(trimethylsilyl)amide (1.0 M in THF, 28 mL, 28 mmol) was slowly added to a solution of 5-bromoindole (5.00 g, 25.5 mmol) in THF (60 mL) at −78° C., under nitrogen atmosphere. The reaction mixture was stirred at −78° C. for 20 minutes, then triisopropylsilylchloride (5.7 mL, 26.8 mmol) was added. The resulting mixture was stirred at −78° C. for 20 minutes, then warmed to room temperature over a period of 1 hour. The reaction was quenched by addition of a saturated aqueous solution of NH$_4$Cl, diluted with water, and the resulting mixture was extracted with EtOAc. The organic layer was separated, dried over MgSO$_4$, filtered and evaporated under reduced pressure to give a crude oil that was purified by flash chromatography (hexane 100%) providing 8.94 g (99% yield) of 5-bromo-1-triisopropylsilanyl-1H-indole as a colorless oil.

In a similar manner, using the appropriate starting material, the following compounds were prepared:
5-Bromo-1-triisopropylsilanyl-1H-indazole (86% yield, yellow solid);
5-Bromo-1-triisopropylsilanyl-1H-pyrrolo[2,3-b]pyridine (87% yield, yellow solid);
5-Bromo-2-methyl-1-triisopropylsilanyl-1H-indole;
5-Bromo-1-triisopropylsilanyl-2,3-dihydro-1H-indole (100% yield, white solid);
5-Bromo-1-(tert-butyl-dimethyl-silanyl)-1H-indole; and
5-Bromo-7-fluoro-1-triisopropylsilanyl-1H-indole.

Preparation 2

(R)-2-Benzyl-pyrrolidine-1,2-dicarboxylic acid 1-tert-butyl ester 2-methyl ester The synthesis of (R)-2-benzyl-pyrrolidine-1,2-dicarboxylic acid 1-tert-butyl ester 2-methyl ester was carried out according to the process shown in Scheme C.

SCHEME C.

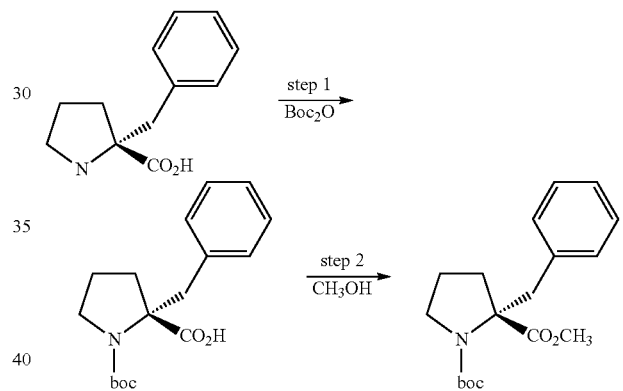

Step 1 (R)-2-Benzyl-pyrrolidine-1,2-dicarboxylic acid 1-tert-butyl ester

A mixture of (R)-2-benzyl-pyrrolidine-2-carboxylic acid (2.07 g, 10.1 mmol) and tetramethylammonium hydroxide pentahydrate (1.83 g, 10.1 mmol) in acetonitrile (100 mL) was stirred under nitrogen for 90 minutes, then (Boc)$_2$O (3.31 g, 15.2 mmol) was added. After 48 hours a second portion of (Boc)$_2$O (1.10 g, 5.0 mmol) was added. After 24 hours the reaction mixture was concentrated in vacuo, then partitioned between ether (100 mL) and water (50 mL). The aqueous phase was washed with ether (50 mL) then acidified to pH 4 with 10% aqueous citric acid (20 mL). The resultant solution was extracted with EtOAc and the combined extracts were washed with brine (30 mL), dried (MgSO$_4$), filtered and concentrated in vacuo to yield (R)-2-benzyl-pyrrolidine-1,2-dicarboxylic acid 1-tert-butyl ester (1.26 g, 4.13 mmol, 41%) as a foam.

Step 2 (R)-2-Benzyl-pyrrolidine-1,2-dicarboxylic acid 1-tert-butyl ester 2-methyl ester To a stirred solution of (R)-2-benzyl-pyrrolidine-1,2-dicarboxylic acid 1-tert-butyl ester (1.23 g, 4.0 mmol) in THF (10 mL) and methanol (10 mL) at 0° C. under nitrogen was added TMS-diazomethane (5.0 mL of a 2.0 M solution in hexanes, 5.0 mmol) dropwise. The reaction mixture was warmed to ambient temperature then concentrated in vacuo to an oil (1.36 g). Purification by chromatography (silica, 5-15% EtOAc in hexanes) gave (R)-2-benzyl-pyrrolidine-1,2-dicarboxylic acid 1-tert-butyl ester 2-methyl ester (1.03 g, 3.23 mmol, 81%) as an oil.

Preparation 3

2-n-Butyl-2-formyl-pyrrolidine-1-carboxylic acid tert-butyl ester

The synthesis of 2-butyl-2-formyl-pyrrolidine-1-carboxylic acid tert-butyl ester was carried out according to the process shown in Scheme D.

SCHEME D

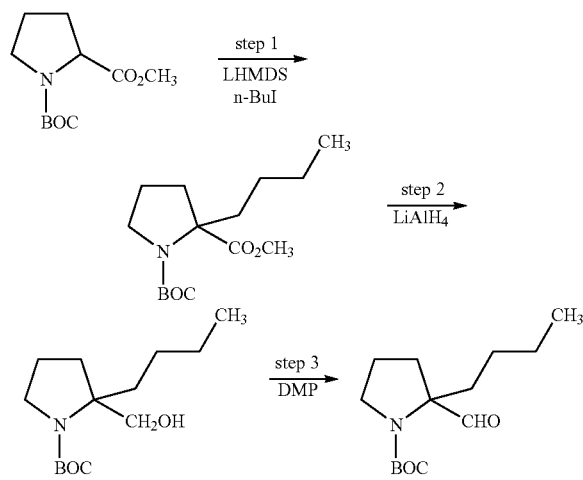

Step 1 2-n-Butyl-pyrrolidine-1,2-dicarboxylic acid 1-tert-butyl ester 2-methyl ester To a stirred solution of pyrrolidine-1,2-dicarboxylic acid 1-tert-butyl ester 2-methyl ester (3.00 g, 13.1 mmol) in THF (50 mL) at −78° C. and under nitrogen was added LHMDS (14.4 mL of 1.0 M solution in THF, 14.4 mmol) dropwise. After 30 minutes, a solution of 1-iodobutane (2.23 mL, 19.7 mmol) in THF (1 mL) was added dropwise. The reaction mixture was stirred for 30 minutes at −78° C., warmed to ambient temperature over 90 minutes, then quenched by the addition of saturated aqueous $NH_4Cl$ and extracted with EtOAc. The combined extracts were washed with saturated aqueous $NaHCO_3$ and brine then dried ($MgSO_4$), filtered and concentrated in vacuo to a yellow oil (4.5 g). Purification by chromatography (silica, 10% EtOAc in hexanes) gave 2-butyl-pyrrolidine-1,2-dicarboxylic acid 1-tert-butyl ester 2-methyl ester (2.57 g, 9.01 mmol, 69%) as a clear colourless oil.

Utilizing the above procedure and the appropriate starting materials the following were similarly prepared:

2-Propyl-pyrrolidine-1,2-dicarboxylic acid 1-tert-butyl ester 2-methyl ester (colourless oil, 85%) using 1-iodopropane;

2-Ethoxymethyl-pyrrolidine-1,2-dicarboxylic acid 1-tert-butyl ester 2-methyl ester (colourless oil, 76%) using chloromethoxy-ethane;

2-(3,3-Difluoro-allyl)-pyrrolidine-1,2-dicarboxylic acid 1-tert-butyl ester 2-methyl ester (colourless oil, 11%) using 1,1,1-trifluoro-3-iodopropane;

2-Isopropoxymethyl-pyrrolidine-1,2-dicarboxylic acid 1-tert-butyl ester 2-ethyl ester (colourless oil, 49%) from chloromethoxyisopropyl ether and pyrrolidine-1,2-dicarboxylic acid 1-tert-butyl ester 2-ethyl ester;

2-Isobutyl-pyrrolidine-1,2-dicarboxylic acid 1-tert-butyl ester 2-ethyl ester (colourless oil, 67%) from 1-iodo-2-methylpropane and pyrrolidine-1,2-dicarboxylic acid 1-tert-butyl ester 2-ethyl ester;

2-Cyclopropylmethyl-pyrrolidine-1,2-dicarboxylic acid 1-tert-butyl ester 2-ethyl ester (colourless oil, 50%) from cyclopropylmethyl bromide and pyrrolidine-1,2-dicarboxylic acid 1-tert-butyl ester 2-ethyl ester;

5,5-Dimethyl-2-propyl-pyrrolidine-1,2-dicarboxylic acid 1-tert-butyl ester 2-methyl ester, (colourless oil, 76%) from 1-iodopropane and 5,5-Dimethyl-pyrrolidine-1,2-dicarboxylic acid 1-tert-butyl ester 2-methyl ester:

(2R,4R)-4-(tert-Butyl-dimethyl-silanyloxy)-2-propyl-pyrrolidine-1,2-dicarboxylic acid 1-tert-butyl ester 2-methyl ester (colourless oil, 26%) and (2S,4R)-4-(tert-butyl-dimethyl-silanyloxy)-2-propyl-pyrrolidine-1,2-dicarboxylic acid 1-tert-butyl ester 2-methyl ester colourless oil, 30%) from 1-iodopropane and (2S,4R)-4-(tert-Butyl-dimethyl-silanyloxy)-pyrrolidine-1,2-dicarboxylic acid 1-tert-butyl ester 2-methyl ester;

2-Propyl-azetidine-1,2-dicarboxylic acid 1-tert-butyl ester 2-methyl ester (colourless oil, 80%) from 1-iodopropane and azetidine-1,2-dicarboxylic acid 1-tert-butyl ester 2-methyl ester;

2-Propyl-piperidine-1,2-dicarboxylic acid 1-tert-butyl ester 2-ethyl ester, (colourless oil, 38%) from 1-iodopropane and piperidine-1,2-dicarboxylic acid 1-tert-butyl ester 2-ethyl ester; and 2-(Tetrahydro-pyran-4-ylmethyl)-pyrrolidine-1,2-dicarboxylic acid 1-tert-butyl ester 2-methyl ester.

Step 2
2-n-Butyl-2-hydroxymethyl-pyrrolidine-1-carboxylic acid tert-butyl ester

To a stirred solution of 2-butyl-pyrrolidine-1,2-dicarboxylic acid 1-tert-butyl ester 2-methyl ester (0.842 g, 2.95 mmol) in THF (30 mL) at 0° C. under nitrogen was added $LiAlH_4$ (2.95 mL of a 1.0 M solution in THF, 2.95 mmol) dropwise. After 15 min the reaction mixture was quenched by the addition of sodium sulfate decahydrate (2.5 g) then filtered. The filter cake was washed with DCM (50 mL) then the combined filtrates were concentrated in vacuo to give 2-butyl-2-hydroxymethyl-pyrrolidine-1-carboxylic acid tert-butyl ester (0.763 g) as a clear, colourless oil that was used directly without further purification.

Utilizing the above procedure and the appropriate starting materials the following were similarly prepared:

2-Hydroxymethyl-2-propyl-pyrrolidine-1-carboxylic acid tert-butyl ester (yellow oil, 94%);

2-Hydroxymethyl-2-isopropoxymethyl-pyrrolidine-1-carboxylic acid tert-butyl ester (colourless oil, 89%);

2-Hydroxymethyl-2-isobutyl-pyrrolidine-1-carboxylic acid tert-butyl ester, (colourless oil, 100%);

2-Cyclopropylmethyl-2-hydroxymethyl-pyrrolidine-1-carboxylic acid tert-butyl ester, colourless oil, 100%);

2-Hydroxymethyl-5,5-dimethyl-2-propyl-pyrrolidine-1-carboxylic acid tert-butyl ester, (colourless oil, 100%);

(2S,4R)-2-Hydroxymethyl-2-propyl-4-(1,1,2,2-tetramethyl-propoxy)-pyrrolidine-1-carboxylic acid tert-butyl ester, (colourless oil, 100%) and 2-Hydroxymethyl-2-(tetrahydro-pyran-4-ylmethyl)-pyrrolidine-1-carboxylic acid tert-butyl ester.

Step 3 2-n-Butyl-2-formyl-pyrrolidine-1-carboxylic acid tert-butyl ester

To a stirred solution of 2-2-butyl-2-hydroxymethyl-pyrrolidine-1-carboxylic acid tert-butyl ester (0.763 g, ca. 2.95 mmol) in DCM (30 mL) at 0° C. under nitrogen was added DMP (2.50 g, 5.90 mmol) in a single portion then the reaction mixture was warmed to ambient temperature. After 14 h the reaction mixture was diluted with DCM (70 mL), washed with 1 N NaOH (2×30 mL) and brine (30 mL) then dried (MgSO$_4$), filtered and concentrated in vacuo. Purification by chromatography (silica, 10-20% EtOAc in hexanes) gave 2-butyl-2-formyl-pyrrolidine-1-carboxylic acid tert-butyl ester (0.359 g, 1.41 mmol, 48%) as a pale yellow oil.

Utilizing the above procedure and the appropriate starting materials the following were similarly prepared:
2-Formyl-2-propyl-pyrrolidine-1-carboxylic acid tert-butyl ester (colourless oil, 92%);
2-Formyl-2-isopropoxymethyl-pyrrolidine-1-carboxylic acid tert-butyl ester (colourless oil, 77%);
2-Formyl-2-isobutyl-pyrrolidine-1-carboxylic acid tert-butyl ester, (colourless oil, 79%);
2-Cyclopropylmethyl-2-formyl-pyrrolidine-1-carboxylic acid tert-butyl ester, (yellow oil, 85%);
2-Formyl-5,5-dimethyl-2-propyl-pyrrolidine-1-carboxylic acid tert-butyl ester, (colourless oil, 85%):
(2S,4R)-4-(tert-Butyl-dimethyl-silanyloxy)-2-formyl-2-propyl-pyrrolidine-1-carboxylic acid tert-butyl ester, (colourless oil, 63%); and
2-Formyl-2-(tetrahydro-pyran-4-ylmethyl)-pyrrolidine-1-carboxylic acid tert-butyl ester.

Preparation 4

2-Ethoxymethyl-2-formyl-pyrrolidine-1-carboxylic acid tert-butyl ester

The synthetic procedure for this preparation is outlined in Scheme E below.

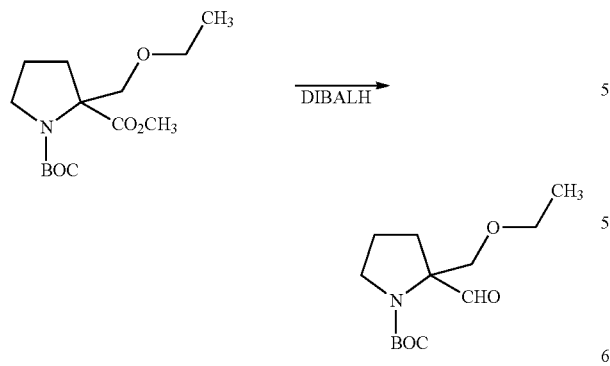

To a stirred solution of 2-ethoxymethyl-pyrrolidine-1,2-dicarboxylic acid 1-tert-butyl ester 2-methyl ester (1.00 g, 3.48 mmol, prepared using the procedure of preparation 3 step 1) in THF (40 mL) at −78° C. under nitrogen was added DIBALH (4.09 mL of 1.7 M solution in PhCH$_3$, 6.96 mmol) dropwise over 15 minutes such that the internal temperature did not exceed −75° C. After 4.5 hours the reaction mixture was quenched by addition of sodium sulfate decahydrate (4 g) and MeOH (0.5 mL) and then warmed to ambient temperature. The reaction mixture was diluted with EtOAc (50 mL) and filtered. The filter cake was washed with EtOAc (200 mL), and the combined filtrates were concentrated in vacuo to a colourless oil. Purification by chromatography (silica, 10-30% EtOAc in hexanes) gave 2-ethoxymethyl-2-formyl-pyrrolidine-1-carboxylic acid tert-butyl ester (0.528 g, 2.05 mmol, 59%) as a clear, colourless oil.

Utilizing the above procedure and the appropriate starting materials the following were similarly prepared:
2-(3,3-Difluoro-allyl)-2-formyl-pyrrolidine-1-carboxylic acid tert-butyl ester (colourless oil, 100%);
(2R,4R)-4-(tert-Butyl-dimethyl-silanyloxy)-2-formyl-2-propyl-pyrrolidine-1-carboxylic acid tert-butyl ester, (colourless oil, 36%);
2-Formyl-2-propyl-azetidine-1-carboxylic acid tert-butyl ester, (colourless oil, 53%); and
2-Hydroxymethyl-2-propyl-piperidine-1-carboxylic acid tert-butyl ester, (colourless oil, 72%).

Preparation 5

4-Formyl-4-propyl-piperidine-1-carboxylic acid tert-butyl ester

The synthetic procedure for this preparation is outlined in Scheme F below.

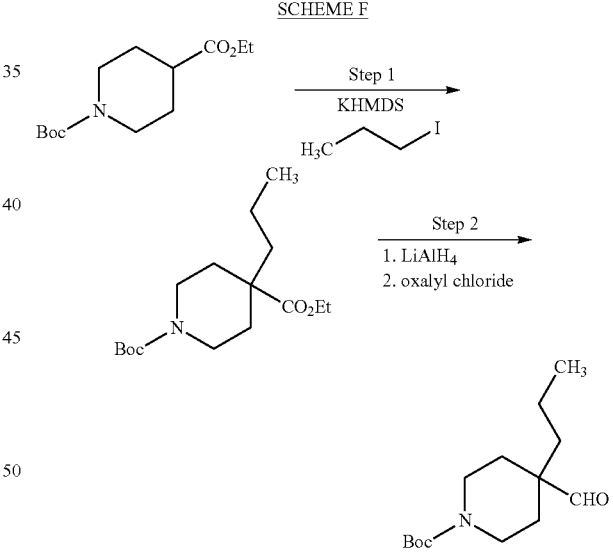

Step 1 4-Propyl-piperidine-1,4-dicarboxylic acid 1-tert-butyl ester 4-ethyl ester To a solution of potassium hexamethyldisilazide (29.1 g, 146 mmol) in THF (200 mL) at −78° C. was added ethyl N-Boc-piperidine-4-carboxylate (25 g, 97 mmol). The reaction mixture was stirred at −78° C. for 30 minutes, then 1-iodopropane (14.2 mL, 146 mmol) was slowly added. The reaction mixture was stirred at −78° C. for a further 20 minutes, then warmed to room temperature and stirred for 1 hour. The reaction was quenched by addition of saturated aqueous NH$_4$Cl solution and extracted with EtOAc. The combined organic extracts were washed with brine, dried over MgSO₄, filtered and evaporated under reduced pressure. The residue was purified by flash chromatography (0% to 50% EtOAc in hexanes) to afford 19.3 g (66%) of 4-propyl-piperidine-1,4-dicarboxylic acid 1-tert-butyl ester 4-ethyl ester as a yellow oil.

Step 2 4-Formyl-4-propyl-piperidine-1-carboxylic acid tert-butyl ester

To a solution of 4-propyl-piperidine-1,4-dicarboxylic acid 1-tert-butyl ester 4-ethyl ester (19.3 g, 64.3 mmol) in THF (120 mL) at 0° C. was slowly added lithium aluminum hydride (1.0 M in THF, 65 mL, 65 mmol). The reaction mixture was stirred at 0° C. for one hour, then quenched by the slow addition of solid Na₂SO₄.10H₂O, and stirred vigorously at room temperature for one hour. The solids were removed via filtration through Celite, rinsing with EtOAc. The filtrate was concentrated under reduced pressure to give a yellow oil.

In a separate flask, oxalyl chloride (5.4 mL, 64.3 mmol) was dissolved in dichloromethane (150 mL) and cooled to −78° C. Dimethylsulfoxide (9.1 mL, 130 mmol) was slowly added and the reaction mixture was stirred at −78° C. for 15 min. The above yellow oil dissolved in dichloromethane (50 mL) was slowly added. After stirring at −78° C. for 15 minutes, Et₃N (45 mL, 322 mmol) was added. The reaction mixture was allowed to warm to room temperature over one hour, then was quenched with H₂O and extracted with dichloromethane. The combined organic extracts were dried over MgSO₄, filtered and concentrated under reduced pressure. The residue was purified by flash chromatography (0% to 50% EtOAc in hexanes) to afford 12.3 g (75%) of 4-formyl-4-propyl-piperidine-1-carboxylic acid tert-butyl ester as a colorless oil.

Example 1

(3-Benzyl-pyrrolidin-3-yl)-(1H-indol-5-yl)-methanone

The synthetic procedure described in this Example was carried out according to the process shown in Scheme G.

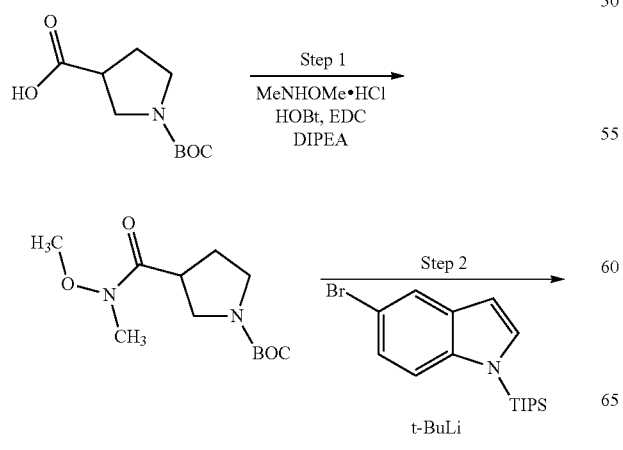

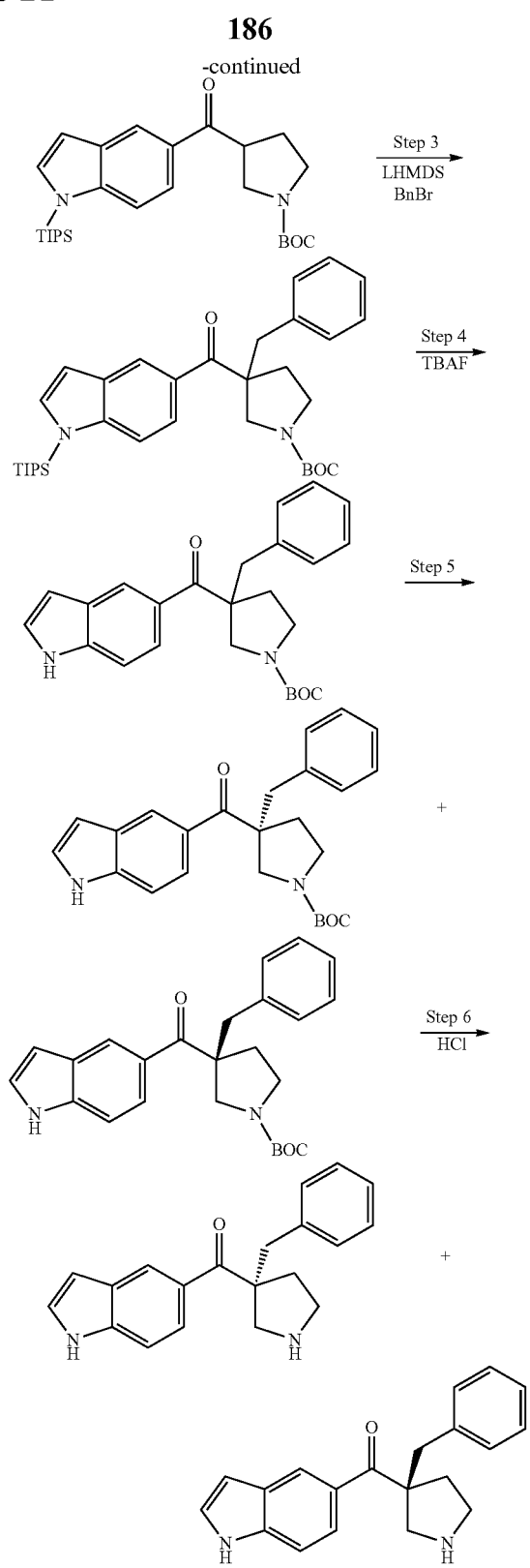

Step 1 3-(Methoxy-methyl-carbamoyl)-pyrrolidine-1-carboxylic acid tert-butyl

Pyrrolidine-1,3-dicarboxylic acid 1-tert-butyl ester (3.00 g, 13.93 mmol), N,O-dimethylhydroxylamine hydrochloride (1.63 g, 16.72 mmol), 1-(3-dimethylaminopropyl)-3-ethylcarbodiimide hydrochloride (2.94 g, 15.32 mmol) and 1-hydroxybenzotriazole (2.07 g, 15.32 mmol) were placed in a 100 mL round bottomed flask and dissolved in DMF (30 mL). Diisopropylethylamine (6.1 mL, 34.82 mmol) was slowly added, and the reaction mixture was stirred at room temperature for 24 hours. The reaction was quenched by addition of water and extracted with ethyl acetate. The combined organic extracts were washed with water and brine, dried over $MgSO_4$, filtered and evaporated under reduced pressure to give 2.60 g (72% yield) of 3-(methoxy-methyl-carbamoyl)-pyrrolidine-1-carboxylic acid tert-butyl ester as a pale yellow oil which was used in the next step without further purification.

Similarly prepared using the procedure of step 1 were:
4-(Methoxy-methyl-carbamoyl)-piperidine-1-carboxylic acid tert-butyl ester;
3-(Methoxy-methyl-carbamoyl)-piperidine-1-carboxylic acid tert-butyl ester;
2-(Methoxy-methyl-carbamoyl)-azetidine-1-carboxylic acid tert-butyl ester; and
3-(Methoxy-methyl-carbamoyl)-azepine-1-carboxylic acid tert-butyl ester.

Step 2 3-(1-Triisopropylsilanyl-1H-indole-5-carbonyl)-pyrrolidine-1-carboxylic acid tert-butyl ester tert-Butyllithium (1.7 M in pentane, 13 mL, 22.13 mmol) was added to a solution of 5-bromo-1-triisopropylsilanyl-1H-indole (3.54 g, 10.06 mmol) in THF (35 mL) at −78° C. under nitrogen atmosphere. The pale yellow reaction mixture was stirred at −78° C. for 15 minutes, then a solution of 3-(methoxy-methyl-carbamoyl)-pyrrolidine-1-carboxylic acid tert-butyl ester (2.60 g, 10.06 mmol) in THF (5 mL) was slowly added. The resulting mixture was stirred at −78° C. for 30 minutes, then allowed to warm to room temperature over a period of 1 hour. The reaction was quenched by addition of a saturated aqueous solution of $NH_4Cl$ and was partitioned between water and EtOAc. The organic layer was dried over $MgSO_4$, filtered and evaporated under reduced pressure. The crude residue was purified by flash chromatography (10% to 25% of EtOAc in hexane) to give 2.66 g (56% yield) of 3-(1-triisopropylsilanyl-1H-indole-5-carbonyl)-pyrrolidine-1-carboxylic acid tert-butyl ester as colorless oil.

Step 3 3-Benzyl-3-(1-triisopropylsilanyl-1H-indole-5-carbonyl)-pyrrolidine-1-carboxylic acid tert-butyl ester Lithium bis(trimethylsilyl)amide (1.0 M in THF, 12.1 mL) was added to a solution of 3-(1-triisopropylsilanyl-1H-indole-5-carbonyl)-pyrrolidine-1-carboxylic acid tert-butyl ester (1.90 g, 4.03 mmol) in THF (25 mL) at 0° C. under nitrogen atmosphere. The reaction mixture was stirred at 0° C. for 10 minutes and then benzyl bromide (1.9 mL, 16.12 mmol) was added. The resulting mixture was warmed to room temperature and stirred for 1.5 hours. The reaction was quenched by addition of a saturated aqueous solution of $NH_4Cl$, then diluted with water and extracted with EtOAc. The organic layer was dried over $MgSO_4$, filtered and evaporated under reduced pressure. The residue was purified by flash chromatography (10% to 20% of EtOAc in hexane) to give 1.55 g (69% yield) of 3-benzyl-3-(1-triisopropylsilanyl-1H-indole-5-carbonyl)-pyrrolidine-1-carboxylic acid tert-butyl ester as a white foam.

Step 4 3-Benzyl-3-(1H-indole-5-carbonyl)-pyrrolidine-1-carboxylic acid tert-butyl ester A solution of tetrabutylammonium fluoride (1.0 M in THF, 1.2 mL) was slowly added at 0° C. to a solution of 3-benzyl-3-(1-triisopropylsilanyl-1H-indole-5-carbonyl)-pyrrolidine-1-carboxylic acid tert-butyl ester (670 mg, 1.19 mmol) in THF (15 mL). The resulting bright yellow mixture was stirred at 0° C. for 20 minutes, then was quenched by addition of water. The resulting mixture was extracted with EtOAc, and the combined organic layers were dried over $MgSO_4$, filtered and evaporated under reduced pressure. The residue was purified by flash chromatography (30% to 50% of EtOAc in hexane) to give 447 mg (93% yield) of 3-benzyl-3-(1H-indole-5-carbonyl)-pyrrolidine-1-carboxylic acid tert-butyl ester as a white foam.

Step 5 Separation of (+)-3-Benzyl-3-(1H-indole-5-carbonyl)-pyrrolidine-1-carboxylic acid tert-butyl ester and (−)-3-Benzyl-3-(1H-indole-5-carbonyl) pyrrolidine-1-carboxylicacid tert-butyl ester The two enantiomers of 3-Benzyl-3-(1H-indole-5-carbonyl)-pyrrolidine-1-carboxylic acid tert-butyl ester were separated by chiral HPLC (using a Chiralpak IA column, with 90/10 hexane/EtOH, 1.4 mL/min.).
Enantiomer A:
$[\alpha]_d=+8.6°$ (5.2 mg/1.0 mL of EtOH).
Enantiomer B:
$[\alpha]_d=-10.2°$ (5.2 mg/1.0 mL of EtOH).

Step 6 (+)-(3-Benzyl-pyrrolidin-3-yl)-(1H-indol-5-yl)-methanone and (−)-(3-Benzyl-pyrrolidin-3-yl)-(1H-indol-5-yl)-methanone A solution of HCl (1.0 M in MeOH, 12 mL) was added to a solution of 3-benzyl-3-(1H-indole-5-carbonyl)-pyrrolidine-1-carboxylic acid tert-butyl ester enantiomer A (257 mg, 0.635 mmol) in MeOH (5 mL). The resulting pale yellow solution was stirred at room temperature for 6 hours, then cooled to 0° C. and quenched by addition of aqueous NaOH (1.0 M). The mixture was diluted with water and extracted with DCM. The combined organic layers were dried over $MgSO_4$, filtered and evaporated under reduced pressure. The residue was purified by flash chromatography (5% to 10% of MeOH in DCM with 0.5% of $NH_4OH$) to give 179 mg (93% yield) of (3-Benzyl-pyrrolidin-3-yl)-(1H-indol-5-yl)-methanone, which was dissolved in a mixture of DCM/MeOH. A solution of HCl (1 M in $Et_2O$) was added, and the resulting mixture was evaporated under reduced pressure and the residue was triturated with $Et_2O$ to give 173 mg of (3-benzyl-pyrrolidin-3-yl)-(1H-indol-5-yl)-methanone hydrochloride enantiomer A as a white powder. MS=305 $[M+H]^+$; $[\alpha]_D=-26.3°$ (5.40 mg/1.0 mL of MeOH).

In a similar manner (3-benzyl-pyrrolidin-3-yl)-(1H-indol-5-yl)-methanone hydrochloride enantiomer B was prepared: $[\alpha]_D=+24.4°$ (5.45 mg/1.0 mL of MeOH).

Utilizing the procedure of Example 1 with the appropriate starting material, the following compounds were prepared:
(3-Benzyl-pyrrolidin-3-yl)-(7-fluoro-1H-indol-5-yl)-methanone hydrochloride, pink powder, MS=324 $[M+H]^+$;
(1H-Indol-5-yl)-[3-(3-methoxy-benzyl)-pyrrolidin-3-yl]-methanone hydrochloride, light pink powder, MS=335 $[M+H]^+$;
3-[3-(1H-Indole-5-carbonyl)-pyrrolidin-3-ylmethyl]-benzonitrile hydrochloride, white solid, MS=330 $[M+H]^+$;
[3-(3-Fluoro-benzyl)-pyrrolidin-3-yl]-(1H-indol-5-yl)-methanone hydrochloride, pink-orange solid, MS=323 $[M+H]^+$;
[3-(4-Fluoro-benzyl)-pyrrolidin-3-yl]-(1H-indol-5-yl)-methanone hydrochloride, red powder, MS=323 $[M+H]^+$;

(1H-Indol-5-yl)-[3-(4-methoxy-benzyl)-pyrrolidin-3-yl]-methanone hydrochloride, MS=335 [M+H]+;

[3-(3,4-Dichloro-benzyl)-pyrrolidin-3-yl]-(1H-indol-5-yl)-methanone hydrochloride, off-white powder, MS=374 [M+H]+;

[3-(2-Fluoro-benzyl)-pyrrolidin-3-yl]-(1H-indol-5-yl)-methanone hydrochloride, pink solid, MS=323 [M+H]+;

(3-Benzyl-pyrrolidin-3-yl)-(2-methyl-1H-indol-5-yl)-methanone hydrochloride, yellow solid, MS=319 [M+H]+;

(3-Benzyl-pyrrolidin-3-yl)-(2,3-dihydro-1H-indol-5-yl)-methanone hydrochloride, light yellow powder, MS=307 [M+H]+;

(4-Benzyl-piperidin-4-yl)-(1H-indol-5-yl)-methanone, off-white powder, MS=319 [M+H]+;

(3-Benzyl-piperidin-3-yl)-(1H-indol-5-yl)-methanone, white solid, MS=319 [M+H]+: the two enantiomers were separated by chiral HPLC on a Chiralpak IB column with 65/35 hexane/EtOH+0.1% DEA, 1.0 ml/min;

Enantiomer A hydrochloride salt (white powder), $[\alpha]_D$=−126.4° (5.12 mg/1.024 mL of MeOH), Enantiomer B hydrochloride salt (white powder), $[\alpha]_D$=+129.4° (5.26 mg/1.052 mL of MeOH).

(1H-Indol-5-yl)-[3-(4-methoxy-benzyl)-piperidin-3-yl]methanone hydrochloride, pale yellow powder, MS=349 [M+H]+;

[3-(3-Fluoro-benzyl)-piperidin-3-yl]-(1H-indol-5-yl)-methanone hydrochloride, white solid, MS=337 [M+H]+;

Additional compounds prepared by the above procedure are shown in Table 1.

Example 2

5-(3-Benzyl-pyrrolidine-3-carbonyl)-1H-indole-3-carbonitrile

The synthetic procedure described in this Example was carried out according to the process shown in Scheme H.

SCHEME H

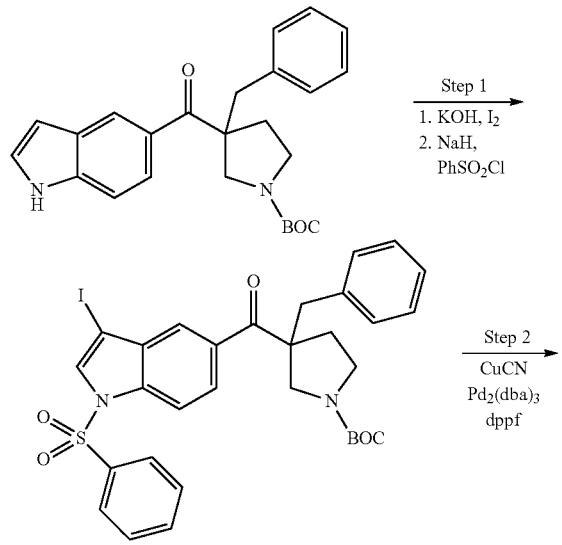

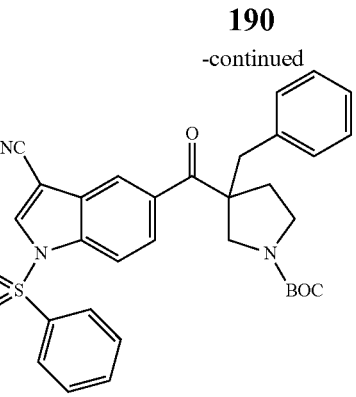

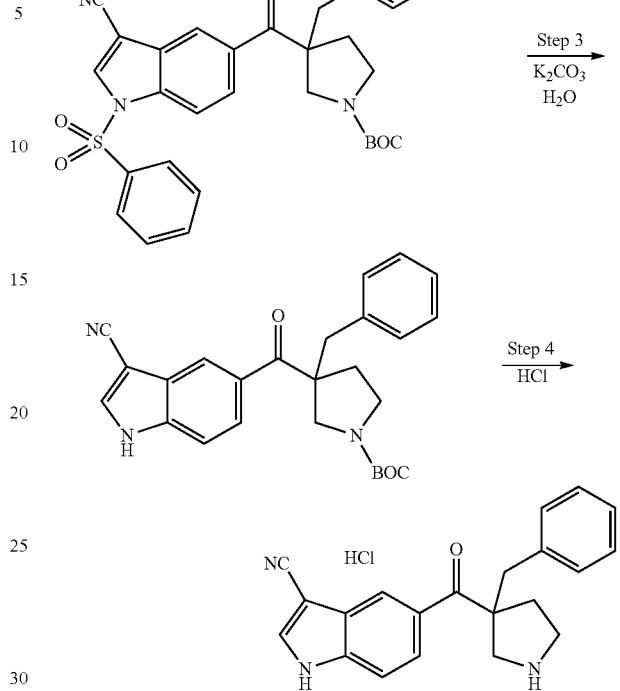

Step 1 3-(1-Benzenesulfonyl-3-iodo-1H-indole-5-carbonyl)-3-benzyl-pyrrolidine-1-carboxylic acid tert-butyl ester Freshly crushed potassium hydroxide (35 mg, 0.617 mmol) was added to a solution of 3-benzyl-3-(1H-indole-5-carbonyl)-pyrrolidine-1-carboxylic acid tert-butyl ester (100 mg, 0.247 mmol) in DMF (1.5 mL). A solution of iodine (63 mg, 0.247 mmol) in DMF (0.5 mL) was then added dropwise, and the reaction mixture was stirred at room temperature for 45 minutes. The reaction was quenched by addition of an aqueous solution of $Na_2S_2O_3$ and diluted with water. The resulting mixture was extracted with EtOAc; the combined organic extracts were washed with water, dried over $MgSO_4$, filtered and evaporated under reduced pressure. The residue was immediately dissolved in DMF (2 mL), and NaH (60% in mineral oil, 12 mg, 0.296 mmol) was added to the solution. The resulting mixture was stirred for 20 minutes, after which benzenesulfonyl chloride (38 μL, 0.296 mmol) was then added dropwise. The reaction mixture was stirred for 30 minutes, then quenched by addition of water. The resulting mixture was extracted with EtOAc, and the combined organic extracts were washed with water, dried over $MgSO_4$, filtered and evaporated under reduced pressure. The residue was purified by flash chromatography (10% to 30% of EtOAc in hexane) to give 150 mg (91% yield) of 3-(1-benzenesulfonyl-3-iodo-1H-indole-5-carbonyl)-3-benzyl-pyrrolidine-1-carboxylic acid tert-butyl ester as a white foam.

Step 2 3-(1-Benzenesulfonyl-3-cyano-1H-indole-5-carbonyl)-3-benzyl-pyrrolidine-1-carboxylic acid tert-butyl ester Copper(I) cyanide (76 mg, 0.852 mmol) was added to a 25 mL round bottom flask charged with 3-(1-benzenesulfonyl- 3-iodo-1H-indole-5-carbonyl)-3-benzyl-pyrrolidine-1-carboxylic acid tert-butyl ester (143 mg, 0.213 mmol), followed by 1,1'-bis(diphenylphosphino)ferrocene (24 mg, 0.043 mmol) and tris(dibenzylideneacetone) dipalladium(0) (10 mg, 0.011 mmol). 1,4-Dioxane (1.5 mL) was then added and the mixture was heated to reflux under nitrogen atmosphere for one hour. The reaction mixture was cooled to room temperature and filtered through a celite pad. The filter cake was rinsed with EtOAc and the filtrate was concentrated under reduced pressure. The residue was purified by flash chromatography (30% of EtOAc in hexane) to give 115 mg (95% yield) of 3-(1-benzenesulfonyl-3-cyano-1H-indole-5-carbonyl)-3-benzyl-pyrrolidine-1-carboxylic acid tert-butyl ester as a pale yellow foam.

Step 3 3-Benzyl-3-(3-cyano-1H-indole-5-carbonyl)-pyrrolidine-1-carboxylic acid tert-butyl ester Water (1 mL) was added to a solution of 3-(1-benzenesulfonyl-3-cyano-1H-indole-5-carbonyl)-3-benzyl-pyrrolidine-1-carboxylic acid tert-butyl ester (100 mg, 0.175 mmol) in MeOH (4 mL), followed by potassium carbonate (73 mg, 0.525 mmol). The reaction mixture was heated at 50° C. for 10 minutes, then cooled to room temperature and diluted with water and brine. The resulting mixture was extracted with DCM, dried over MgSO$_4$, filtered and evaporated under reduced pressure. The residue was purified by flash chromatography (30% to 50% of EtOAc in hexane) to give 3-benzyl-3-(3-cyano-1H-indole-5-carbonyl)-pyrrolidine-1-carboxylic acid tert-butyl ester as white foamy solid.

Step 4 5-(3-Benzyl-pyrrolidine-3-carbonyl)-1H-indole-3-carbonitrile

A solution of HCl (1.0 M in MeOH, 8 mL) was slowly added at 0° C. to a solution of 3-benzyl-3-(3-cyano-1H-indole-5-carbonyl)-pyrrolidine-1-carboxylic acid tert-butyl ester (169 mg, 0.393 mmol) in MeOH (2 mL). The resulting pale yellow mixture was stirred at room temperature for 4 hours, then was quenched by addition of 0° C. aqueous NaOH (1.0 M). The resulting mixture was diluted with water and extracted with DCM. The combined organic extracts were dried over MgSO$_4$, filtered and evaporated under reduced pressure. The crude was purified by flash chromatography (MeOH in DCM with 0.5% of NH$_4$OH) to give 42 mg of 5-(3-Benzyl-pyrrolidine-3-carbonyl)-1H-indole-3-carbonitrile as a white foamy solid. This product was dissolved in DCM and a solution of HCl (1.0 M in Et$_{20}$, 1 equivalent) was added. MeOH was added and the resulting mixture was evaporated under reduced pressure. The residue was triturated with Et$_2$O and 32 mg of 5-(3-benzyl-pyrrolidine-3-carbonyl)-1H-indole-3-carbonitrile hydrochloride was collected as a white solid; MS=330 [M+H]$^+$.

Additional compounds prepared by the above procedure are shown in Table 1.

Example 3

(1H-Indazol-5-yl)-(3-propyl-pyrrolidin-3-yl)-methanone hydrochloride

The synthetic procedure described in this Example was carried out according to the process shown in Scheme I.

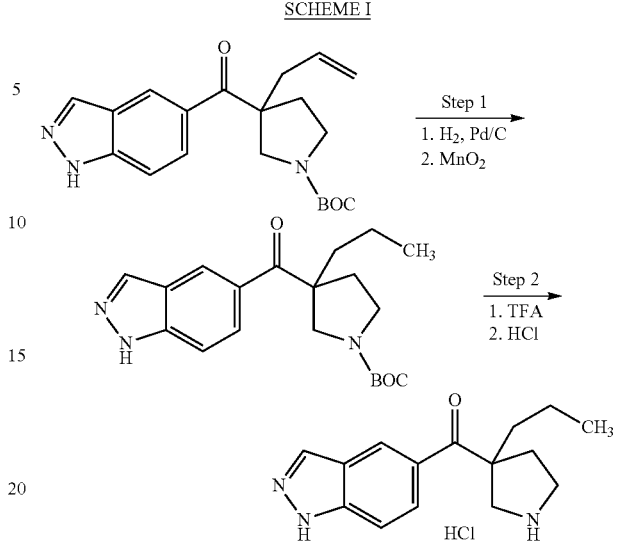

SCHEME I

Step 1 5-(3-Propyl-pyrrolidine-3-carbonyl)-indazole-1-carboxylic acid tert-butyl ester 5-(3-Allyl-pyrrolidine-3-carbonyl)-indazole-1-carboxylic acid tert-butyl ester was prepared as described in steps 3 and 4 of Example 1, but replacing benzyl bromide with allyl iodide. Pd/C (10%, Degussa catalyst type E101 NE/W, 100 mg) was added to a solution of 5-(3-allyl-pyrrolidine-3-carbonyl)-indazole-1-carboxylic acid tert-butyl ester (200 mg, 0.56 mmol) in MeOH (10 mL). The resulting mixture was stirred under hydrogen atmosphere (balloon pressure) for 2.5 hours. The reaction mixture was then filtered through a celite pad and the filtrate was evaporated under reduced pressure to give 207 mg of crude 5-[hydroxy-(3-propyl-pyrrolidin-3-yl)-methyl]-indazole-1-carboxylic acid tert-butyl ester as an off-white foam. This material was dissolved in toluene (8 mL) and activated manganese dioxide (85%, 240 mg, 2.80 mmol) was added. The resulting mixture was heated at 100° C. for 3 hours, then cooled to room temperature and filtered through a celite pad. The filtrate was evaporated under reduced pressure, and the resulting residue was purified by flash chromatography to give 86 mg of 5-(3-propyl-pyrrolidine-3-carbonyl)-indazole-1-carboxylic acid tert-butyl ester as a white foamy solid.

Step 2 (1H-Indazol-5-yl)-(3-propyl-pyrrolidin-3-yl)-methanone hydrochloride 5-(3-Propyl-pyrrolidine-3-carbonyl)-indazole-1-carboxylic acid tert-butyl ester was deprotected following the procedure described in step 4 of Example 2, (1H-indazol-5-yl)-(3-propyl-pyrrolidin-3-yl)-methanone hydrochloride was obtained as a white powder; MS=258 [M+H]$^+$.

Utilizing the above described procedure and the appropriate starting material, the following compounds were prepared:

(1H-Indol-5-yl)-(3-propyl-pyrrolidin-3-yl)-methanone hydrochloride, MS=257 [M+H]+;

(3-Butyl-pyrrolidin-3-yl)-(1H-indol-5-yl)-methanone hydrochloride, MS=271 [M+H]+; and (1H-Indol-5-yl)-[3-(3-methyl-butyl)-pyrrolidin-3-yl]-methanone hydrochloride, MS=285 [M+H]+.

Additional compounds prepared by the above procedure are shown in Table 1.

Example 4

(1H-Indol-5-yl)-(3-phenyl-pyrrolidin-3-yl)-methanone

The synthetic procedure described in this Example was carried out according to the process shown in Scheme J.

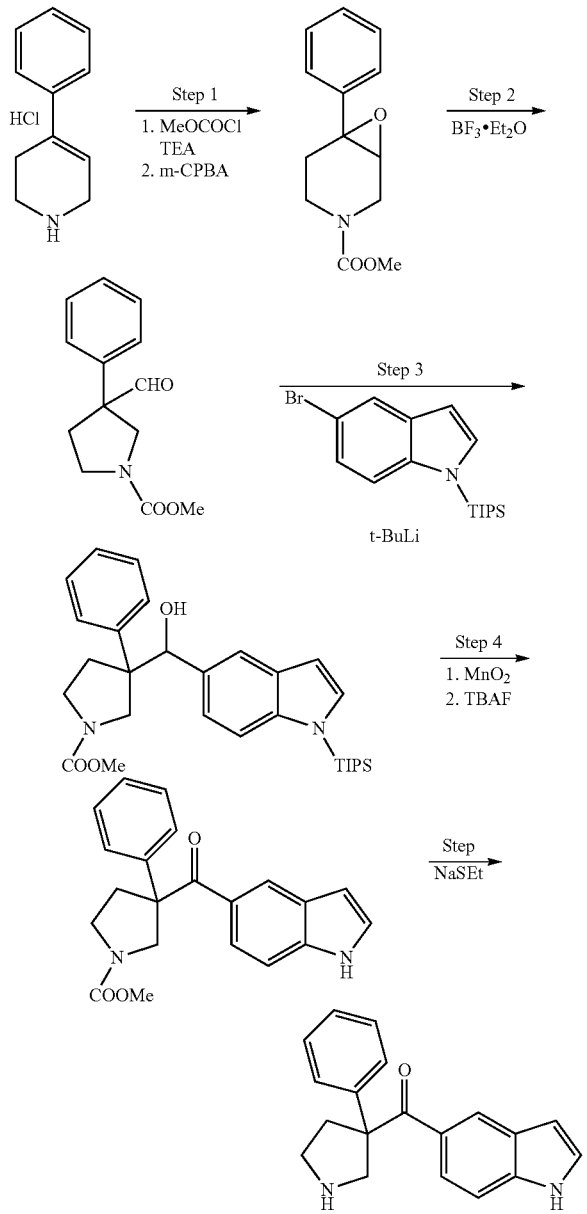

Step 1 6-Phenyl-7-oxa-3-aza-bicyclo[4.1.0]heptane-3-carboxylic acid methyl ester Triethylamine (2.6 mL, 19.15 mmol) was added to a suspension of 4-phenyl-1,2,3,6-tetrahydropyridine hydrochloride (1.50 g, 7.66 mmol) in DCM (30 mL). The resulting mixture was stirred for 5 minutes until complete dissolution of the solids, then was cooled to 0° C., and methyl chloroformate (0.65 mL, 8.43 mmol) was added dropwise. A thick white precipitate formed. The reaction mixture was warmed to room temperature and stirred for 1 hour, then was quenched by addition of water, and extracted with DCM. The combined organic extracts were dried over MgSO$_4$, filtered and evaporated under reduced pressure to give 1.75 g of 4-phenyl-3,6-dihydro-2H-pyridine-1-carboxylic acid methyl ester as a pale yellow oil. This crude product (7.66 mmol) was dissolved in chloroform (30 mL) and 3-chloroperoxybenzoic acid (77%, 2.22 g, 9.95 mmol) was added. The resulting solution was stirred at room temperature for 18 hours. An aqueous solution of Na$_2$SO$_3$ (20%, 30 mL) was added and the resulting mixture was vigorously stirred for 1 hour. The phases were separated and the aqueous layer was extracted with DCM. The combined organic extracts were washed with a saturated aqueous solution of NaHCO$_3$, dried over MgSO$_4$, filtered and evaporated under reduced pressure to give a pale yellow oil. This crude oil was purified by flash chromatography (10% to 20% of EtOAc in hexane) to give 1.68 g (94% 2 steps yield) of 6-phenyl-7-oxa-3-aza-bicyclo[4.1.0]heptane-3-carboxylic acid methyl ester as a colorless oil.

Step 2 3-Formyl-3-phenyl-pyrrolidine-1-carboxylic acid methyl ester

Boron trifluoride diethyl etherate (1.82 mL, 14.40 mmol) was slowly added at room temperature to a solution of 6-phenyl-7-oxa-3-aza-bicyclo[4.1.0]heptane-3-carboxylic acid methyl ester (1.68 g, 7.20 mmol). A slightly exothermic reaction was observed and after 5 minutes the reaction mixture was quenched by slow addition of saturated aqueous NaHCO$_3$ (50 mL). The resulting mixture was extracted with EtOAc, and the combined organic extracts were washed with water, dried over MgSO$_4$, filtered and evaporated under reduced pressure to give 1.63 g (97% yield) of 3-formyl-3-phenyl-pyrrolidine-1-carboxylic acid methyl ester as a pale yellow oil which was used without further purification.

Step 3 3-[Hydroxy-(1-triisopropylsilanyl-1H-indol-5-yl)-methyl]-3-phenyl-pyrrolidine-1-carboxylic acid methyl ester tert-Butyllithium (1.7 M in pentane, 8.9 mL, 15.10 mmol) was added at −78° C., under nitrogen atmosphere to a solution of 5-bromo-1-triisopropylsilanyl-1H-indole (2.42 g, 6.86 mmol) in THF (25 mL). The resulting pale yellow solution was stirred at −78° C. for 15 minutes, then a solution of 3-formyl-3-phenyl-pyrrolidine-1-carboxylic acid methyl ester (1.60 g, 6.86 mmol) in THF (5 mL) was then slowly added. The reaction mixture was stirred at −78° C. for 30 minutes and then warmed to room temperature over a period of 1 hour. The reaction was quenched by addition of a saturated aqueous solution of NH$_4$Cl and diluted with water. The resulting mixture was extracted with EtOAc, and the combined organic extracts were dried over MgSO$_4$, filtered and evaporated under reduced pressure. The residue was purified by flash chromatography (10% to 50% of EtOAc in hexane) to give 1.76 g (51% yield) of 3-[hydroxy-(1-triisopropylsilanyl-1H-indol-5-yl)-methyl]-3-phenyl-pyrrolidine-1-carboxylic acid methyl ester as a white foamy solid.

Step 4 3-(1H-Indole-5-carbonyl)-3-phenyl-pyrrolidine-1-carboxylic acid methyl ester Manganese dioxide (85%, 256 mg, 2.95 mmol) was added to a solution of 3-[hydroxy-(1-triisopropylsilanyl-1H-indol- 5-yl)-methyl]-3-phenyl-pyrrolidine-1-carboxylic acid methyl ester (300 mg, 0.59 mmol) in toluene (8 mL). The reaction mixture was heated at 100° C. for 2 hours, then cooled to room temperature and filtered through a celite pad. The filtrate was evaporated under reduced pressure to give 326 mg of 3-phenyl-3-(1-triisopropylsilanyl-1H-indole-5-carbonyl)-pyrrolidine-1-carboxylic acid methyl ester as a colorless foamy oil. A portion of this product (298 mg, 0.59 mmol) was dissolved in THF (8 mL) and a solution of tetrabutylammonium fluoride (1.0 M in THF, 0.60 mL, 0.59 mmol) was added at 0° C. The reaction mixture was stirred at 0° C. for 20 minutes, then was quenched by addition of water. The resulting mixture was extracted with EtOAc, and the combined organic extracts were dried over MgSO$_4$, filtered and evaporated under reduced pressure. The residue was purified by flash chromatography (30% to 50% of EtOAc in hexane) to give 167 mg (81% 2 steps yield) of 3-(1H-indole-5-carbonyl)-3-phenyl-pyrrolidine-1-carboxylic acid methyl ester as a white foam.

4-(1H-Indole-5-carbonyl)-4-phenyl-piperidine-1-carboxylic acid tert-butyl ester was prepared following the procedure described above using 4-formyl-4-phenyl-piperidine-1-carboxylic acid tert-butyl ester (prepared as described in Preparation 5).

Step 5 (1H-Indol-5-yl)-(3-phenyl-pyrrolidin-3-yl)-methanone

Sodium ethanethiolate (113 mg, 1.35 mmol) was added to a solution of 3-(1H-indole-5-carbonyl)-3-phenyl-pyrrolidine-1-carboxylic acid methyl ester (157 mg, 0.45 mmol) in DMF (3 mL). The resulting mixture was heated at 100° C. for 2 hours and then at 120° C. for 2 further hours. The reaction mixture was cooled to room temperature and quenched by addition of water. The resulting mixture was extracted with EtOAc, and the combined organic extracts were washed with water, dried over MgSO$_4$, filtered and evaporated under reduced pressure to give 230 mg of an oil that was purified by flash chromatography (MeOH/DCM/NH$_4$OH) to give 15 mg of (1H-indol-5-yl)-(3-phenyl-pyrrolidin-3-yl)-methanone; MS=291 [M+H]$^+$.

Similarly prepared was (1H-Indol-5-yl)-(4-phenyl-piperidin-4-yl)-methanone, MS=305 [M+H]$^+$.

Additional compounds prepared by the above procedure are shown in Table 1.

Example 5

(3-Benzyl-pyrrolidin-3-yl)-(1-methyl-1H-indol-5-yl)-methanone

The synthetic procedure described in this Example was carried out according to the process shown in Scheme K.

SCHEME K

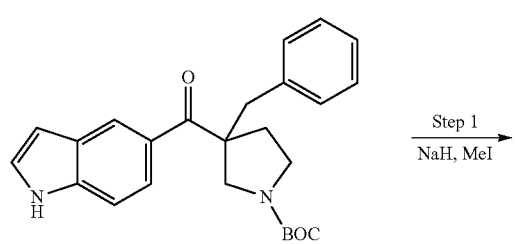

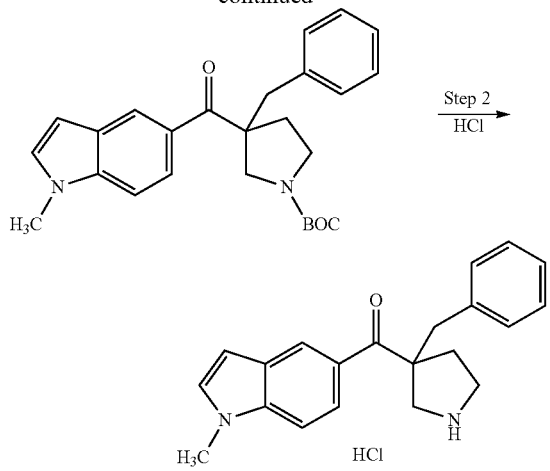

Step 1 3-Benzyl-3-(1-methyl-1H-indole-5-carbonyl)-pyrrolidine-1-carboxylic acid tert-butyl ester Sodium hydride (60% in mineral oil, 12 mg, 0.296 mmol) was added at room temperature to a solution of 3-benzyl-3-(1H-indole-5-carbonyl)-pyrrolidine-1-carboxylic acid tert-butyl ester (100 mg, 0.247 mmol) in DMF (3 mL). The resulting mixture was stirred at room temperature for 20 minutes, and then methyliodide (18 µL, 0.296 mmol) was added. The reaction mixture was then stirred for 30 minutes, then quenched by addition of water and extracted with EtOAc. The combined organic extracts were washed with water and brine, dried over MgSO$_4$, filtered and evaporated under reduced pressure to give 105 mg of 3-benzyl-3-(1-methyl-1H-indole-5-carbonyl)-pyrrolidine-1-carboxylic acid tert-butyl ester as a white foam that was used without further purification.

Step 2 (3-Benzyl-pyrrolidin-3-yl)-(1-methyl-1H-indol-5-yl)-methanone

3-Benzyl-3-(1-methyl-1H-indole-5-carbonyl)-pyrrolidine-1-carboxylic acid tert-butyl ester was deprotected as described in Example 1, Step 4 to give (3-Benzyl-pyrrolidin-3-yl)-(1-methyl-1H-indol-5-yl)-methanone as a hydrochloride salt; MS=319 [M+H]$^+$.

Additional compounds prepared by the above procedure are shown in Table 1.

Example 6

(3-Benzyl-pyrrolidin-3-yl)-(3,4-dichloro-phenyl)-methanone

The synthetic procedure described in this Example was carried out according to the process shown in Scheme L.

SCHEME L

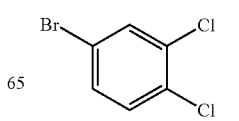

+

Step 1
3-(3,4-Dichloro-benzoyl)-pyrrolidine-1-carboxylic acid tert-butyl ester

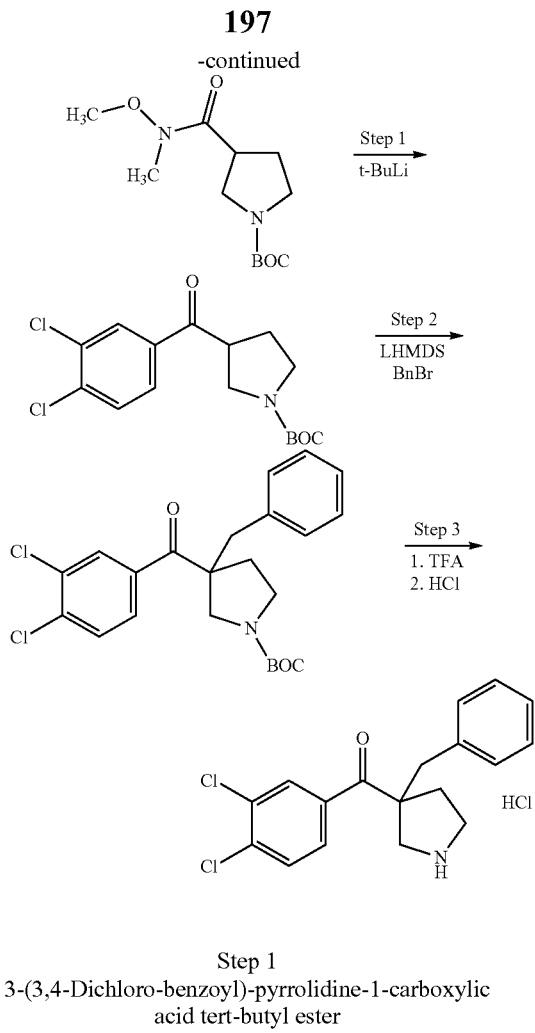

tert-Butyllithium (1.7 M in pentane, 2.5 mL, 4.25 mmol) was added at −78° C. to a solution of 4-bromo-1,2-dichlorobenzene (435 mg, 1.93 mmol) in THF (10 mL) under nitrogen atmosphere. The resulting solution was stirred at −78° C. for 15 minutes, and then a solution of 3-(methoxy-methyl-carbamoyl)-pyrrolidine-1-carboxylic acid tert-butyl ester (500 mg, 1.93 mmol) in THF (2 mL) was slowly added. The reaction mixture was stirred at −78° C. for 20 minutes and then warmed up to room temperature over a period of 30 minutes. The reaction was quenched by addition of saturated aqueous NH$_4$Cl, then diluted with water and extracted with EtOAc. The combined organic extracts were dried over MgSO$_4$, filtered and evaporated under reduced pressure to give an oil that was purified by flash chromatography (10% to 30% of EtOAc in hexane) to give 143 mg (22% yield) of 3-(3,4-dichloro-benzoyl)-pyrrolidine-1-carboxylic acid tert-butyl ester as a colorless oil.

Step 2 3-Benzyl-3-(3,4-dichloro-benzoyl)-pyrrolidine-1-carboxylic acid tert-butyl ester Benzyl bromide (0.19 mL, 1.60 mmol) was added to a solution of 3-(3,4-dichloro-benzoyl)-pyrrolidine-1-carboxylic acid tert-butyl ester (138 mg, 0.40 mmol) in THF (5 mL), and then lithium bis(trimethylsilyl)amide (1.0 M, in THF, 1.2 mL, 1.20 mmol) was slowly added at room temperature. The reaction mixture was stirred at room temperature for 1.5 hours, then was quenched by addition of saturated aqueous NH$_4$Cl, diluted with water, and extracted with EtOAc. The combined organic extracts were dried over MgSO$_4$, filtered and evaporated under reduced pressure. The residue was purified by flash chromatography (10% to 20% of EtOAc in hexane) to give 40 mg (23% yield) of 3-benzyl-3-(3,4-dichloro-benzoyl)-pyrrolidine-1-carboxylic acid tert-butyl ester as a colorless oil.

Step 3 3-Benzyl-pyrrolidin-3-yl)-(3,4-dichloro-phenyl)-methanone

Trifluoroacetic acid (0.3 mL) was added at room temperature to a solution of 3-benzyl-3-(3,4-dichloro-benzoyl)-pyrrolidine-1-carboxylic acid tert-butyl ester (40 mg, 0.092 mmol) in DCM (3 mL). The reaction mixture was stirred at room temperature for 1 hour, then poured into aqueous NaOH (1.0 M), diluted with water and extracted with DCM. The combined organic extracts were dried over MgSO$_4$, filtered and evaporated under reduced pressure. The residue was purified by flash chromatography (3% to 10% of MeOH in DCM+ 0.5% of NH$_4$OH) to give 15 mg (48% yield) of 3-benzyl-pyrrolidin-3-yl)-(3,4-dichloro-phenyl)-methanone as a yellow oil. This material was dissolved in DCM and a solution of HCl (1.0 M in Et$_2$O, 1.1 equivalents) was added, the resulting mixture was concentrated under reduced pressure and the residue was triturated with Et$_2$O to give 17 mg of 3-benzyl-pyrrolidin-3-yl)-(3,4-dichloro-phenyl)-methanone hydrochloride as a white solid; MS=334 [M+H]$^+$.

Additional compounds prepared by the above procedure are shown in Table 1.

Example 7

5-(3-Benzyl-pyrrolidine-3-carbonyl)-1,3-dihydro-indol-2-one hydrochloride

The synthetic procedure described in this Example was carried out according to the process shown in Scheme M.

SCHEME M

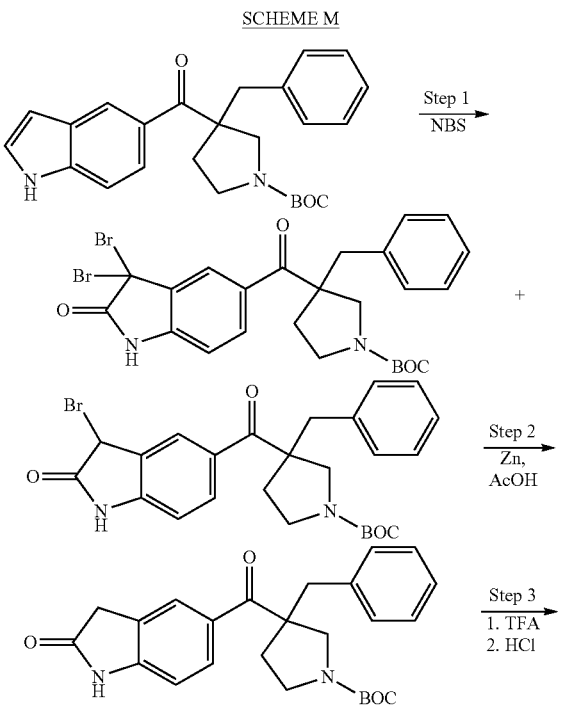

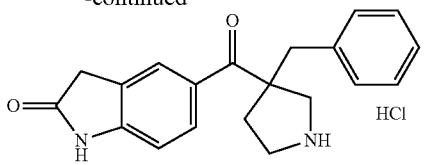

Step 1 3-Benzyl-3-(3,3-dibromo-2-oxo-2,3-dihydro-1H-indole-5-carbonyl)-pyrrolidine-1-carboxylic acid tert-butyl ester and 3-Benzyl-3-(3-bromo-2-oxo-2,3-dihydro-1H-indole-5-carbonyl)-pyrrolidine-1-carboxylic acid tert-butyl ester Freshly recrystallized N-bromosuccinimide (278 mg, 1.56 mmol) was added in portions, over a period of 5 minutes at room temperature, to a solution of 3-benzyl-3-(1H-indole-5-carbonyl)-pyrrolidine-1-carboxylic acid tert-butyl ester (210 mg, 0.52 mmol) in a mixture of t-BuOH/water (5% water, 8.40 mL). The reaction mixture was stirred for 1.5 hours at room temperature and then concentrated under reduced pressure. The residue was partitioned between water and DCM, and the combined organic extracts were dried over $MgSO_4$, filtered and evaporated under reduced pressure. The residue was purified by flash chromatography (30% to 60% of EtOAc in hexane) to give 129 mg (43% yield) of 3-benzyl-3-(3,3-dibromo-2-oxo-2,3-dihydro-1H-indole-5-carbonyl)-pyrrolidine-1-carboxylic acid tert-butyl ester as a pale yellow foamy solid, and 67 mg (26% yield) of 3-benzyl-3-(3-bromo-2-oxo-2,3-dihydro-1H-indole-5-carbonyl)-pyrrolidine-1-carboxylic acid tert-butyl ester as a pale yellow foamy solid.

Step 2 3-Benzyl-3-(2-oxo-2,3-dihydro-1H-indole-5-carbonyl)-pyrrolidine-1-carboxylic acid tert-butyl ester Zinc powder (130 mg, 2.00 mmol) was added to a solution of 3-benzyl-3-(3,3-dibromo-2-oxo-2,3-dihydro-1H-indole-5-carbonyl)-pyrrolidine-1-carboxylic acid tert-butyl ester (115 mg, 0.20 mmol) in acetic acid (4 mL). The reaction mixture was stirred vigorously at room temperature for 1 hour. Solids were removed by filtration, and the filtrate was concentrate under reduced pressure to give 3-benzyl-3-(2-oxo-2,3-dihydro-1H-indole-5-carbonyl)-pyrrolidine-1-carboxylic acid tert-butyl ester as a foam. The same procedure was repeated using the 3-benzyl-3-(3-bromo-2-oxo-2,3-dihydro-1H-indole-5-carbonyl)-pyrrolidine-1-carboxylic acid tert-butyl ester to provide additional 3-benzyl-3-(2-oxo-2,3-dihydro-1H-indole-5-carbonyl)-pyrrolidine-1-carboxylic acid tert-butyl ester.

Step 3 5-(3-Benzyl-pyrrolidine-3-carbonyl)-1,3-dihydro-indol-2-one hydrochloride 3-Benzyl-3-(2-oxo-2,3-dihydro-1H-indole-5-carbonyl)-pyrrolidine-1-carboxylic acid tert-butyl ester was deprotected following the procedure described in Example 3 to give 5-(3-Benzyl-pyrrolidine-3-carbonyl)-1,3-dihydro-indol-2-one hydrochloride as an off-white powder; MS=321 $[M+H]^+$.

Additional compounds prepared by the above procedure are shown in Table 1.

Example 8

(2-Benzyl-pyrrolidin-2-yl)-(1H-indol-5-yl)-methanone

The synthetic procedure described in this Example was carried out according to the process shown in Scheme N.

SCHEME N

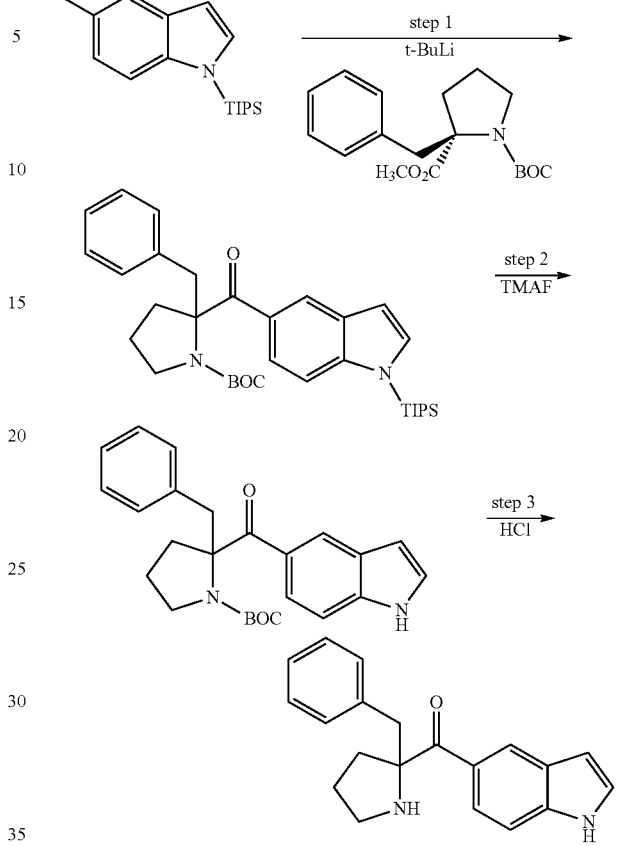

Step 1 2-Benzyl-2-(1-triisopropylsilanyl-1H-indole-5-carbonyl)-pyrrolidine-1-carboxylic acid tert-butyl ester To a stirred solution of 5-bromo-1-triisopropylsilanyl-1H-indole (0.55 g, 1.57 mmol) in THF (10 mL) at −78° C. under nitrogen atmosphere was added tert-butyllithium (2.02 mL of 1.55 M solution in pentanes, 3.13 mmol) dropwise. After one hour, the reaction mixture was added rapidly to a cold (−78° C.) solution of (R)-2-benzyl-pyrrolidine-1,2-dicarboxylic acid 1-tert-butyl ester 2-methyl ester (0.50 g, 3.13 mmol) in THF (10 mL). The reaction mixture was stirred at −78° C. for one hour, then warmed to room temperature and stirred for two hours. The reaction mixture was quenched by the addition of saturated aqueous $NH_4Cl$ (20 mL) then extracted with EtOAc. The combined extracts were washed with brine then dried ($MgSO_4$), filtered and concentrated in vacuo. Purification by chromatography (silica, 0-20% EtOAc in hexanes) gave 2-benzyl-2-(1-triisopropylsilanyl-1H-indole-5-carbonyl)-pyrrolidine-1-carboxylic acid tert-butyl ester (0.145 g, 0.259 mmol, 16%) as a colourless gum.

Utilizing the appropriate starting materials the following compound was also prepared:
2-Butyl-2-(1-triisopropylsilanyl-1H-indazole-5-carbonyl)-pyrrolidine-1-carboxylic acid tert-butyl ester, (yellow oil, 31%).

Step 2 2-Benzyl-2-(1H-indole-5-carbonyl)-pyrrolidine-1-carboxylic acid tert-butyl ester To a stirred solution of 2-benzyl-2-(1-triisopropylsilanyl-1H-indole-5-carbonyl)-pyrrolidine-1-carboxylic acid tert-butyl ester (0.145 g, 0.259 mmol) in THF (5 mL) at ambient temperature under nitrogen was added TMAF (0.026 g, 0.285 mmol). After one hour, the reaction mixture was concentrated in vacuo. Purification of the residue by chromatography (silica, 25-50% EtOAc in hexanes) gave 2-benzyl-2-(1H-indole-5-carbonyl)-pyrrolidine-1-carboxylic acid tert-butyl ester (0.045 g, 0.111 mmol, 43%) as a colourless foam.

Utilizing the appropriate starting materials the following compound was also prepared:

2-Butyl-2-(1H-indazole-5-carbonyl)-pyrrolidine-1-carboxylic acid tert-butyl ester (yellow solid, 25%).

Step 3 (2-Benzyl-pyrrolidin-2-yl)-(1H-indol-5-yl)-methanone

A solution of 2-benzyl-2-(1H-indole-5-carbonyl)-pyrrolidine-1-carboxylic acid tert-butyl ester (0.045 g, 0.111 mmol) in 1N HCl in MeOH (2.2 mL) was stirred for 14 hours at ambient temperature under nitrogen. Aqueous NaOH (4 N, 0.6 mL) was added and the reaction mixture was extracted into DCM. The combined extracts were washed with brine then dried (MgSO$_4$), filtered and concentrated in vacuo. Purification of the residue by chromatography (silica, 0-10% of a 9:1 MeOH:NH$_4$OH solution in DCM) gave (2-benzyl-pyrrolidin-2-yl)-(1H-indol-5-yl)-methanone (0.021 g, 0.069 mmol, 62%) as a colourless solid, MS=305 [M+H]$^+$.

Utilizing the appropriate starting materials the following compound was also prepared:

(2-Butyl-pyrrolidin-2-yl)-(1H-indazol-5-yl)-methanone, (yellow solid, 100%), MS=306 [M+H]$^+$.

Additional compounds prepared by the above procedure are shown in Table 1.

Example 9

(2-Butyl-pyrrolidin-2-yl)-(3,4-dichloro-phenyl)-methanone

The synthetic procedure described in this Example was carried out according to the process shown in Scheme O.

SCHEME O

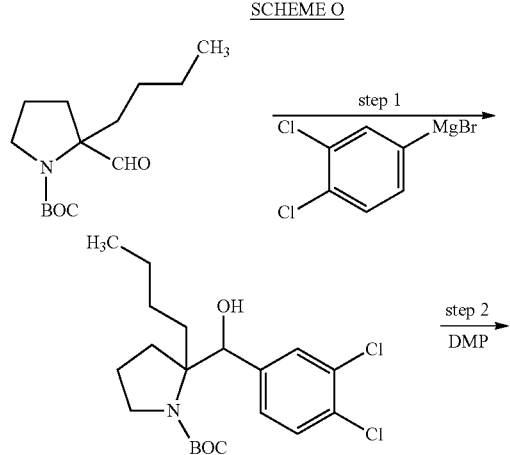

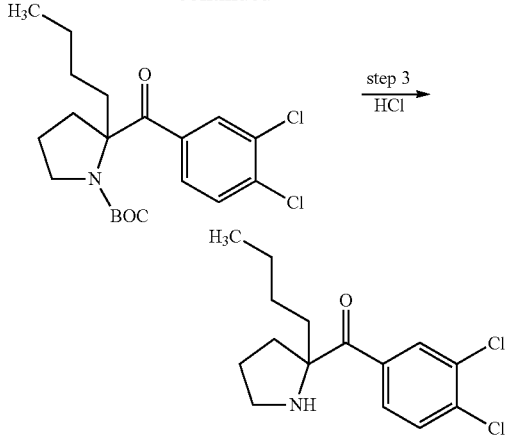

Step 1 2-Butyl-2-[(3,4-dichloro-phenyl)-hydroxy-methyl]-pyrrolidine-1-carboxylic acid tert-butyl ester To a stirred solution of 2-butyl-2-formyl-pyrrolidine-1-carboxylic acid tert-butyl ester (0.753 g, 2.95 mmol) in THF (12 mL) at 0° C. and under nitrogen was added 3,4-dichlorophenylmagnesium bromide (11.8 mL of a 0.5 M solution in pentanes, 5.9 mmol) dropwise over 10 minutes. After 20 minutes, the reaction mixture was quenched by the addition of saturated aqueous NH$_4$Cl (30 mL) then extracted with EtOAc. The combined extracts were washed with brine then dried (MgSO$_4$), filtered and concentrated in vacuo to a yellow oil (1.9 g). Purification by chromatography (silica, 5-20% EtOAc in hexanes) gave 2-butyl-2-[(3,4-dichloro-phenyl)-hydroxy-methyl]-pyrrolidine-1-carboxylic acid tert-butyl ester (0.548 g, 1.36 mmol, 46%) as a colourless gum and as an inseparable mixture of diastereomers Utilizing the appropriate starting materials the following compounds were also prepared:

2-[(3,4-Dichloro-phenyl)-hydroxy-methyl]-2-propyl-pyrrolidine-1-carboxylic acid tert-butyl ester (pale yellow oil, 47%);

2-[(3,4-Dichloro-phenyl)-hydroxy-methyl]-2-ethoxymethyl-pyrrolidine-1-carboxylic acid tert-butyl ester (colourless oil, 59%);

2-[(3,4-Dichloro-phenyl)-hydroxy-methyl]-2-(3,3-difluoro-allyl)-pyrrolidine-1-carboxylic acid tert-butyl ester (colourless gum, 42%);

2-[(3,4-Dichloro-phenyl)-hydroxy-methyl]-5,5-dimethyl-2-propyl-pyrrolidine-1-carboxylic acid tert-butyl ester, (colourless foam, 81%);

(2R,4R)-4-(tert-Butyl-dimethyl-silanyloxy)-2-[(3,4-dichloro-phenyl)-hydroxy-methyl]-2-propyl-pyrrolidine-1-carboxylic acid tert-butyl ester, (colourless gum, 70%);

(2S,4R)-4-(tert-Butyl-dimethyl-silanyloxy)-2-[(3,4-dichloro-phenyl)-hydroxy-methyl]-2-propyl-pyrrolidine-1-carboxylic acid tert-butyl ester, (colourless oil, 45%);

2-[(3,4-Dichloro-phenyl)-hydroxy-methyl]-2-propyl-azetidine-1-carboxylic acid tert-butyl ester, (colourless oil, 21%) as a single diasteromer;

2-[(3,4-Dichloro-phenyl)-hydroxy-methyl]-2-propyl-piperidine-1-carboxylic acid tert-butyl ester (colourless oil, 10%).

Step 2 2-Butyl-2-(3,4-dichloro-benzoyl)-pyrrolidine-1-carboxylic acid tert-butyl ester To a stirred solution of 2-butyl-2-[(3,4-dichloro-phenyl)-hydroxy-methyl]-pyrrolidine-1-carboxylic acid tert-butyl ester (0.520 g, 1.29 mmol) in DCM (20 mL) at 0° C. under nitrogen was added DMP (0.658 g, 1.55 mmol) in a single portion. The reaction mixture was warmed to ambient temperature and stirred for 30 minutes, then diluted with DCM, washed with 1 N NaOH and brine, then dried (MgSO$_4$), filtered and concentrated in vacuo to a yellow oil (0.62 g). Purification by chromatography (silica, 10-20% EtOAc in hexanes) gave 2-butyl-2-(3,4-dichloro-benzoyl)-pyrrolidine-1-carboxylicacid tert-butyl ester (0.441 g, 1.10 mmol, 85%) as a clear colourless gum.

Utilizing the appropriate starting materials the following compounds were also prepared:

2-(3,4-Dichloro-benzoyl)-2-propyl-pyrrolidine-1-carboxylic acid tert-butyl ester (white solid, 88%);

2-(3,4-Dichloro-benzoyl)-2-ethoxymethyl-pyrrolidine-1-carboxylic acid tert-butyl ester (colourless residue, 75%);

2-(3,4-Dichloro-benzoyl)-2-(3,3-difluoro-allyl)-pyrrolidine-1-carboxylic acid tert-butyl ester (yellow oil, 81%);

2-(3,4-Dichloro-benzoyl)-5,5-dimethyl-2-propyl-pyrrolidine-1-carboxylic acid tert-butyl ester, (colourless gum, 83%);

(2R,4R)-4-(tert-Butyl-dimethyl-silanyloxy)-2-(3,4-dichloro-benzoyl)-2-propyl-pyrrolidine-1-carboxylic acid tert-butyl ester, (colourless gum, 73%);

(2S,4R)-4-(tert-Butyl-dimethyl-silanyloxy)-2-(3,4-dichloro-benzoyl)-2-propyl-pyrrolidine-1-carboxylic acid tert-butyl ester, (colourless oil, 83%);

2-(3,4-Dichloro-benzoyl)-2-propyl-azetidine-1-carboxylic acid tert-butyl ester, (colourless residue, 58%);

2-(3,4-Dichloro-benzoyl)-2-propyl-piperidine-1-carboxylic acid tert-butyl ester, (colourless oil, 80%).

Step 3 (2-Butyl-pyrrolidin-2-yl)-(3,4-dichloro-phenyl)-methanone

A solution of 2-butyl-2-(3,4-dichloro-benzoyl)-pyrrolidine-1-carboxylic acid tert-butyl ester (0.435 g, 1.09 mmol) in 1N HCl in MeOH (10.9 mL) was stirred at ambient temperature under nitrogen for 14 hours. The reaction mixture was concentrated in vacuo, then redissolved in DCM and concentrated in vacuo to remove excess HCl. Purification by chromatography (silica, 0-10% MeOH in DCM) gave (2-butyl-pyrrolidin-2-yl)-(3,4-dichloro-phenyl)-methanone (0.249 g, 0.740 mmol, 68%) as a white powder, MS=300 [M+H]$^+$.

Utilizing the appropriate starting materials the following compounds were prepared in similar fashion:

(3,4-Dichloro-phenyl)-(2-propyl-pyrrolidin-2-yl)-methanone (off-white solid, 81%); MS=286 [M+H]$^+$;

(3,4-Dichloro-phenyl)-(2-ethoxymethyl-pyrrolidin-2-yl)-methanone (white solid, 99%); MS=302 [M+H]$^+$;

(3,4-Dichloro-phenyl)$_{4-2}$-(3,3-difluoro-allyl)-pyrrolidin-2-yd-methanone (white powder, 97%); MS=320 [M+H]$^+$;

(3,4-Dichloro-phenyl)-(5,5-dimethyl-2-propyl-pyrrolidin-2-yl)-methanone, (pale yellow powder, 97%); MS=314 [M+H]$^+$;

(3,4-Dichloro-phenyl)-(2-propyl-azetidin-2-yl)-methanone (white powder, 30%) after analytical HPLC purification; MS=272 [M+H]$^+$; and (3,4-Dichloro-phenyl)-(2-propyl-piperidin-2-yl)-methanone, (yellow solid, 97%), MS=300 [M+H]$^+$.

Additional compounds prepared by the above procedure are shown in Table 1.

Example 10

(4-Amino-3-chloro-phenyl)-(2-butyl-pyrrolidin-2-yl)-methanone

The synthetic procedure described in this Example was carried out according to the process shown in Scheme P.

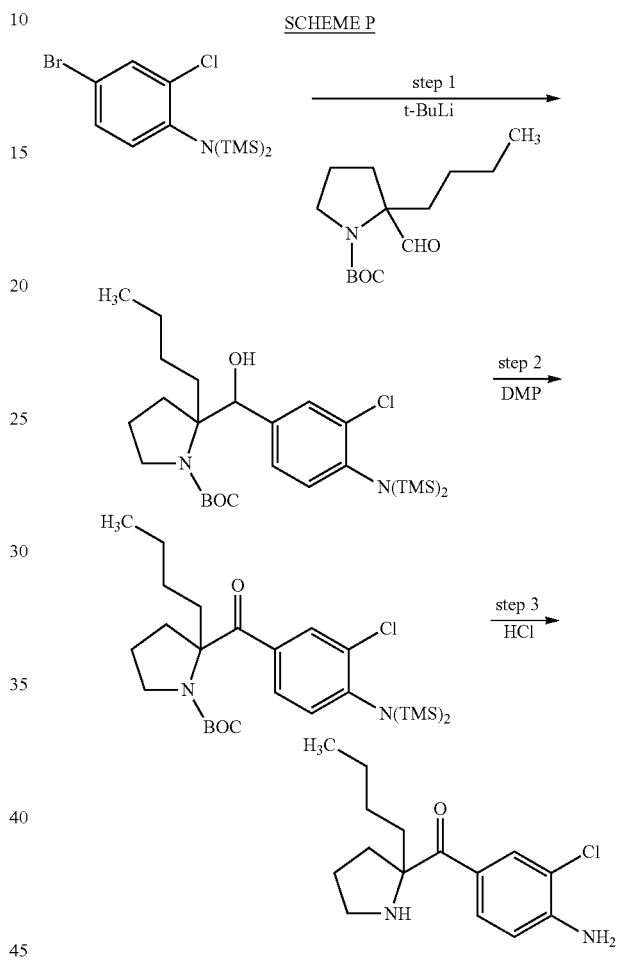

SCHEME P

Step 1 2-Butyl-2-{[3-chloro-4-(1,1,1,3,3,3-hexamethyl-disilazan-2-yl)-phenyl]-hydroxy-methyl}-pyrrolidine-1-carboxylic acid tert-butyl ester To a stirred solution of 2-(4-bromo-2-chloro-phenyl)-1,1,1,3,3,3-hexamethyl-disilazane (0.484 g, 1.38 mmol) in ether (14 mL) at −78° C. and under nitrogen was added tert-butyl-lithium (2.03 mL, 1.43 M solution in pentanes, 2.91 mmol) dropwise. After 90 minutes, a solution of 2-butyl-2-formyl-pyrrolidine-1-carboxylic acid tert-butyl ester (0.353 g, 1.38 mmol) in ether (3 mL) was added to the reaction mixture dropwise. After one hour, the reaction mixture was warmed to ambient temperature and stirred at ambient temperature for 30 minutes. The reaction mixture was quenched by the addition of saturated aqueous NH$_4$Cl (10 mL) and extracted with EtOAc. The combined extracts were washed with brine, then dried (MgSO$_4$), filtered, and concentrated in vacuo to an oil (0.75 g). Purification by chromatography (silica, 5-20% EtOAc in hexanes) gave 2-butyl-2-{[3-chloro-4-(1,1,1,3,3,3-hexamethyl-disilazan-2-yl)-phenyl]-hydroxy-methyl}-pyrrolidine-1-carboxylic acid tert-butyl ester (0.357 g, 0.678 mmol, 49%) as a colourless oil.

Utilizing the appropriate starting materials the following compounds were also prepared:

2-{[3-Chloro-4-(1,1,1,3,3,3-hexamethyl-disilazan-2-yl)-phenyl]-hydroxy-methyl}-2-propyl-pyrrolidine-1-carboxylic acid tert-butyl ester (colourless foam, 43%);

2-[Hydroxy-(1-triisopropylsilanyl-1H-indazol-5-yl)-methyl]-2-propyl-pyrrolidine-1-carboxylic acid tert-butyl ester, (yellow foam, 50%);

2-{[1-(tert-Butyl-dimethyl-silanyl)-7-fluoro-1H-indol-5-yl]-hydroxy-methyl}-2-propyl-pyrrolidine-1-carboxylic acid tert-butyl ester, (white solid, 49%); and 2-Cyclopropylmethyl-2-[hydroxy-(1-triisopropylsilanyl-1H-indazol-5-yl)-methyl]-pyrrolidine-1-carboxylic acid tert-butyl ester, (colourless gum, 62%).

Step 2 2-Butyl-2-[3-chloro-4-(1,1,1,3,3,3-hexamethyl-disilazan-2-yl)-benzoyl]-pyrrolidine-1-carboxylic acid tert-butyl ester To a stirred solution of 2-butyl-2-{[3-chloro-4-(1,1,1,3,3,3-hexamethyl-disilazan-2-yl)-phenyl]-hydroxy-methyl}-pyrrolidine-1-carboxylic acid tert-butyl ester (0.357 g, 0.678 mmol) in DCM (10 mL) at ambient temperature under nitrogen was added DMP (0.575 g, 1.36 mmol) in a single portion. After one hour the reaction mixture was diluted with DCM, washed with 1 N NaOH and brine, then dried (MgSO$_4$), filtered and concentrated in vacuo to a brown residue (0.290 g). Purification by chromatography (silica, 10% EtOAc in hexanes) gave 2-butyl-2-[3-chloro-4-(1,1,1,3,3,3-hexamethyl-disilazan-2-yl)-benzoyl]-pyrrolidine-1-carboxylic acid tert-butyl ester (0.208 g, 0.397 mmol, 58%) as a clear colourless residue.

Utilizing the appropriate starting materials the following compounds were also prepared:

2-[3-Chloro-4-(1,1,1,3,3,3-hexamethyl-disilazan-2-yl)-benzoyl]-2-propyl-pyrrolidine-1-carboxylic acid tert-butyl ester, (yellow oil, 96%);

2-Propyl-2-(1-triisopropylsilanyl-1H-indazole-5-carbonyl)-pyrrolidine-1-carboxylic acid tert-butyl ester, (yellow foam, 77%);

2-[1-(tert-Butyl-dimethyl-silanyl)-7-fluoro-1H-indole-5-carbonyl]-2-propyl-pyrrolidine-1-carboxylic acid tert-butyl ester, (yellow oil, 75%);

2-Cyclopropylmethyl-2-(1-triisopropylsilanyl-1H-indazole-5-carbonyl)-pyrrolidine-1-carboxylic acid tert-butyl ester, (colourless gum, 27%).

Step 3 (4-Amino-3-chloro-phenyl)-(2-butyl-pyrrolidin-2-yl)-methanone

A solution of 2-butyl-2-[3-chloro-4-(1,1,1,3,3,3-hexamethyl-disilazan-2-yl)-benzoyl]-pyrrolidine-1-carboxylic acid tert-butyl ester (0.205 g, 0.391 mmol) in methanolic 1N HCl (7.8 mL) was stirred at 50° C. under nitrogen for 2 hours. The reaction mixture was concentrated in vacuo to yield (4-amino-3-chloro-phenyl)-(2-butyl-pyrrolidin-2-yl)-methanone (0.249 g, quantitative yield) as a light brown powder and as a monohydrochloride salt.

Utilizing the appropriate starting materials the following compounds were also prepared by the above procedure:

(4-Amino-3-chloro-phenyl)-(2-propyl-pyrrolidin-2-yl)-methanone, (beige solid, 83%), MS=267 [M+H]$^+$;

(1H-Indazol-5-yl)-(2-propyl-pyrrolidin-2-yl)-methanone, (yellow solid, 57%), MS=258 [M+H]$^+$;

(7-Fluoro-1H-indol-5-yl)-(2-propyl-pyrrolidin-2-yl)-methanone (light brown foam, 60%), MS=275 [M+H]$^+$;

(2-Cyclopropylmethyl-pyrrolidin-2-yl)-(1H-indazol-5-yl)-methanone (white powder, 99%), MS=270 [M+H]$^+$.

Additional compounds prepared by the above procedure are shown in Table 1.

Example 11

(2-propyl-pyrrolidin-2-yl)-(1H-pyrrolo[2,3-b]pyridin-5-yl)-methanone

The synthetic procedure described in this Example was carried out according to the process shown in Scheme Q.

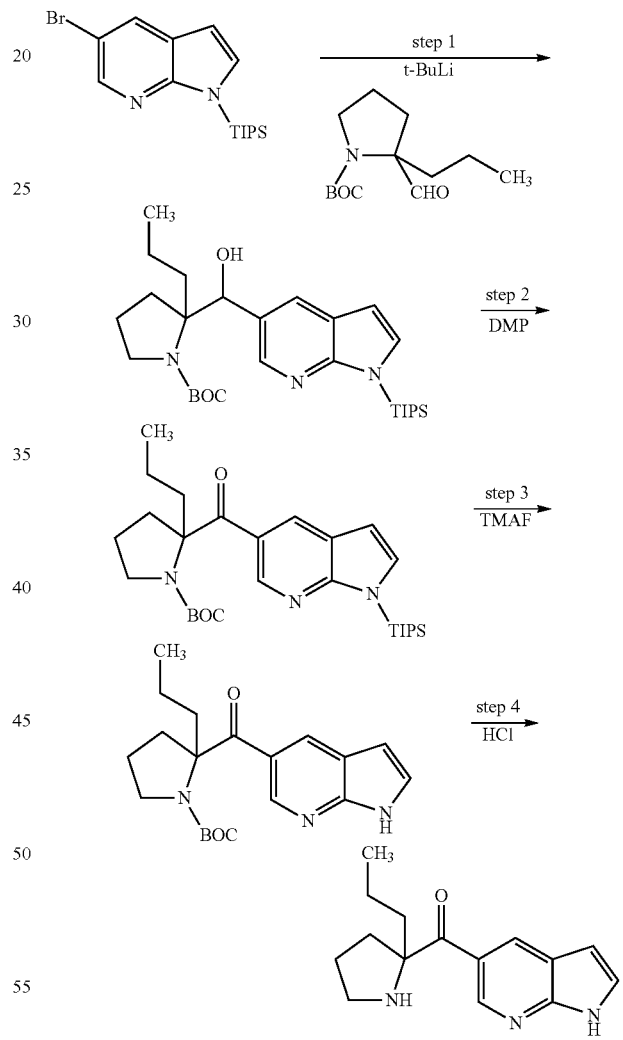

SCHEME Q

Step 1 2-[Hydroxy-(1-triisopropylsilanyl-1H-pyrrolo[2,3-b]pyridin-5-yl)-methyl]-2-propyl-pyrrolidine-1-carboxylic acid tert-butyl ester To a stirred solution of 5-bromo-1-triisopropylsilanyl-1H-pyrrolo[2,3-b]pyridine (0.587 g, 1.66 mmol) in ether (20 mL) at −78° C. and under nitrogen was added tert-butyllithium (2.30 mL of 1.51 M solution in pentanes, 3.49 mmol) dropwise. After 90 minutes, a solution of 2-formyl-2-propyl-pyrrolidine-1-carboxylic acid tert-butyl ester (0.400 g, 1.66 mmol) in ether (1 mL) was added to the reaction mixture dropwise. After stirring for one hour, the reaction mixture was warmed to ambient temperature over 30 minutes. The reaction mixture was quenched by the addition of saturated aqueous $NH_4Cl$ (20 mL) then extracted with EtOAc. The combined extracts were washed with saturated aqueous $NaHCO_3$ and brine, then dried ($MgSO_4$), filtered and concentrated in vacuo to a yellow oil (0.90 g). Purification by chromatography (silica, 5-20% EtOAc in hexanes) gave 2-[hydroxy-(1-triisopropylsilanyl-1H-pyrrolo[2,3-b]pyridin-5-yl)-methyl]-2-propyl-pyrrolidine-1-carboxylic acid tert-butyl ester (0.576 g, 1.12 mmol, 53%) as a colourless gum.

Utilizing the appropriate starting materials the following compounds were also prepared:
2-[Hydroxy-(1-triisopropylsilanyl-1H-indazol-5-yl)-methyl]-2-isopropoxymethyl-pyrrolidine-1-carboxylic acid tert-butyl ester, (yellow oil, 79%); and
2-[Hydroxy-(1-triisopropylsilanyl-1H-indazol-5-yl)-methyl]-2-isobutyl-pyrrolidine-1-carboxylic acid tert-butyl ester, (colourless oil, 56%).

Step 2 2-Propyl-2-(1-triisopropylsilanyl-1H-pyrrolo [2,3-b]pyridine-5-carbonyl)-pyrrolidine-1-carboxylic acid tert-butyl ester To a stirred solution of 2-[hydroxy-(1-triisopropylsilanyl-1H-pyrrolo[2,3-b]pyridin-5-yl)-methyl]-2-propyl-pyrrolidine-1-carboxylic acid tert-butyl ester (0.528 g, 1.03 mmol) in DCM (15 mL) at ambient temperature under nitrogen was added DMP (0.652 g, 1.54 mmol) in a single portion. After 90 minutes the reaction mixture was diluted with DCM, washed with 1 N NaOH and brine, then dried ($MgSO_4$), filtered and concentrated in vacuo to a brown oil. Purification by chromatography (silica, 5 to 10% EtOAc in hexanes) gave 2-propyl-2-(1-triisopropylsilanyl-1H-pyrrolo[2,3-b]pyridine-5-carbonyl)-pyrrolidine-1-carboxylic acid tert-butyl ester (0.415 g, 0.809 mmol, 79%) as a yellow gum.

Utilizing the appropriate starting materials the following compounds were also prepared:
2-Isopropoxymethyl-2-(1-triisopropylsilanyl-1H-indazole-5-carbonyl)-pyrrolidine-1-carboxylic acid tert-butyl ester, (yellow solid, 96%); and
2-Isobutyl-2-(1-triisopropylsilanyl-1H-indazole-5-carbonyl)-pyrrolidine-1-carboxylic acid tert-butyl ester, (colourless gum, 49%).

Step 3 2-Propyl-2-(1H-pyrrolo[2,3-b]pyridine-5-carbonyl)-pyrrolidine-1-carboxylic acid tert-butyl ester To a stirred solution of 2-propyl-2-(1-triisopropylsilanyl-1H-pyrrolo[2,3-b]pyridine-5-carbonyl)-pyrrolidine-1-carboxylic acid tert-butyl ester (0.415 g, 0.809 mmol) in THF (7.5 mL) at ambient temperature under nitrogen was added TMAF (0.753 g, 8.09 mmol). The reaction mixture was stirred for one hour, then diluted with saturated aqueous $NaHCO_3$ (30 mL) and water (15 mL) and extracted with EtOAc. The combined organic extracts were washed with brine, dried ($MgSO_4$), filtered, and concentrated in vacuo to a pale yellow gum. Purification by chromatography (silica, 50 to 100% EtOAc in hexanes) gave 2-propyl-2-(1H-pyrrolo[2, 3-b]pyridine-5-carbonyl)-pyrrolidine-1-carboxylic acid tert-butyl ester (0.247 g, 0.692 mmol, 86%) as a colourless foam.

Utilizing the appropriate starting materials the following compounds were also prepared:

2-(1H-Indazole-5-carbonyl)-2-isopropoxymethyl-pyrrolidine-1-carboxylic acid tert-butyl ester, white foam, 68%);
2-(1H-Indazole-5-carbonyl)-2-isobutyl-pyrrolidine-1-carboxylic acid tert-butyl ester, (yellow foam, 30%);
(2R,4R)-2-(3,4-Dichloro-benzoyl)-4-hydroxy-2-propyl-pyrrolidine-1-carboxylic acid tert-butyl ester, (colourless residue, 79%);
(2S,4R)-2-(3,4-Dichloro-benzoyl)-4-hydroxy-2-propyl-pyrrolidine-1-carboxylic acid tert-butyl ester, (colourless gum, 79%).

Step 4 (2-Propyl-pyrrolidin-2-yl)-(1H-pyrrolo[2,3-b] pyridin-5-yl)-methanone

A solution of 2-propyl-2-(1H-pyrrolo[2,3-b]pyridine-5-carbonyl)-pyrrolidine-1-carboxylic acid tert-butyl ester (0.240 g, 0.672 mmol) in 1N methanolic HCl (10.1 mL) was stirred at 20° C. under nitrogen for 18 hours. The reaction mixture was concentrated in vacuo then triturated with DCM (5 mL) and concentrated in vacuo to yield (2-propyl-pyrrolidin-2-yl)-(1H-pyrrolo[2,3-b]pyridin-5-yl)-methanone (0.215 g, 0.652 mmol, 97%) as a white powder and as a monohydrochloride salt, MS=258 $[M+H]^+$.

Utilizing the appropriate starting materials the following compounds were also prepared:
(1H-Indazol-5-yl)-(2-isopropoxymethyl-pyrrolidin-2-yl)-methanone, (white solid, 94%), MS=288 $[M+H]^+$;
(1H-Indazol-5-yl)-(2-isobutyl-pyrrolidin-2-yl)-methanone, (yellow powder, 100%), MS=272 $[M+H]^+$;
(3,4-Dichloro-phenyl)-((2R,4R)-4-hydroxy-2-propyl-pyrrolidin-2-yl)-methanone, (white solid, 61%), MS=302 $[M+H]^+$; and
(3,4-Dichloro-phenyl)-((2S,4R)-4-hydroxy-2-propyl-pyrrolidin-2-yl)-methanone, (white solid, 97%), MS=302 $[M+H]^+$.

Additional compounds prepared by the above procedure are shown in Table 1.

Example 12

(5,6-Dichloro-pyridin-2-yl)-(2-propyl-pyrrolidin-2-yl)-methanone

The synthetic procedure described in this Example was carried out according to the process shown in Scheme R.

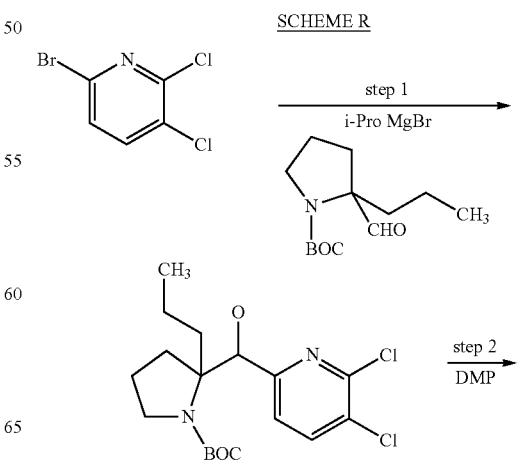

209

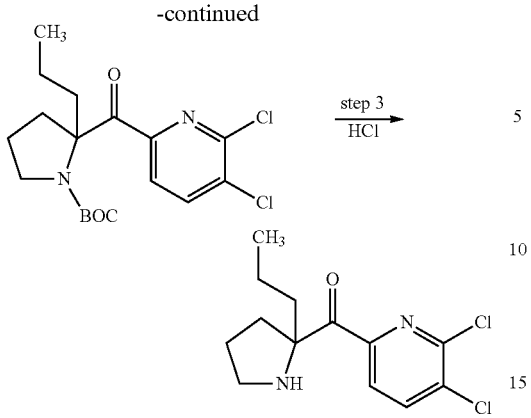

Step 1 2-[(5,6-Dichloro-pyridin-2-yl)-hydroxy-methyl]-2-propyl-pyrrolidine-1-carboxylic acid tert-butyl ester To a stirred solution of 2-bromo-5,6-dichloro-pyridine (0.500 g, 2.20 mmol) in THF (6 mL) at 0° C. and under nitrogen was added isopropylmagnesium chloride (1.21 mL of a 2 M solution in THF, 2.42 mmol) dropwise. After 2 hours, a solution of 2-formyl-2-propyl-pyrrolidine-1-carboxylic acid tert-butyl ester (0.317 g, 1.32 mmol) in THF (1 mL) was added to the reaction mixture dropwise. After 30 minutes, the reaction mixture was warmed to ambient temperature and stirred for one hour, then quenched by the addition of saturated aqueous NH$_4$Cl (10 mL) and extracted with EtOAc. The combined organic extracts were washed with brine, dried (MgSO$_4$), filtered, and concentrated in vacuo. Purification of the residue by chromatography (silica, 0 to 40% EtOAc in hexanes) gave 2-[(5,6-dichloro-pyridin-2-yl)-hydroxy-methyl]-2-propyl-pyrrolidine-1-carboxylic acid tert-butyl ester (0.289 g, 0.745 mmol, 56%) as a yellow oil and as an inseparable mixture of diastereomers.

Utilizing the appropriate starting materials, 2-[(4,5-Dichloro-pyridin-2-yl)-hydroxy-methyl]-2-propyl-pyrrolidine-1-carboxylic acid tert-butyl ester (orange oil, 19%) was also prepared using the above procedure.

Step 2 2-(5,6-Dichloro-pyridine-2-carbonyl)-2-propyl-pyrrolidine-1-carboxylic acid tert-butyl ester To a stirred solution of 2-[(5,6-dichloro-pyridin-2-yl)-hydroxy-methyl]-2-propyl-pyrrolidine-1-carboxylic acid tert-butyl ester (0.288 g, 0.742 mmol) in DCM (12 mL) at 0° C. under nitrogen was added DMP (0.315 g, 0.742 mmol) in a single portion. The reaction mixture was stirred for one hour, then was quenched with a 1:1 mixture of 10% aqueous Na$_2$S$_2$O$_3$ and saturated aqueous NaHCO$_3$ (50 mL), and extracted with DCM (3×30 mL). The combined organic phases were concentrated in vacuo to give 2-(5,6-dichloro-pyridine-2-carbonyl)-2-propyl-pyrrolidine-1-carboxylic acid tert-butyl ester (0.280 g, 0.725 mmol, 98%) as a yellow solid that was used directly without further purification.

Utilizing the appropriate starting materials, 2-(4,5-Dichloro-pyridine-2-carbonyl)-2-propyl-pyrrolidine-1-carboxylic acid tert-butyl ester (colourless oil, 43%) was also prepared.

Step 3 (5,6-Dichloro-pyridin-2-yl)-(2-propyl-pyrrolidin-2-yl)-methanone

A solution of 2-(5,6-dichloro-pyridine-2-carbonyl)-2-propyl-pyrrolidine-1-carboxylic acid tert-butyl ester (0.280 g,

210

0.725 mmol) in 1N HCl in MeOH (3 mL) was stirred at ambient temperature under nitrogen for 20 hours. The reaction mixture was concentrated in vacuo and the resulting residue was purified by chromatography (silica, 0 to 30% MeOH in DCM) to yield (5,6-dichloro-pyridin-2-yl)-(2-propyl-pyrrolidin-2-yl)-methanone (0.167 g, 0.522 mmol, 72%) as a yellow solid and as a monohydrochloride salt, MS=287 [M+H]$^+$.

Utilizing the appropriate starting material, (4,5-Dichloro-pyridin-2-yl)-(2-propyl-pyrrolidin-2-yl)-methanone (yellow gum, 37%) was also prepared, MS=287 [M+H]$^+$.

Additional compounds prepared by the above procedure are shown in Table 1.

Example 13

(3,4-Dichloro-5-fluoro-phenyl)-(2-propyl-pyrrolidin-2-yl)-methanone

The synthetic procedure described in this Example was carried out according to the process shown in Scheme S.

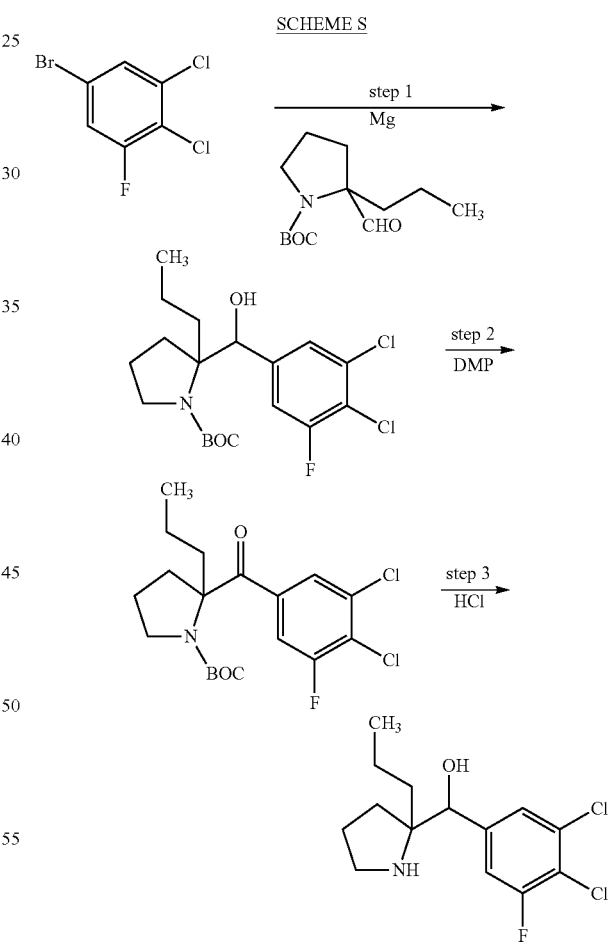

Step 1 2-[(3,4-Dichloro-5-fluoro-phenyl)-hydroxy-methyl]-2-propyl-pyrrolidine-1-carboxylic acid tert-butyl ester A stirred mixture of 3,4-dichloro-5-fluorophenyl bromide (1.38 g, 5.66 mmol) and magnesium turnings (0.145 g, 5.94 mmol) in THF (8 mL) was heated at reflux under nitrogen for 30 minutes, then cooled to 0° C. To the reaction mixture was added a solution of 2-formyl-2-propyl-pyrrolidine-1-carboxylic acid tert-butyl ester (0.682 g, 2.38 mmol) in THF (2 mL) dropwise over 15 minutes. The cold reaction mixture was stirred for one hour, then quenched by the addition of saturated aqueous NH$_4$Cl (20 mL) and extracted with EtOAc. The combined organic extracts were washed with brine, dried (MgSO$_4$), filtered and concentrated in vacuo to a yellow oil (1.7 g). Purification by chromatography (silica, 0 to 20% EtOAc in hexanes) gave 2-[(3,4-dichloro-5-fluoro-phenyl)-hydroxy-methyl]-2-propyl-pyrrolidine-1-carboxylic acid tert-butyl ester (0.571 g, 1.41 mmol, 50%) as a white solid.

Step 2 2-(3,4-Dichloro-5-fluoro-benzoyl)-2-propyl-pyrrolidine-1-carboxylic acid tert-butyl ester To a stirred solution of 2-[(3,4-dichloro-5-fluoro-phenyl)-hydroxy-methyl]-2-propyl-pyrrolidine-1-carboxylic acid tert-butyl ester (0.533 g, 1.31 mmol) in DCM (20 mL) at 0° C. under nitrogen was added DMP (0.557 g, 1.55 mmol) in a single portion. The reaction mixture was warmed to ambient temperature and stirred for 90 minutes. A second portion of DMP (0.110 g, 0.26 mmol) was added, and the reaction mixture was stirred for 30 minutes, then diluted with DCM, washed with 1 N NaOH, brine (20 mL), dried (MgSO$_4$), filtered and concentrated in vacuo to a clear colourless oil (0.55 g). Purification by chromatography (silica, 5-20% EtOAc in hexanes) gave 2-(3,4-dichloro-5-fluoro-benzoyl)-2-propyl-pyrrolidine-1-carboxylic acid tert-butyl ester (0.358 g, 0.886 mmol, 68%) as a clear colourless gum.

Step 3 (3,4-Dichloro-5-fluoro-phenyl)-(2-propyl-pyrrolidin-2-yl)-methanone

A solution of 2-(3,4-dichloro-5-fluoro-benzoyl)-2-propyl-pyrrolidine-1-carboxylic acid tert-butyl ester (0.346 g, 0.856 mmol) in 1N methanolic HCl (8.6 mL) was stirred at ambient temperature under nitrogen for 15 hours. The reaction mixture was concentrated in vacuo then redissolved in DCM and re-concentrated in vacuo to remove excess HCl, furnishing (3,4-dichloro-5-fluoro-phenyl)-(2-propyl-pyrrolidin-2-yl)-methanone (0.294 g, quantitative yield) as a white powder, MS=304 [M+H]$^+$.

Additional compounds prepared by the above procedure are shown in Table 1.

Example 14

(3,4-Dichloro-phenyl)-((2R,4S)-4-fluoro-2-propyl-pyrrolidin-2-yl)-methanone and (3,4-Dichloro-phenyl)-((2S,4S)-4-fluoro-2-propyl-pyrrolidin-2-yl)-methanone The synthetic procedure described in this Example was carried out according to the process shown in Scheme T.

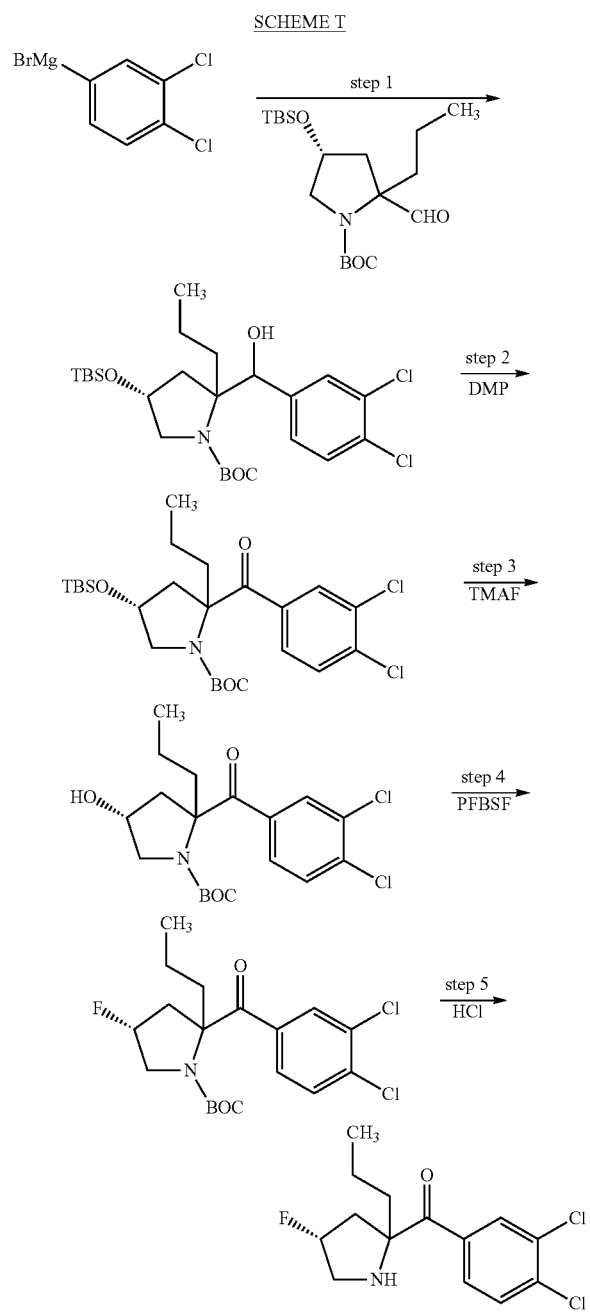

Step 1 (R)-4-(tert-Butyl-dimethyl-silanyloxy)-2-propyl-2-[(3,4-dichloro-phenyl)-hydroxy-methyl]-pyrrolidine-1-carboxylic acid tert-butyl ester (R)-4-(tert-Butyl-dimethyl-silanyloxy)-2-propyl-2-[(3,4-dichloro-phenyl)-hydroxy-methyl]-pyrrolidine-1-carboxylic acid tert-butyl ester was prepared by reaction of 3,4-dichlorophenyl magnesium bromide with (R)-4-(tert-Butyl-dimethyl-silanyloxy)-2-formyl-2-propyl-pyrrolidine-1-carboxylic acid tert-butyl ester following the procedure of step 1 of Example 11.

Step 2 (R)-4-(tert-Butyl-dimethyl-silanyloxy)-2-propyl-2-(3,4-dichloro-benzoyl)-pyrrolidine-1-carboxylic acid tert-butyl ester (R)-4-(tert-Butyl-dimethyl-silanyloxy)-2-propyl-2-(3,4-dichloro-benzoyl)-pyrrolidine-1-carboxylic acid tert-butyl ester was prepared by oxidation of (R)-4-(tert-Butyl-dimethyl-silanyloxy)-2-propyl-2-[(3,4-dichloro-phenyl)-hydroxy-methyl]-pyrrolidine-1-carboxylic acid tert-butyl ester with DMP following the procedure of step 2 of Example 11.

Step 3 (R)-2-(3,4-Dichloro-benzoyl)-4-hydroxy-2-propyl-pyrrolidine-1-carboxylic acid tert-butyl ester (R)-2-(3,4-Dichloro-benzoyl)-4-hydroxy-2-propyl-pyrrolidine-1-carboxylic acid tert-butyl ester was prepared by treating (R)-4-(tert-Butyl-dimethyl-silanyloxy)-2-propyl-2-(3,4-dichloro-benzoyl)-pyrrolidine-1-carboxylic acid tert-butyl ester with TMAF following the procedure of step 3 of Example 11.

Step 4 (S)-2-(3,4-Dichloro-benzoyl)-4-fluoro-2-propyl-pyrrolidine-1-carboxylic acid tert-butyl ester To a stirred solution of (R)-2-(3,4-dichloro-benzoyl)-4-hydroxy-2-propyl-pyrrolidine-1-carboxylic acid tert-butyl ester (0.222 g, 0.554 mmol) in THF (3 mL) at ambient temperature under nitrogen was added perfluorobutanesulfonyl fluoride (0.195 mL, 1.11 mmol), triethylamine trihydrofluoride (0.181 mL, 1.11 mmol) and triethylamine (0.46 mL, 3.32 mmol). The reaction mixture was stirred for 18 hours, then filtered through a pad of silica, washed with EtOAc, and concentrated in vacuo to give (S)-2-(3,4-dichloro-benzoyl)-4-fluoro-2-propyl-pyrrolidine-1-carboxylic acid tert-butyl ester (0.222 g, 0.551 mmol, 99%) as a yellow foam that was used directly in the next step without further purification.

Step 5 (3,4-Dichloro-phenyl)-((2R,4S)-4-fluoro-2-propyl-pyrrolidin-2-yl)-methanone and (3,4-Dichloro-phenyl)-((2S,4S)-4-fluoro-2-propyl-pyrrolidin-2-yl)-methanone A solution of (S)-2-(3,4-dichloro-benzoyl)-4-fluoro-2-propyl-pyrrolidine-1-carboxylic acid tert-butyl ester (0.220 g, 0.545 mmol) in 1N methanolic HCl (3 mL) was stirred at 20° C. under nitrogen for 18 hours. The reaction mixture was concentrated in vacuo then purified by chromatography (silica, 0 to 20% MeOH in DCM) to yield (3,4-dichloro-phenyl)-((2R,4S)-4-fluoro-2-propyl-pyrrolidin-2-yl)-methanone (0.048 g, 0.158 mmol, 29%) as a first fraction (yellow oil) then (3,4-dichloro-phenyl)-((2S,4S)-4-fluoro-2-propyl-pyrrolidin-2-yl)-methanone (0.072 g, 0.238 mmol, 44%) as a second fraction (yellow oil), each as a monohydrochloride salt, MS=304 [M+H]$^+$.

Additional compounds prepared by the above procedure are shown in Table 1.

Example 15

(1H-Indol-5-yl)-(2-propyl-pyrrolidin-2-yl)-methanone

The synthetic procedure described in this Example was carried out according to the process shown in Scheme U.

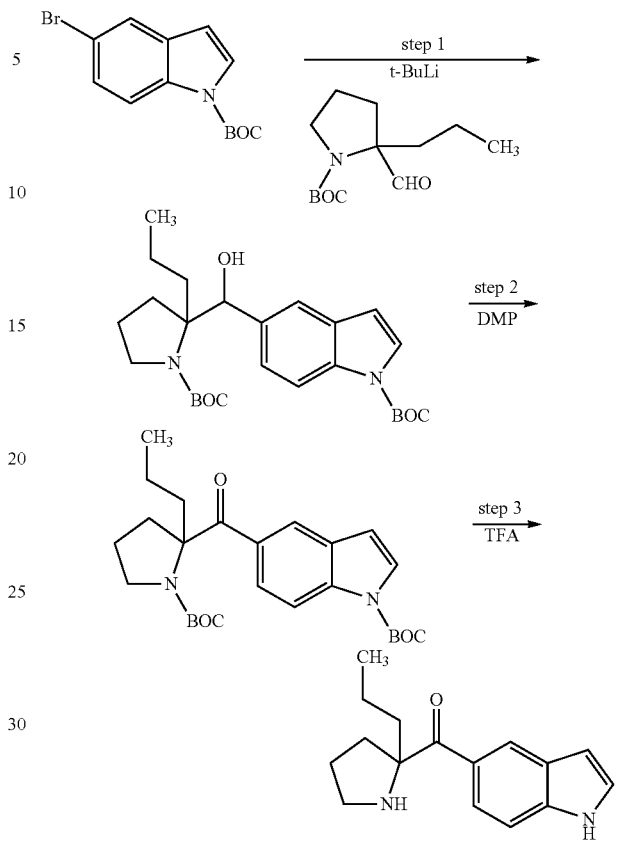

SCHEME U

Step 1 5-[(1-tert-Butoxycarbonyl-2-propyl-pyrrolidin-2-yl)-hydroxy-methyl]-indole-1-carboxylic acid tert-butyl ester To a stirred solution of 5-bromo-indole-1-carboxylic acid tert-butyl ester (0.700 g, 2.37 mmol) in ether (20 mL) at −78° C. and under nitrogen was added tert-butyllithium (3.64 mL of 1.43 M solution in pentanes, 5.21 mmol) dropwise. After 30 minutes, a solution of 2-formyl-2-propyl-pyrrolidine-1-carboxylic acid tert-butyl ester (0.569 g, 2.37 mmol) in ether (5 mL) was added to the reaction mixture dropwise. The reaction mixture was stirred for one hour, then quenched by the addition of saturated aqueous NH$_4$Cl, and extracted with EtOAc. The combined organic extracts were washed with saturated aqueous NaHCO$_3$ and brine, then dried (MgSO$_4$), filtered and concentrated in vacuo. Purification by chromatography (silica, 0-60% EtOAc in hexanes) gave 5-[(1-tert-butoxycarbonyl-2-propyl-pyrrolidin-2-yl)-hydroxy-methyl]-indole-1-carboxylic acid tert-butyl ester (0.466 g, 1.02 mmol, 43%) as a yellow oil.

Step 2 5-(1-tert-Butoxycarbonyl-2-propyl-pyrrolidine-2-carbonyl)-indole-1-carboxylic acid tert-butyl ester To a stirred solution of 5-[(1-tert-butoxycarbonyl-2-propyl-pyrrolidin-2-yl)-hydroxy-methyl]-indole-1-carboxylic acid tert-butyl ester (0.460 g, 1.00 mmol) in DCM (10 mL) at 0° C. under nitrogen was added DMP (0.652 g, 1.54 mmol) in a single portion. The reaction mixture warmed to ambient temperature and stirred for 90 minutes, then diluted with DCM, washed with a 1:1 mixture of 10% aqueous $Na_2S_2O_5$ and $NaHCO_3$, followed by brine, then dried ($MgSO_4$), filtered and concentrated in vacuo to a yellow oil. Purification by chromatography (silica, 0 to 80% EtOAc in hexanes) gave 5-(1-tert-butoxycarbonyl-2-propyl-pyrrolidine-2-carbonyl)-indole-1-carboxylic acid tert-butyl ester (0.132 g, 0.289 mmol, 29%) as a yellow oil.

Step 3 (1H-Indol-5-yl)-(2-propyl-pyrrolidin-2-yl)-methanone

To a stirred solution of 5-(1-tert-butoxycarbonyl-2-propyl-pyrrolidine-2-carbonyl)-indole-1-carboxylic acid tert-butyl ester (0.132 g, 0.289 mmol) in DCM (3 mL) at 20° C. under nitrogen was added TFA (1 mL). After 14 hours the reaction mixture was quenched with saturated aqueous $NaHCO_3$ and extracted with DCM. The combined organic phases were concentrated in vacuo then purified by chromatography (silica, 0 to 30% MeOH in DCM) to furnish (1H-indol-5-yl)-(2-propyl-pyrrolidin-2-yl)-methanone (0.053 g, 0.207 mmol, 72%) as a beige foam, MS=257 [M+H]+.

Additional compounds prepared by the above procedure are shown in Table 1.

Example 16 exo-(3,4-Dichloro-phenyl)-(2-propyl-8-aza-bicyclo[3.2.1]oct-2-yl)-methanone The synthetic procedure described in this Example was carried out according to the process shown in Scheme V.

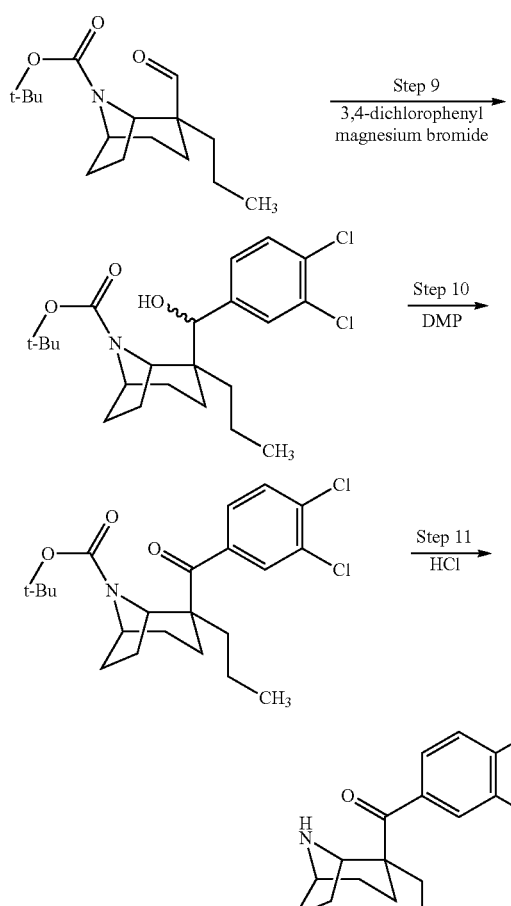

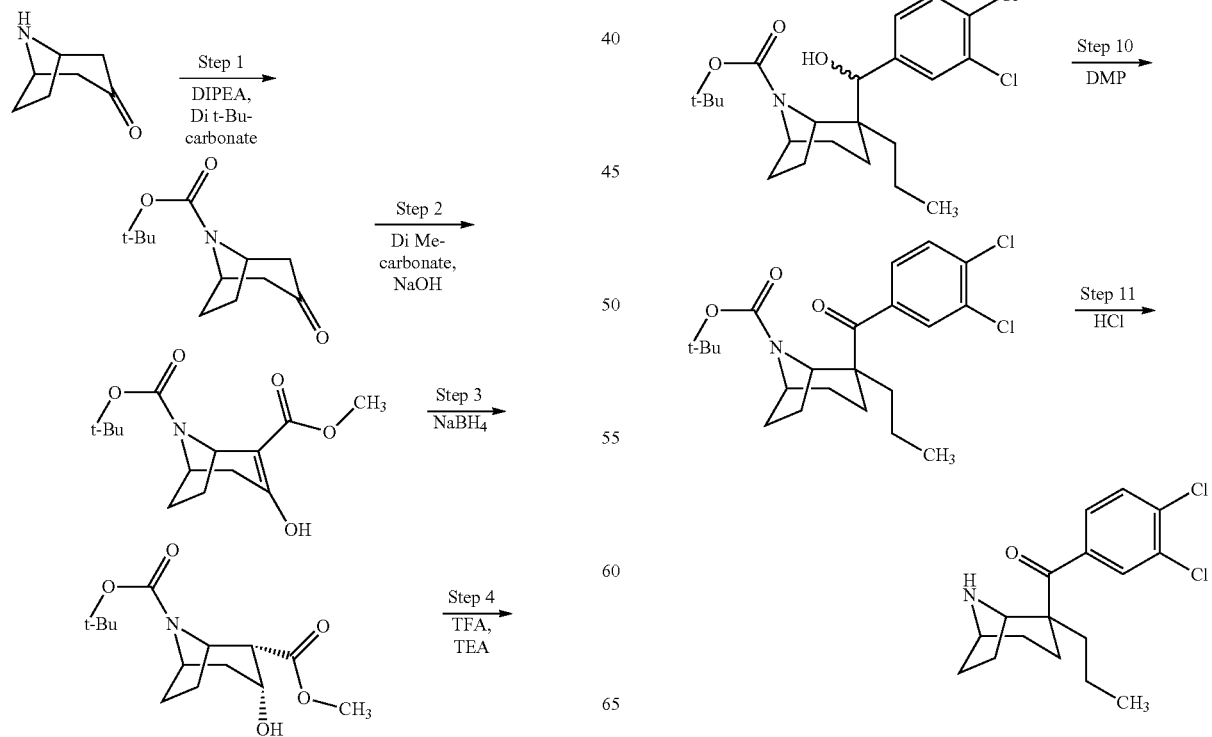

Step 1
3-Oxo-8-azabicyclo[3.2.1]octane-8-carboxylic acid tert-butyl ester 8-Azabicyclo[3.2.1]octan-3-one hydrochloride (nortropinone hydrochloride, 10.0 g, 62 mmol) was dissolved in 1,4-dioxane (200 mL) and water (50 mL). N,N-diisopropylethylamine (20.0 g, 155 mmol) and di-tert-butyldicarbonate (20.3 g, 93 mmol) were added, and the reaction mixture was stirred at room temperature for three hours. The mixture was diluted with water and extracted with ethyl acetate. The combined organic extracts were with water and brine, dried over sodium sulfate, filtered, and concentrated under reduced pressure. The residue was purified by flash chromatography (silica gel, ethyl acetate/hexane) to provide 3-oxo-8-azabicyclo[3.2.1]octane-8-carboxylic acid tert-butyl ester as an off-white solid, 14 g (99% yield).

Step 2 3-Hydroxy-8-azabicyclo[3.2.1]oct-2-ene-2,8-dicarboxylic acid 8-tert-butyl ester 2-methyl ester 3-Oxo-8-azabicyclo[3.2.1]octane-8-carboxylic acid tert-butyl ester from Step 1 (14.1 g, 62 mmol) was dissolved in cyclohexane (550 mL), to which was added dimethyl carbonate (12.4 g, 137 mmol), followed by sodium hydride (5.0 g, 125 mmol) and methanol (0.2 mL). The reaction mixture was stirred at reflux for 15 hours, then cooled to room temperature, and water (25 mL) was added. The reaction mixture was concentrated under reduced pressure to a volume of 50 mL, which was then partitioned between ethyl acetate and saturated aqueous ammonium chloride. The combined organic extracts were washed with water and brine, dried over sodium sulfate, filtered, and concentrated under reduced pressure. The residue was purified by flash chromatography (silica gel, ethyl acetate/hexane) to provide 3-hydroxy-8-azabicyclo[3.2.1]oct-2-ene-2,8-dicarboxylic acid 8-tert-butyl ester 2-methyl ester as a light yellow oil (15.4 g, 87% yield).

Step 3 endo-3-Hydroxy-8-azabicyclo[3.2.1]octane-2,8-dicarboxylic acid 8-tert-butyl ester exo-2-methyl ester 3-Hydroxy-8-azabicyclo[3.2.1]oct-2-ene-2,8-dicarboxylic acid 8-tert-butyl ester 2-methyl ester from Step 2 (15.4 g, 54 mmol) was dissolved in methanol (350 mL). The resulting solution was cooled in an acetonitrile/dry ice bath (−45° C.). Sodium borohydride (5.15 g, 136 mmol, 10-40 mesh) was added, and the reaction mixture was stirred at −45° C. for 1.5 hours, after which time saturated aqueous ammonium chloride (50 mL) was added. The mixture was warmed to room temperature and then concentrated under reduced pressure to a volume of 50 mL, which was then partitioned between dichloromethane and saturated aqueous ammonium chloride. The combined organic layers were dried over sodium sulfate, filtered and concentrated under reduced pressure. The residue was purified by flash chromatography (silica gel, ethyl acetate/hexane) to provide endo-3-hydroxy-8-azabicyclo[3.2.1]octane-2,8-dicarboxylic acid 8-tert-butyl ester exo-2-methyl ester as a colorless oil (8.1 g, 52% yield).

Step 4
8-Azabicyclo[3.2.1]oct-2-ene-2,8-dicarboxylic acid 8-tert-butyl ester 2-methyl ester Endo-3-hydroxy-8-azabicyclo[3.2.1]octane-2,8-dicarboxylic acid 8-tert-butyl ester exo-2-methyl ester from Step 3 (8.1 g, 28 mmol) was dissolved in 1,2-dichloroethane (120 mL), to which was added triethylamine (17.2 g, 170 mmol) and trifluoroacetic anhydride (17.8 g, 85 mmol). The reaction mixture was stirred at room temperature for 15 hours, then aqueous saturated sodium bicarbonate (150 mL) and dichloromethane (280 mL) were added. The organic phase was separated and washed with brine. The combined organic layers were dried over sodium sulfate, filtered and concentrated under reduced pressure. The residue was purified by flash chromatography (silica gel, ethyl acetate/hexane) to provide 8-azabicyclo[3.2.1]oct-2-ene-2,8-dicarboxylic acid 8-tert-butyl ester 2-methyl ester as a yellow oil (6.0 g, 79% yield).

Step 5 8-Azabicyclo[3.2.1]octane-2,8-dicarboxylic acid 8-tert-butyl ester 2-methyl ester 8-Azabicyclo[3.2.1]oct-2-ene-2,8-dicarboxylic acid 8-tert-butyl ester 2-methyl ester from Step 4 (5.9 g, 22 mmol) was dissolved in ethanol (100 mL), to which palladium (10% on charcoal, 0.59 g) was added. The resulting mixture was shaken under an atmosphere of hydrogen (50 psi) for 2 hours at room temperature, and was then filtered through a bed of Celite, which was washed with ethyl acetate. The filtrate was concentrated under reduced pressure, and the resulting residue was purified by flash chromatography (silica gel, ethyl acetate/hexane) to provide 8-azabicyclo[3.2.1]octane-2,8-dicarboxylic acid 8-tert-butyl ester 2-methyl ester as a mixture of endo and exo isomers as a colorless oil (5.8 g, 97% yield).

Step 6 2-Propyl-8-aza-bicyclo[3.2.1]octane-2,8-dicarboxylic acid 8-tert-butyl ester 8-Azabicyclo[3.2.1]octane-2,8-dicarboxylic acid 8-tert-butyl ester 2-methyl ester as a mixture of endo and exo isomers from Step 5 (1.0 g, 3.7 mmol) was dissolved in tetrahydrofuran (30 mL), and 1-iodopropane (3.2 g, 19 mmol) was added. The resulting solution was cooled to −76° C. and treated dropwise over 15 minutes with solution of potassium bis(trimethylsilyl) amide in toluene (0.5 M, 11.1 mL, 5.6 mmol). Stirring was continued at −76° C. for 1.5 hours, and the reaction mixture was then allowed to warm slowly to 0° C. over 3 hours. Saturated aqueous ammonium chloride was added, and the resulting mixture was extracted with ethyl acetate. The combined organic extracts were washed with water and brine, dried over sodium sulfate, filtered, and concentrated under reduced pressure. The residue was purified by flash chromatography (silica gel, ethyl acetate/hexane) to provide 2-propyl-8-aza-bicyclo[3.2.1]octane-2,8-dicarboxylic acid 8-tert-butyl ester 2-methyl ester as a mixture of endo and exo isomers as a pale yellow oil (0.99 g, 85% yield).

Step 7 2-hydroxymethyl-2-propyl-8-azabicyclo[3.2.1]octane-8-carboxylic acid tert-butyl ester 2-Propyl-8-aza-bicyclo[3.2.1]octane-2,8-dicarboxylic acid 8-tert-butyl ester 2-methyl ester (mixture of endo and exo isomers from Step 6, 0.98 g, 3.1 mmol) was dissolved in tetrahydrofuran (15 mL), and the resulting mixture was cooled to 0° C. A solution of lithium aluminum hydride in tetrahydrofuran (1 M, 3.3 mL, 3.3 mmol) in tetrahydrofuran was added dropwise over 10 minutes, and stirring was continued at 0° C. for 1.5 hours. A saturated aqueous solution of potassium sodium tartrate (10 mL) was added, and the mixture was warmed to room temperature and stirred for 15 hours. Additional saturated aqueous solution of potassium sodium tartrate (10 mL) was added, and the mixture was extracted with ethyl acetate. The combined organic extracts were washed with water and brine, dried over sodium sulfate, filtered, and concentrated under reduced pressure. The residue was purified by flash chromatography (silica gel, ethyl acetate/hexane) to provide 2-hydroxymethyl-2-propyl-8-azabicyclo[3.2.1]octane-8-carboxylic acid tert-butyl ester as a separable mixture of endo and exo isomers, both as colorless oils (0.68 g and 0.17 g, 76% and 19% yield, respectively).

Step 8 exo-2-Formyl-2-propyl-8-azabicyclo[3.2.1]octane-8-carboxylic acid tert-butyl ester exo-2-Hydroxymethyl-2-propyl-8-azabicyclo[3.2.1]octane-8-carboxylic acid tert-butyl ester from Step 7 (0.67 g, 2.4 mmol) was dissolved in dichloromethane (25 mL). The solution was cooled to 0° C., and Dess-Martin periodinane (1.0 g, 2.4 mmol) was added. Stirring was continued for 5 minutes at 0° C., followed by 1.5 hours at room temperature. To the reaction mixture was added to diethyl ether (50 mL) and aqueous sodium hydroxide (1 M, 20 mL), followed by additional diethyl ether (30 mL). The phases were separated, and the organic phase was washed with water and brine. The combined organic layers dried over sodium sulfate, and concentrated under reduced pressure. The residue was purified by flash chromatography (silica gel, ethyl acetate/hexane) to provide exo-2-formyl-2-propyl-8-azabicyclo[3.2.1]octane-8-carboxylic acid tert-butyl ester as a colorless oil (0.61 g, 90% yield).

Step 9 exo-2-[(3,4-Dichlorophenyl)-hydroxymethyl]-2-propyl-8-azabicyclo[3.2.1]octane-8-carboxylic acid tert-butyl ester exo-2-Formyl-2-propyl-8-azabicyclo[3.2.1]octane-8-carboxylic acid tert-butyl ester from Step 8 (0.45 g, 1.6 mmol) was dissolved in tetrahydrofuran (4 mL). The resulting solution was cooled to 0° C., and a solution 3,4-dichlorophenyl-magnesium bromide in tetrahydrofuran (0.5 M, 6.4 mL, 3.2 mmol) was added dropwise over 10 minutes. Stirring was continued at 0° C. for 1.5 hours, then aqueous saturated ammonium chloride (20 mL) was added. The resulting mixture was extracted with ethyl acetate, and the combined organic extracts were washed with water and brine, dried over sodium sulfate, filtered, and concentrated under reduced pressure. The residue was purified by flash chromatography (silica gel, ethyl acetate/hexane) to provide exo-2-[(3,4-dichlorophenyl)-hydroxymethyl]-2-propyl-8-azabicyclo[3.2.1]octane-8-carboxylic acid tert-butyl ester as a mixture of epimers as a white solid (0.57 g, 83% yield).

Step 10 exo-2-(3,4-Dichlorobenzoyl)-2-propyl-8-azabicyclo[3.2.1]octane-8-carboxylic acid tert-butyl ester exo-2-[(3,4-dichlorophenyl)-hydroxymethyl]-2-propyl-8-azabicyclo[3.2.1]octane-8-carboxylic acid tert-butyl ester as a mixture of epimers from Step 9 (0.56 g, 1.3 mmol) was suspended in acetonitrile (14 mL). Dichloromethane (4 mL) was added, and to the resulting homogeneous solution was added Dess-Martin periodinane (0.56 g, 1.3 mmol), followed by stirring at room temperature for 1 hour. To the reaction mixture was added diethyl ether (80 mL) and aqueous sodium hydroxide (1 M, 20 mL). The phases were separated, and the combined organic extracts were washed with water and brine, dried over sodium sulfate, filtered, and concentrated under reduced pressure. The residue was purified by flash chromatography (silica gel, ethyl acetate/hexane) to provide exo-2-(3,4-dichlorobenzoyl)-2-propyl-8-azabicyclo[3.2.1]octane-8-carboxylic acid tert-butyl ester as an off-white solid (0.53 g, 95% yield).

Step 11 exo-(3,4-dichloro-phenyl)-(2-propyl-8-azabicyclo[3.2.1]oct-2-yl)methanone exo-2-(3,4-Dichlorobenzoyl)-2-propyl-8-azabicyclo[3.2.1]octane-8-carboxylic acid tert-butyl ester from Step 10 (0.15 g, 0.35 mmol) was dissolved in a solution of hydrogen chloride in methanol (1 M, 3.5 mL), and the resulting solution was stirred at 40° C. for two hours. The reaction mixture was concentrated under reduced pressure to provide exo-(3,4-dichloro-phenyl)-(2-propyl-8-azabicyclo[3.2.1]oct-2-yl)methanone hydrochloride as a white foam (0.13 g, 99% yield).

Similarly prepared from endo-2-hydroxymethyl-2-propyl-8-azabicyclo[3.2.1]octane-8-carboxylic acid tert-butyl ester from Step 7, following Steps 8-11, was endo-(3,4-dichloro-phenyl)-(2-propyl-8-azabicyclo[3.2.1]oct-2-yl)methanone hydrochloride, MS=326 [M+H]$^+$ Additional compounds prepared by the above procedure are shown in Table 1.

Example 17

(5-Fluoro-1H-indol-2-yl)-(4-propyl-piperidin-4-yl)-methanone

The synthetic procedure described in this Example was carried out according to the process shown in Scheme W.

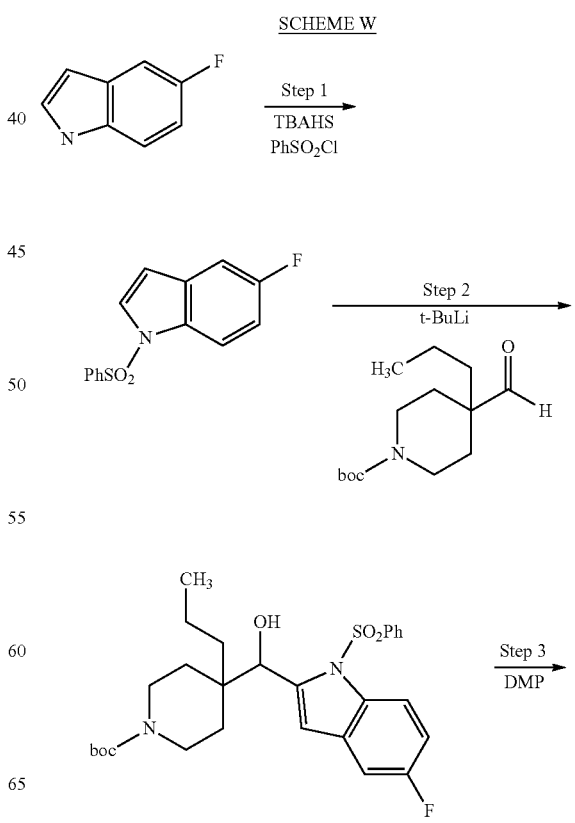

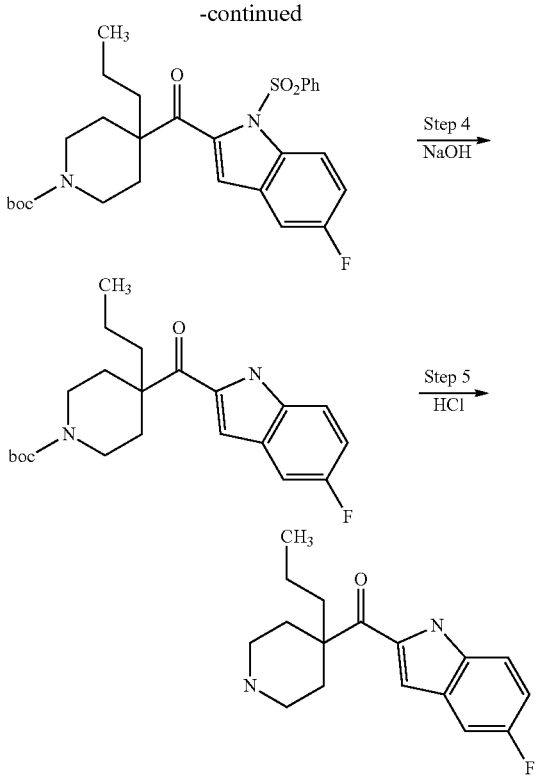

Step 1 1-Benzenesulfonyl-5-fluoro-1H-indole

To a 0° C. solution of 5-fluoroindole (10 g, 74 mmol) and tetrabutyl ammonium hydrogen sulfate (3.8 g, 11 mmol) in 200 mL of toluene was added 200 mL 50% aqueous NaOH, followed by addition of benzene sulfonylchloride (14 mL, 111 mmol). The reaction mixture was allowed to warm to room temperature overnight. The reaction mixture was extracted with ethyl acetate and washed with 1 M HCl, aqueous sodium bicarbonate, water and brine. The organic layer was dried over magnesium sulfate, filtered and concentrated in vacuo. The remaining residue was recrystallized from ethyl acetate and hexanes to afford 19 g (96% yield) of 1-benzenesulfonyl-5-fluoro-1H-indole as a white crystalline solid.

Step 2 4-[(1-Benzenesulfonyl-5-fluoro-1H-indol-2-yl)-hydroxy-methyl]-4-propyl-piperidine-1-carboxylic acid tert-butyl ester To a −78° C. solution of 1-benzenesulfonyl-5-fluoro-1H-indole (539 mg, 1.96 mmol) in 30 mL THF, t-BuLi (1.5 mL, 2.54 mmol) was slowly added. The reaction mixture was stirred for 30 minutes, then a solution of 4-formyl-4-propyl-piperidine-1-carboxylic acid tert-butyl ester (500 mg, 1.96 mmol) in 5 mL THF was added. The reaction was allowed to stir for 2 hours at −78° C. and was then warmed to −20° C. and quenched with a saturated aqueous solution of ammonium chloride. The reaction mixture was extracted with ethyl acetate and the combined organic layers were washed with brine, dried (MgSO$_4$), filtered and concentrated onto silica. The material was chromatographed over a 25 g Thomson column eluting with 20% ethyl acetate 80% hexanes to afford 4-[(1-benzenesulfonyl-5-fluoro-1H-indol-2-yl)-hydroxy-methyl]-4-propyl-piperidine-1-carboxylic acid tert-butyl ester (319 mg, 0.6 mmol) in a 53% yield as a beige foam.

Step 3 4-(1-benzenesulfonyl-5-fluoro-1H-indole-2-carbonyl)-4-propyl-piperidine-1-carboxylic acid tert-butyl ester To a solution of 4-[(1-benzenesulfonyl-5-fluoro-1H-indol-2-yl)-hydroxy-methyl]-4-propyl-piperidine-1-carboxylic acid tert-butyl ester (319 mg, 0.6 mmol) in 20 mL of dichloromethane was added Dess-Martin periodinane (255 mg, 0.6 mmol). The reaction was stirred for 30 minutes at room temperature, and then quenched with a 1:1 mixture of 5% aqueous Na$_2$S$_2$O$_3$: saturated aqueous NaHCO$_3$. The mixture was stirred until all solids were dissolved, then extracted with diethyl ether. The combined organic layers were washed with saturated aqueous NaHCO$_3$, and brine, dried (MgSO$_4$), filtered and concentrated in vacuo to afford crude 4-(1-benzenesulfonyl-5-fluoro-1H-indole-2-carbonyl)-4-propyl-piperidine-1-carboxylic acid tert-butyl ester (300 mg, 0.57 mmol) as a beige solid in a 95% yield.

Step 4 4-(5-Fluoro-1H-indole-2-carbonyl)-4-propyl-piperidine-1-carboxylic acid tert-butyl ester To a solution of 4-(1-benzenesulfonyl-5-fluoro-1H-indole-2-carbonyl)-4-propyl-piperidine-1-carboxylic acid tert-butyl ester (290 mg, 0.55 mmol) in 30 mL of methanol was added 10 mL of 1M NaOH. The reaction mixture was warmed to 80° C. and was allowed to stir for one hour, then was concentrated in vacuo to remove the methanol. The remaining residue was extracted with ethyl acetate, and the combined organic layers were washed with brine, dried (MgSO$_4$), filtered and concentrated in vacuo to afford a yellow colored oil. The oil was chromatographed over a 12 g SiO2 column eluting with 20% ethyl Acetate, 80% hexanes to afford 4-(5-fluoro-1H-indole-2-carbonyl)-4-propyl-piperidine-1-carboxylic acid tert-butyl ester 162 mg as a white solid in 76% yield.

Step 5 (5-Fluoro-1H-indol-2-yl)-(4-propyl-piperidin-4-yl)-methanone 4-(5-fluoro-1H-indole-2-carbonyl)-4-propyl-piperidine-1-carboxylic acid tert-butyl ester 162 mg was dissolved in 1 M methanolic HCl and stirred at room temperature for 24 hours. The solvent was removed to afford an oil which was precipitated from diethyl ether to give (5-fluoro-1H-indol-2-yl)-(4-propyl-piperidin-4-yl)-methanone; hydrochloride 132 mg as a solid in 97% yield, MS=289 [M+H]$^+$.

Additional compounds prepared by the above procedure are shown in Table 1.

Example 18

(4-Propyl-piperidin-4-yl)-quinolin-2-yl-methanone

The synthetic procedure described in this Example was carried out according to the process shown in Scheme X.

SCHEME X

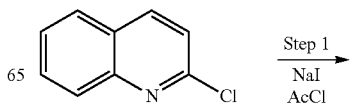

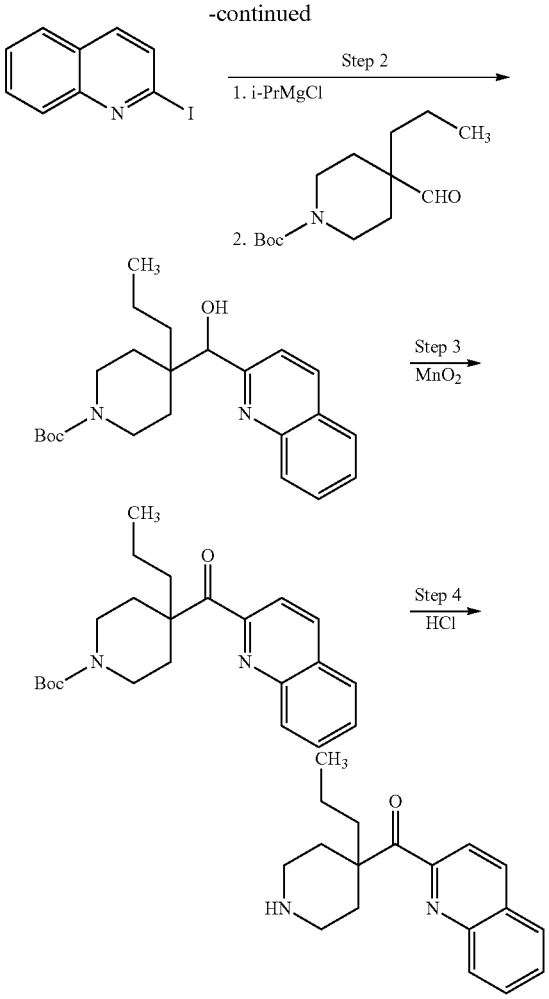

ous NH4Cl solution, and extracted with EtOAc. The combined organic extracts were washed with brine, dried over MgSO4, filtered and concentrated under reduced pressure. The residue was purified by flash chromatography (0% to 20% EtOAc in hexanes) to afford 190 mg (19%) of 4-(hydroxy-quinolin-2-yl-methyl)-4-propyl-piperidine-1-carboxylic acid tert-butyl ester as a yellow oil.

Step 3 4-Propyl-4-(quinoline-2-carbonyl)-piperidine-1-carboxylic acid tert-butyl ester To a solution of 4-(hydroxy-quinolin-2-yl-methyl)-4-propyl-piperidine-1-carboxylic acid tert-butyl ester (190 mg, 0.5 mmol) in toluene (5 mL) was added manganese (IV) oxide (activated, 260 mg, 3.0 mmol). The reaction mixture was heated at 100° C. for 3 hours, then cooled to room temperature and filtered through Celite, rinsing with EtOAc. The filtrate was concentrated and purified by flash chromatography (0% to 20% EtOAc in hexanes) to provide 124 mg (67%) of 4-propyl-4-(quinoline-2-carbonyl)-piperidine-1-carboxylic acid tert-butyl ester as a colorless oil.

Step 4
(4-Propyl-piperidin-4-yl)-quinolin-2-yl-methanone

4-Propyl-4-(quinoline-2-carbonyl)-piperidine-1-carboxylic acid tert-butyl ester (124 mg, 0.32 mmol) was dissolved in a solution of anhydrous 1.0M HCl in MeOH (5 mL). The reaction mixture was stirred at room temperature for 15 hours then concentrated under reduced pressure to afford 82 mg (80%) of (4-propyl-piperidin-4-yl)-quinolin-2-yl-methanone hydrochloride as a yellow solid, MS=283 [M+H]+.

Additional compounds prepared by the above procedure are shown in Table 1.

Step 1 2-Iodoquinoline

2-Iodoquinoline was prepared according to the procedure of Kimber, et. al. (*Tetrahedron* 2000, 56, 3575). To a solution of 2-chloroquinoline (10.0 g, 61.5 mmol) in CH3CN (100 mL) was added sodium iodide (14 g, 92.3 mmol) and acetyl chloride (8.8 mL, 123 mmol). The reaction mixture was stirred at 100° C. for 5 hours, then cooled to room temperature and quenched with 10% aqueous K2CO3 (100 mL) and 5% aqueous NaHSO3 (50 mL). The aqueous layer was extracted twice with dichloromethane then the combined organic extracts were dried over MgSO4, filtered and concentrated under reduced pressure. The residue was purified by flash chromatography (0% to 20% EtOAc in hexanes) to provide 9.7 g (70%) of 2-iodoquinoline as a yellow solid.

Step 2 4-(Hydroxy-quinolin-2-yl-methyl)-4-propyl-piperidine-1-carboxylic acid tert-butyl ester To a solution of 2-iodoquinoline (670 mg, 2.6 mmol) in THF (10 mL) at 0° C. was slowly added isopropyl magnesium chloride (2.0 M in THF, 1.6 mL, 3.2 mmol). The reaction mixture was stirred at 0° C. for 30 minutes, then a solution of 4-formyl-4-propyl-piperidine-1-carboxylic acid tert-butyl ester (670 mg, 2.6 mmol) in THF (3 mL) was slowly added. The reaction mixture was stirred at 0° C. for 30 minutes, then warmed to room temperature, quenched with saturated aque- Example 19

[3-(3,3-Dimethyl-butyl)-pyrrolidin-3-yl]-(5-fluoro-benzo[b]thiophen-3-yl)-methanone The synthetic procedure described in this Example was carried out according to the process shown in Scheme Y.

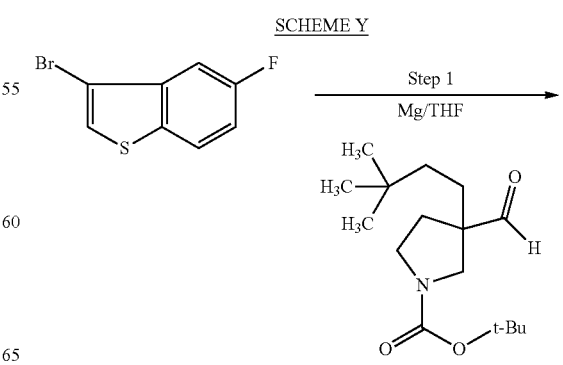

225

-continued

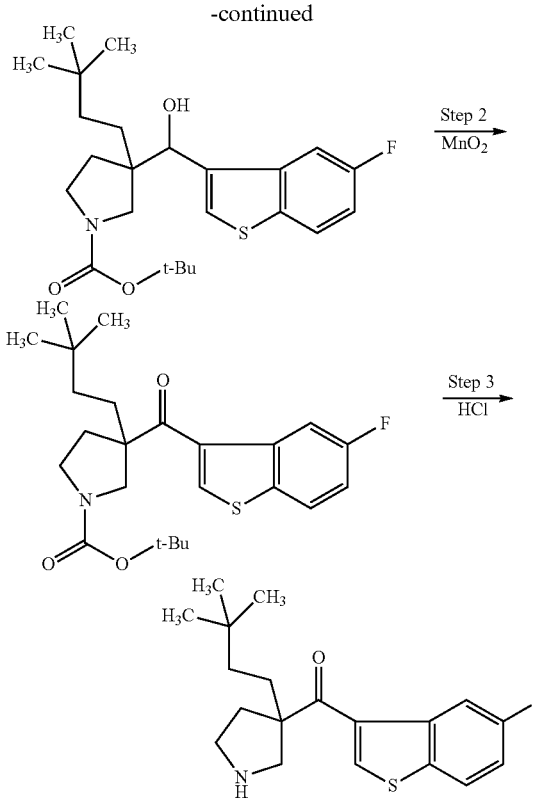

Step 1 3-(3,3-Dimethyl-butyl)-3-[(5-fluoro-benzo[b]
thiophen-3-yl)-hydroxy-methyl]-pyrrolidine-1-carboxylic acid tert butyl ester A mixture of 3-bromo-5-fluoro-benzothiophene (0.4 g, 1.73 mmoles), magnesium (0.051 g, 2.1 mmoles) and a few particles of iodine in anhydrous tetrahydrofuran (10 nil) was refluxed for 7 hours, and then cooled in an ice bath. To the reaction mixture was slowly added a solution of 3-(3,3-dimethyl-butyl)-3-formyl-pyrrolidine-1-carboxylic acid tert-butyl ester (0.39 g, 1.38 mmoles) in anhydrous tetrahydrofuran (9 ml). The reaction mixture was stirred at ice bath temperature for one hour and quenched with saturated aqueous ammonium chloride solution. The aqueous solution was extracted into ethylacetate which was washed with brine and dried over anhydrous sodium sulfate. After removal of drying agent, the organic solution was concentrated under reduced pressure. The residue was purified by silica gel chromatography (0 to 20% ethyl acetate in hexane) to yield 3-(3,3-dimethyl-butyl)-3-[(5-fluoro-benzo[b]thiophen-3-yl)-hydroxy-methyl]-pyrrolidine-1-carboxylic acid tert butyl ester as yellow foam (0.13 g, 21%), MS=436 [M+H]+, Step 2 3-(3,3-Dimethyl-butyl)-3-(5-fluoro-benzo[b]
thiophene-3-carbonyl)-pyrrolidine-1-carboxylic acid tert-butyl ester 3-(3,3-Dimethyl-butyl)-3-(5-fluoro-benzo[b]thiophene-3-carbonyl)-pyrrolidine-1-carboxylic acid tert-butyl ester was prepared from 3-(3,3-dimethyl-butyl)-3-[(5-fluoro-benzo[b]thiophen-3-yl)-hydroxy-methyl]-pyrrolidine-1-carboxylic acid tert butyl ester by oxidation with MnO2 using the procedure of step 3 of Example 18.

226

Step 3 [3-(3,3-Dimethyl-butyl)-pyrrolidin-3-yl]-(5-fluoro-benzo[b]thiophen-3-yl)-methanone

[3-(3,3-Dimethyl-butyl)-pyrrolidin-3-yl]-(5-fluoro-benzo[b]thiophen-3-yl)-methanone was prepared from 3-(3,3-Dimethyl-butyl)-3-(5-fluoro-benzo[b]thiophene-3-carbonyl)-pyrrolidine-1-carboxylic acid tert-butyl ester using the procedure of step 4 of Example 18, MS=334 [M+H]+.

Additional compounds prepared by the above procedure are shown in Table 1.

Example 20

(7-Fluoro-benzo[b]thiophen-2-yl)-[3-(tetrahydro-pyran-4-ylmethyl)-pyrrolidin-3-yl]-methanone The synthetic procedure described in this Example was carried out according to the process shown in Scheme Z.

SCHEME Z

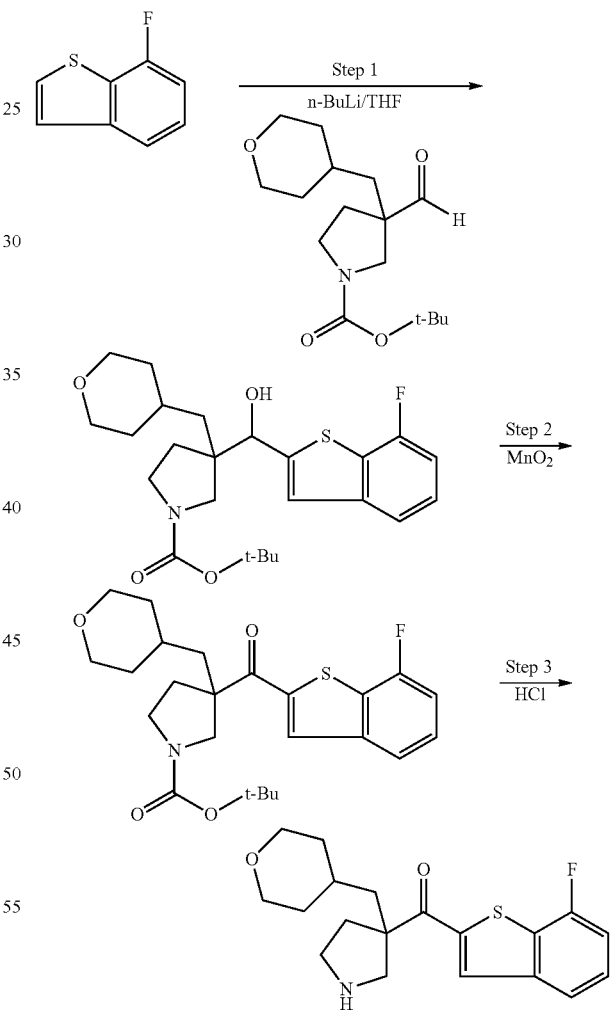

Step 1 3-[7-Fluoro-benzo[b]thiophen-2-yl)-hydroxy-methyl]-3-(tetrahydro-pyran-4-ylmethyl)-pyrrolidine-1-carboxylic acid tert-butyl ester To a solution of 7-fluoro-benzothiophene (0.22 g, 1.44 mmoles) in anhydrous tetrahydrofuran (10 ml) at −78° C. was added dropwise a solution of n-BuLi in hexane (1.6M, 0.9 ml, 1.44 mmoles). The reaction mixture was stirred at −78° C. for one hour, and then a solution of 3-formyl-3-(tetrahydro-pyran-4-ylmethyl)-pyrrolidine-1-carboxylic acid tert-butyl ester (0.3 g, 1.01 mmoles) in anhydrous tetrahydrofuran (5 ml) was then added. The reaction mixture was stirred at −78° C. for 3 hours, quenched with saturated aqueous ammonium chloride, and partitioned between ethyl acetate and saturated aqueous ammonium chloride solution. The organic phase was washed with brine, dried over anhydrous sodium sulfate, filtered, and concentrated under reduced pressure. The residue was purified by silica gel chromatography (10 to 45% ethyl acetate in hexane) to yield 3-[(7-Fluoro-benzo[b]thiophen-2-yl)-hydroxy-methyl]-3-(tetrahydro-pyran-4-yl-methyl)-pyrrolidine-1-carboxylic acid tert-butyl ester as a colorless semisolid (0.138 g, 30%). MS=450 [M+H]+.

Step 2 3-(7-Fluoro-benzo[b]thiophene-2-carbonyl)-3-(tetrahydro-pyran-4-ylmethyl)-pyrrolidine-1-carboxylic acid tert-butyl ester 3-(7-Fluoro-benzo[b]thiophene-2-carbonyl)-3-(tetrahydro-pyran-4-ylmethyl)-pyrrolidine-1-carboxylic acid tert-butyl ester was prepared from 3-[(7-fluoro-benzo[b]thiophen-2-yl)-hydroxy-methyl]-3-(tetrahydro-pyran-4-ylmethyl)-pyrrolidine-1-carboxylic acid tert-butyl ester by oxidation with MnO$_2$ using the procedure of step 3 of Example 18.

Step 3 (7-Fluoro-benzo[b]thiophen-2-yl)-[3-(tetrahydro-pyran-4-ylmethyl)-pyrrolidin-3-yl]-methanone (7-Fluoro-benzo[b]thiophen-2-yl)-[3-(tetrahydro-pyran-4-ylmethyl)-pyrrolidin-3-yl]-methanone was prepared from 3-(7-Fluoro-benzo[b]thiophene-2-carbonyl)-3-(tetrahydro-pyran-4-ylmethyl)-pyrrolidine-1-carboxylic acid tert-butyl ester using the procedure of step 4 of Example 18, MS=348 [M+H]+.

Additional compounds prepared by the above procedure are shown in Table 1.

Example 21

(4-Chloro-5-methyl-thiophen-2-yl)-(3-propyl-pyrrolidin-3-yl)-methanone

The synthetic procedure described in this Example was carried out according to the process shown in Scheme AA.

SCHEME AA

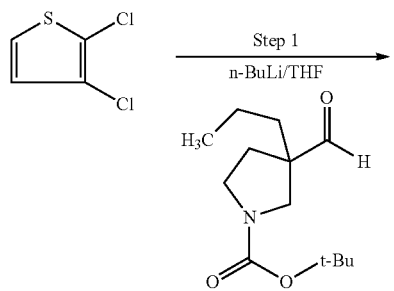

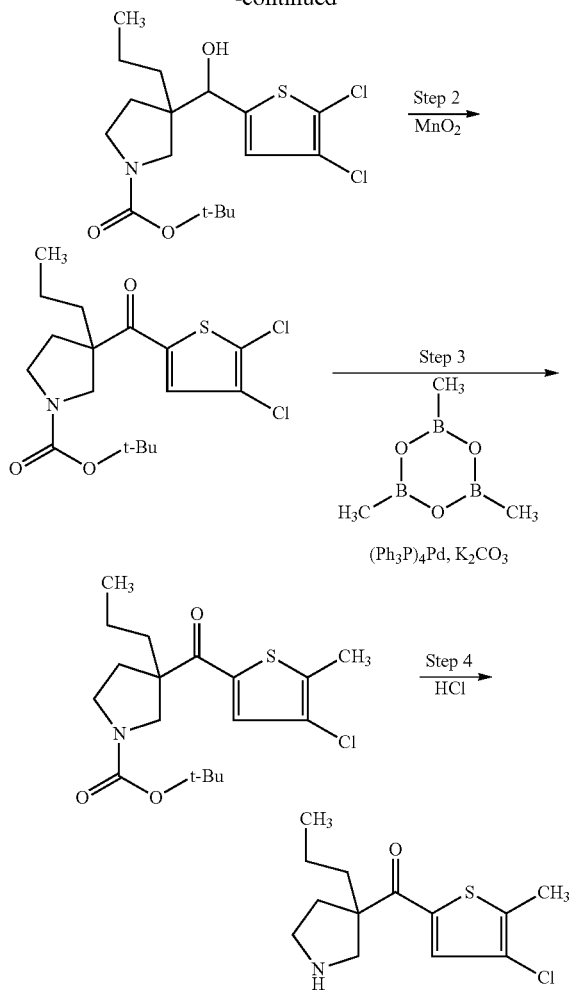

Step 1 3-[(4,5-Dichloro-thiophen-2-yl)-hydroxy-methyl]-3-propyl-pyrrolidine-1-carboxylic acid tert-butyl ester 3-[(4,5-Dichloro-thiophen-2-yl)-hydroxy-methyl]-3-propyl-pyrrolidine-1-carboxylic acid tert-butyl ester was prepared from 2,3-dichloro-thiophene and 3-formyl-3-propyl-pyrrolidine-1-carboxylic acid tert-butyl ester using the procedure of step 1 of Example 20.

Step 2 3-(4,5-Dichloro-thiophene-2-carbonyl)-3-propyl-pyrrolidine-1-carboxylic acid tert-butyl ester A mixture of 3-[(4,5-dichloro-thiophen-2-yl)-hydroxy-methyl]-3-propyl-pyrrolidine-1-carboxylic acid tert-butyl ester (0.423 g, 1.07 mmoles) and manganese(IV) oxide (1.3 g, 12.7 mmoles) in toluene (20 ml) was refluxed for 2 hours and filtered through a celite pad. The filtrate was washed with brine, dried over anhydrous sodium sulfate, filtered and concentrated under reduced pressure. The residue was purified by silica gel chromatography (10% ethyl acetate in hexane) to yield 3-(4,5-dichloro-thiophene-2-carbonyl)-3-propyl-pyrrolidine-1-carboxylic acid tert-butyl ester as pale yellow solid (0.27 g, 64%). M+Na: 414.

Step 3 3-(4-Chloro-5-methyl-thiophene-2-carbonyl)-3-propyl-pyrrolidine-1-carboxylic acid tert-butyl ester A mixture of 3-(4,5-dichloro-thiophene-2-carbonyl)-3-propyl-pyrrolidine-1-carboxylic acid tert-butyl ester (0.2 g, 0.512 mmoles), trimethylboroxine (0.24 g, 1.91 mmoles), potassium carbonate (0.22 g, 1.59 mmoles), and tetrakis(triphenylphosphine)palladium(0) (0.06 g, 0.051 mmoles) in dioxane (10 ml) was refluxed for three hours, then cooled to room temperature. The mixture was filtered through celite and the filtrate was concentrated under reduced pressure. The residue was purified by silica gel chromatography (0 to 10% ethyl acetate in hexane) to yield 3-(4-chloro-5-methyl-thiophene-2-carbonyl)-3-propyl-pyrrolidine-1-carboxylic acid tert-butyl ester as a solid (0.166 g, 87%). M+Na: 394

Step 4 (4-Chloro-5-methyl-thiophen-2-yl)-(3-propyl-pyrrolidin-3-yl)-methanone A solution of 3-(4-chloro-5-methyl-thiophene-2-carbonyl)-3-propyl-pyrrolidine-1-carboxylic acid tert-butyl ester (0.16 g, 0.43 mmoles) in a mixed solvent of methanol and dichloromethane (3 ml/3 ml) was added a solution of hydrochloride acid in anhydrous ether (1M, 10 ml). The solution was stirred at room temperature over night, and concentrated under reduced pressure. The residue was triturated with hexanes and diethyl ether to yield (4-chloro-5-methyl-thiophen-2-yl)-(3-propyl-pyrrolidin-3-yl)-methanone hydrochloride as solid (0.129 g, 97%). $[M+H]^+$: 272

Similarly prepared, by omitting step 3, was (4,5-dichloro-thiophen-2-yl)-(3-propyl-pyrrolidin-3-yl)-methanone, MS=292 $[M+H]^+$.

Additional compounds prepared by the above procedure are shown in Table 1.

Example 22

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |

-continued

Topical Formulation

| Ingredients | grams |
|---|---|
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 23

Screening for Human Serotonin Transporter (hSERT) Antagonists Using a Scintillation Proximity Assay (SPA)

The screening assay of this example was used to determine the affinity of ligands at the hSERT transporter by competition with [$^3$H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 µg/ml G418 and 2 mM L-Glutamine) and incubated at 37° C. with 5% $CO_2$. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay $IC_{50}/K_i$ determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the [$^3$H]-Citalopram radioligand was added at 50 µl/well. Membrane and beads were prepared to a ratio of 10 µg:0.7 mg, with 0.7 mg PVT-WGA Amersham beads (Cat# RPQ0282V) added per well. 130 µl of the membrane:bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for human serotonin transporter. For example, naphthalen-2-yl-(3-propyl-pyrrolidin-3-yl)-methanone exhibited a pKi of approximately 9.82 using the above assay.

Example 24

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine. As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 µg/ml G418 and 2 mM L-Glutamine) and incubated at 37° C. with 5% $CO_2$. Cells were released from culture flasks using PBS for 1-2 minutes.

The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube ($7.5 \times 10^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v). and stored at −80° C.

$^3$[H] Nisoxetine radioligand (Amersham Cat. # TRK942 or Perkin Elmer Cat. # NET1084, specific activity: 70-87 Ci/mmol, stock concentration: 1.22e-5 M, final concentration: 8.25e-9 M), and 50 mM Tris-HCl, 300 mM NaCl, (pH 7.4) buffers were used for Scintillation Proximity Assay $IC_{50}$/$K_i$ determination. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the radioligand was added at 50 µl/well. Membrane and beads were prepared to a ratio of 10 µg: 0.7 mg, with 0.7 mg PVT-WGA Amersham beads (Cat#RPQ0282V) added per well. 130 µA of the membrane:bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human norepinephrine transporter. For example, (7-Fluoro-1H-indol-5-yl)-[(S)-3-(3-methyl-butyl)-pyrrolidin-3-yl]-methanone exhibited a pKi of approximately 9.2 using the above assay.

Example 25

Screening for Compounds Active at Human Dopamine Transporter Using a Scintillation Proximity Assay (SPA)

This assay was used to determine the affinity of ligands for the dopamine transporter by competition with [$^3$H]-Vanoxerine.

HEK-293 cells (Tatsumi et al., Eur. J. Pharmacol. 1997, 30, 249-258) stably expressing recombinant hDAT were maintained with media (DMEM hi glucose with 10% FBS, 300 µg/ml G418 and 2 mM L-Glutamine) and incubated at 37° C. with 5% $CO_2$. Cells were plated four hours prior to experiment by placing approximately 30,000 cells per well (in PBS) on white, opaque Cell-Tak coated 96 well plates. Extra buffer was apriated from the cell plates using an ELx405 plate washer.

$^3$-[H] vanoxerine (GBR 12909) radioligand, specific activity approximately 59 Ci/mmol, stock concentration, 400 nM, and 50 mM Tris-HCl, 300 mM NaCl, (pH 7.4) buffers were used for Scintillation Proximity Assay $IC_{50}$/$K_i$ determination. Compounds of the invention were diluted from 10 mM to 0.1 nM FAC (10 point curves, whole log/half log dilutions) via a Beckman Biomek 2000 using a 10-point dilution protocol. The mixtures were allowed to stand at room temperature for 30 minutes, and were then counted on a Packard TopCount LCS, a generic SPA counting protocol settings, Count Time (min.): 0.40, Background Subtract: none, Half-Life Correction: none, Quench Indicator: tSIS, Platemap blank subtraction: none, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human dopamine transporter. For example, [(S)-3-(3,3-Dimethyl-butyl)-pyrrolidin-3-yl]-(7-fluoro-1H-indol-5-yl)-methanone exhibited a pKi of approximately 9.2 using the above assay.

Example 26

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 µl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 mM bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 27

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 28

Cold Allodynia in Rats with a Chronic Constriction Injury of the Sciatic Nerve The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I:

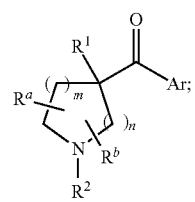

or a pharmaceutically acceptable salt thereof,
wherein:
  m is 1;
  n is 2;
  Ar is:
    optionally substituted phenyl;
  $R^1$ is:
    hetero-$C_{1-6}$alkyl;
    halo-$C_{1-6}$alkyl;
    $C_{3-7}$cycloalkyl-$C_{1-6}$alkyl;
    $C_{1-6}$alkyl-$C_{3-6}$cycloalkyl-$C_{1-6}$alkyl; or
    aryl-$C_{1-3}$alkyl;
  $R^2$ is:
    hydrogen; or
    $C_{1-6}$alkyl; and
  $R^a$ and $R^b$ each independently is:
    hydrogen;
    $C_{1-6}$alkyl; or
    or $R^a$ and $R^b$ together form a $C_{1-2}$alkylene;
provided that when m is 1, n is 2 and Ar is optionally substituted phenyl, then $R^1$ is not methyl or ethyl.

2. The compound of claim 1, wherein $R^1$ is:
   $C_{3-6}$alkyl;
   $C_{3-6}$cycloalkyl-$C_{1-6}$alkyl; or
   $C_{1-6}$-alkyl-$C_{1-3}$cycloalkyl-$C_{1-6}$alkyl.

3. The compound of claim 1, wherein $R^1$ is $C_{3-6}$alkyl.

4. The compound of claim 1, wherein $R^2$ is hydrogen.

5. The compound of claim 1, wherein $R^a$ and $R^b$ are hydrogen.

6. The compound of claim 1, wherein said compound is of formula IX:

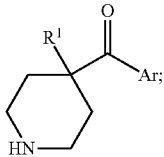

IX wherein Ar and $R^1$ are as recited in claim 1.

7. The compound of claim 6, wherein:
   $R^1$ is:
      $C_{3-6}$alkyl;
      $C_{3-6}$cycloalkyl-$C_{1-6}$alkyl; or
      $C_{1-6}$-alkyl-$C_{1-3}$cycloalkyl-$C_{1-6}$alkyl; and
   Ar is phenyl substituted one, two or three times with groups independently selected from:
      halo;
      amino;
      $C_{1-6}$alkyl;
      $C_{3-6}$cycloalkyl;
      $C_{1-6}$alkylcarbonyl;
      $C_{1-6}$alkylsulfonyl;
      $C_{1-6}$alkylsulfanyl;
      halo-$C_{1-6}$alkyl;
      $C_{1-6}$alkoxy;
      halo-$C_{1-6}$alkoxy;
      $C_{1-6}$alkoxy-$C_{1-6}$alkyl;
      hydroxy;
      cyano;
      optionally substituted phenyl;
      optionally substituted phenoxy;
      phenylsulfonyl; or
      optionally substituted heteroaryl.

8. The compound of claim 7, wherein $R^1$ is $C_{3-6}$alkyl.

9. The compound of claim 8, wherein Ar is phenyl substituted at the 3- and 4-positions with groups independently selected from:
   halo;
   amino;
   $C_{1-6}$alkyl;
   halo-$C_{1-6}$alkyl;
   $C_{1-6}$alkoxy;
   hydroxy; or
   cyano.

10. The compound of claim 9, wherein Ar is phenyl substituted at the 3- and 4-positions with halo or amino.

11. The compound of claim 9, wherein Ar is phenyl substituted at the 3- and 4-positions with halo.

12. A pharmaceutical composition comprising a compound of claim 1 and a pharmaceutically acceptable carrier.

* * * * *